US006943001B2

(12) United States Patent
Zhao et al.

(10) Patent No.: US 6,943,001 B2
(45) Date of Patent: Sep. 13, 2005

(54) EPOXIDE HYDROLASES, NUCLEIC ACIDS ENCODING THEM AND METHODS FOR MAKING AND USING THEM

(75) Inventors: Lishan Zhao, Carlsbad, CA (US); Eric J. Mathur, Carlsbad, CA (US); David Weiner, Del Mar, CA (US); Toby Richardson, San Diego, CA (US); Aileen Milan, San Diego, CA (US); Mark J. Burk, San Diego, CA (US); Bin Han, San Diego, CA (US); Jay M. Short, Rancho Santa Fe, CA (US)

(73) Assignee: Diversa Corporation, San Diego, CA (US)

( * ) Notice: Subject to any disclaimer, the term of this patent is extended or adjusted under 35 U.S.C. 154(b) by 0 days.

(21) Appl. No.: 10/272,490

(22) Filed: Oct. 10, 2002

(65) Prior Publication Data

US 2003/0148490 A1 Aug. 7, 2003

Related U.S. Application Data

(63) Continuation-in-part of application No. 10/214,473, filed on Aug. 5, 2002.
(60) Provisional application No. 60/309,478, filed on Aug. 3, 2001, and provisional application No. 60/393,978, filed on Jul. 3, 2002.

(51) Int. Cl.[7] .......................... C12N 9/14; C12N 15/54; C12Q 1/34; C07K 2/04
(52) U.S. Cl. ..................... 435/195; 435/18; 435/252.3; 435/325; 435/410; 435/254.1; 435/255.1; 435/320.1; 536/23.2; 536/24.33
(58) Field of Search ............................ 435/195, 320.1, 435/252.7, 18, 325, 410, 254.1, 255.1; 536/23.2, 24.3, 24.33

(56) References Cited

U.S. PATENT DOCUMENTS

| | | | |
|---|---|---|---|
| 4,558,004 A | 12/1985 | Hammock et al. .............. 435/4 |
| 5,387,742 A | 2/1995 | Cordell .......................... 800/2 |
| 5,445,956 A | 8/1995 | Hammock et al. .......... 435/195 |
| 5,573,933 A | 11/1996 | Seamark et al. ......... 435/172.3 |
| 5,605,793 A | 2/1997 | Stemmer ........................ 435/6 |
| 5,635,369 A | 6/1997 | Pompon et al. ............. 435/69.1 |
| 5,705,647 A | 1/1998 | Babu et al. .................. 546/146 |
| 5,759,765 A | 6/1998 | Harris et al. .................... 435/4 |
| 5,795,737 A | 8/1998 | Seed et al. .................. 435/69.1 |
| 5,811,238 A | 9/1998 | Stemmer et al. ................ 435/6 |
| 5,824,514 A | 10/1998 | Kauffman et al. .......... 435/91.1 |
| 5,830,721 A | 11/1998 | Stemmer et al. .......... 435/172.1 |
| 5,834,252 A | 11/1998 | Stemmer et al. ............ 435/91.1 |
| 5,939,250 A | 8/1999 | Short .............................. 435/4 |
| 5,955,358 A | 9/1999 | Huse .......................... 435/328 |
| 5,955,496 A | 9/1999 | Hammock et al. .......... 514/477 |
| 5,965,408 A | 10/1999 | Short .......................... 435/91.1 |
| 6,037,160 A | 3/2000 | Wisnewski et al. .......... 435/195 |
| 6,057,103 A | 5/2000 | Short .............................. 435/6 |
| 6,143,542 A | 11/2000 | Wisnewski et al. .......... 435/195 |
| 6,150,415 A | 11/2000 | Hammock et al. .......... 514/588 |
| 6,153,397 A | 11/2000 | Wisnewski et al. ........... 435/18 |
| 6,174,695 B1 | 1/2001 | Hammock et al. ............. 435/18 |
| 6,287,861 B1 | 9/2001 | Stemmer et al. ............ 435/440 |
| 6,287,862 B1 | 9/2001 | delCardayre et al. ....... 435/440 |
| 6,291,242 B1 | 9/2001 | Stemmer .................... 435/440 |
| 6,361,974 B1 | 3/2002 | Short et al. ................. 435/69.1 |
| 6,372,469 B1 | 4/2002 | Arahira et al. .............. 435/195 |
| 6,379,938 B1 | 4/2002 | Dauvrin et al. ............. 435/158 |
| 6,387,668 B1 | 5/2002 | Lutje Spelberg et al. ... 435/155 |
| 6,537,776 B1 | 3/2003 | Short ........................ 435/69.1 |

FOREIGN PATENT DOCUMENTS

| | | |
|---|---|---|
| WO | WO 98/53081 | 11/1988 |
| WO | WO 94/03588 | 2/1994 |
| WO | WO 98/02554 | 1/1998 |
| WO | WO 99/21972 | 5/1999 |
| WO | WO 00/09682 | 2/2000 |
| WO | WO 00/20573 | 4/2000 |
| WO | WO 00/29846 | 5/2000 |
| WO | WO 00/37619 | 6/2000 |
| WO | WO 00/40569 | 7/2000 |
| WO | WO 00/48593 | 8/2000 |
| WO | WO 99/06059 | 10/2000 |
| WO | WO 01/07623 | 2/2001 |
| WO | WO 01/10438 | 2/2001 |
| WO | WO 01/46476 | 6/2001 |

OTHER PUBLICATIONS

Misawa, E., et al. (1998) Acc. No. CAJ4332.*
Vipey, V., et al. (2000) Acc. No. AZ578947.*
Strausberg (2000) Acc. No. BF434120.*
Steinreiber, A. and Faber, K., "Microbial epoxide hydrolases for preparative biotransformations", Curr. Opin. Biotechnol. vol. 12, pp. 552–558, 2001.
Zhi–Xian Wang et al., "An Efficient Catalytic Asymmetric Epoxidation Method," J. Am. Chem. Soc. vol. 119, pp. 11224–11235, 1997.
Tokunaga, M. Asymmetric Catalysis with Water: Efficient Kinetic Resolution of Terminal Epoxides by Means of Catalytic Hydrolysis Science 1997, vol. 277, pp. 936–938, 1997.
Morisseau, C. Proc. Natl. Acad. Sci. vol. 96, pp. 8849–8854, 1999.
Swaving, J., "Microbial transformation of epoxices", Enzyme and Microbial Technology, vol. 22, pp. 19–26, 1998.
Patten, et al., "Applications of DNA shuffling to pharmaceuticals and vaccines", Current Opinion in Biotechnology, vol. 8, pp. 724–733, 1997.

(Continued)

Primary Examiner—Charles L. Patterson, Jr.
(74) Attorney, Agent, or Firm—Morrison & Foerster LLP

(57) ABSTRACT

The invention is directed to polypeptides having epoxide hydrolase activity, polynucleotides encoding the polypeptides, antibodies that bind to these polypeptides, and methods for making and using these polynucleotides and polypeptides. The epoxide hydrolases are used to catalyze the hydrolysis of epoxides and arene oxides to their corresponding diols.

58 Claims, 14 Drawing Sheets

OTHER PUBLICATIONS

Nardini, M., "The X-ray Structure of Epoxide Hydrolase from *Agrobacterium radiobacter* AD1", vol. 274, No. 21, pp. 14579–14586, 1999.

Ling, M.M., "Approaches to DNA Mutagenesis: An Overview", *Analytical Biochemistry*, vol. 254, pp. 157–178, 1997.

Goswami, A., "Stereospecific enzymatic hydrolysis of racemic epoxide: a process for making chiral epoxide", *Tetrahedron:Asymmetry*, vol. 10, pp. 3167–3175, 1999.

Genzel, Y., "Microbiological transformations. Part 46: Preparation of enantiopure (S)–2pyridyloxirane via epoxide hydrolase–catalysed kinetic resolution", *Tetrahedron:Asymmetry*, vol. 11, pp. 3041–3044, 2000.

Cleij, M., "Microbiological transformatioons. Part 42: A two–liquid–phase preparative scale process for an epoxide hydrolase catalysed resolution of para–bromo–α–methyl styrene oxide. Occurrence of a surprising enantioselectivity enhancement", *Tetrahedron:Asymmetry*, vol. 9, pp. 1839–1842, 1998.

Argiriadi, M., "Detoxification of environmental mutagens and carcinogens: Structure, mechanism, and evolution of liver epoxide hydrolase", *Proc. Natl. Acad. Sci.*, vol. 96, pp. 10637–10642, 1999.

Archelas, A., "Synthetic applications of epoxide hydrolases", *Current Opinion in Chemical Biology*, vol. 5, pp. 112–119, 2001.

Crameri, A., "DNA shuffling of a family of genes from diverse species accelerates directed evolution", *Nature*, vol. 391, pp. 288–291, 1998.

Rice, G., "Random PCR mutagenesis screening of secreted proteins by directed expression in mammalian cells", *Proc. Natl. Acad. Sci.*, vol. 89, pp. 5467–5471, 1992.

Arkin, A., "An algorithm for protein engineering: Simulations of recursive ensemble mutagenesis", *Proc. Natl. Acad. Sci.*, vol. 89, pp. 7811–7815, 1992.

Stemmer, W., "DNA shuffling by random fragmentation and reassembly: In vitro recombination for molecular evolution", *Proc. Natl. Acad. Sci.* vol. 91, pp. 10740–10751, 1994.

Orru, R.V.A., "Stereoselectivities of microbial epoxide hydrolases", *Current Opinion in Chemical Biology*, vol. 3, pp. 16–21, 1999.

Weijers, C.A.G.M., Enantioselective hydrolysis of unbranched aliphatic 1,2–epoxides by *Rhodotorula glutinis*, *Tetrahedron:Asymmetry*, vol. 9, pp. 467–473, 1998.

Weijers, C.A.G.M., "Enantiselective hydrolysis of aryl, alicyclic and aliphatic epoxides by *Rhodotorula glutinis*", *Tetrahedron:Asymmetry*, vol. 8, No. 4, pp. 639–647, 1997.

Wu, M., "An Efficient Formal Synthesis of Balanol via the Asymmetric Epoxide Ring Opening Reaction", *Tetrahedron Letters*, vol. 38, No. 10, pp. 1693–1696, 1997.

Kim, B.M., "Synthesis of a Chiral Aziridine Derivative as a Versatile Intermediate for HIV Protease Inhibitors", *Organic Letters*, vol. 3, No. 15, pp. 2349–2351, 2001.

Jacobsen, E.N., "Asymmetric Catalysis of Epoxide Ring–Opening Reactions", *Acc. Chem. Res.*, vol. 33, pp. 421–431, 2000.

Schaus, S. E., Dynamic Kinetic Resolution of Epichlorohydrin via Enantioselective Catalytic Ring Opening with $TMSN_3$, Practical Synthesis of Aryl Oxazolidinone Antibacterial Agents, *Tetrahedron Letters*, vol. 37, No. 44, pp. 7937–7940, 1996.

Xu, Z., "Process Research and Development for an Efficient Synthesis of the HIV Protease Inhibitor BMS–23632", *Organic Process Research & Development*, vol. 6, pp. 323–328, 2002.

Ikunaka, M., "A Process in Need is a Process Indeed: Scalable Enantioselective Synthesis of Chiral Compounds for the Pharmaceutical Industry", *Chem. Eur. M.*, vol. 9, No. 2, pp. 378–388, 2003.

Yu, D., "Synthesis and Antibacterial Activity of Linezolid Analogues", *Bioorganic & Medicinal Chemistry Letters*, vol. 12, pp. 857–859, 2002.

Hechtberger, P., "Asymmetric Hydrolysis of Epoxides using an Immobilized Enzyme Preparation from *Phodococcus* sp.", *Tetrahedron:Asymmetry*, vol. 4, No. 6, pp. 1161–1164, 1993.

Spelberg, J.H.L., "Biocatalytic Potential of the Epoxide Hydolase from *Agrobacterium radiobacter* AD1 and a Mutant with Enhanced Enantioselectivity", *Adv. Synth. Catal.*, vol. 344, No. 9, pp. 980–985, 2002.

Sagawa, S., "Catalytic Asymmetric Aminolysis of 3,5,8–Trioxabicyclo [5.1.0] octane Providing an Optically Pure 2–Amino–1,3,4–butanetriol Equivalent", *J. Org. Chem.*, vol. 64, pp. 4962–4965, 1999.

Zook, S., "A concise synthesis of the HIV–protease inhibitor nelfinavir via an unusual tetrahydrofuran rearrangement", *Tetrahedron Letter*, vol. 41, pp. 7017–7021, 2000.

Inaba, T., "A Practical Synthesis of Nelfinavir, an HIV–Protease Inhibitor, Using a Novel Chiral C4 Building Block: (5R,6S)–2,2–Dimethyl–5–hydroxy–1, 3–dioxepan–6–ylammonium Acetate", *J. Org. Chem.*, vol. 64, pp. 7582–7583, 1998.

Weijers, C.A.G.M., "Epoxide hydrolase from yeasts and other sources, versatile tools in biocatalysis", *Journal of Molecular Catalysis B–Enzymatic*, vol. 6, pp. 199–214, 1999.

Cleij, A., "Microbiological Transformations 43. Epoxide Hydrolases as Tools for the Synthesis of Enantiopure α–Methylstyrene Oxides: A New and Efficient Synthesis of (S)–Ibuprofen", *J. Org. Chem.*, vol. 64, pp. 5029–2035, 1999.

Genzel, Y., "Microbiological Tarnsformations. 47. A Step toward a Green Chemistry Preparation of Enantiopure (S)–2–,–3–, and –4–Pyridyloxirane via an Epoxide Hydrolase catalyzed Kinetic Resolution", *J. Org. Chem.*, vol. 66, pp. 538–543, 2001.

Wang, G., "A Simple three–step method for preparing homochiral 5–trityloxymethyl–2–oxazolidinones from optically active 3–hydroxy–β–butyrolactones", *Tetrahedron: Asymmetry*, vol. 11, pp. 4429–4432, 2000.

Inaba, T., "(1S)–1–[(4R)–2,2–Dimethyl–1, 3–dioxolan–4–yl]–2–hydroxyethylammonium Benzoate, A Versatile Building Block for Chiral 2–Aminoalkanols: Concise Synthesis and Application to Nelfinavir, a Potent HIV–Protease Inhibitor", *J. Org. Chem.*, vol. 65, pp. 1623–1628, 2000.

Lupattelli, P., "Single Route to Chiral syn–and anti–2–Amino–1,2–diphenylethanols via a New Stereodivergent Opening of trans–1,2–Diphenyloxirane", *J. Org. Chem.*, vol. 68, pp.3360–3362, 2003.

Schaus, S.E., "Practical Synthesis of Enantipure Cyclic 1,2–Amino Alcohols via Catalytic Asymmetric Ring Opening of Meso Epoxides", *J. Org. Chem.*, vol. 62, pp. 4197–4199, 1997.

Rink, R., "Primary Structure and Catalytic Mechanism of the Epoxide Hydrolase from Agrobacterium radiobacter AD1*" *The Journal of Biological Chemistry* vol. 272 No. 23 pp. 14650–14657, 1997.

Rink, R., "Kinectic Mechanism of the Enantioselective Conversion of Styrene Oxide by Epoxide Hydrolase from Agrobacterium radiobacter Ad1", *Biochemistry*, vol. 37, pp. 18119–18127, 1998.

Rink, R., Mutation of Tyrosine Residues Involved in the Alkylation Half Reaction of Epoxide Hydrolase from *Agrobacterium radiobacter* AD1 Results in Improved Enantioselectivity *J. Am. Chem. Soc.*, vol. 121, pp. 7417–7418, 1999.

Rink, R., "Tyrosine Residues Serve as Proton Donor in the Catalytic Mechanism of Epoxide Hydrolase from *Agrobacterium radiobacter*", *Biochemistry*, vol. 39, pp. 5600–5613, 2000.

Van Den Wijnegaard, A., "Degradation of Epichlorohydrin and Halohydrins by Bacterial Cultures Isolated from Freshwater Sediment", *Journal of General Microbiology*, vol. 135, pp. 2199–2208, 1989.

Jacobs, M.H.J., "Characterization of the epoxide hydrolase from an epichlorohydrin–degrading Pseudomonas sp.", *Eur. J. Biochem.* vol. 202, pp. 1217–1222, 1991.

Van Der Werf, MJ, "*Rhodococcus erythropolis* DCL14 Contains a Novel Degradation Pathway for Limonene", *Applied and Environmental Microbiology*, vol. 65, No. 5, pp. 2092–2102, 1999.

Barbirato, F., "The *Rhodococcus erythropolis* DCL14 limonene–1,2–epoxide hydrolase gene encodes an enzyme belonging to a novel class of epoxide hydrolases", *FEBS Letters*, vol. 483, pp. 293–296, 1998.

Mischitz, N., "Regioselectivity of Rhodococcus NCIMB 11216 Epoxide Hydrolase: Applicability of E–Values for Description of Enantioselectivity Depends on Substrate Structure", *Tetrahedron:Asymmetry*, vol. 7, No. 7, pp. 2041–2046, 1996.

Visser, H., "Cloning and characterization of an epoxide hydrolase–encoding gene from rhodotorula glutinis", *Appl. Microbiol. Biotechnol*, vol. 53, pp. 415–419, 2000.

Choi, W.J., "Continuous production of enantiopure 1,2–epoxyhexane by yeast epoxide hydrolase in a two–phase membrane bioreactor", *Appl Microbiol Biotechnol*, vol. 54, pp. 641–646, 2000.

Guengerich, F. P., "Alcohol Dehydrogenase–Coupled Spectrophotometric Assay of Epoxide Hydrates Activity", *Analytical Biochemistry*, vol. 104, pp. 445–451, 1980.

Hasegawa, L.S., "Spectrophotometric Assay for Mammalian Cytosolic Epoxide Hydrolase Using TRNA–Stillbene Oxide as the Substrate", *Biochemical Pharmacology*, vol. 31, No. 11, pp. 1979–1984, 1982.

Bhatnagar, T., "A Spectrophotometric method to assay epoxide hydrolase activity", *J. Biochem. Biophys. Methods,* vol. 50, pp. 1–13, 2001.

De Raadt, A., "Chemoselective Enzymatic Hydrolysis of Aliphatic and Alicyclic Nitrates", *J. Chem. Soc. Perkin Trans.*, pp. 137–140, 1992.

Wixtrom, R. N., "Continuous Spectrophotometric Assays for Cytosolic Epoxide Hydrolase", *Analytical Biochemistry*, vol. 174, pp. 291–299, 1988.

Dansette, P., "Continuous Fluorometric Assay of Epoxide Hydrase Activity", *Analytical Biochemistry*, vol. 97, pp. 340–345, 1979.

Gill, S., "Rapid and sensitive enzyme–linked immunosorbent assay for the microsomal epoxide hydrolase", *Carcinogenesis*, vol. 3, pp. 1307–1310, 1982.

Watabe, T., "Photometric Assay of the Hepatic Epoxide Hydrolase Activity with Safrole Oxide (SAFO) as Substrate", *Biochemical Pharmacology*, vol. 23, pp. 2839–2844, 1974.

Oesch, F., "A Highly Sensitive Assay for Epoxide Hydrolase Using an Endogenous Epoxide as Substrate: 16α, 17α–Epoxyandrost–4–en–3–one", *Analytical Biochemistry*, vol. 117, pp. 223–230, 1981.

Black, H.S., "A Practical Radiochromatographic Assay For Cholesterol Epoxide Hydrase", *Analytical Biochemistry*, vol. 94, pp. 383–385, 1979.

Hukkelhoven, M.W.A.C., "A sensitive fluorometric assay for epoxide hydratase", *FEBS Letters*, vol. 144, No. 1, pp. 104–108, 1982.

Mullin, C.A., "A Rapid Radiometric Assay for Mammalian Cytosolic Epoxide Hydrolase", *Analytical Biochemistry*, vol. 106, pp. 476–485, 1980.

Craven, A.C.C., "The Assay of Microsomal Epoxide Hyrolase in Normal and Pathological Human Liver", *Biochemical Pharmacology*, vol. 31, No. 7, pp. 1321–1324, 1982.

Gill, S., "Radiometric Assays for Mammalian Epoxide Hydrolase and Glutathione S–Transferase", *Analytical Biochemistry*, vol. 131, pp. 273–282, 1983.

Herrero, M.E., "Fluorometric Microassay to Quantify Microsomal Epoxide Hydrolase in 96–Well Plates", *Analytical Biochemistry*, vol. 230, pp. 154–158, 1995.

Faber, K., "Hydrolysis of Epoxides", vol. 11.2, pp. 579–608.

Armstrong, R., "Nucleophilic Epoxide Opening", pp. 51–71.

Archelas, A., "Biocatalytic Approaches for the Synthesis of Enantiopure Epoxides", *Top Curr Chem* vol. 200, pp. 160–191, 1999.

Kroutil, W., "Stereoselective Syntheses Using Microbial Epoxide Hydrolases", pp. 205–237.

Chiappe, C., "Enantioselective hydrolasis of epoxides: the employment of the soluble fraction from *Victa sativa* seedlings", *Journal of Molecular Catalysis B: Enzymatic*, vol. 14, pp. 125–129, 2001.

Archelas, A., "Synthesis of Enantiopure Epoxides Through Biocatalytic Approaches", *Annu Rev. Microbiol.*, vol. 51, pp. 491–525, 1997.

Omiecinski C., "Epoxide hydrolase—polymorphism and role in toxicology", *Toxicology Letters*, vol. 112–113, pp. 365–370, 2000.

Choi, W.J., "Resolution of 1,2–epoxyhexane by *Rhodotorula glutinis* using a two–phase membrane bioreactor", *Appl Microbiol Biotechnol*, vol. 53, pp. 7–11, 1999.

Katsuki, T., "Catalytic asymmetric oxidations using optically active (salen) manganese (III) complexes as catalysts", *Coordination Chemistry Reviews*, vol. 140, pp. 189–214, 1995.

Badalassi, F., "A Versatile Periodate–Coupled Fluorogenic Assay for Hydrolytic Enzymes", *Arnew. Chem. Intl. Ed.*, vol. 39, No. 22, pp. 4067–4070, 2000.

Guerard, J., "Transketolase–Mediated Synthesis of 4–Deoxy–D–fructose 6–Phosphate by Epoxide Hydrolase–catalysed Resolution of 1,1–Diethoxy–3,4–epoxybutane", *Eur. J. Org. Chem.* pp. 3399–3402, 1999.

Armstrong, R. N., "Kinetic and Chemical Mechanism of Epoxide Hydrolase", *Drug Metabolism Reviews*, Rev. 1999, vol. 31, pp. 71–86.

Kroutil, W., "Deracemization of (+)–cis–2,3–Epoxyheptane via Enanticonvergent Biocatalytic Hydrolysis using Nocardia EH1–Epoxide Hydrolase", *Tetrahedron Letters,* vol. 37, No. 46, pp. 8379–8382, 1996.

Archer, I. V. J., Chemoenzymic Resolution and Deracemisation of (+)–1–Methyl–1,2–epoxycycohexane; the synthesis of (1–s,2–s–1–methylcyclohexane–1,2 diol) *Tetrahedron Letters,* vol. 37, No. 48, pp. 8819–8822, 1996.

Zou, J., et al., "Structore of Aspergillus niiger epoxide hydrolase at 1.8 Å resolution: implications for the structure and function of the mammalian microsomal class of epoxide hydrolase", *Structure,* vol. 8, pp. 111–12, 2000.

Besse, P., "Chemical and Biological Synthesis of Chiral Epoxides", *Tetrahedron,* vol. 50, No. 30, pp. 8885–8927, 1994.

Hacking, A. J., "Disruption of the Fucose Pathway as a Consequence of Genetic Adaptation to Propanediol as a Carbon Source in E. coli", *Journal of Bacteriology,* vol. 126, No. 3, pp. 1166–1172, 1976.

Arnold, F.H., "Proteiin engineering for unusual environments", *Current Opinion in Biotechnology* vol. 4, pp.450–455, 1993.

Smith, M., "In vitro mutagenesis", *Ann. Rev. Genet.* vol. 19, pp. 423–462, 1985.

Crameri, A., "Construction and evolution of antibody–phage libraries by DNA shuffling", *Nature Medicine,* vol. 2, No. 1, pp. 100–103, 1996.

Crameri, A., "Combinatorial Multiple Cassette Mutagenesis Creates All the Permutations of Mutant and Wild–Type Sequences", *BioTechniques,* vol. 18, No. 2, pp. 194–196, 1995.

Jacobsen, E. N., "Asymmetric Catalytic Epoxidation of Unfunctionalized Olefins", In *Catalytic Asymmetric Synthesis,* Ojima, I. Ed.: VCH: New York, pp. 159–202, 1993.

Johnson, R. A., Sharples, K. B., "Catalytic asymmetric Dihydroxylation", In *Catalytic Asymmetric Synthesis:* Ojima, I. Ed.; VCH: New York, pp. 227–272, 1993.

Johnson, R. A.: Sharpless, K. B., "Catalytic asymmetric epoxidation of allylic alcohols", In *Catalytic Asymmetric Synthesis:* Ojima, E. Ed.: VCH: New York.: pp. 103–158, 1993.

Arand, M., "Cloning and molecular characterization of a soluble epoxide hydrolase from Aspergillus niger that is related to mammalian microsomal epoxide hydrolase", *Biochem. J.,* vol. 344, pp. 273–280, 1999.

\* cited by examiner docetaxel: $R_1 = {}^tBu$, $R_2 = H$ paclitaxel: $R_1 = $ phenyl, $R_2 = $ acetyl

| | Chemical Methods | $\overset{R}{\underset{}{\triangle}}{}^O$ | $\overset{R_1}{\underset{R_2}{\triangle}}{}^O$ | $\overset{R_2 \quad R_1}{\underset{O}{\triangle}}$ | $\overset{R_1 \quad R_3}{\underset{R_2 \quad O}{\triangle}}$ | $\overset{R_1 \quad R_3}{\underset{R_2 \; O \; R_4}{\triangle}}$ |
|---|---|---|---|---|---|---|
| Alkene | Sharpless epoxidation (Ti-tartrate) | (√) Allylic alcohol | (√) Allylic alcohol | (√) Allylic Alcohol | (√) Allylic Alcohol | (√) Allylic alcohol |
| | Katsuki-Jacobsen epoxidation (Mn-Salen) | | | √ cis-conjugated | √ conjugated | |
| | Shi-epoxidation (Oxone/chiral ketone) | | | √ trans- | √ | |
| Epoxides | Jacobsen hydrolytic kinetic resolution (Co-Salen) | √ | | | | |

*FIG. 6*

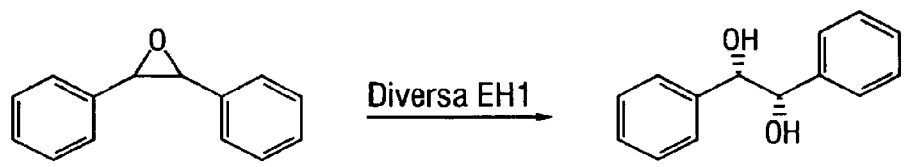

> 97% ee
99% conversion

*FIG. 7* mono-substituted | 2,2-disubstituted | 2,3-disubstituted | trisubstituted | styrene-oxides > 90% ee
85% yld glycidol R=OH
propene oxide R=H glycerol R=OH
propane diol R=H

SEQUENCE LISTING

<160> NUMBER OF SEQ ID NOS: 94

<210> SEQ ID NO 1
<211> LENGTH: 1353
<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(102)

<400> SEQUENCE: 1

-continued

```
atgtcaaaca acgctcccca atcctcgtcg cgccgccatt tcgtcggcgt ggccgctgcg      60
gcgctcgcga caggctcgct gagccggctc gcctttgcca acgcattccc gactgtcggc     120
acgatcacgg aacccgccaa tggcgacaag gcagcgctgc gcccgttccg cgttcacatt     180
cctgaagcgc agctcgtcga catgcggcgg cgcatcaagg cgacgcgctg gccggaccgc     240
gaaaccgtgc ccgacgaatc gcagggtatt cagctcgcca ccatccaggg actcgcccaa     300
tactgggcga ccggatacga ctggcgtaaa tgcgaggcgc gactgaattc gtatccgcaa     360
ttcatcacgg agatcgacgg actcgatatc catttcatcc atgtgcgctc gaagcacgcc     420
gacgccatgc cgttgatcgt cacgcatgga tggcccgggt cggtcatcga acagttcaag     480
atcatcgatc cgctcgtcaa tccgaccgcg tacggcgcgc cggcatcgga tgccttccat     540
ctcgtgattc cctctttgcc cggttacggc ttttcggcca gaccgaccac gacgggatgg     600
ggaccggagc gcaccgcacg cgcgtgggtc accttgatga aacgcctcgg ctatgagcgt     660
tttgcttcgc agggcggcga tctcggcggg atcgtcacga acatcatggc caaacaggcg     720
ccgcccgaac tgatcggcat tcatgtgaac ttccctgcct ccgttccagc ggagattctg     780
aagtcgctgg ctgccggtga atcgatgccc gccggattat cggacgagga aaagcacgcg     840
tatgagcagt tgagtgccaa cttcaagaag aagcgcggct acgcattcga aatgggcacg     900
cgcccgcaga cgctttacgg actcgccgac tcacccatcg cgctggcttc ctggctactc     960
gaccacggcg acggctacgg ccagcccgcg gctgcgctga gcgcggccgt ccttggtcac    1020
cccgtcaacg gtcactcagc aggcgcgctg acgcgagacg acatactcga cgacatcacg    1080
ctttactggc tgaccaacac cggtatctcg gcagcgcgtt tctactggga gtcgcatgcg    1140
aacttctttc tcgcagccga cgtcaatgtg cctgctgccg tgagcgcatt tcccggagaa    1200
aattaccagg cgccgaagag ctggacggaa aaggcctatc acaagctgat ttacttcaac    1260
aagcccgaaa cgggcggcca cttcgcggca tgggaagagc cgatgatctt cgcgaatgaa    1320
gtgcgctcgg ggttaaggcc cttgcgcgcg tga                                1353
```

<210> SEQ ID NO 2
<211> LENGTH: 450
<212> TYPE: PRT
<213> ORGANISM: Unknown
<220> FEATURE:
<223> OTHER INFORMATION: Obtained from an environmental source
<220> FEATURE:
<221> NAME/KEY: SIGNAL
<222> LOCATION: (1)...(34)

<400> SEQUENCE: 2

```
Met Ser Asn Asn Ala Pro Gln Ser Ser Arg Arg His Phe Val Gly
  1               5                  10                  15

Val Ala Ala Ala Leu Ala Thr Gly Ser Leu Ser Arg Leu Ala Phe
                 20                  25                  30

Ala Asn Ala Phe Pro Thr Val Gly Thr Ile Thr Glu Pro Ala Asn Gly
             35                  40                  45

Asp Lys Ala Ala Leu Arg Pro Phe Arg Val His Ile Pro Glu Ala Gln
 50                  55                  60

Leu Val Asp Met Arg Arg Arg Ile Lys Ala Thr Arg Trp Pro Asp Arg
 65                  70                  75                  80

Glu Thr Val Pro Asp Glu Ser Gln Gly Ile Gln Leu Ala Thr Ile Gln
                 85                  90                  95

Gly Leu Ala Gln Tyr Trp Ala Thr Gly Tyr Asp Trp Arg Lys Cys Glu
            100                 105                 110
```

```
Ala Arg Leu Asn Ser Tyr Pro Gln Phe Ile Thr Glu Ile Asp Gly Leu
            115                 120                 125

Asp Ile His Phe Ile His Val Arg Ser Lys His Ala Asp Ala Met Pro
        130                 135                 140

Leu Ile Val Thr His Gly Trp Pro Gly Ser Val Ile Glu Gln Phe Lys
145                 150                 155                 160

Ile Ile Asp Pro Leu Val Asn Pro Thr Ala Tyr Gly Pro Ala Ser
                165                 170                 175

Asp Ala Phe His Leu Val Ile Pro Ser Leu Pro Gly Tyr Gly Phe Ser
            180                 185                 190

Ala Arg Pro Thr Thr Thr Gly Trp Gly Pro Glu Arg Thr Ala Arg Ala
            195                 200                 205

Trp Val Thr Leu Met Lys Arg Leu Gly Tyr Glu Arg Phe Ala Ser Gln
            210                 215                 220

Gly Gly Asp Leu Gly Gly Ile Val Thr Asn Ile Met Ala Lys Gln Ala
225                 230                 235                 240

Pro Pro Glu Leu Ile Gly Ile His Val Asn Phe Pro Ala Ser Val Pro
                245                 250                 255

Ala Glu Ile Leu Lys Ser Leu Ala Ala Gly Glu Ser Met Pro Ala Gly
                260                 265                 270

Leu Ser Asp Glu Glu Lys His Ala Tyr Glu Gln Leu Ser Ala Asn Phe
            275                 280                 285

Lys Lys Lys Arg Gly Tyr Ala Phe Glu Met Gly Thr Arg Pro Gln Thr
            290                 295                 300

Leu Tyr Gly Leu Ala Asp Ser Pro Ile Ala Leu Ala Ser Trp Leu Leu
305                 310                 315                 320

Asp His Gly Asp Gly Tyr Gly Gln Pro Ala Ala Leu Ser Ala Ala
                325                 330                 335

Val Leu Gly His Pro Val Asn Gly His Ser Ala Gly Ala Leu Thr Arg
                340                 345                 350

Asp Asp Ile Leu Asp Asp Ile Thr Leu Tyr Trp Leu Thr Asn Thr Gly
            355                 360                 365

Ile Ser Ala Ala Arg Phe Tyr Trp Glu Ser His Ala Asn Phe Phe Leu
370                 375                 380

Ala Ala Asp Val Asn Val Pro Ala Ala Val Ser Ala Phe Pro Gly Glu
385                 390                 395                 400

Asn Tyr Gln Ala Pro Lys Ser Trp Thr Glu Lys Ala Tyr His Lys Leu
                405                 410                 415

Ile Tyr Phe Asn Lys Pro Glu Thr Gly Gly His Phe Ala Ala Trp Glu
                420                 425                 430

Glu Pro Met Ile Phe Ala Asn Glu Val Arg Ser Gly Leu Arg Pro Leu
            435                 440                 445

Arg Ala
    450

<210> SEQ ID NO 3
<211> LENGTH: 831
<212> TYPE: DNA
<213> ORGANISM: Bacterial

<400> SEQUENCE: 3
atgcgggtgc agctgtccga ggtgaacctc gacgtcgagg tgagcgggga ggggccggcc    60
gtgctgctcg tgcacggctt ccccgacagc catcgtctgt ggcgtcatca ggtcgcggcg   120
```

-continued

```
ctgaacgacg ccggtttcac cacggtcgcg cccaccctgc ggggcttcgg cgcctcggac      180
cgccccgagg gcggccccgc ggcgtaccac ccgggcaggc acgtcgccga cctggtcgag      240
ctcctggcgc acctcgacct cgaccgggtc catctggtgg ccacgactg gggttcgggc       300 atcgcgcagg ccctgaccca gttctacccg gaccgggtgg ggagcctgag catcctgtcc      360
gtcggccatc tggcgtcgat ccggtcggcg ggctgggagc agaagcagcg gtcctggtac      420
atgcttctgt tccagctggc cggggtggcc gaggactggc tggcgcggga cgacttcgcg      480
aacatgcggg agatgctggg cgagcacccg gacgccgagt ccgcgatcga ggcgctgcgc      540
gcgcccggag cgctgacggc cgcgctggac atctaccgcg cgggcctgcc gcctgaggtg      600
ctgttcggcg cggacgcgcc ggcggtgccg ctgccggagt cggtcccggt gctgggcctg      660
tggtcgaccg gcgaccgttt cctcaccgag cgctcgatgg cggggacggc cgagtacgtc      720
gccgggccgt ggcgctacga gcgcgtcgag gacgcgggcc actggctgca gctcgaccag      780
ccggagaggg tcaacgaact gctgctctcc ttcctcaagg agaacggcta g               831
```

<210> SEQ ID NO 4
<211> LENGTH: 276
<212> TYPE: PRT
<213> ORGANISM: Bacterial

<400> SEQUENCE: 4

```
Met Arg Val Gln Leu Ser Glu Val Asn Leu Asp Val Glu Val Ser Gly
 1               5                  10                  15

Glu Gly Pro Ala Val Leu Leu Val His Gly Phe Pro Asp Ser His Arg
            20                  25                  30

Leu Trp Arg His Gln Val Ala Ala Leu Asn Asp Ala Gly Phe Thr Thr
        35                  40                  45

Val Ala Pro Thr Leu Arg Gly Phe Gly Ala Ser Asp Arg Pro Glu Gly
    50                  55                  60

Gly Pro Ala Ala Tyr His Pro Gly Arg His Val Ala Asp Leu Val Glu
65                  70                  75                  80

Leu Leu Ala His Leu Asp Leu Asp Arg Val His Leu Val Gly His Asp
                85                  90                  95

Trp Gly Ser Gly Ile Ala Gln Ala Leu Thr Gln Phe Tyr Pro Asp Arg
            100                 105                 110

Val Arg Ser Leu Ser Ile Leu Ser Val Gly His Leu Ala Ser Ile Arg
        115                 120                 125

Ser Ala Gly Trp Glu Gln Lys Gln Arg Ser Trp Tyr Met Leu Leu Phe
    130                 135                 140

Gln Leu Ala Gly Val Ala Glu Asp Trp Leu Ala Arg Asp Asp Phe Ala
145                 150                 155                 160

Asn Met Arg Glu Met Leu Gly Glu His Pro Asp Ala Glu Ser Ala Ile
                165                 170                 175

Glu Ala Leu Arg Ala Pro Gly Ala Leu Thr Ala Ala Leu Asp Ile Tyr
            180                 185                 190

Arg Ala Gly Leu Pro Pro Glu Val Leu Phe Gly Ala Asp Ala Pro Ala
        195                 200                 205

Val Pro Leu Pro Glu Ser Val Pro Val Leu Gly Leu Trp Ser Thr Gly
    210                 215                 220

Asp Arg Phe Leu Thr Glu Arg Ser Met Ala Gly Thr Ala Glu Tyr Val
225                 230                 235                 240

Ala Gly Pro Trp Arg Tyr Glu Arg Val Glu Asp Ala Gly His Trp Leu
                245                 250                 255
```

```
Gln Leu Asp Gln Pro Glu Arg Val Asn Glu Leu Leu Leu Ser Phe Leu
            260                 265                 270

Lys Glu Asn Gly
        275

<210> SEQ ID NO 5
<211> LENGTH: 963
<212> TYPE: DNA
<213> ORGANISM: Unknown
<220> FEATURE:
<223> OTHER INFORMATION: Obtained from an environmental source

<400> SEQUENCE: 5
atgaggccaa cctccacacc cgagggcccc ggctccgtct ccggggcacc caacctcccg      60
gaggggttcg ccgacacctt caccagcagg tacgtcgacg ccggtgagct gcgtctccat     120
gcagttaccg gcggcgaagg cccgcccctg ctcctcgtcc acgggtggcc cgagacctgg     180
tacgcctggc ggatggtgat gccggcgttg gccgagcact tcgaggtgat cgcggtcgac     240
cagcgcgggg tcgggctgtc cgacaagccc gaggacggat acgacagcac aagcctcgcc     300
aacgacctcg tcggactgat ggacgcgctc ggccatgagc ggttcgcact gtatggaacc     360
gacactggaa tgccgatcgc ctatgcactg gctgcggacc agccggaccg aatcgaccgt     420 tgatcgtct cggaggcccc gcttccggc gtgactccct caccacctttt gctcctcccg      480 ccccaactca ctgccaagtt ctggcacctg atgttcaacc agctccccgc cgaggtgaac     540
gaggcgctcg tcaggggcg ggaggacatc ttcttcgggg cggagttcga cgcctctgcc      600
gggacgaaga agctgccagc cgacatcgtg aggtactaca tcgatacggt cgcgaccgac     660
cccgaccatc tgcgcgggag cttcgggttc taccggggcga tcccgaccac gatcgcgcag    720
aacgagcagc ggaagacacg gcgtctgccc atgcccgttc tcgcgatcgg cggggaggag    780
agcggtggag aagggccggg gaacgcgatg aagctcgtcg cagacgacgt gcagaccctg    840
gtcctcgcgg gcagcggcca ctgggtcgcc gagcaggcgc ctcacgcgct gctggcggcg    900
ctgagcgagt cctggctcc ctacctcgag gaagcgactg cacaggtagg agcggcccgc     960
tga                                                                  963

<210> SEQ ID NO 6
<211> LENGTH: 320
<212> TYPE: PRT
<213> ORGANISM: Unknown
<220> FEATURE:
<223> OTHER INFORMATION: Obtained from an environmental source

<400> SEQUENCE: 6

Met Arg Pro Thr Ser Thr Pro Glu Gly Pro Gly Ser Val Ser Gly Ala
1               5                   10                  15

Pro Asn Leu Pro Glu Gly Phe Ala Asp Thr Phe Thr Ser Arg Tyr Val
            20                  25                  30

Asp Ala Gly Glu Leu Arg Leu His Ala Val Thr Gly Gly Glu Gly Pro
        35                  40                  45

Pro Leu Leu Leu Val His Gly Trp Pro Glu Thr Trp Tyr Ala Trp Arg
    50                  55                  60

Met Val Met Pro Ala Leu Ala Glu His Phe Glu Val Ile Ala Val Asp
65                  70                  75                  80

Gln Arg Gly Val Gly Leu Ser Asp Lys Pro Glu Asp Gly Tyr Asp Ser
                85                  90                  95
```

```
Thr Ser Leu Ala Asn Asp Leu Val Gly Leu Met Asp Ala Leu Gly His
        100                 105                 110

Glu Arg Phe Ala Leu Tyr Gly Thr Asp Thr Gly Met Pro Ile Ala Tyr
        115                 120                 125

Ala Leu Ala Ala Asp Gln Pro Asp Arg Ile Asp Arg Leu Ile Val Ser
    130                 135                 140

Glu Ala Pro Leu Pro Gly Val Thr Pro Ser Pro Leu Leu Leu Pro
145                 150                 155                 160

Pro Gln Leu Thr Ala Lys Phe Trp His Leu Met Phe Asn Gln Leu Pro
                165                 170                 175

Ala Glu Val Asn Glu Ala Leu Val Arg Gly Arg Glu Asp Ile Phe Phe
            180                 185                 190

Gly Ala Glu Phe Asp Ala Ser Ala Gly Thr Lys Lys Leu Pro Ala Asp
        195                 200                 205

Ile Val Arg Tyr Tyr Ile Asp Thr Val Ala Thr Asp Pro Asp His Leu
    210                 215                 220

Arg Gly Ser Phe Gly Phe Tyr Arg Ala Ile Pro Thr Thr Ile Ala Gln
225                 230                 235                 240

Asn Glu Gln Arg Lys Thr Arg Arg Leu Pro Met Pro Val Leu Ala Ile
                245                 250                 255

Gly Gly Glu Glu Ser Gly Gly Glu Gly Pro Gly Asn Ala Met Lys Leu
            260                 265                 270

Val Ala Asp Asp Val Gln Thr Leu Val Leu Ala Gly Ser Gly His Trp
        275                 280                 285

Val Ala Glu Gln Ala Pro His Ala Leu Leu Ala Leu Ser Glu Phe
    290                 295                 300

Leu Ala Pro Tyr Leu Glu Glu Ala Thr Ala Gln Val Gly Ala Ala Arg
305                 310                 315                 320

<210> SEQ ID NO 7
<211> LENGTH: 897
<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(63)

<400> SEQUENCE: 7
atgtcgcccc gttcgattcc tgctctggct ctactgctct gttcgactgt ctccgctttg      60
gccgccgatt tcgaatcgcg cgtgaagcat ggctacgccg actccaacgg cgtgaagatt     120
cactacgcca cgatcggcag cgggccgctg atcgtgatga tccacggctt ccccgacttc     180
tggtacacgt ggcgcaagca gatggagggt tgtcggaca agtaccaatg cgtggccatc      240
gaccagcgcg gctataaccct cagcgacaag ccgcaggggcg tcgagaacta cgacatgagc    300
ctgctggtgg gcgacgtcat cgccgtgatc aagcacctgg gcaaagacaa ggccatcatc    360
gtcggtcacg actggggcgg ggcggtcgca tggcagctgg ctctgaacgc gccccagtat    420
gtcgaccgcc taatcattct taacctccca tacccgcgcg gcatcatgcg cgagctggct    480
cacaacccca gcaacaagc cgccagcgcc tacgcccgca attttcagac tgagggcgcg    540
gaagccatga tcaagccgga gcaactggcc ttctgggtca ccgatgccga ggccaagccg    600
aaatacgtgg aggcctttca gcgctcggac atcaaggcca tgctgaacta ctacaagcgc    660
aactacccgc gagagccgta tcaggaaaac acctcgccgg tggtgaagac gcagatgccc    720
```

-continued

```
gtgctcatgt tccacggtct caaagacacc gcgctgctct ccgacgcgct caacaacacc    780
tgggactgga tgggcaaaga cctcaccctg gtgaccatcc ctgattccgg ccacttcgtg    840
cagcaagatg cagccgacct ggtgacgcgg atgatgcggg cgtggctgga acgttga      897
```

```
<210> SEQ ID NO 8
<211> LENGTH: 298
<212> TYPE: PRT
<213> ORGANISM: Unknown
<220> FEATURE:
<223> OTHER INFORMATION: Obtained from an environmental source
<220> FEATURE:
<221> NAME/KEY: SIGNAL
<222> LOCATION: (1)...(21)

<400> SEQUENCE: 8
```

```
Met Ser Pro Arg Ser Ile Pro Ala Leu Ala Leu Leu Leu Cys Ser Thr
 1               5                  10                  15

Val Ser Ala Leu Ala Ala Asp Phe Glu Ser Arg Val Lys His Gly Tyr
            20                  25                  30

Ala Asp Ser Asn Gly Val Lys Ile His Tyr Ala Thr Ile Gly Ser Gly
        35                  40                  45

Pro Leu Ile Val Met Ile His Gly Phe Pro Asp Phe Trp Tyr Thr Trp
    50                  55                  60

Arg Lys Gln Met Glu Gly Leu Ser Asp Lys Tyr Gln Cys Val Ala Ile
65                  70                  75                  80

Asp Gln Arg Gly Tyr Asn Leu Ser Asp Lys Pro Gln Gly Val Glu Asn
                85                  90                  95

Tyr Asp Met Ser Leu Leu Val Gly Asp Val Ile Ala Val Ile Lys His
            100                 105                 110

Leu Gly Lys Asp Lys Ala Ile Ile Val Gly His Asp Trp Gly Gly Ala
        115                 120                 125

Val Ala Trp Gln Leu Ala Leu Asn Ala Pro Gln Tyr Val Asp Arg Leu
    130                 135                 140

Ile Ile Leu Asn Leu Pro Tyr Pro Arg Gly Ile Met Arg Glu Leu Ala
145                 150                 155                 160

His Asn Pro Lys Gln Gln Ala Ala Ser Ala Tyr Ala Arg Asn Phe Gln
                165                 170                 175

Thr Glu Gly Ala Glu Ala Met Ile Lys Pro Gln Leu Ala Phe Trp
            180                 185                 190

Val Thr Asp Ala Glu Ala Lys Pro Lys Tyr Val Glu Ala Phe Gln Arg
    195                 200                 205

Ser Asp Ile Lys Ala Met Leu Asn Tyr Tyr Lys Arg Asn Tyr Pro Arg
210                 215                 220

Glu Pro Tyr Gln Glu Asn Thr Ser Pro Val Val Lys Thr Gln Met Pro
225                 230                 235                 240

Val Leu Met Phe His Gly Leu Lys Asp Thr Ala Leu Leu Ser Asp Ala
                245                 250                 255

Leu Asn Asn Thr Trp Asp Trp Met Gly Lys Asp Leu Thr Leu Val Thr
            260                 265                 270

Ile Pro Asp Ser Gly His Phe Val Gln Gln Asp Ala Ala Asp Leu Val
        275                 280                 285

Thr Arg Met Met Arg Ala Trp Leu Glu Arg
    290                 295
```

```
<210> SEQ ID NO 9
<211> LENGTH: 1209
```

<212> TYPE: DNA
<213> ORGANISM: Unknown
<220> FEATURE:
<223> OTHER INFORMATION: Obtained from an environmental source

<400> SEQUENCE: 9

```
atgagtgtcg ttacagaaca cactgacaag accgctattc gtccgttcaa gatcaatgtg      60
ccggaggcgg aacctgaagga tttgcacagg cgcatccagg cgaccaagtt tcccgaacgc    120
gagacggttc cggatgccac gcagggcgtg cagcttgcca cggttcaggc cctcgcgcag    180
tattgggcga aagactacaa ctggcacaag tgtgagtcga ggctgaatgc actgccgcag    240
ttcatgaccg agattgaggg gctcgacatt catttcattc acgttcgttc gaagcatccg    300
aacgcgctgc cggtcatcgt gacgcacggc tggccaggat cgatcgtcga gcagttgaag    360
atcatcgatc cgctgacgaa tccgacggcg catggtggaa gcgcatcgga cgccttcgac    420
gtggtggtcc cgtccatgcc cggctatgga tactccggca agcctaccgc cgccgggtgg    480
aatcccgttc gcatcgcgcg tgcctgggtt gtgctgatga agcgcctggg ttacacgaag    540
ttcgtagccc aagtggtgac ctggggcgca gtcgtcgtcg acatgatggg gctacaagca    600
cctcctgagt tgctaggtat ccacaccaac atgcctggca tctttccgac cgacattgac    660
caggcggctt cggcggcgc accgacgcca ggagggtttt cacccgacga gaaagttgct    720
tacgagcgtg tgcgcttcgt ctatcaaaag ggagtcgcct acggttttcca gatgggctt    780
cgaccgcaga cactgtacgc aatcggggac tcaccggttg gctcgcggc ctatttcctt    840
gatcacgacg cccggagcta tgagctgatc gcacgcgtct ttcaaggaca ggccgaaggc    900
ctcacgcgcg atgacatcct ggacaacgtc acgatcacgt ggttgacgaa caccgccgtc    960
tctggcgctc gcctctattg ggagtattgg ggcaaagggt cgtacttcag cgccaagggc   1020
gtctccatcc cggttgccgt gagcgtgttc cctgacgaac tctatcccgc ccccagagc   1080
tggacagagc gcgcctatcc gaaactgatg tacttcaaga agcacaacaa gggcgggcac   1140
ttcgcggcat gggaacagcc acaactcttg tctgaggacc tgcgcgaggg cttccgatcg   1200
ttgcggtag                                                            1209
```

<210> SEQ ID NO 10
<211> LENGTH: 402
<212> TYPE: PRT
<213> ORGANISM: Unknown
<220> FEATURE:
<223> OTHER INFORMATION: Obtained from an environmental source

<400> SEQUENCE: 10

```
Met Ser Val Val Thr Glu His Thr Asp Lys Thr Ala Ile Arg Pro Phe
  1               5                  10                  15

Lys Ile Asn Val Pro Glu Ala Asp Leu Lys Asp Leu His Arg Arg Ile
             20                  25                  30

Gln Ala Thr Lys Phe Pro Glu Arg Glu Thr Val Pro Asp Ala Thr Gln
         35                  40                  45

Gly Val Gln Leu Ala Thr Val Gln Ala Leu Ala Gln Tyr Trp Ala Lys
     50                  55                  60

Asp Tyr Asn Trp His Lys Cys Glu Ser Arg Leu Asn Ala Leu Pro Gln
 65                  70                  75                  80

Phe Met Thr Glu Ile Glu Gly Leu Asp Ile His Phe Ile His Val Arg
                 85                  90                  95

Ser Lys His Pro Asn Ala Leu Pro Val Ile Val Thr His Gly Trp Pro
            100                 105                 110
```

-continued

Gly Ser Ile Val Glu Gln Leu Lys Ile Ile Asp Pro Leu Thr Asn Pro
            115                 120                 125

Thr Ala His Gly Gly Ser Ala Ser Asp Ala Phe Asp Val Val Pro
        130                 135                 140

Ser Met Pro Gly Tyr Gly Tyr Ser Gly Lys Pro Thr Ala Ala Gly Trp
145                 150                 155                 160

Asn Pro Val Arg Ile Ala Arg Ala Trp Val Val Leu Met Lys Arg Leu
                165                 170                 175

Gly Tyr Thr Lys Phe Val Ala Gln Gly Gly Asp Trp Gly Ala Val Val
            180                 185                 190

Val Asp Met Met Gly Leu Gln Ala Pro Pro Glu Leu Leu Gly Ile His
        195                 200                 205

Thr Asn Met Pro Gly Ile Phe Pro Thr Asp Ile Asp Gln Ala Ala Phe
        210                 215                 220

Gly Gly Ala Pro Thr Pro Gly Gly Phe Ser Pro Asp Glu Lys Val Ala
225                 230                 235                 240

Tyr Glu Arg Val Arg Phe Val Tyr Gln Lys Gly Val Ala Tyr Gly Phe
                245                 250                 255

Gln Met Gly Leu Arg Pro Gln Thr Leu Tyr Ala Ile Gly Asp Ser Pro
            260                 265                 270

Val Gly Leu Ala Ala Tyr Phe Leu Asp His Asp Ala Arg Ser Tyr Glu
        275                 280                 285

Leu Ile Ala Arg Val Phe Gln Gly Gln Ala Glu Gly Leu Thr Arg Asp
        290                 295                 300

Asp Ile Leu Asp Asn Val Thr Ile Thr Trp Leu Thr Asn Thr Ala Val
305                 310                 315                 320

Ser Gly Ala Arg Leu Tyr Trp Glu Tyr Trp Gly Lys Gly Ser Tyr Phe
                325                 330                 335

Ser Ala Lys Gly Val Ser Ile Pro Val Ala Val Ser Val Phe Pro Asp
            340                 345                 350

Glu Leu Tyr Pro Ala Pro Gln Ser Trp Thr Glu Arg Ala Tyr Pro Lys
        355                 360                 365

Leu Met Tyr Phe Lys Lys His Asn Lys Gly Gly His Phe Ala Ala Trp
        370                 375                 380

Glu Gln Pro Gln Leu Leu Ser Glu Asp Leu Arg Glu Gly Phe Arg Ser
385                 390                 395                 400

Leu Arg

<210> SEQ ID NO 11
<211> LENGTH: 981
<212> TYPE: DNA
<213> ORGANISM: Unknown
<220> FEATURE:
<223> OTHER INFORMATION: Obtained from an environmental source

<400> SEQUENCE: 11
atgagcaaca cacacgtcgc cgccgggacg gagatccgcc ccttcaccgt cgaggtcgcc    60
caagacgagt tggacgacct cagccgtcgc atctcggcga cgcgctggcc cgaggaggag   120
accgtcgagg atcagtcgca gggcgtgccg ctggcgacga tgcaggagct cgtccgctac   180
tggggctccg agtacgactt cggaaggctg gaggcacggt gaacgccttc cctcagttc    240 atcaccgaga tcgacggcct cgacatccac ttcatccacg ttcgctcgcc ggaggagaac   300
gcgctgccga tcatcctcac gcacggctgg ccgggctcgt tcatcgagat gctgaacgtg   360

```
atcgggccac tgtccgaccc gaccgcgcac ggcggcgacg cggaggacgc gttcgacgtc    420
gtggttccgt ccatcccggg ctacgggttc tcggggaagc cgagcgcgac cgggtgggac    480
ccggttcaca tcgcgcgcgc gtggatcgcc ctgatggagc gcctcggccc tgaccgctac    540
gtcgcgcagg gcggcgactg gggcgcgcag atcacggatg tgatgggtgc ggaggcgccg    600
ccggaactgg cggggatccc gggctttttac accaagacgg gcttcggcac gcaggtcgcc    660
gaagggaagg aagtgaaaga gttcgagggc gagcaatata tactcgagcg cgggattcgc    720
gccgacctct cgatcgtcaa gggatggaag gccgacgaga ccggcaatct catgttccgc    780
aagacaacgc gaaacttcaa cctgccggct gcgacctgcg ggaaggtgtg cctcgccgag    840
gtggaagaga tcgtcccggt cggctcgctt gatcccgact gcatccacct gccctcgatc    900
tatgtgaacc ggttgatcga tggctcgccc tacgagaaga agatcgagtt ccggaccgtc    960
cgtcagcacg aggcggcatg a                                              981
```

```
<210> SEQ ID NO 12
<211> LENGTH: 326
<212> TYPE: PRT
<213> ORGANISM: Unknown
<220> FEATURE:
<223> OTHER INFORMATION: Obtained from an environmental source

<400> SEQUENCE: 12

Met Ser Asn Thr His Val Ala Ala Gly Thr Glu Ile Arg Pro Phe Thr
1               5                   10                  15

Val Glu Val Ala Gln Asp Glu Leu Asp Asp Leu Ser Arg Arg Ile Ser
            20                  25                  30

Ala Thr Arg Trp Pro Glu Glu Thr Val Glu Asp Gln Ser Gln Gly
        35                  40                  45

Val Pro Leu Ala Thr Met Gln Glu Leu Val Arg Tyr Trp Gly Ser Glu
    50                  55                  60

Tyr Asp Phe Gly Arg Leu Glu Ala Arg Leu Asn Ala Phe Pro Gln Phe
65                  70                  75                  80

Ile Thr Glu Ile Asp Gly Leu Asp Ile His Phe Ile His Val Arg Ser
                85                  90                  95

Pro Glu Glu Asn Ala Leu Pro Ile Ile Leu Thr His Gly Trp Pro Gly
            100                 105                 110

Ser Phe Ile Glu Met Leu Asn Val Ile Gly Pro Leu Ser Asp Pro Thr
        115                 120                 125

Ala His Gly Gly Asp Ala Glu Asp Ala Phe Asp Val Val Pro Ser
    130                 135                 140

Ile Pro Gly Tyr Gly Phe Ser Gly Lys Pro Ser Ala Thr Gly Trp Asp
145                 150                 155                 160

Pro Val His Ile Ala Arg Ala Trp Ile Ala Leu Met Glu Arg Leu Gly
                165                 170                 175

Pro Asp Arg Tyr Val Ala Gln Gly Gly Asp Trp Gly Ala Gln Ile Thr
            180                 185                 190

Asp Val Met Gly Ala Glu Ala Pro Glu Leu Ala Gly Ile Pro Gly
        195                 200                 205

Phe Tyr Thr Lys Thr Gly Phe Gly Thr Gln Val Ala Glu Gly Lys Glu
    210                 215                 220

Val Lys Glu Phe Glu Gly Glu Gln Tyr Ile Leu Glu Arg Gly Ile Arg
225                 230                 235                 240

Ala Asp Leu Ser Ile Val Lys Gly Trp Lys Ala Asp Glu Thr Gly Asn
                245                 250                 255
```

Leu Met Phe Arg Lys Thr Thr Arg Asn Phe Asn Leu Pro Ala Ala Thr
             260                 265                 270

Cys Gly Lys Val Cys Leu Ala Glu Val Glu Glu Ile Val Pro Val Gly
         275                 280                 285

Ser Leu Asp Pro Asp Cys Ile His Leu Pro Ser Ile Tyr Val Asn Arg
     290                 295                 300

Leu Ile Asp Gly Ser Pro Tyr Glu Lys Lys Ile Glu Phe Arg Thr Val
305                 310                 315                 320

Arg Gln His Glu Ala Ala
                325

<210> SEQ ID NO 13
<211> LENGTH: 930
<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(60)

<400> SEQUENCE: 13

| | | | | | |
|---|---|---|---|---|---|
| atgatttcgc | tcttcgcccc | cggaatcctc | gccatcgcgc | tcggcagcgc | gcaggcgccg | 60 |
| cgcgacgatg | tgttcgatcg | cgtgacgcac | ggttacgcga | cgtcggatgg | cggcgtgaag | 120 |
| atccactacg | cgtcgctcgg | ccaggggccg | ctcgtggtga | tgatccacgg | cttcccggat | 180 |
| ttctggtact | cgtggcggcg | ccagatgcaa | gcgttgtcgg | atcgctatca | ggtggtcgcc | 240 |
| atcgatcagc | gcggctacaa | cctgagcgac | aagcccaagg | gcgtcgacgc | ctacgacatg | 300 |
| cgcctgctcg | tcggcgacgt | cgccgctgtg | atccgcagcc | tcggcaaaga | caaagccacg | 360 |
| atcgtcggcc | acgactgggg | cggcatcgtc | gcatggaact | tcgcgatgaa | cctgccccag | 420 |
| atgaccgaga | acctgatcat | cctgaacctg | ccgcatccga | acggccttgc | ccgggagctc | 480 |
| aagaacaatc | ccgatcagat | caagaacagt | gagtacgcgc | gcaacttcca | gaccaagtcg | 540 |
| ccgtccgatc | cgaccgtgtt | cttcggcagg | ccgatgacgg | cggagaacct | ggcgggctgg | 600 |
| gtccgcgatc | ccgaggcgcg | caagcggtac | gtcgaggcgt | tccagaagtc | cgatttcgag | 660 |
| gcgatgctga | actactacaa | gcggaactac | ccgcgcggcg | cgggcgcgga | cgcgccgacg | 720 |
| ccgccgccgc | tcccgaaggt | gaagatgccg | gtgctgatgt | tcacgggct | caacgacacc | 780 |
| gcgttgaacg | cgtcgggact | gaacgacacg | tggcagtggc | tggagaagga | tctgacgctc | 840 |
| gtcacggttc | cgggctcggg | acacttcgtg | cagcaggatg | cggccgacct | cgtcgccaac | 900 |
| acgatgaagt | ggtggctcgc | gatgcgttga | | | | 930 |

<210> SEQ ID NO 14
<211> LENGTH: 309
<212> TYPE: PRT
<213> ORGANISM: Unknown
<220> FEATURE:
<223> OTHER INFORMATION: Obtained from an environmental source
<220> FEATURE:
<221> NAME/KEY: SIGNAL
<222> LOCATION: (1)...(20)

<400> SEQUENCE: 14

Met Ile Ser Leu Phe Ala Pro Gly Ile Leu Ala Ile Ala Leu Gly Ser
1               5                   10                  15

Ala Gln Ala Pro Arg Asp Asp Val Phe Asp Arg Val Thr His Gly Tyr
            20                  25                  30

-continued

```
Ala Thr Ser Asp Gly Gly Val Lys Ile His Tyr Ala Ser Leu Gly Gln
         35                  40                  45

Gly Pro Leu Val Val Met Ile His Gly Phe Pro Asp Phe Trp Tyr Ser
 50                  55                  60

Trp Arg Arg Gln Met Gln Ala Leu Ser Asp Arg Tyr Gln Val Val Ala
 65                  70                  75                  80

Ile Asp Gln Arg Gly Tyr Asn Leu Ser Asp Lys Pro Lys Gly Val Asp
                 85                  90                  95

Ala Tyr Asp Met Arg Leu Leu Val Gly Asp Val Ala Ala Val Ile Arg
             100                 105                 110

Ser Leu Gly Lys Asp Lys Ala Thr Ile Val Gly His Asp Trp Gly Gly
         115                 120                 125

Ile Val Ala Trp Asn Phe Ala Met Asn Leu Pro Gln Met Thr Glu Asn
 130                 135                 140

Leu Ile Ile Leu Asn Leu Pro His Pro Asn Gly Leu Ala Arg Glu Leu
145                 150                 155                 160

Lys Asn Asn Pro Asp Gln Ile Lys Asn Ser Glu Tyr Ala Arg Asn Phe
                 165                 170                 175

Gln Thr Lys Ser Pro Ser Asp Pro Thr Val Phe Phe Gly Arg Pro Met
             180                 185                 190

Thr Ala Glu Asn Leu Ala Gly Trp Val Arg Asp Pro Glu Ala Arg Lys
         195                 200                 205

Arg Tyr Val Glu Ala Phe Gln Lys Ser Asp Phe Glu Ala Met Leu Asn
 210                 215                 220

Tyr Tyr Lys Arg Asn Tyr Pro Arg Gly Ala Gly Ala Asp Ala Pro Thr
225                 230                 235                 240

Pro Pro Pro Leu Pro Lys Val Lys Met Pro Val Leu Met Phe His Gly
                 245                 250                 255

Leu Asn Asp Thr Ala Leu Asn Ala Ser Gly Leu Asn Asp Thr Trp Gln
             260                 265                 270

Trp Leu Glu Lys Asp Leu Thr Leu Val Thr Val Pro Gly Ser Gly His
         275                 280                 285

Phe Val Gln Gln Asp Ala Ala Asp Leu Val Ala Asn Thr Met Lys Trp
 290                 295                 300

Trp Leu Ala Met Arg
305
```

<210> SEQ ID NO 15
<211> LENGTH: 870
<212> TYPE: DNA
<213> ORGANISM: Unknown
<220> FEATURE:
<223> OTHER INFORMATION: Obtained from an environmental source

<400> SEQUENCE: 15

```
gtgagagcag gtagggttcg ggcgcgcggg atcgagttcg cgacgctgga ggagggcaac      60
ggtccgctcg tcctctgcct gcacgggttc cccgatcatc cccgctcgtt ccggcaccag     120
ctgccggcgc tcgcgaaggc cggattccgc gcggtcgcgc ccgcgctccg tggctacgcg     180
ccgaccgggc cggcccccga cggccgctat cagtcggcgg cgctcgccat ggatgccgtc     240
gcgctgatcg aggcactcgg ttacgacgac gcggtcgtct cgggcacgac ctggggcgcg     300
accgccgcct acggcgccgc gctcgccgca ccgcagcggg tccgcaagct cgtcaccgcc     360
gcggtgccgt acggcccgca ggtggtcggc tcgttcatga ccagctacga ccagcagcgc     420
```

-continued

```
cggtcctggt acatgttctt ctttcagacg ccgttcgccg acgccgccgt cgcgcacgac    480
gacttcgcgt tcctcgagcg gctgtggcgc gattggtcgc cgggctggaa gtacccaccc    540
gaagagatgg ccgcgctcaa agagacgttc cgccagcccg gcgtgctgga ggccgcactc    600
ggctactacc gcgccgcctt caatccggcg ctgcaggacc ccgagctcgc ggcgttgcag    660
ggccggatga tgacggaccc gatcgaggtg ccgggcctga tgctgcacgg cgccgccgac    720
ggttgcatgg gcgctgagct cgtcgagggg atggcggcgc tcttcccgcg cggcctccgc    780
gtcgaaatcg tcccgggaac gggccacttc ctgcaccagg aagcccccga tcggatcaat    840
ccgatcgtcc tcgacttcct gcggtcgtag                                    870
```

<210> SEQ ID NO 16
<211> LENGTH: 289
<212> TYPE: PRT
<213> ORGANISM: Unknown
<220> FEATURE:
<223> OTHER INFORMATION: Obtained from an environmental source

<400> SEQUENCE: 16

```
Met Arg Ala Gly Arg Val Arg Ala Arg Gly Ile Glu Phe Ala Thr Leu
  1               5                  10                  15

Glu Glu Gly Asn Gly Pro Leu Val Leu Cys Leu His Gly Phe Pro Asp
                 20                  25                  30

His Pro Arg Ser Phe Arg His Gln Leu Pro Ala Leu Ala Lys Ala Gly
             35                  40                  45

Phe Arg Ala Val Ala Pro Ala Leu Arg Gly Tyr Ala Pro Thr Gly Pro
 50                  55                  60

Ala Pro Asp Gly Arg Tyr Gln Ser Ala Ala Leu Ala Met Asp Ala Val
 65                  70                  75                  80

Ala Leu Ile Glu Ala Leu Gly Tyr Asp Asp Ala Val Val Phe Gly His
                 85                  90                  95

Asp Trp Gly Ala Thr Ala Ala Tyr Gly Ala Ala Leu Ala Ala Pro Gln
            100                 105                 110

Arg Val Arg Lys Leu Val Thr Ala Ala Val Pro Tyr Gly Pro Gln Val
            115                 120                 125

Val Gly Ser Phe Met Thr Ser Tyr Asp Gln Gln Arg Arg Ser Trp Tyr
130                 135                 140

Met Phe Phe Gln Thr Pro Phe Ala Asp Ala Ala Val Ala His Asp
145                 150                 155                 160

Asp Phe Ala Phe Leu Glu Arg Leu Trp Arg Asp Trp Ser Pro Gly Trp
                165                 170                 175

Lys Tyr Pro Pro Glu Glu Met Ala Ala Leu Lys Glu Thr Phe Arg Gln
            180                 185                 190

Pro Gly Val Leu Glu Ala Ala Leu Gly Tyr Tyr Arg Ala Ala Phe Asn
            195                 200                 205

Pro Ala Leu Gln Asp Pro Glu Leu Ala Ala Leu Gln Gly Arg Met Met
        210                 215                 220

Thr Asp Pro Ile Glu Val Pro Gly Leu Met Leu His Gly Ala Ala Asp
225                 230                 235                 240

Gly Cys Met Gly Ala Glu Leu Val Glu Gly Met Ala Ala Leu Phe Pro
                245                 250                 255

Arg Gly Leu Arg Val Glu Ile Val Pro Gly Thr Gly His Phe Leu His
            260                 265                 270

Gln Glu Ala Pro Asp Arg Ile Asn Pro Ile Val Leu Asp Phe Leu Arg
            275                 280                 285
```

Ser

<210> SEQ ID NO 17
<211> LENGTH: 1350
<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(72)

<400> SEQUENCE: 17

```
atggcgaggg tcaatcgacg gttgacggtt ttcggactcg tagtcgcgct gtcggtcgtg      60
ggcgcacggg cggctcagac ccagcgtgcg tcgaactcct tcgctgcagg cgcgggcgcg     120
aagactgcct caggcgaagc gatcgtgcct ttcaagatcc atgttcccga ctctgtcgtg     180
gccgacctga agcagcggct ccagcgcgcc cggtttgcgg acgagattcc cgaggtggga     240
tgggactatg gcacgaacct ggcctatctc aaggagctcg tgacgtactg gcgcgacaag     300
tacgactggc gggctcagga gcggcgcctc aaccagtacg accaattcaa gacgaacatc     360
gacgggctcg acatccactt cattcatcaa cgatcgaagg tgccgaacgc caagcccctc     420
ctgctgctga acgggtggcc gagctcgatc gaggagtaca cgaaggtcat cggtcctctc     480
actgacccgg ccgcccacgg cggccgcacc accgacgcct tcacgtcgt catcccgtcg     540
atgccgggct acggcttctc ggacaaaccg cgcgagcgcg gctacaaccc cgagcgcatg     600
gcaagcgtat gggtgaagct gatggcgcgc tcggataca cgcgttacct gacgcatggc     660
agcgattggg gaatcgcggt agccacgcac ctcgccctga agacccgggg catctggcg     720
gcgcttcatc ttgcgggctg cccgggcggc ctgatcgggc agtctccgtc acggcccgca     780
ggcgcgcccc cgccgccacc agccccccg cctccagccg cgccagtctc cgcgaatctg     840
gggtatcagg aaatacaaac gaccaagccg cagacactcg gccacgggct gagtgattca     900
cccctggggc tcgcgtcgtg gattatcgac aagtggcagt cctggaccga tcacgatggc     960
gatctcgaga aggtctacac caaagaccag ctgctgacga atgtcatgat ttactgggtc    1020
accaactcag gggcgtcttc ggctcgcttg tactacgaga cgagacatgt ggatggacgg    1080
ctgctgccga cctttttcga aactttctt ccgaagcttc ccgagggccg cgtcaacgtt    1140
ccaaccggat gcgggacgtt tccctcgcag tacgatcgcc gcgacattcc gatcagcatg    1200
aacactgcag cagcacgcac ggctgctgag gcccgctaca acgtggtcta tctgacgatt    1260
tcgccacacg gaggccactt tccggcgctc gagcagccgc aggtctgggc cgacgacatt    1320
cgagcgttct tccgcgatcg gccactgtaa                                     1350
```

<210> SEQ ID NO 18
<211> LENGTH: 449
<212> TYPE: PRT
<213> ORGANISM: Unknown
<220> FEATURE:
<223> OTHER INFORMATION: Obtained from an environmental source
<220> FEATURE:
<221> NAME/KEY: SIGNAL
<222> LOCATION: (1)...(24)

<400> SEQUENCE: 18

Met Ala Arg Val Asn Arg Arg Leu Thr Val Phe Gly Leu Val Val Ala
 1               5                  10                  15

Leu Ser Val Val Gly Ala Arg Ala Ala Gln Thr Gln Arg Ala Ser Asn

-continued

```
                 20                  25                  30
Ser Phe Ala Ala Gly Ala Gly Ala Lys Thr Ala Ser Gly Glu Ala Ile
             35                  40                  45

Val Pro Phe Lys Ile His Val Pro Asp Ser Val Val Ala Asp Leu Lys
 50                  55                  60

Gln Arg Leu Gln Arg Ala Arg Phe Ala Asp Glu Ile Pro Glu Val Gly
 65                  70                  75                  80

Trp Asp Tyr Gly Thr Asn Leu Ala Tyr Leu Lys Glu Leu Val Thr Tyr
             85                  90                  95

Trp Arg Asp Lys Tyr Asp Trp Arg Ala Gln Glu Arg Arg Leu Asn Gln
             100                 105                 110

Tyr Asp Gln Phe Lys Thr Asn Ile Asp Gly Leu Asp Ile His Phe Ile
             115                 120                 125

His Gln Arg Ser Lys Val Pro Asn Ala Lys Pro Leu Leu Leu Leu Asn
             130                 135                 140

Gly Trp Pro Ser Ser Ile Glu Glu Tyr Thr Lys Val Ile Gly Pro Leu
145                 150                 155                 160

Thr Asp Pro Ala Ala His Gly Arg Thr Thr Asp Ala Phe His Val
             165                 170                 175

Val Ile Pro Ser Met Pro Gly Tyr Gly Phe Ser Asp Lys Pro Arg Glu
             180                 185                 190

Arg Gly Tyr Asn Pro Glu Arg Met Ala Ser Val Trp Val Lys Leu Met
             195                 200                 205

Ala Arg Leu Gly Tyr Thr Arg Tyr Leu Thr His Gly Ser Asp Trp Gly
             210                 215                 220

Ile Ala Val Ala Thr His Leu Ala Leu Lys Asp Pro Gly His Leu Ala
225                 230                 235                 240

Ala Leu His Leu Ala Gly Cys Pro Gly Gly Leu Ile Gly Gln Ser Pro
             245                 250                 255

Ser Arg Pro Ala Gly Ala Pro Pro Pro Pro Ala Pro Pro Pro Pro
             260                 265                 270

Ala Ala Pro Val Ser Ala Asn Leu Gly Tyr Gln Glu Ile Gln Thr Thr
             275                 280                 285

Lys Pro Gln Thr Leu Gly His Gly Leu Ser Asp Ser Pro Leu Gly Leu
             290                 295                 300

Ala Ser Trp Ile Ile Asp Lys Trp Gln Ser Trp Thr Asp His Asp Gly
305                 310                 315                 320

Asp Leu Glu Lys Val Tyr Thr Lys Asp Gln Leu Leu Thr Asn Val Met
             325                 330                 335

Ile Tyr Trp Val Thr Asn Ser Gly Ala Ser Ser Ala Arg Leu Tyr Tyr
             340                 345                 350

Glu Thr Arg His Val Asp Gly Arg Leu Leu Pro Thr Phe Phe Glu Asn
             355                 360                 365

Phe Leu Pro Lys Leu Pro Glu Gly Arg Val Asn Val Pro Thr Gly Cys
             370                 375                 380

Gly Thr Phe Pro Ser Gln Tyr Asp Arg Arg Asp Ile Pro Ile Ser Met
385                 390                 395                 400

Asn Thr Ala Ala Ala Arg Thr Ala Ala Glu Ala Arg Tyr Asn Val Val
                 405                 410                 415

Tyr Leu Thr Ile Ser Pro His Gly Gly His Phe Pro Ala Leu Glu Gln
             420                 425                 430

Pro Gln Val Trp Ala Asp Asp Ile Arg Ala Phe Phe Arg Asp Arg Pro
             435                 440                 445
```

Leu

<210> SEQ ID NO 19
<211> LENGTH: 981
<212> TYPE: DNA
<213> ORGANISM: Unknown
<220> FEATURE:
<223> OTHER INFORMATION: Obtained from an environmental source

<400> SEQUENCE: 19

```
atgagcgaag taaaacatcg cgaggtagat acgaacggta tccgcatgca catcgctgaa      60
agcgggacgg gcccgttggt gttgctgtgc catggttttc ccgaatcttg gtattcgtgg     120
cgccaccagt tggatgcggt cgcagaagct ggattccacg tggttgcacc tgacatgcga     180
ggttatggcc taactgagag tccagaagaa atcgaccggt acaccctcct ccatttggtc     240
ggggatatgg tcggcctgct ggacgctctt ggggaggaga gggcggtgat tgctgggcac     300
gattggggtg ctccggtcgc gtggcacgcc gctcttctac gccccgatcg cttccgcggt     360
gtgatcggct tgagcgtgcc cttcacgccg cggcggcctg cacgcccac cagcatgatg     420
cctcagacgg aagacgcgtt gttctatcaa ctttacttcc aatctccagg cgttgcggaa     480
gcggagttcg agcgcgacgt tcgtctaagc atccgaagcc tcctctactc cgcttccggg     540
gatgctccac gttgggaaaa ccgtgaaggg gctcgagagg aagttggtat ggtaccgcgc     600
cgaggtggct actttcgcg gttgatgaac cctgcctcgt tgccgccttg gatcaccgag     660
gcggacgtgg acttctacgt gagcgagttc acgcgcacgg gatttcgcgg gccactgaac     720
tggtaccgca atatcgaccg caactgggaa ctcctagcac ccatggcggc aacgacagtg     780
tcagtcccgg ggctgtacat cgcaggcgac cgcgatctcg ttttggcttt tcgtgggatg     840
gaccagatca tcgccagcct gtccaagttt gtaccgcggc ttcagggaac agtcgtgctc     900
ccaggttgcg gtcattggac ccagcaggaa cgggcccgag aggtcacgaa ggccatgatt     960
gacttcgccc ggcgacttta g                                               981
```

<210> SEQ ID NO 20
<211> LENGTH: 326
<212> TYPE: PRT
<213> ORGANISM: Unknown
<220> FEATURE:
<223> OTHER INFORMATION: Obtained from an environmental source

<400> SEQUENCE: 20

Met Ser Glu Val Lys His Arg Glu Val Asp Thr Asn Gly Ile Arg Met
 1               5                  10                  15

His Ile Ala Glu Ser Gly Thr Gly Pro Leu Val Leu Leu Cys His Gly
            20                  25                  30

Phe Pro Glu Ser Trp Tyr Ser Trp Arg His Gln Leu Asp Ala Val Ala
        35                  40                  45

Glu Ala Gly Phe His Val Val Ala Pro Asp Met Arg Gly Tyr Gly Leu
    50                  55                  60

Thr Glu Ser Pro Glu Glu Ile Asp Arg Tyr Thr Leu Leu His Leu Val
65                  70                  75                  80

Gly Asp Met Val Gly Leu Leu Asp Ala Leu Gly Glu Glu Arg Ala Val
                85                  90                  95

Ile Ala Gly His Asp Trp Gly Ala Pro Val Ala Trp His Ala Ala Leu
            100                 105                 110

Leu Arg Pro Asp Arg Phe Arg Gly Val Ile Gly Leu Ser Val Pro Phe

```
                    115                 120                 125
Thr Pro Arg Arg Pro Ala Arg Pro Thr Ser Met Met Pro Gln Thr Glu
        130                 135                 140

Asp Ala Leu Phe Tyr Gln Leu Tyr Phe Gln Ser Pro Gly Val Ala Glu
145                 150                 155                 160

Ala Glu Phe Glu Arg Asp Val Arg Leu Ser Ile Arg Ser Leu Leu Tyr
                165                 170                 175

Ser Ala Ser Gly Asp Ala Pro Arg Trp Glu Asn Arg Glu Gly Ala Arg
            180                 185                 190

Glu Glu Val Gly Met Val Pro Arg Arg Gly Gly Leu Leu Ser Arg Leu
        195                 200                 205

Met Asn Pro Ala Ser Leu Pro Pro Trp Ile Thr Glu Ala Asp Val Asp
210                 215                 220

Phe Tyr Val Ser Glu Phe Thr Arg Thr Gly Phe Arg Gly Pro Leu Asn
225                 230                 235                 240

Trp Tyr Arg Asn Ile Asp Arg Asn Trp Glu Leu Leu Ala Pro Met Ala
                245                 250                 255

Ala Thr Thr Val Ser Val Pro Gly Leu Tyr Ile Ala Gly Asp Arg Asp
            260                 265                 270

Leu Val Leu Ala Phe Arg Gly Met Asp Gln Ile Ile Ala Ser Leu Ser
        275                 280                 285

Lys Phe Val Pro Arg Leu Gln Gly Thr Val Val Leu Pro Gly Cys Gly
        290                 295                 300

His Trp Thr Gln Gln Glu Arg Ala Arg Glu Val Thr Lys Ala Met Ile
305                 310                 315                 320

Asp Phe Ala Arg Arg Leu
                325

<210> SEQ ID NO 21
<211> LENGTH: 810
<212> TYPE: DNA
<213> ORGANISM: Unknown
<220> FEATURE:
<223> OTHER INFORMATION: Obtained from an environmental source

<400> SEQUENCE: 21
gtgagagtag aggcagacgg cgtcgggatc tcgtacgagg tgaccggaca gggacggccg      60
gtgatcctgc tgcacggctt cccagactcg ggacggcttt ggcgcaacca ggtgccggct     120
ttggctgagg ccggcttcca ggtgatcgtc cctgacctgc gcgggtacgg gcagtccgat     180
aagccagagg ccgtcgatgc gtactccctt ccggccctgg ccggggacgt catggcggta     240
ctggctgatg cgggcgtcga tcgggcccac gtcgtgggcc acgactgggg tgcgcgcgctc    300 ggctgggtgc tggcctcgct cgtgcccgac cgggtcgatc acctcgccgt tctgtcggtc     360
ggccatcccg cgaccttccg caggacgctg cacagaacg agaagtcctg gtacatgctt      420
ctcttccagt tcgcgggcat cgccgagcac tggctcagcg acaacgactg gccaacttc      480 cgcgcctggg cgcggcaccc tgacaccgac gcagtcatca gcgacctcga ggcgaccaag     540
tccctgacgc ctgcgctgaa ctggtatcgc gccaatgtcc cgcccgagtc ctggaccgcg     600
cctccgctgg ctcttcctgc cgtgcccgcc ccgtgatgg ggatctggag caccggcgac      660
atagccctga ccgagaagca gatgacggac tcgcaggaga acgtcagcgg cccgtggcgg     720
tacgagcgga tcgatggccc tggccactgg atgcagctcg aggctccgga gacgatcagc     780
cgcctgctcc tcgactttct ccctgcctag                                      810
```

<210> SEQ ID NO 22
<211> LENGTH: 269
<212> TYPE: PRT
<213> ORGANISM: Unknown
<220> FEATURE:
<223> OTHER INFORMATION: Obtained from an environmental source

<400> SEQUENCE: 22

Met Arg Val Glu Ala Asp Gly Val Gly Ile Ser Tyr Glu Val Thr Gly
1               5                   10                  15

Gln Gly Arg Pro Val Ile Leu Leu His Gly Phe Pro Asp Ser Gly Arg
            20                  25                  30

Leu Trp Arg Asn Gln Val Pro Ala Leu Ala Glu Ala Gly Phe Gln Val
        35                  40                  45

Ile Val Pro Asp Leu Arg Gly Tyr Gly Gln Ser Asp Lys Pro Glu Ala
    50                  55                  60

Val Asp Ala Tyr Ser Leu Pro Ala Leu Ala Gly Asp Val Met Ala Val
65                  70                  75                  80

Leu Ala Asp Ala Gly Val Asp Arg Ala His Val Val Gly His Asp Trp
                85                  90                  95

Gly Ala Ala Leu Gly Trp Val Leu Ala Ser Leu Val Pro Asp Arg Val
            100                 105                 110

Asp His Leu Ala Val Leu Ser Val Gly His Pro Ala Thr Phe Arg Arg
        115                 120                 125

Thr Leu Ala Gln Asn Glu Lys Ser Trp Tyr Met Leu Leu Phe Gln Phe
    130                 135                 140

Ala Gly Ile Ala Glu His Trp Leu Ser Asp Asn Asp Trp Ala Asn Phe
145                 150                 155                 160

Arg Ala Trp Ala Arg His Pro Asp Thr Asp Ala Val Ile Ser Asp Leu
                165                 170                 175

Glu Ala Thr Lys Ser Leu Thr Pro Ala Leu Asn Trp Tyr Arg Ala Asn
            180                 185                 190

Val Pro Pro Glu Ser Trp Thr Ala Pro Pro Leu Ala Leu Pro Ala Val
        195                 200                 205

Pro Ala Pro Val Met Gly Ile Trp Ser Thr Gly Asp Ile Ala Leu Thr
    210                 215                 220

Glu Lys Gln Met Thr Asp Ser Gln Glu Asn Val Ser Gly Pro Trp Arg
225                 230                 235                 240

Tyr Glu Arg Ile Asp Gly Pro Gly His Trp Met Gln Leu Glu Ala Pro
                245                 250                 255

Glu Thr Ile Ser Arg Leu Leu Leu Asp Phe Leu Pro Ala
            260                 265

<210> SEQ ID NO 23
<211> LENGTH: 1233
<212> TYPE: DNA
<213> ORGANISM: Unknown
<220> FEATURE:
<223> OTHER INFORMATION: Obtained from an environmental source

<400> SEQUENCE: 23
atgaccccga ccgttgcgac aaaaaccagc gaccagcaga cagcggagaa gacagcgatt      60
cggccgtttc gcatcaacgt tcccgacgcg gaactgaccg acctgcgcag gcgcgtcagc     120
gcgacgaggt ggcccgaacg cgagacggtt ccggatcaaa cgcagggcgt gcagctcgcg     180
acggttcaac agcttgcgcg ttattgggcg accgagtacg actggcgtaa gtgcgaggcg     240

-continued

```
aggctgaatg ccctgccgca gttcatcacg gagatcgatg gctggatat ccacttcatt       300 cacgtgcgct cgaagcacga tcgcgcgttg ccgctcatcg tcacgcacgg atggcctggc       360
tccatcgtcg agcagctgaa gatcatcgat ccgctcacca atcccacggc ccatggcggc       420
accgcgtccg acgccttcga cgtcgtgatc ccgtcgatgc ccggctacgg tgttcaggc        480 cggccgtcga ccaccggctg ggacgtcgca cacatcgcgc gcgcgtgggt ggtgctcatg       540
aaacgcctcg gctactcgaa gttcgcggcg cagggtggcg attggggcgc gattgtggtc       600
gatcagatgg gcgtccaggc ggctccggaa ttgatcggca ttcacaccaa catgcctggt       660
atctttcccg cggacatcga tcaggcggcg tttgccggga agccggcgcc atcgggtctg       720
tcagccgacg agaaagttgc gtacgagcgc ttgctgttcg tgtatcaaaa gggaatcggg       780
tacggatatc agatgggact gcgaccgcag acgctgtacg aatcgccga ttcacccgtc        840 ggcctggcgg cgtatttct cgatcacgac gcgcgcagtc tcgatctgat ctcgcgcgtc        900
ttcgcgggag cgtccgaggg cctctcacgc gatgacgtcc tcgacaacgt cacgatcgcc       960
tggttgacga acacgggggt gtccggcggc cgtctctact gggagaacta tggcaagctc      1020
ggattcttca atgtcaaagg cgtatcgatc ccggtggccg tgagcgtgtt ccccgacgag      1080
ctctatccag cgccgcggag ctggacggag aaggcgtatc cgaaactgat ccacttcaac      1140
aaggtcgaca agggcggaca cttcgcggcc ttcgagcagc cgaagctctt gtccgacgag      1200
attcgcacgg gtctgaagtc tctgcgcacc tga                                    1233
```

<210> SEQ ID NO 24
<211> LENGTH: 410
<212> TYPE: PRT
<213> ORGANISM: Unknown
<220> FEATURE:
<223> OTHER INFORMATION: Obtained from an environmental source

<400> SEQUENCE: 24

```
Met Thr Pro Thr Val Ala Thr Lys Thr Ser Asp Gln Gln Thr Ala Glu
  1               5                  10                  15

Lys Thr Ala Ile Arg Pro Phe Arg Ile Asn Val Pro Asp Ala Glu Leu
             20                  25                  30

Thr Asp Leu Arg Arg Arg Val Ser Ala Thr Arg Trp Pro Glu Arg Glu
         35                  40                  45

Thr Val Pro Asp Gln Thr Gln Gly Val Gln Leu Ala Thr Val Gln Gln
     50                  55                  60

Leu Ala Arg Tyr Trp Ala Thr Glu Tyr Asp Trp Arg Lys Cys Glu Ala
 65                  70                  75                  80

Arg Leu Asn Ala Leu Pro Gln Phe Ile Thr Glu Ile Asp Gly Leu Asp
                 85                  90                  95

Ile His Phe Ile His Val Arg Ser Lys His Asp Arg Ala Leu Pro Leu
            100                 105                 110

Ile Val Thr His Gly Trp Pro Gly Ser Ile Val Glu Gln Leu Lys Ile
        115                 120                 125

Ile Asp Pro Leu Thr Asn Pro Thr Ala His Gly Thr Ala Ser Asp
    130                 135                 140

Ala Phe Asp Val Val Ile Pro Ser Met Pro Gly Tyr Gly Cys Ser Gly
145                 150                 155                 160

Arg Pro Ser Thr Thr Gly Trp Asp Val Ala His Ile Ala Arg Ala Trp
                165                 170                 175

Val Val Leu Met Lys Arg Leu Gly Tyr Ser Lys Phe Ala Ala Gln Gly
            180                 185                 190
```

```
Gly Asp Trp Gly Ala Ile Val Val Asp Gln Met Gly Val Gln Ala Ala
            195                 200                 205

Pro Glu Leu Ile Gly Ile His Thr Asn Met Pro Gly Ile Phe Pro Ala
    210                 215                 220

Asp Ile Asp Gln Ala Ala Phe Ala Gly Lys Pro Ala Pro Ser Gly Leu
225                 230                 235                 240

Ser Ala Asp Glu Lys Val Ala Tyr Glu Arg Leu Leu Phe Val Tyr Gln
                245                 250                 255

Lys Gly Ile Gly Tyr Gly Tyr Gln Met Gly Leu Arg Pro Gln Thr Leu
            260                 265                 270

Tyr Gly Ile Ala Asp Ser Pro Val Gly Leu Ala Ala Tyr Phe Leu Asp
        275                 280                 285

His Asp Ala Arg Ser Leu Asp Leu Ile Ser Arg Val Phe Ala Gly Ala
    290                 295                 300

Ser Glu Gly Leu Ser Arg Asp Asp Val Leu Asp Asn Val Thr Ile Ala
305                 310                 315                 320

Trp Leu Thr Asn Thr Gly Val Ser Gly Gly Arg Leu Tyr Trp Glu Asn
                325                 330                 335

Tyr Gly Lys Leu Gly Phe Phe Asn Val Lys Gly Val Ser Ile Pro Val
            340                 345                 350

Ala Val Ser Val Phe Pro Asp Glu Leu Tyr Pro Ala Pro Arg Ser Trp
        355                 360                 365

Thr Glu Lys Ala Tyr Pro Lys Leu Ile His Phe Asn Lys Val Asp Lys
    370                 375                 380

Gly Gly His Phe Ala Ala Phe Glu Gln Pro Lys Leu Leu Ser Asp Glu
385                 390                 395                 400

Ile Arg Thr Gly Leu Lys Ser Leu Arg Thr
                405                 410

<210> SEQ ID NO 25
<211> LENGTH: 870
<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(81)

<400> SEQUENCE: 25
atgtccgaac cctggaagca tcacgccaaa gttgtcaacg gctttcgtat gcactatgtc      60
attgccggtt ccggctaccc actcgtattt ctgcatggct ggccccagag ttggtatgag     120
tggcgaaaga tcattccggc actcgctgag aagttcacgg taattgcccc ggacctacgc     180
ggattgggag attctgaacg tcctctcaca gggtatgata acgtaccct  ggcctcagat     240 gtgtacgagt tggtgaaatc cctgggcttc agcaaaattg gctcactgg  ccatgactgg     300 ggtggtgccg tagcgttcta ctttgcttac gatcatccag atggtcga  acgcttgctg     360 attctcgaca tggtgccagg ttacgggcgc aaaggtgggt caatgaccct cgccaagca     420 cagcgctatt ggcacgcgtt ctttcacggt ggcatgccag acttagctga aaagctggtc     480
agcgccaacg tcgaagccta cttaagccat ttctacactt cgaccacgta caactacagt     540
ccaaatgtgt tcagtgcaga agatatagcc gaatacgtgc gcgtatattc cgctccaggg     600
gcgatccgtg ccgggtttca atactatcgt gctgcgttgc aagaagacct tgacaacctc     660
agcagctgca cagaaaaact gaaaatgcct gtgctcgcat ggggaggcga agcattcatg     720
```

```
ggcaacgttg taccggtgtg gcagacggtc gccgagaacg tacaaggagg cgagctcaag      780
cagtgtggcc acttcatcgc ggaggagaaa cctgagttcg ccactcaaca gcgctggaa       840 tttttcgcgc cgctccgggg agcaaagtag                                       870
```

```
<210> SEQ ID NO 26
<211> LENGTH: 289
<212> TYPE: PRT
<213> ORGANISM: Unknown
<220> FEATURE:
<223> OTHER INFORMATION: Obtained from an environmental source
<220> FEATURE:
<221> NAME/KEY: SIGNAL
<222> LOCATION: (1)...(27)

<400> SEQUENCE: 26
```

```
Met Ser Glu Pro Trp Lys His His Ala Lys Val Val Asn Gly Phe Arg
 1               5                  10                  15

Met His Tyr Val Ile Ala Gly Ser Gly Tyr Pro Leu Val Phe Leu His
             20                  25                  30

Gly Trp Pro Gln Ser Trp Tyr Glu Trp Arg Lys Ile Ile Pro Ala Leu
         35                  40                  45

Ala Glu Lys Phe Thr Val Ile Ala Pro Asp Leu Arg Gly Leu Gly Asp
     50                  55                  60

Ser Glu Arg Pro Leu Thr Gly Tyr Asp Lys Arg Thr Leu Ala Ser Asp
 65                  70                  75                  80

Val Tyr Glu Leu Val Lys Ser Leu Gly Phe Ser Lys Ile Gly Leu Thr
                 85                  90                  95

Gly His Asp Trp Gly Gly Ala Val Ala Phe Tyr Phe Ala Tyr Asp His
            100                 105                 110

Pro Glu Met Val Glu Arg Leu Leu Ile Leu Asp Met Val Pro Gly Tyr
        115                 120                 125

Gly Arg Lys Gly Gly Ser Met Asp Leu Arg Gln Ala Gln Arg Tyr Trp
    130                 135                 140

His Ala Phe Phe His Gly Gly Met Pro Asp Leu Ala Glu Lys Leu Val
145                 150                 155                 160

Ser Ala Asn Val Glu Ala Tyr Leu Ser His Phe Tyr Thr Ser Thr Thr
                165                 170                 175

Tyr Asn Tyr Ser Pro Asn Val Phe Ser Ala Glu Asp Ile Ala Glu Tyr
            180                 185                 190

Val Arg Val Tyr Ser Ala Pro Gly Ala Ile Arg Ala Gly Phe Gln Tyr
        195                 200                 205

Tyr Arg Ala Ala Leu Gln Glu Asp Leu Asp Asn Leu Ser Ser Cys Thr
    210                 215                 220

Glu Lys Leu Lys Met Pro Val Leu Ala Trp Gly Glu Ala Phe Met
225                 230                 235                 240

Gly Asn Val Val Pro Val Trp Gln Thr Val Ala Glu Asn Val Gln Gly
                245                 250                 255

Gly Glu Leu Lys Gln Cys Gly His Phe Ile Ala Glu Lys Pro Glu
            260                 265                 270

Phe Ala Thr Gln Gln Ala Leu Glu Phe Phe Ala Pro Leu Arg Gly Ala
        275                 280                 285

Lys
```

```
<210> SEQ ID NO 27
<211> LENGTH: 1299
```

<212> TYPE: DNA
<213> ORGANISM: Unknown
<220> FEATURE:
<223> OTHER INFORMATION: Obtained from an environmental source

<400> SEQUENCE: 27

| | | | | | |
|---|---|---|---|---|---|
| atgacacgcg | actcactcca | actcgccgcc | gtcgcgttgg | ccatggtgct | cgccggcgcc | 60 |
| ttcgcgattc | ccgggtgggc | gcaaaccacc | gtcggcagcg | atgcctcgat | ccgtcccttc | 120 |
| aagatccaag | tgccgcaagc | ctcgctcgac | gacctgcgcc | ggcgtattgc | ggcaacgcgc | 180 |
| tggcccgaca | aggagaccgt | cgacaacgca | tcccagggcg | cgcagcttgc | gcagatgcag | 240 |
| gagctcgtga | ggtactgggg | cacgagctac | gactggcgca | aggccgaggc | gaagctcaac | 300 |
| gcgttgccgc | aattcacgac | caacatcgac | ggcgtcgaca | ttcatttcat | ccacgtgcgc | 360 |
| tcgcgtcatc | ccaatgcgct | gcccgtcatc | attacgcacg | gctggcccgg | atcggtgatc | 420 |
| gagcagctca | gctcatcga | tccgctcacg | gatccgaccg | cgcacggcgg | cagcgccgac | 480 |
| gacgcgttcg | acgtcgtcat | tccgtcggtg | ccgggctacg | ggttttccgg | caagccgacc | 540 |
| ggcaccgggt | gggatccgga | tcgcatcgcg | cgcgcgtggg | cggagctcat | gaaacgcctc | 600 |
| ggctacacac | gttatgtcgc | gcaaggcggc | gactggggct | cgccgatctc | gagcgcgatg | 660 |
| gcgcggcagg | gagcgccggg | gttgctcggt | attcacatca | acctgcctgc | gacggtgccg | 720 |
| ccggaagcag | ccgccgcgct | cggggtggc | ccgctgccgg | cagggcttc | cgacaaggaa | 780 |
| cgcgccgcga | tcgacacgct | catggcttat | gccaaggccg | gcaacgcctc | gtacttcacg | 840 |
| atgttgacgg | cgcgcccgca | aaccgtcggt | tacggcgcga | acgactcgcc | gacgggcctt | 900 |
| gcggcctgga | tcctcgtgca | tccgggtttc | aggcaatggt | cgtacggcgt | cgatccgacg | 960 |
| gagtcgccga | gcaaggacga | cgtgctcgac | gacatcacgc | tgtattggct | caccgggacc | 1020 |
| gcgacctcgg | ccggccggct | gtactgggag | aacggcgcgc | gcggcagcgt | catcgtcgcc | 1080 |
| gccgcgcaga | agaccggcga | gatctcgctt | ccggtcgcga | tcacggtgtt | tcccgacgac | 1140 |
| gtctatcgcg | cgccggagac | ctgggcgcgg | cgcgcgtacc | gcaacctcgt | ctacttccac | 1200 |
| gaagtggaca | agggcggaca | tttcgcagcg | tgggaacagc | ccgagctgtt | cagcgccgag | 1260 |
| ctgcgcgctg | cgttcaggcc | gctgcgcgag | gcgcactga | | | 1299 |

<210> SEQ ID NO 28
<211> LENGTH: 432
<212> TYPE: PRT
<213> ORGANISM: Unknown
<220> FEATURE:
<223> OTHER INFORMATION: Obtained from an environmental source

<400> SEQUENCE: 28

Met Thr Arg Asp Ser Leu Gln Leu Ala Ala Val Ala Leu Ala Met Val
1               5                   10                  15

Leu Ala Gly Ala Phe Ala Ile Pro Gly Trp Ala Gln Thr Thr Val Gly
            20                  25                  30

Ser Asp Ala Ser Ile Arg Pro Phe Lys Ile Gln Val Pro Gln Ala Ser
        35                  40                  45

Leu Asp Asp Leu Arg Arg Arg Ile Ala Ala Thr Arg Trp Pro Asp Lys
    50                  55                  60

Glu Thr Val Asp Asn Ala Ser Gln Gly Ala Gln Leu Ala Gln Met Gln
65                  70                  75                  80

Glu Leu Val Arg Tyr Trp Gly Thr Ser Tyr Asp Trp Arg Lys Ala Glu
                85                  90                  95

```
Ala Lys Leu Asn Ala Leu Pro Gln Phe Thr Thr Asn Ile Asp Gly Val
            100                 105                 110

Asp Ile His Phe Ile His Val Arg Ser Arg His Pro Asn Ala Leu Pro
            115                 120                 125

Val Ile Ile Thr His Gly Trp Pro Gly Ser Val Ile Glu Gln Leu Lys
130                 135                 140

Leu Ile Asp Pro Leu Thr Asp Pro Thr Ala His Gly Gly Ser Ala Asp
145                 150                 155                 160

Asp Ala Phe Asp Val Val Ile Pro Ser Val Pro Gly Tyr Gly Phe Ser
            165                 170                 175

Gly Lys Pro Thr Gly Thr Gly Trp Asp Pro Asp Arg Ile Ala Arg Ala
            180                 185                 190

Trp Ala Glu Leu Met Lys Arg Leu Gly Tyr Thr Arg Tyr Val Ala Gln
            195                 200                 205

Gly Gly Asp Trp Gly Ser Pro Ile Ser Ser Ala Met Ala Arg Gln Gly
            210                 215                 220

Ala Pro Gly Leu Leu Gly Ile His Ile Asn Leu Pro Ala Thr Val Pro
225                 230                 235                 240

Pro Glu Ala Ala Ala Leu Gly Gly Gly Pro Leu Pro Ala Gly Leu
            245                 250                 255

Ser Asp Lys Glu Arg Ala Ala Ile Asp Thr Leu Met Ala Tyr Ala Lys
            260                 265                 270

Ala Gly Asn Ala Ser Tyr Phe Thr Met Leu Thr Ala Arg Pro Gln Thr
            275                 280                 285

Val Gly Tyr Gly Ala Asn Asp Ser Pro Thr Gly Leu Ala Ala Trp Ile
            290                 295                 300

Leu Val His Pro Gly Phe Arg Gln Trp Ser Tyr Gly Val Asp Pro Thr
305                 310                 315                 320

Glu Ser Pro Ser Lys Asp Asp Val Leu Asp Asp Ile Thr Leu Tyr Trp
            325                 330                 335

Leu Thr Gly Thr Ala Thr Ser Ala Gly Arg Leu Tyr Trp Glu Asn Gly
            340                 345                 350

Ala Arg Gly Ser Val Ile Val Ala Ala Gln Lys Thr Gly Glu Ile
            355                 360                 365

Ser Leu Pro Val Ala Ile Thr Val Phe Pro Asp Val Tyr Arg Ala
370                 375                 380

Pro Glu Thr Trp Ala Arg Arg Ala Tyr Arg Asn Leu Val Tyr Phe His
385                 390                 395                 400

Glu Val Asp Lys Gly Gly His Phe Ala Ala Trp Gln Pro Glu Leu
            405                 410                 415

Phe Ser Ala Glu Leu Arg Ala Ala Phe Arg Pro Leu Arg Glu Ala His
            420                 425                 430

<210> SEQ ID NO 29
<211> LENGTH: 981
<212> TYPE: DNA
<213> ORGANISM: Unknown
<220> FEATURE:
<223> OTHER INFORMATION: Obtained from an environmental source

<400> SEQUENCE: 29
atgcatgaga taaagcatcg cgttgtcgaa acgaatggca tccgcatgca cgtcgctgag    60
tgcggggtgg gtccgcttgt gctcctgtgt cacgggtttc ccgagtgttg gtattcgtgg   120
cgccatcagt tgccggccct cgcggaagct ggattccacg tcgtcgcgcc tgacatgcga   180
```

```
ggctacggcg agacagaccg gccacaggaa atcgaggagt acacgctcct gcatttagtt      240
ggtgacatga taggtctgct cgacgttttg ggtgcagaaa gcgcggtgat cgccggccac      300
gattggggtg ccccggtggc gtggcattct gcgcttctac gcccagatcg gttccgcgcc      360
gtcatcggct tgagcgtacc gttcaggccg agactccccg tgcgcccgac tagcgtcatg      420
cctcagaccg acgacgcgct cttctaccag ctttacttcc aaacttcagg catcgccgag      480
gcggagttcg agcgcgacgt ccggctgagc atccgcagcc tcctctattc ggcttcgggc      540
gatgcgccgc gtcgcgataa caccggaatg cctggtggcg aagtcggaat ggtgccacgc      600
caaggtggtt tcctctcgcg cctgataaat cccgcatcgc tacccactg gctcaccgac       660
gcggacgtag acttctacgt gaaggagttc acgcgcacag gatttcgcgg cggtctgaac      720
tggtaccgca acatcgaccg caattgggag ctcttggcgc ccttcactgc ggcgcgtgtg      780
tccgtccccg cactctttgt cgccggcgac cgcgatctcg tagtcgcctt cgtgggatg       840
gaccaactca tccccaatct ggcgaagttt gtcccgcagc tccttggcac cctcatgctc      900
ccaggctgcg gccactggac ccaacaggaa tgtccgcgcg aggtcaatga cgccatgctc      960
gatttccttc gtcggctgta g                                                981

<210> SEQ ID NO 30
<211> LENGTH: 326
<212> TYPE: PRT
<213> ORGANISM: Unknown
<220> FEATURE:
<223> OTHER INFORMATION: Obtained from an environmental source

<400> SEQUENCE: 30
```

Met His Glu Ile Lys His Arg Val Val Glu Thr Asn Gly Ile Arg Met
1               5                   10                  15

His Val Ala Glu Cys Gly Val Gly Pro Leu Val Leu Cys His Gly
            20                  25                  30

Phe Pro Glu Cys Trp Tyr Ser Trp Arg His Gln Leu Pro Ala Leu Ala
        35                  40                  45

Glu Ala Gly Phe His Val Val Ala Pro Asp Met Arg Gly Tyr Gly Glu
    50                  55                  60

Thr Asp Arg Pro Gln Glu Ile Glu Glu Tyr Thr Leu Leu His Leu Val
65                  70                  75                  80

Gly Asp Met Ile Gly Leu Leu Asp Val Leu Gly Ala Glu Ser Ala Val
                85                  90                  95

Ile Ala Gly His Asp Trp Gly Ala Pro Val Ala Trp His Ser Ala Leu
            100                 105                 110

Leu Arg Pro Asp Arg Phe Arg Ala Val Ile Gly Leu Ser Val Pro Phe
        115                 120                 125

Arg Pro Arg Leu Pro Val Arg Pro Thr Ser Val Met Pro Gln Thr Asp
    130                 135                 140

Asp Ala Leu Phe Tyr Gln Leu Tyr Phe Gln Thr Ser Gly Ile Ala Glu
145                 150                 155                 160

Ala Glu Phe Glu Arg Asp Val Arg Leu Ser Ile Arg Ser Leu Leu Tyr
                165                 170                 175

Ser Ala Ser Gly Asp Ala Pro Arg Arg Asp Asn Thr Gly Met Pro Gly
            180                 185                 190

Gly Glu Val Gly Met Val Pro Arg Gln Gly Gly Phe Leu Ser Arg Leu
        195                 200                 205

Ile Asn Pro Ala Ser Leu Pro His Trp Leu Thr Asp Ala Asp Val Asp
    210                 215                 220

```
Phe Tyr Val Lys Glu Phe Thr Arg Thr Gly Phe Arg Gly Gly Leu Asn
225                 230                 235                 240

Trp Tyr Arg Asn Ile Asp Arg Asn Trp Glu Leu Leu Ala Pro Phe Thr
            245                 250                 255

Ala Ala Arg Val Ser Val Pro Ala Leu Phe Val Ala Gly Asp Arg Asp
        260                 265                 270

Leu Val Val Ala Phe Arg Gly Met Asp Gln Leu Ile Pro Asn Leu Ala
    275                 280                 285

Lys Phe Val Pro Gln Leu Leu Gly Thr Leu Met Leu Pro Gly Cys Gly
    290                 295                 300

His Trp Thr Gln Gln Glu Cys Pro Arg Glu Val Asn Asp Ala Met Leu
305                 310                 315                 320

Asp Phe Leu Arg Arg Leu
            325
```

<210> SEQ ID NO 31
<211> LENGTH: 894
<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(51)

<400> SEQUENCE: 31

```
atgaagcgta tggttctaaa acagcaatc gccctgcttg cgtcggatgc agccgagggt      60
ggcgagttcg agtcgcgggt gacgcatggt tacgccgatt cttcggggt aaaaatccac     120 tatgccagca tgggcaaggg tccactggta gtgatggtcc acgtttccc cgatttctgg    180 tacacctggc gggcacaaat ggaagcactt tccgattcgt tccaatgtgt tgccatcgac    240
caacgcggat acaatttgag cgacaagccc atcggcgtcg agaactacgg cgtccgcctg    300
ttggtcggag acgtttcggc ggtgataaaa aagctgggca agaaaaggc gatcctggtt     360 ggacatgact ggggcgggct ggttgcctgg caattcgcgc tcacccaacc gcaaatgacc    420
gagcggctca tcattctgaa tttgccgcat cctcggggcc tgctgcgcga gttggcccag    480
aatccgcaac agcagaagaa cagccagtat gcacgggact tcagcaacc cgaggccgcc    540 tcgaaattga cggccgagca gcttgccttc tgggtgaaag atgcggaggc ccggaccaag    600
tacatcgaag cgttcaaacg ctccgatttt gaggcgatgc tcaactatta caagcgcaac    660
tacccgcgcg agccttacac cgaggatact tcgccagtgg taaaggtgca ggtgcctgtt    720
cttatgattc atgggttagg cgacacggct ttgctgcccg gcgcgctcaa caacacgtgg    780
gattggttgg agaaagattt gacgctggtc acgattcctg gcgccggcca cttcgttcaa    840
caggacgccg ctgaattggt gtcgcgctcg atgagagcat ggttgctgcg ctga          894
```

<210> SEQ ID NO 32
<211> LENGTH: 297
<212> TYPE: PRT
<213> ORGANISM: Unknown
<220> FEATURE:
<223> OTHER INFORMATION: Obtained from an environmental source
<220> FEATURE:
<221> NAME/KEY: SIGNAL
<222> LOCATION: (1)...(17)

<400> SEQUENCE: 32

Met Lys Arg Met Val Leu Lys Thr Ala Ile Ala Leu Leu Ala Ser Asp

```
                1               5                  10                 15
           Ala Ala Glu Gly Gly Glu Phe Glu Ser Arg Val Thr His Gly Tyr Ala
                           20                  25                 30
           Asp Ser Ser Gly Val Lys Ile His Tyr Ala Ser Met Gly Lys Gly Pro
                       35                  40                  45
           Leu Val Val Met Val His Gly Phe Pro Asp Phe Trp Tyr Thr Trp Arg
                50                  55                  60
           Ala Gln Met Glu Ala Leu Ser Asp Ser Phe Gln Cys Val Ala Ile Asp
            65                  70                  75                  80
           Gln Arg Gly Tyr Asn Leu Ser Asp Lys Pro Ile Gly Val Glu Asn Tyr
                            85                  90                  95
           Gly Val Arg Leu Leu Val Gly Asp Val Ser Ala Val Ile Lys Lys Leu
                           100                 105                 110
           Gly Lys Glu Lys Ala Ile Leu Val Gly His Asp Trp Gly Gly Leu Val
                       115                 120                 125
           Ala Trp Gln Phe Ala Leu Thr Gln Pro Gln Met Thr Glu Arg Leu Ile
                       130                 135                 140
           Ile Leu Asn Leu Pro His Pro Arg Gly Leu Leu Arg Glu Leu Ala Gln
           145                 150                 155                 160
           Asn Pro Gln Gln Gln Lys Asn Ser Gln Tyr Ala Arg Asp Phe Gln Gln
                           165                 170                 175
           Pro Glu Ala Ala Ser Lys Leu Thr Ala Glu Gln Leu Ala Phe Trp Val
                       180                 185                 190
           Lys Asp Ala Glu Ala Arg Thr Lys Tyr Ile Glu Ala Phe Lys Arg Ser
                       195                 200                 205
           Asp Phe Glu Ala Met Leu Asn Tyr Tyr Lys Arg Asn Tyr Pro Arg Glu
                       210                 215                 220
           Pro Tyr Thr Glu Asp Thr Ser Pro Val Val Lys Val Gln Val Pro Val
           225                 230                 235                 240
           Leu Met Ile His Gly Leu Gly Asp Thr Ala Leu Leu Pro Gly Ala Leu
                           245                 250                 255
           Asn Asn Thr Trp Asp Trp Leu Glu Lys Asp Leu Thr Leu Val Thr Ile
                       260                 265                 270
           Pro Gly Ala Gly His Phe Val Gln Gln Asp Ala Ala Glu Leu Val Ser
                       275                 280                 285
           Arg Ser Met Arg Ala Trp Leu Leu Arg
                       290                 295

<210> SEQ ID NO 33
<211> LENGTH: 1377
<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(123)

<400> SEQUENCE: 33
atgcagctcg aaaaagcgca gtacatgccc gccttagcgt catcgcacac ttggcgcagc      60
tttcttcgct acataacagt cgcgtgcttt ttgggcattt tcctgctcgg cgctcagagc     120
tacgcccaga ccggtaggac cgccatcgcg gaggcctccg tcagcagctc gcttcctgcg     180
aagccgcctg cagcgaccga agataaggcg atccgtcctt tccgcgtcca cgtcccacaa     240
gaggcgctcg acgacctcag ccgtcgcctc gcggcgacgc gcttgcctga ccaggagacc     300
```

-continued

```
gtcaacgatc gatcgcaggg caatcagttg gcaacgatga aggaactcgt gcggtattgg    360
cagacaggct acgactggcg caaggcggag cagaaactga acgcattgcc gcagtttgtt    420
acgacgatag acggcctaga catccatttc atccacgtcc gctcgaaaca tcccaacgcg    480
atgccactca ttatcacgca cggctggcct ggatcgatat ttgaattact aaaggttatc    540
ggcccgctta ccgatccgac ggcgttcggc agcggcgcgg aagatgcctt cgacgtcgtg    600
atcccgtcga tgcctggcta tggcttctcc ggcaagccga cggacgccgg ttgggacccc    660
gaacacatcg cgcgagtctg gcggagctg atgaagcgcc tcggatacac ccgctacgtc     720
gcccagggcg gcgactgggg ctcccccgtc tccagcgcga tggcgcgcca ggcgccggcg    780
ggactgctcg gcatccacgt caacttgccg gcggctatac cgcccgacgt gggcagggcg    840
ctcaacgccg gcgggcccgc gccggcggga ctctccgaga aggagcgcgc ggcgtttgac    900
gcgctcgtca cgttcaacac gaagaacagg gcctactcgg tgatgatggc cacgcggccg    960
cagacgatag gctacgcctt gacgattct ccggcgggc ttgcggcctg gatatatgac     1020
tacaacaacg gcgagcccga gcgctcactg accaaagacg agatgctgga cgacatcacg    1080
ctgtactggc tgacgaacag cgcgacctcg gcggcgcggc tgtactggga gaacagcgga    1140
cgaagccttc tttctgtggc cgcgcagaag accgccgaga tctcgctccc agtggccatc    1200
acggtatttc cgggagagat ctatcgagcc ccggagacgt gggcccggct cgcctatcgc    1260
aacctgatct actttcacga ggtcgacagg ggcggacact tcgcggcctg ggaagagccg    1320
gagcttttct ccgccgagtt gcgcgccgcc ttcagatcac ttcagaaaca gcaatga      1377
```

<210> SEQ ID NO 34
<211> LENGTH: 458
<212> TYPE: PRT
<213> ORGANISM: Unknown
<220> FEATURE:
<223> OTHER INFORMATION: Obtained from an environmental source
<220> FEATURE:
<221> NAME/KEY: SIGNAL
<222> LOCATION: (1)...(42)

<400> SEQUENCE: 34

```
Met Gln Leu Glu Lys Ala Gln Tyr Met Pro Ala Leu Ala Ser Ser His
 1               5                  10                  15

Thr Trp Arg Ser Phe Leu Arg Tyr Ile Thr Val Ala Cys Phe Leu Gly
            20                  25                  30

Ile Phe Leu Leu Gly Ala Gln Ser Tyr Ala Gln Thr Gly Arg Thr Ala
        35                  40                  45

Ile Ala Glu Ala Ser Val Ser Ser Leu Pro Ala Lys Pro Pro Ala
    50                  55                  60

Ala Thr Glu Asp Lys Ala Ile Arg Pro Phe Arg Val His Val Pro Gln
65                  70                  75                  80

Glu Ala Leu Asp Asp Leu Ser Arg Arg Leu Ala Ala Thr Arg Leu Pro
                85                  90                  95

Asp Gln Glu Thr Val Asn Asp Arg Ser Gln Gly Asn Gln Leu Ala Thr
            100                 105                 110

Met Lys Glu Leu Val Arg Tyr Trp Gln Thr Gly Tyr Asp Trp Arg Lys
        115                 120                 125

Ala Glu Gln Lys Leu Asn Ala Leu Pro Gln Phe Val Thr Thr Ile Asp
    130                 135                 140

Gly Leu Asp Ile His Phe Ile His Val Arg Ser Lys His Pro Asn Ala
145                 150                 155                 160
```

Met Pro Leu Ile Ile Thr His Gly Trp Pro Gly Ser Ile Phe Glu Leu
            165                 170                 175

Leu Lys Val Ile Gly Pro Leu Thr Asp Pro Thr Ala Phe Gly Ser Gly
            180                 185                 190

Ala Glu Asp Ala Phe Asp Val Val Ile Pro Ser Met Pro Gly Tyr Gly
            195                 200                 205

Phe Ser Gly Lys Pro Thr Asp Ala Gly Trp Asp Pro Glu His Ile Ala
            210                 215                 220

Arg Val Trp Ala Glu Leu Met Lys Arg Leu Gly Tyr Thr Arg Tyr Val
225                 230                 235                 240

Ala Gln Gly Gly Asp Trp Gly Ser Pro Val Ser Ser Ala Met Ala Arg
            245                 250                 255

Gln Ala Pro Ala Gly Leu Leu Gly Ile His Val Asn Leu Pro Ala Ala
            260                 265                 270

Ile Pro Pro Asp Val Gly Arg Ala Leu Asn Ala Gly Gly Pro Ala Pro
            275                 280                 285

Ala Gly Leu Ser Glu Lys Glu Arg Ala Ala Phe Asp Ala Leu Val Thr
            290                 295                 300

Phe Asn Thr Lys Asn Arg Ala Tyr Ser Val Met Met Ala Thr Arg Pro
305                 310                 315                 320

Gln Thr Ile Gly Tyr Ala Leu Thr Asp Ser Pro Ala Gly Leu Ala Ala
            325                 330                 335

Trp Ile Tyr Asp Tyr Asn Asn Gly Glu Pro Glu Arg Ser Leu Thr Lys
            340                 345                 350

Asp Glu Met Leu Asp Asp Ile Thr Leu Tyr Trp Leu Thr Asn Ser Ala
            355                 360                 365

Thr Ser Ala Ala Arg Leu Tyr Trp Glu Asn Ser Gly Arg Ser Leu Leu
370                 375                 380

Ser Val Ala Ala Gln Lys Thr Ala Glu Ile Ser Leu Pro Val Ala Ile
385                 390                 395                 400

Thr Val Phe Pro Gly Glu Ile Tyr Arg Ala Pro Glu Thr Trp Ala Arg
            405                 410                 415

Leu Ala Tyr Arg Asn Leu Ile Tyr Phe His Glu Val Asp Arg Gly Gly
            420                 425                 430

His Phe Ala Ala Trp Glu Glu Pro Glu Leu Phe Ser Ala Glu Leu Arg
            435                 440                 445

Ala Ala Phe Arg Ser Leu Gln Lys Gln Gln
450                 455

<210> SEQ ID NO 35
<211> LENGTH: 858
<212> TYPE: DNA
<213> ORGANISM: Unknown
<220> FEATURE:
<223> OTHER INFORMATION: Obtained from an environmental source

<400> SEQUENCE: 35
atgaacttca ataccgtcga ggtcacaggc cttaagatct tctaccgcga ggccgggaac      60
ccgtcaaagc cggccatcgt cctgctgcac gggttccctt cgtcctcgta ctcattccac     120
gatctcattc cgctcctgtc ggatcgtttt catgtcattg cgccggacta ccccggcatg     180
gggtacagcg aagcgccacc cacgggcgca atgcgcccga ctttcgacga tatggtgaag     240
gccatggaca catttatcgc ccaatgtgcc cctgggccgg tcatcttgta catgcatgac     300
atcggcggcc ccatcggctt gcgaatcgcg gcggcacacc cggagaggat cgcgggcctg     360

```
atctttcaga acttcacgat ttcgatggag ggttggaacc cggagcgtct caaggtctac    420
gagcggcttg gcggtccgga aaccccggag aatctggccg aaaccgagca attcgcaacc    480
gtagaacgca gtgcgtttct tcataagagg ggcgcgcatc ggcccgaggc cctgaatccg    540
gacagttggg cgattgatgc ctatgccttc tcgatcccgg ccagccgcgc ctttatgtcg    600
agcttgttta tgaatgtcac cagcaacatt ccgcactatc cggaatggca ggcatatctg    660
aaagaccggc agccgagatc gctgatcgtg tgggggcaaa atgacccggt tttctcgccg    720
gcagctccgg aaaccgtcaa gaggctcttg ccggcggcga gggttcattc tttcaacggc    780
ggacacttcg tgctcgacga atacgccgaa ccgatcgccg cggcgatcat cgagacgttt    840
gccggagaca agaaatga                                                  858
```

<210> SEQ ID NO 36
<211> LENGTH: 285
<212> TYPE: PRT
<213> ORGANISM: Unknown
<220> FEATURE:
<223> OTHER INFORMATION: Obtained from an environmental source

<400> SEQUENCE: 36

```
Met Asn Phe Asn Thr Val Glu Val Thr Gly Leu Lys Ile Phe Tyr Arg
 1               5                  10                  15

Glu Ala Gly Asn Pro Ser Lys Pro Ala Ile Val Leu Leu His Gly Phe
            20                  25                  30

Pro Ser Ser Ser Tyr Ser Phe His Asp Leu Ile Pro Leu Leu Ser Asp
        35                  40                  45

Arg Phe His Val Ile Ala Pro Asp Tyr Pro Gly Met Gly Tyr Ser Glu
    50                  55                  60

Ala Pro Pro Thr Gly Ala Met Arg Pro Thr Phe Asp Asp Met Val Lys
65                  70                  75                  80

Ala Met Asp Thr Phe Ile Ala Gln Cys Ala Pro Gly Pro Val Ile Leu
                85                  90                  95

Tyr Met His Asp Ile Gly Gly Pro Ile Gly Leu Arg Ile Ala Ala Ala
            100                 105                 110

His Pro Glu Arg Ile Ala Gly Leu Ile Phe Gln Asn Phe Thr Ile Ser
        115                 120                 125

Met Glu Gly Trp Asn Pro Glu Arg Leu Lys Val Tyr Glu Arg Leu Gly
    130                 135                 140

Gly Pro Glu Thr Pro Glu Asn Leu Ala Glu Thr Glu Gln Phe Ala Thr
145                 150                 155                 160

Val Glu Arg Ser Ala Phe Leu His Lys Arg Gly Ala His Arg Pro Glu
                165                 170                 175

Ala Leu Asn Pro Asp Ser Trp Ala Ile Asp Ala Tyr Ala Phe Ser Ile
            180                 185                 190

Pro Ala Ser Arg Ala Phe Met Ser Ser Leu Phe Met Asn Val Thr Ser
        195                 200                 205

Asn Ile Pro His Tyr Pro Glu Trp Gln Ala Tyr Leu Lys Asp Arg Gln
    210                 215                 220

Pro Arg Ser Leu Ile Val Trp Gly Gln Asn Asp Pro Val Phe Ser Pro
225                 230                 235                 240

Ala Ala Pro Glu Thr Val Lys Arg Leu Leu Pro Ala Ala Arg Val His
                245                 250                 255

Ser Phe Asn Gly Gly His Phe Val Leu Asp Glu Tyr Ala Glu Pro Ile
            260                 265                 270
```

```
Ala Ala Ala Ile Ile Glu Thr Phe Ala Gly Asp Lys Lys
        275                 280                 285
```

<210> SEQ ID NO 37
<211> LENGTH: 1206
<212> TYPE: DNA
<213> ORGANISM: Unknown
<220> FEATURE:
<223> OTHER INFORMATION: Obtained from an environmental source

<400> SEQUENCE: 37

```
atgacccaga cgacaacccg ccctgccatc cgctccttcg aggtctcctt tcccgatgaa      60
gcactcgcgg acctccgccg gcgcttagca gcgacgcgct ggccggagaa agagaccgtc     120
gccgacaact cacaaggcgt cccgctggtc aacatgcagc agctggcccg ctactgggcg     180
gccgaatacg actggcgcaa gacggaggcg aagctcaacg ccttgcccca attcctgact     240
gaaatcgacg gctgggcat tcacttcatt cacgtccgct cgcgccatga gaacgccctg     300
ccgatcatca tcacgcacgg ctggccgggc tcgattatcg agcagctcaa gatcatcgag     360
ccgctcacca acccgaccgc ctctggcggt agcgccgaag acgccttcca cgtggtcatc     420
ccttcgctgc ccggctatgg cttttccggc aagccggcgg cgccgggctg gaacccaatc     480
accatcgcaa ctgcctggac cacactgatg aaacgccttg gctactcccg cttcgtcgcc     540
cagggcggcg actgggcaa cgccgtatcg gagatcatgc ccttgcaggc tcctcccgaa     600
ctggtcggca tccacaccaa catggcggcc accgttccgg ccaacgtcgc gaaggcgctc     660
gcattccacg agggcccgcc ttccggcctt tcgcccgaag agtcctccgc ctggagccag     720
ctggactact tttacaagaa gggcctgggc tacgccctgg agatgaatac ccggccccag     780
accctgtacg gctggcgga ttcgccggtt ggcctggccg cctggatgct cgaccacgac     840
attcgcagcc aggagctaat cgcccgcgtc tttgacggac agtcggaggg cctatctaaa     900
gaggacgtga tcgagaacgt caccctctac tggctgacga gcaccgcgat tcctcggcg     960
cgcctctact gggataccgc tcaacttggc ggtggcgggt ttttcgacgt ccgaggtatc    1020
aagattccgg tcgccgtcag cgccttcccg gatgagatct acacgccgcc ccgcagttgg    1080
gccgaggcgg cctacccgaa gctcatccat tacaaccggc tcgacaaagg cggccacttc    1140
gccgcctggg aacaaccgca gctcttctcg tccgagctgc gcgcagcatt tagaactttg    1200
cgctag                                                               1206
```

<210> SEQ ID NO 38
<211> LENGTH: 401
<212> TYPE: PRT
<213> ORGANISM: Unknown
<220> FEATURE:
<223> OTHER INFORMATION: Obtained from an environmental source

<400> SEQUENCE: 38

```
Met Thr Gln Thr Thr Thr Arg Pro Ala Ile Arg Ser Phe Glu Val Ser
  1               5                  10                  15

Phe Pro Asp Glu Ala Leu Ala Asp Leu Arg Arg Arg Leu Ala Ala Thr
             20                  25                  30

Arg Trp Pro Glu Lys Glu Thr Val Ala Asp Asn Ser Gln Gly Val Pro
         35                  40                  45

Leu Val Asn Met Gln Gln Leu Ala Arg Tyr Trp Ala Ala Glu Tyr Asp
     50                  55                  60

Trp Arg Lys Thr Glu Ala Lys Leu Asn Ala Leu Pro Gln Phe Leu Thr
 65                  70                  75                  80
```

```
Glu Ile Asp Gly Leu Gly Ile His Phe Ile His Val Arg Ser Arg His
                    85                  90                  95

Glu Asn Ala Leu Pro Ile Ile Thr His Gly Trp Pro Gly Ser Ile
            100                 105                 110

Ile Glu Gln Leu Lys Ile Ile Glu Pro Leu Thr Asn Pro Thr Ala Ser
            115                 120                 125

Gly Gly Ser Ala Glu Asp Ala Phe His Val Val Ile Pro Ser Leu Pro
130                 135                 140

Gly Tyr Gly Phe Ser Gly Lys Pro Ala Ala Pro Gly Trp Asn Pro Ile
145                 150                 155                 160

Thr Ile Ala Thr Ala Trp Thr Thr Leu Met Lys Arg Leu Gly Tyr Ser
                165                 170                 175

Arg Phe Val Ala Gln Gly Gly Asp Trp Gly Asn Ala Val Ser Glu Ile
                180                 185                 190

Met Ala Leu Gln Ala Pro Pro Glu Leu Val Gly Ile His Thr Asn Met
                195                 200                 205

Ala Ala Thr Val Pro Ala Asn Val Ala Lys Ala Leu Ala Phe His Glu
210                 215                 220

Gly Pro Pro Ser Gly Leu Ser Pro Glu Glu Ser Ser Ala Trp Ser Gln
225                 230                 235                 240

Leu Asp Tyr Phe Tyr Lys Lys Gly Leu Gly Tyr Ala Leu Glu Met Asn
                245                 250                 255

Thr Arg Pro Gln Thr Leu Tyr Gly Leu Ala Asp Ser Pro Val Gly Leu
                260                 265                 270

Ala Ala Trp Met Leu Asp His Asp Ile Arg Ser Gln Glu Leu Ile Ala
                275                 280                 285

Arg Val Phe Asp Gly Gln Ser Glu Gly Leu Ser Lys Glu Asp Val Ile
                290                 295                 300

Glu Asn Val Thr Leu Tyr Trp Leu Thr Ser Thr Ala Ile Ser Ser Ala
305                 310                 315                 320

Arg Leu Tyr Trp Asp Thr Ala Gln Leu Gly Gly Gly Phe Phe Asp
                325                 330                 335

Val Arg Gly Ile Lys Ile Pro Val Ala Val Ser Ala Phe Pro Asp Glu
                340                 345                 350

Ile Tyr Thr Pro Pro Arg Ser Trp Ala Glu Ala Ala Tyr Pro Lys Leu
                355                 360                 365

Ile His Tyr Asn Arg Leu Asp Lys Gly Gly His Phe Ala Ala Trp Glu
                370                 375                 380

Gln Pro Gln Leu Phe Ser Ser Glu Leu Arg Ala Ala Phe Arg Thr Leu
385                 390                 395                 400

Arg

<210> SEQ ID NO 39
<211> LENGTH: 1383
<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(114)

<400> SEQUENCE: 39
atgacctcag agaaactgca gtacccggcg agaactcaaa cgacccgcct tagcgccgcc      60
gcggcggccg ggcttgcctc gggacttctc gtcttctctt gcccgaatta cggccagacc     120
```

-continued

```
accaccgatc gtgggagcgc gatcgtcgcc caggcgtctg cgcagcgcgc ggcagcggaa      180
gatccatcga tccgcccctt caaggtgcaa ataccgcaag ccgcgctcga cgacctgcgc      240
cggcgcatca acgccacgcg ctggcccgac aaggagaccg tcgccgacga gtcgcagggt      300
gcgcagttgg cgaggctcca ggagctggtt cgctactggg gcagcggcta cgactggcgc      360
aagctggaag cgaagctgaa tgccctgccg caattcacga cgaccatcga cggtgtcgag      420
attcacttca tccacgtccg ctctcgtcac aagaatgcgc tcccggtgat cgtcacccac      480
gggtggccgg gatccgtcgt cgagcaactc aagatcatcg gcccgctcac ggatccaacc      540
gcccatggcg gcagcgccga ggatgctttc gacgtcgtga tcccgtccct gccaggttac      600
ggcttctccg gcaagccaac cggtaccggc tgggaccccg accgaatcgc gcgagcctgg      660
gcggagctga tgaagcgcct cgggtacacc cgctacgtcg cccagggcgg cgactgggdt      720
gcccccatca cgagcgcgat ggcacgccag aaagcggcgg gattgcaggg tatccacgtc      780
aacctgcccg caacgctgcc gcccgaggtg actgcagcgc tcggcaccgg cgggcctgcg      840
ccggcgggac tctccgagaa ggaaagcgca gtgttcgagg cactgaagaa gtacggcatg      900
acggggaact cggcctactt cacgatgatg acggcgcggc cgcagacggt cggctatggc      960
gcgacggact caccggccgg cctcgcggca tggatcctcg tgcatccagg cttcgcccag     1020
tggagatacg gcgccgatcc aaagcagtcg ccgactaagg acgacgtgct cgacgacatc     1080
acgctgtact ggctgacgaa caccgcggcg tcggcggcgc ggctgtactg ggagaacggc     1140
gcacgaggca gcgtcattgc cgccgcgccg cagaaaacct ccgaaatctc gctgcccgtg     1200
gccattacgg ttttcccgga cgacgtctat cgagccccgg agtcatgggc ccggcgggca     1260 tacccccaacc tgacctattt ccacgaggtc gacaagggcg acatttcgc cgcgtgggag     1320 cagccggaac tcttcgcggc cgagctgcgc gccgcgttca agccacttcg gggggtgcaa     1380
tga                                                                  1383
```

<210> SEQ ID NO 40
<211> LENGTH: 460
<212> TYPE: PRT
<213> ORGANISM: Unknown
<220> FEATURE:
<223> OTHER INFORMATION: Obtained from an environmental source
<220> FEATURE:
<221> NAME/KEY: SIGNAL
<222> LOCATION: (1)...(38)

<400> SEQUENCE: 40

```
Met Thr Ser Glu Lys Leu Gln Tyr Pro Ala Arg Thr Gln Thr Thr Arg
 1               5                  10                  15

Leu Ser Ala Ala Ala Ala Gly Leu Ala Ser Gly Leu Leu Val Phe
            20                  25                  30

Ser Cys Pro Asn Tyr Gly Gln Thr Thr Thr Asp Arg Gly Ser Ala Ile
        35                  40                  45

Val Ala Gln Ala Ser Ala Gln Arg Ala Ala Glu Asp Pro Ser Ile
    50                  55                  60

Arg Pro Phe Lys Val Gln Ile Pro Gln Ala Ala Leu Asp Asp Leu Arg
65                  70                  75                  80

Arg Arg Ile Asn Ala Thr Arg Trp Pro Asp Lys Glu Thr Val Ala Asp
                85                  90                  95

Glu Ser Gln Gly Ala Gln Leu Ala Arg Leu Gln Glu Leu Val Arg Tyr
            100                 105                 110
```

```
Trp Gly Ser Gly Tyr Asp Trp Arg Lys Leu Glu Ala Lys Leu Asn Ala
        115                 120                 125

Leu Pro Gln Phe Thr Thr Thr Ile Asp Gly Val Glu Ile His Phe Ile
    130                 135                 140

His Val Arg Ser Arg His Lys Asn Ala Leu Pro Val Ile Val Thr His
145                 150                 155                 160

Gly Trp Pro Gly Ser Val Val Glu Gln Leu Lys Ile Ile Gly Pro Leu
                165                 170                 175

Thr Asp Pro Thr Ala His Gly Gly Ser Ala Glu Asp Ala Phe Asp Val
            180                 185                 190

Val Ile Pro Ser Leu Pro Gly Tyr Gly Phe Ser Gly Lys Pro Thr Gly
        195                 200                 205

Thr Gly Trp Asp Pro Asp Arg Ile Ala Arg Ala Trp Ala Glu Leu Met
    210                 215                 220

Lys Arg Leu Gly Tyr Thr Arg Tyr Val Ala Gln Gly Gly Asp Trp Gly
225                 230                 235                 240

Ala Pro Ile Thr Ser Ala Met Ala Arg Gln Lys Ala Ala Gly Leu Gln
                245                 250                 255

Gly Ile His Val Asn Leu Pro Ala Thr Leu Pro Pro Glu Val Thr Ala
            260                 265                 270

Ala Leu Gly Thr Gly Gly Pro Ala Pro Ala Gly Leu Ser Glu Lys Glu
        275                 280                 285

Ser Ala Val Phe Glu Ala Leu Lys Lys Tyr Gly Met Thr Gly Asn Ser
    290                 295                 300

Ala Tyr Phe Thr Met Met Thr Ala Arg Pro Gln Thr Val Gly Tyr Gly
305                 310                 315                 320

Ala Thr Asp Ser Pro Ala Gly Leu Ala Ala Trp Ile Leu Val His Pro
                325                 330                 335

Gly Phe Ala Gln Trp Arg Tyr Gly Ala Asp Pro Lys Gln Ser Pro Thr
            340                 345                 350

Lys Asp Asp Val Leu Asp Asp Ile Thr Leu Tyr Trp Leu Thr Asn Thr
        355                 360                 365

Ala Ala Ser Ala Ala Arg Leu Tyr Trp Glu Asn Gly Ala Arg Gly Ser
    370                 375                 380

Val Ile Ala Ala Pro Gln Lys Thr Ser Glu Ile Ser Leu Pro Val
385                 390                 395                 400

Ala Ile Thr Val Phe Pro Asp Asp Val Tyr Arg Ala Pro Glu Ser Trp
                405                 410                 415

Ala Arg Arg Ala Tyr Pro Asn Leu Thr Tyr Phe His Glu Val Asp Lys
            420                 425                 430

Gly Gly His Phe Ala Ala Trp Glu Gln Pro Glu Leu Phe Ala Ala Glu
        435                 440                 445

Leu Arg Ala Ala Phe Lys Pro Leu Arg Gly Val Gln
450                 455                 460

<210> SEQ ID NO 41
<211> LENGTH: 972
<212> TYPE: DNA
<213> ORGANISM: Unknown
<220> FEATURE:
<223> OTHER INFORMATION: Obtained from an environmental source

<400> SEQUENCE: 41
atggagccga ccttgcacga acttcgcctc gagacactgc aggtgggcgc actgcgcatg      60
cgtgtggcca gccagggcag cggcccgctt gtgctgctat gtcatggctt tccggagtcg     120
```

-continued

```
tggtactcct ggcgacatca gttggcggcg ctcgccgccg cgggcttccg cgccgtcgca      180
cccgatatgc gcggctatgg cggcaccgat gcgccgcccg atgcggactc gtacacgatg      240
ctgcatcttg tcggcgacat ggtcgaactc gtcaacgtgc tcggtgaaag cgaggcggtg      300
atcgttggcc acgattgggg cgcgccggtc gcctggaatt cggcgatgtt gcggccagat      360
ctgtttcgtg cggtggtcgg catgagcgtg ccgtttcatc cgcctgcacg ggaggatttg      420
cttagcgcac tggatcggca aggatacga acattctata tgcagtactt ccagacgccc      480
ggtgtagccg agcatgagtt cgaggccgat ccagaagccg cgattcgacg catcacattc      540
agcatgtcgg gcgacggacc cgagcgcgtc gtggcgggaa tattggcccc cggcgcaggt      600
tttctcgaca acacggtcga tcccgagacg ctgccaggct ggctcaccag cgaagagatc      660
gcttatgtgg cgggcgagtt cgcgcgcacg ggtttcagag gcggcctcaa ctggtaccgc      720
ggcattcgac gctcgtcgga actgatggcg catggcgag cgccgtgat ccgtcagcct      780 tcgatgttcg tggccggcgc gagagacgac gttctcaagt ttccgggctc gcaggcgcgt      840
atcgagaatc tgacacgcgt gctgcccgga ttgcgtggct gccatattct cgatggcgcg      900
ggtcattgga ttcagcggga acgttcggcc gaagtgaatg acttgctagt tgcgttcttg      960
aagggactgt aa                                                          972
```

<210> SEQ ID NO 42
<211> LENGTH: 323
<212> TYPE: PRT
<213> ORGANISM: Unknown
<220> FEATURE:
<223> OTHER INFORMATION: Obtained from an environmental source

<400> SEQUENCE: 42

```
Met Glu Pro Thr Leu His Glu Leu Arg Leu Glu Thr Leu Gln Val Gly
 1               5                  10                  15

Ala Leu Arg Met Arg Val Ala Ser Gln Gly Ser Gly Pro Leu Val Leu
            20                  25                  30

Leu Cys His Gly Phe Pro Glu Ser Trp Tyr Ser Trp Arg His Gln Leu
        35                  40                  45

Ala Ala Leu Ala Ala Ala Gly Phe Arg Ala Val Ala Pro Asp Met Arg
    50                  55                  60

Gly Tyr Gly Gly Thr Asp Ala Pro Pro Asp Ala Asp Ser Tyr Thr Met
65                  70                  75                  80

Leu His Leu Val Gly Asp Met Val Glu Leu Val Asn Val Leu Gly Glu
                85                  90                  95

Ser Glu Ala Val Ile Val Gly His Asp Trp Gly Ala Pro Val Ala Trp
            100                 105                 110

Asn Ser Ala Met Leu Arg Pro Asp Leu Phe Arg Ala Val Val Gly Met
        115                 120                 125

Ser Val Pro Phe His Pro Pro Ala Arg Glu Asp Leu Leu Ser Ala Leu
    130                 135                 140

Asp Arg Gln Gly Ile Arg Thr Phe Tyr Met Gln Tyr Phe Gln Thr Pro
145                 150                 155                 160

Gly Val Ala Glu His Glu Phe Glu Ala Asp Pro Glu Ala Ala Ile Arg
                165                 170                 175

Arg Ile Thr Phe Ser Met Ser Gly Asp Gly Pro Glu Arg Val Val Ala
            180                 185                 190

Gly Ile Leu Ala Pro Gly Ala Gly Phe Leu Asp Asn Thr Val Asp Pro
        195                 200                 205
```

```
Glu Thr Leu Pro Gly Trp Leu Thr Ser Glu Ile Ala Tyr Val Ala
    210                 215                 220

Gly Glu Phe Ala Arg Thr Gly Phe Arg Gly Leu Asn Trp Tyr Arg
225                 230                 235                 240

Gly Ile Arg Arg Ser Ser Glu Leu Met Ala Ala Trp Arg Gly Ala Val
                245                 250                 255

Ile Arg Gln Pro Ser Met Phe Val Ala Gly Ala Arg Asp Asp Val Leu
            260                 265                 270

Lys Phe Pro Gly Ser Gln Ala Arg Ile Glu Asn Leu Thr Arg Val Leu
        275                 280                 285

Pro Gly Leu Arg Gly Cys His Ile Leu Asp Gly Ala Gly His Trp Ile
    290                 295                 300

Gln Arg Glu Arg Ser Ala Glu Val Asn Asp Leu Leu Val Ala Phe Leu
305                 310                 315                 320

Lys Gly Leu
```

<210> SEQ ID NO 43
<211> LENGTH: 858
<212> TYPE: DNA
<213> ORGANISM: Unknown
<220> FEATURE:
<223> OTHER INFORMATION: Obtained from an environmental source

<400> SEQUENCE: 43

```
atgacggccc gctcggacgt cgatctcgac gacgtgaccc tcgcgtgcgt agtcgaaggc      60
gaaggccccg tcgtcctcgc cgtacacggc ttcccggacg acgcgtcgac gtttcgcgga     120
caggtgccgg ccctcgtcgc ggccggatac caggtcgtgt gcccgacctt gcgcggctac     180
gcgccgagcg gcgtccctcg gtcgcgtcgc tacgacgccg cggcgctcgc gcgcgacgtc     240
gtgggcctcg ccgatcggtt ctcgccgcgc gctcctgcgc gcctcgtcgg tcatgactgg     300
ggtgcggtcg cggcgttcgc cgcggtggca ctagcgccca cgcgcttctc gcacatggtc     360
acgatggcgg tcccacacac cgccgcgttc gcgaggaact tcggccccgc gcaggcgcgg     420
cgctcctggt acatggggct gttccagctt ccgggagtgg cggaggcgcg gctcgaggcc     480
gatgacttcg cgctcgtcga gcggctgtgg cgcgactggt cgcctggcta ccgcgcctcg     540
agcgacgagc tccgctcggt gaaggacggc ctccgcgggc gcgtgtccga agcgctgggg     600
tactaccgcg cgctccggtc gcccgccgcg ctcttcggcg aagcgcggcg gctcgcgttc     660
gcgcgcgtcg gcgtacggtc ccttcacctg cacgcgccg acgacggctg cgtcggcgtc     720
gactccacgc gcggcgccga gcgcttctac gacgcgcctt accggctcga cgtcgtcgag     780
ggcgccggcc acttcctgca gcgcgagaag cccgacgtcg tgaacgcgtc cctcctcgcg     840
ttcttcaagg cttcttga                                                  858
```

<210> SEQ ID NO 44
<211> LENGTH: 285
<212> TYPE: PRT
<213> ORGANISM: Unknown
<220> FEATURE:
<223> OTHER INFORMATION: Obtained from an environmental source

<400> SEQUENCE: 44

```
Met Thr Ala Arg Ser Asp Val Asp Leu Asp Asp Val Thr Leu Ala Cys
  1               5                  10                  15

Val Val Glu Gly Glu Gly Pro Val Val Leu Ala Val His Gly Phe Pro
                20                  25                  30
```

```
Asp Asp Ala Ser Thr Phe Arg Gly Gln Val Pro Ala Leu Val Ala Ala
         35                  40                  45
Gly Tyr Gln Val Val Cys Pro Thr Leu Arg Gly Tyr Ala Pro Ser Gly
     50                  55                  60
Val Pro Arg Ser Arg Arg Tyr Asp Ala Ala Leu Ala Arg Asp Val
 65              70                  75                  80
Val Gly Leu Ala Asp Arg Phe Ser Pro Arg Ala Pro Ala Arg Leu Val
                 85                  90                  95
Gly His Asp Trp Gly Val Ala Ala Phe Ala Val Ala Leu Ala
            100                 105                 110
Pro Thr Arg Phe Ser His Met Val Thr Met Ala Val Pro His Thr Ala
            115                 120                 125
Ala Phe Ala Arg Asn Phe Gly Pro Ala Gln Ala Arg Arg Ser Trp Tyr
        130                 135                 140
Met Gly Leu Phe Gln Leu Pro Gly Val Ala Glu Ala Arg Leu Glu Ala
145                 150                 155                 160
Asp Asp Phe Ala Leu Val Glu Arg Leu Trp Arg Asp Trp Ser Pro Gly
                165                 170                 175
Tyr Arg Ala Ser Ser Asp Glu Leu Arg Ser Val Lys Asp Gly Leu Arg
            180                 185                 190
Gly Arg Val Ser Glu Ala Leu Gly Tyr Tyr Arg Ala Leu Arg Ser Pro
        195                 200                 205
Ala Ala Leu Phe Gly Glu Ala Arg Arg Leu Ala Phe Ala Arg Val Gly
    210                 215                 220
Val Arg Ser Leu His Leu His Gly Ala Asp Asp Gly Cys Val Gly Val
225                 230                 235                 240
Asp Ser Thr Arg Gly Ala Glu Arg Phe Tyr Asp Ala Pro Tyr Arg Leu
                245                 250                 255
Asp Val Val Glu Gly Ala Gly His Phe Leu Gln Arg Glu Lys Pro Asp
            260                 265                 270
Val Val Asn Ala Ser Leu Leu Ala Phe Phe Lys Ala Ser
        275                 280                 285

<210> SEQ ID NO 45
<211> LENGTH: 771
<212> TYPE: DNA
<213> ORGANISM: Unknown
<220> FEATURE:
<223> OTHER INFORMATION: Obtained from an environmental source

<400> SEQUENCE: 45
atgcgggttg agatcgaggg aagcggcaag ccgatcgtga tggtccacgg ctggccggac      60
acgtaccggc tctgggatgg ccaggtgatg gcgctcgccg accgctatca atgcgtgcgc     120
ttcactttgc cgggcttcga cgtatcgcag ccgaagcgtg cctacacggt ggacgaagtc     180
gtcgatgcaa tccgtggcgt cgtcgagcag gccggcggca aggtgacctt gatgctgcac     240
gactgggggtt gcctgtacgg ctaccagttt gcgatgcgct accgcagct cgtcgggcgc     300
gttgtcggcg tcgacatcgg cgacgcgggc tcacgcgcgc acctgggcga gctgggcgcg     360
cggggccggt tgatgatcct cgcctaccag tattggctgg ccctcgcgtg gcgcatcggc     420
ggacgcgcgg gtgacggcat gtcgcgcgcc atggcgcggc tcctgcgctg cccgaccgat     480
ccgcgccgca tcggcgcgca gatggcctat ccgtatgccg tgcgctggtt cggcgccgcg     540
ggcggcttcc agggcctgcg cgtcttcaag cccgaagtgc cgatgctttt catctacggc     600
```

```
gagaagaagc cggtgatgtt tcattcgcgc gcgtgggccg agcgcctggc ggcgcgcccg    660
gcaagccggg tcatcgccat gccgaccggg cactggatca tggtcacgag gcgcgaggcg    720
ttcaacgagg ccgtgcggac gtggcttgcc gagaccgacg ccctggcatg a             771
```

```
<210> SEQ ID NO 46
<211> LENGTH: 256
<212> TYPE: PRT
<213> ORGANISM: Unknown
<220> FEATURE:
<223> OTHER INFORMATION: Obtained from an environmental source

<400> SEQUENCE: 46
```

```
Met Arg Val Glu Ile Glu Gly Ser Gly Lys Pro Ile Val Met Val His
  1               5                  10                  15

Gly Trp Pro Asp Thr Tyr Arg Leu Trp Asp Gly Gln Val Met Ala Leu
                 20                  25                  30

Ala Asp Arg Tyr Gln Cys Val Arg Phe Thr Leu Pro Gly Phe Asp Val
             35                  40                  45

Ser Gln Pro Lys Arg Ala Tyr Thr Val Asp Glu Val Val Asp Ala Ile
         50                  55                  60

Arg Gly Val Val Glu Gln Ala Gly Gly Lys Val Thr Leu Met Leu His
 65                  70                  75                  80

Asp Trp Gly Cys Leu Tyr Gly Tyr Gln Phe Ala Met Arg Tyr Pro Gln
                 85                  90                  95

Leu Val Gly Arg Val Val Gly Val Asp Ile Gly Asp Ala Gly Ser Arg
                100                 105                 110

Ala His Leu Gly Glu Leu Gly Ala Arg Gly Arg Leu Met Ile Leu Ala
            115                 120                 125

Tyr Gln Tyr Trp Leu Ala Leu Ala Trp Arg Ile Gly Gly Arg Ala Gly
        130                 135                 140

Asp Gly Met Ser Arg Ala Met Ala Arg Leu Leu Arg Cys Pro Thr Asp
145                 150                 155                 160

Pro Arg Arg Ile Gly Ala Gln Met Ala Tyr Pro Tyr Ala Val Arg Trp
                165                 170                 175

Phe Gly Ala Ala Gly Gly Phe Gln Gly Leu Arg Val Phe Lys Pro Glu
                180                 185                 190

Val Pro Met Leu Phe Ile Tyr Gly Glu Lys Lys Pro Val Met Phe His
            195                 200                 205

Ser Arg Ala Trp Ala Glu Arg Leu Ala Ala Arg Pro Ala Ser Arg Val
        210                 215                 220

Ile Ala Met Pro Thr Gly His Trp Ile Met Val Thr Arg Arg Glu Ala
225                 230                 235                 240

Phe Asn Glu Ala Val Arg Thr Trp Leu Ala Glu Thr Asp Ala Leu Ala
                245                 250                 255
```

```
<210> SEQ ID NO 47
<211> LENGTH: 897
<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(63)

<400> SEQUENCE: 47
atgaaaactg ctgtactgaa aacggcagcc gccctggttg cggctgatgt agtccagggc    60
```

-continued

```
gccgacttcg aagcgcgcgt cacccacgcc tatgcggatt cgaacggggt caaaattcac    120
tatgccacca tcggcaacgg gcccttaatg gtgatgatcc atgggttttcc cgatttctgg    180 tactcctggc gggcacaaat ggaggcgctt tcggacaagt tccagtgcgt ggccatcgac    240
cagcgcggct acaaccagag cgacaaacca caaggagttg agaactacag ccttcggttc    300
ctcgtggggg atgtcgccgc ggtcatcaaa tcattaggga agacaaggc catcatcgtc    360 ggccacgatt ggggcggcct cgtggcgtgg caattcgcgc tgtaccagcc ccagatgacc    420
gagcgcctga tcatcctgaa cctgccgcat ccgcgcggtc tgaaccgtga actggcccgc    480
aacccgcaac aacagaagaa cagccaatat gcgcgcgatt tccagcaacc ggacgcggcg    540
tcgaaactca ccgccgaaca gctcgccttc tgggtcaaag atcctgaggc ccgcgcaaaa    600
tacattgaag cattcaagcg ctcggacttc gaagcgatgc tcaactatta caagcggaac    660
tatcccaacg agccatacac cgaggacacc tcgccgctcg ccaataaagt gcgaatgccg    720
gtcctgatga ttcacgggtt ggaagacaag tggttgctgt ccggcgcgct caacaacacc    780
tgggagtggc tggataatga cctgacgctg gtcacggttc cgagagcagg gcacttcgtg    840
caacaggacg ccgccgagct ggtctcgcgt tcgatgcgcg cctggctgct cgcgctaa       897
```

<210> SEQ ID NO 48
<211> LENGTH: 298
<212> TYPE: PRT
<213> ORGANISM: Unknown
<220> FEATURE:
<223> OTHER INFORMATION: Obtained from an environmental source
<220> FEATURE:
<221> NAME/KEY: SIGNAL
<222> LOCATION: (1)...(21)

<400> SEQUENCE: 48

```
Met Lys Thr Ala Val Leu Lys Thr Ala Ala Leu Val Ala Ala Ala Asp
 1               5                  10                  15

Val Val Gln Gly Ala Asp Phe Glu Ala Arg Val Thr His Ala Tyr Ala
                20                  25                  30

Asp Ser Asn Gly Val Lys Ile His Tyr Ala Thr Ile Gly Asn Gly Pro
            35                  40                  45

Leu Met Val Met Ile His Gly Phe Pro Asp Phe Trp Tyr Ser Trp Arg
        50                  55                  60

Ala Gln Met Glu Ala Leu Ser Asp Lys Phe Gln Cys Val Ala Ile Asp
65                  70                  75                  80

Gln Arg Gly Tyr Asn Gln Ser Asp Lys Pro Gln Gly Val Glu Asn Tyr
                85                  90                  95

Ser Leu Arg Phe Leu Val Gly Asp Val Ala Val Ile Lys Ser Leu
            100                 105                 110

Gly Lys Asp Lys Ala Ile Ile Val Gly His Asp Trp Gly Gly Leu Val
        115                 120                 125

Ala Trp Gln Phe Ala Leu Tyr Gln Pro Gln Met Thr Glu Arg Leu Ile
    130                 135                 140

Ile Leu Asn Leu Pro His Pro Arg Gly Leu Asn Arg Glu Leu Ala Arg
145                 150                 155                 160

Asn Pro Gln Gln Gln Lys Asn Ser Gln Tyr Ala Arg Asp Phe Gln Gln
                165                 170                 175

Pro Asp Ala Ala Ser Lys Leu Thr Ala Glu Gln Leu Ala Phe Trp Val
            180                 185                 190

Lys Asp Pro Glu Ala Arg Ala Lys Tyr Ile Glu Ala Phe Lys Arg Ser
        195                 200                 205
```

```
Asp Phe Glu Ala Met Leu Asn Tyr Tyr Lys Arg Asn Tyr Pro Asn Glu
        210                 215                 220

Pro Tyr Thr Glu Asp Thr Ser Pro Leu Ala Asn Lys Val Arg Met Pro
225                 230                 235                 240

Val Leu Met Ile His Gly Leu Glu Asp Lys Trp Leu Ser Gly Ala
                245                 250                 255

Leu Asn Asn Thr Trp Glu Trp Leu Asp Asn Asp Leu Thr Leu Val Thr
                260                 265                 270

Val Pro Arg Ala Gly His Phe Val Gln Gln Asp Ala Ala Glu Leu Val
            275                 280                 285

Ser Arg Ser Met Arg Ala Trp Leu Leu Arg
290                 295
```

<210> SEQ ID NO 49
<211> LENGTH: 996
<212> TYPE: DNA
<213> ORGANISM: Unknown
<220> FEATURE:
<223> OTHER INFORMATION: Obtained from an environmental source

<400> SEQUENCE: 49

```
atgatcgaga tgccgccgtt acagttcgcc cagactaaca atattcgcat gggttactac      60
gaagccggtc ccaaaaccga tacgccgccg gtgatcctgt gtcacggctg ccggagatc     120
gcgtttcgt ggcgccatca gatcaaggcg ctcagcgaag ccggcatccg ggtgatcgcg     180
ccggatcagc gcggctatgg cgcgaccgac cggcctgaac ttgtcgagtc ctacgatatc     240
gagcatttga ccggggatct cgttggcctg ctggatcatc tcgagatcga caaggctgtc     300
ttcgtcggcc acgactgggg cggattcgtc gtctggcaga tgccgctgcg gcatatcgat     360
cgtgttgccg gcgtcgtcgg cgtcaacacg ccgcatacca accgcccgtg ggctgacccg     420
atcgaactcc tgcgtcagcg tttcggcgag cagatgtata tcgtgcagtt tcaggacccc     480
gcgcgcggtg cggacaagat attcaacagc cgggtcgaac agaccttcga tgccttcatg     540
cgcaagccgg tcccgcgcgg cgacggcacg ccgcccgagg agccggtggc aggcgtcggc     600
gcttcaccga gactcaatct ggcatttccg cagatgatcg ccggctacga tgcgaaacac     660
gatccgcgga cgccgatcct gtcgccggag gaaaagaagg tgttcgtcga caccttcacc     720
aaaaccggct tcaccggcgg catcaactgg taccgcaaca tgtcccgtaa ctggcaacgc     780
tcggctggca tcgactatac ggtgcgggtg ccgtcgctga tgatcatggc tgaaaacgat     840
caggtgttgc cgccgtcttc ggccgatggc atggaaaaat tgattcccga cctcgaaaaa     900
tatctggttc gcggcagcgg ccattggacg cagcaggaaa agccggaaga aatcagcgcc     960
aagctgatcg aatggcgtag aaggcgattc ggatag                               996
```

<210> SEQ ID NO 50
<211> LENGTH: 331
<212> TYPE: PRT
<213> ORGANISM: Unknown
<220> FEATURE:
<223> OTHER INFORMATION: Obtained from an environmental source

<400> SEQUENCE: 50

```
Met Ile Glu Met Pro Pro Leu Gln Phe Ala Gln Thr Asn Asn Ile Arg
 1               5                  10                  15

Met Gly Tyr Tyr Glu Ala Gly Pro Lys Thr Asp Thr Pro Val Ile
            20                  25                  30
```

```
Leu Cys His Gly Trp Pro Glu Ile Ala Phe Ser Trp Arg His Gln Ile
            35                  40                  45

Lys Ala Leu Ser Glu Ala Gly Ile Arg Val Ile Ala Pro Asp Gln Arg
        50                  55                  60

Gly Tyr Gly Ala Thr Asp Arg Pro Glu Leu Val Glu Ser Tyr Asp Ile
65                  70                  75                  80

Glu His Leu Thr Gly Asp Leu Val Gly Leu Leu Asp His Leu Glu Ile
                85                  90                  95

Asp Lys Ala Val Phe Val Gly His Asp Trp Gly Gly Phe Val Val Trp
                100                 105                 110

Gln Met Pro Leu Arg His Ile Asp Arg Val Ala Gly Val Val Gly Val
            115                 120                 125

Asn Thr Pro His Thr Asn Arg Pro Trp Ala Asp Pro Ile Glu Leu Leu
        130                 135                 140

Arg Gln Arg Phe Gly Glu Gln Met Tyr Ile Val Gln Phe Gln Asp Pro
145                 150                 155                 160

Ala Arg Gly Ala Asp Lys Ile Phe Asn Ser Arg Val Glu Gln Thr Phe
                165                 170                 175

Asp Ala Phe Met Arg Lys Pro Val Pro Arg Gly Asp Gly Thr Pro Pro
            180                 185                 190

Glu Glu Pro Val Ala Gly Val Gly Ala Ser Pro Arg Leu Asn Leu Ala
        195                 200                 205

Phe Pro Gln Met Ile Ala Gly Tyr Asp Ala Lys His Asp Pro Arg Thr
    210                 215                 220

Pro Ile Leu Ser Pro Glu Glu Lys Lys Val Phe Val Asp Thr Phe Thr
225                 230                 235                 240

Lys Thr Gly Phe Thr Gly Gly Ile Asn Trp Tyr Arg Asn Met Ser Arg
                245                 250                 255

Asn Trp Gln Arg Ser Ala Gly Ile Asp Tyr Thr Val Arg Val Pro Ser
            260                 265                 270

Leu Met Ile Met Ala Glu Asn Asp Gln Val Leu Pro Pro Ser Ser Ala
        275                 280                 285

Asp Gly Met Glu Lys Leu Ile Pro Asp Leu Glu Lys Tyr Leu Val Arg
    290                 295                 300

Gly Ser Gly His Trp Thr Gln Gln Glu Lys Pro Glu Glu Ile Ser Ala
305                 310                 315                 320

Lys Leu Ile Glu Trp Arg Arg Arg Phe Gly
                325                 330
```

<210> SEQ ID NO 51
<211> LENGTH: 1230
<212> TYPE: DNA
<213> ORGANISM: Unknown
<220> FEATURE:
<223> OTHER INFORMATION: Obtained from an environmental source

<400> SEQUENCE: 51

```
atggcccaag ccattgctac accacacggc agcgagcagg ccgctgacaa gaccgctatg      60
cgaccgtttc gtgtgaatgt tccggaagcg gaactgaccg aattgcgccg gcgtatcacc     120
gcgacgcgat tcccggagaa ggaaaccgtc gccgatccgt cgcagggcgt gcaactcgcc     180
gtcattcaag cgctcgcgca gtattgggcg accgattaca actggcggag gtgcgaggcg     240
caactgaact ctcatcccca attcatcacg gagatcgatg ggttggacat ccacttcatt     300
cacgtccgct cgagacatga agatgcgatg ccgctcatcg tcacccacgg ctggcccggc     360
```

-continued

```
tcgccgatcg agcagctgaa gatcatcgat ccactgacca accccacggc tcacggcgcc      420
agcgcgtcgg acgccttcca cgtggtgatc ccgtcgatgg ccggctacgg gttttcaggc      480
aagcccacga cgcccggttg ggaccccgct cacatggcgc gggcgtgggt ggagctgatg      540
aagcgcctcg gtacagccg gttcgcggcg caaggcggtg attggggtgg gttcgtcaca       600
aacttgatgg ctcaacaggc acctccggag ttgatcggca tccatctgaa cttctccggt      660
gccgcgcccc gtgacgttgc caaggcgctt gagactggcg gccgccgcc ggccggtctc       720 tcggctgagg agctgcgggc atacgaccag atggcgttcc tttaccggca cgtccctacg      780
caactgatga tggccgcaca cccgcaaact ctgtacgggt tggcggactc gcccgtcgcc      840
cttgccgcct ggatgatcga ccacgacgtg gccagctacg gcacattgt gaaactcttt       900 gtcgatgggg agccctacgg cgacctcaca cgggacgaca tcctcgacaa catcacctc       960 tcctggttga cgaacacggg cgtgtccagc gctcgtctct atgtggaata taagggcggc     1020
ttcttcaacg actacaacat ctccattccg actgccgtaa gcgtcttccc tgaggaggtc     1080
taccaagctc cgcggagttg gaccgagcgc gcctaccgca atctcatcca cttcaacgag     1140
ctcccgaagg gcggtcattt tgcggcctgg gaacagccgc aactgttttc agaagaagtt     1200
cgggcgggct tcaggtcgct gcgcggatag                                      1230
```

<210> SEQ ID NO 52
<211> LENGTH: 409
<212> TYPE: PRT
<213> ORGANISM: Unknown
<220> FEATURE:
<223> OTHER INFORMATION: Obtained from an environmental source

<400> SEQUENCE: 52

```
Met Ala Gln Ala Ile Ala Thr Pro His Gly Ser Glu Gln Ala Ala Asp
  1               5                  10                  15

Lys Thr Ala Met Arg Pro Phe Arg Val Asn Val Pro Glu Ala Glu Leu
             20                  25                  30

Thr Glu Leu Arg Arg Arg Ile Thr Ala Thr Arg Phe Pro Glu Lys Glu
         35                  40                  45

Thr Val Ala Asp Pro Ser Gln Gly Val Gln Leu Ala Val Ile Gln Ala
     50                  55                  60

Leu Ala Gln Tyr Trp Ala Thr Asp Tyr Asn Trp Arg Arg Cys Glu Ala
 65                  70                  75                  80

Gln Leu Asn Ser His Pro Gln Phe Ile Thr Glu Ile Asp Gly Leu Asp
                 85                  90                  95

Ile His Phe Ile His Val Arg Ser Arg His Glu Asp Ala Met Pro Leu
            100                 105                 110

Ile Val Thr His Gly Trp Pro Gly Ser Pro Ile Glu Gln Leu Lys Ile
        115                 120                 125

Ile Asp Pro Leu Thr Asn Pro Thr Ala His Gly Ala Ser Ala Ser Asp
    130                 135                 140

Ala Phe His Val Val Ile Pro Ser Met Ala Gly Tyr Gly Phe Ser Gly
145                 150                 155                 160

Lys Pro Thr Thr Pro Gly Trp Asp Pro Ala His Met Ala Arg Ala Trp
                165                 170                 175

Val Glu Leu Met Lys Arg Leu Gly Tyr Ser Arg Phe Ala Ala Gln Gly
            180                 185                 190

Gly Asp Trp Gly Gly Phe Val Thr Asn Leu Met Ala Gln Gln Ala Pro
        195                 200                 205
```

-continued

```
  Pro Glu Leu Ile Gly Ile His Leu Asn Phe Ser Gly Ala Ala Pro Arg
      210                 215                 220

Asp Val Ala Lys Ala Leu Glu Thr Gly Gly Pro Pro Ala Gly Leu
  225                 230                 235                 240

Ser Ala Glu Glu Leu Arg Ala Tyr Asp Gln Met Ala Phe Leu Tyr Arg
                      245                 250                 255

His Val Pro Thr Gln Leu Met Met Ala Ala His Pro Gln Thr Leu Tyr
                  260                 265                 270

Gly Leu Ala Asp Ser Pro Val Ala Leu Ala Ala Trp Met Ile Asp His
                  275                 280                 285

Asp Val Ala Ser Tyr Gly His Ile Val Lys Leu Phe Val Asp Gly Glu
      290                 295                 300

Pro Tyr Gly Asp Leu Thr Arg Asp Ile Leu Asp Asn Ile Thr Leu
  305                 310                 315                 320

Ser Trp Leu Thr Asn Thr Gly Val Ser Ser Ala Arg Leu Tyr Val Glu
                  325                 330                 335

Tyr Lys Gly Gly Phe Phe Asn Asp Tyr Asn Ile Ser Ile Pro Thr Ala
                  340                 345                 350

Val Ser Val Phe Pro Glu Glu Val Tyr Gln Ala Pro Arg Ser Trp Thr
                  355                 360                 365

Glu Arg Ala Tyr Arg Asn Leu Ile His Phe Asn Glu Leu Pro Lys Gly
      370                 375                 380

Gly His Phe Ala Ala Trp Glu Gln Pro Gln Leu Phe Ser Glu Glu Val
  385                 390                 395                 400

Arg Ala Gly Phe Arg Ser Leu Arg Gly
                  405
```

<210> SEQ ID NO 53
<211> LENGTH: 1143
<212> TYPE: DNA
<213> ORGANISM: Unknown
<220> FEATURE:
<223> OTHER INFORMATION: Obtained from an environmental source

<400> SEQUENCE: 53

```
atggtcgagc cgttccgcgt cgacgtaccc gacgaggtcc tcgacgacct gcgcgcgcgg      60
ctcgcccgca cgcgcctgcc gaaccaggtc gacggcgcag gctgggacca gggcaccgag     120
ctcggctacc tccgggagct cctcgcgtac tggcaggacg ggttcgactg gcgcgcgcag     180
gaggcgcggc tcaacgcgtt cgaccagtac gtcaccgaag tcgacgggca cgcatccac     240
ttcatccatc accgctcgcc ggaacccgat gcggtgccgc tgctcgtgag ccacggctgg     300
ccgggctcgg tcgtcgagtt cctcgacgtg atcggcccgc tcaccgaccc gcgcgcgcac     360
gggggcgacc cggccgacgc cttccacgtc gtcgcccgt cgctgcccgg attcgccttc     420
tccggtccga cgcacgagcg gggctggcac ccagtcgca tcgccgccgc gtacgtgcag     480
ctcatggccg acctcggcta cgaccgctac ggcgcgcaag gcggcgactg gggctccatc     540
gtgtgtgcga gcgtggccga tctcgatgcc gagcacgtgg ccggactgca cctcaacttc     600
gtgaccgtgc cgaagccggc cgacgcgaag ttcgaggacc tcaccgccga agagcagcac     660
gccctcgcgg cccagagcga gtggcgcacc accggcgccg gctaccagga gatccagggc     720
acgaagccgc agtcgctcgg ctacggcctc gacgactcgc cggcgggcct cgcggcatgg     780
atcgtcgaga agttcggcgc gtggtccgac ggcgctccgt atccggacgc gtcgttcacg     840
cgcgaccagc tgctcacgaa catcaccacg tactgggtga cggccaccgc gacctcgtcg     900
```

-continued

```
gcccgcatct actacgagat gcggcagatc ggtcgcggcg cgttgccaca ggagtacgtc      960
gcggtaccta ctggcattgc gaacttcccg ggcgaggtca cccggacgcc gcgttcgtgg     1020
gtggagcacc ggtacaacgt cacgcactgg acgaaccacg accggggcgg ccacttcgcg     1080
gcgatgcagg tgcccgacct cttcgtcgac gacgtgcgtg cattcttccg cccactgcgc     1140
tga                                                                   1143
```

<210> SEQ ID NO 54
<211> LENGTH: 380
<212> TYPE: PRT
<213> ORGANISM: Unknown
<220> FEATURE:
<223> OTHER INFORMATION: Obtained from an environmental source

<400> SEQUENCE: 54

```
Met Val Glu Pro Phe Arg Val Asp Val Pro Asp Glu Val Leu Asp Asp
  1               5                  10                  15

Leu Arg Ala Arg Leu Ala Arg Thr Arg Leu Pro Asn Gln Val Asp Gly
                 20                  25                  30

Ala Gly Trp Asp Gln Gly Thr Glu Leu Gly Tyr Leu Arg Glu Leu Leu
             35                  40                  45

Ala Tyr Trp Gln Asp Gly Phe Asp Trp Arg Ala Gln Glu Ala Arg Leu
         50                  55                  60

Asn Ala Phe Asp Gln Tyr Val Thr Glu Val Asp Gly Gln Arg Ile His
 65                  70                  75                  80

Phe Ile His His Arg Ser Pro Glu Pro Asp Ala Val Pro Leu Leu Val
                 85                  90                  95

Ser His Gly Trp Pro Gly Ser Val Val Glu Phe Leu Asp Val Ile Gly
            100                 105                 110

Pro Leu Thr Asp Pro Arg Ala His Gly Gly Asp Pro Ala Asp Ala Phe
        115                 120                 125

His Val Val Ala Pro Ser Leu Pro Gly Phe Ala Phe Ser Gly Pro Thr
    130                 135                 140

His Glu Arg Gly Trp His Pro Arg Arg Ile Ala Ala Ala Tyr Val Gln
145                 150                 155                 160

Leu Met Ala Asp Leu Gly Tyr Asp Arg Tyr Gly Ala Gln Gly Gly Asp
                165                 170                 175

Trp Gly Ser Ile Val Cys Ala Ser Val Ala Asp Leu Asp Ala Glu His
            180                 185                 190

Val Ala Gly Leu His Leu Asn Phe Val Thr Val Pro Lys Pro Ala Asp
        195                 200                 205

Ala Lys Phe Glu Asp Leu Thr Ala Glu Glu Gln His Ala Leu Ala Ala
    210                 215                 220

Gln Ser Glu Trp Arg Thr Thr Gly Ala Gly Tyr Gln Glu Ile Gln Gly
225                 230                 235                 240

Thr Lys Pro Gln Ser Leu Gly Tyr Gly Leu Asp Asp Ser Pro Ala Gly
                245                 250                 255

Leu Ala Ala Trp Ile Val Glu Lys Phe Gly Ala Trp Ser Asp Gly Ala
            260                 265                 270

Pro Tyr Pro Asp Ala Ser Phe Thr Arg Asp Gln Leu Leu Thr Asn Ile
        275                 280                 285

Thr Thr Tyr Trp Val Thr Ala Thr Ala Ser Ser Ala Arg Ile Tyr
    290                 295                 300

Tyr Glu Met Arg Gln Ile Gly Arg Gly Ala Leu Pro Gln Glu Tyr Val
305                 310                 315                 320
```

```
Ala Val Pro Thr Gly Ile Ala Asn Phe Pro Gly Glu Val Thr Arg Thr
                325                 330                 335

Pro Arg Ser Trp Val Glu His Arg Tyr Asn Val Thr His Trp Thr Asn
            340                 345                 350

His Asp Arg Gly Gly His Phe Ala Ala Met Gln Val Pro Asp Leu Phe
        355                 360                 365

Val Asp Asp Val Arg Ala Phe Phe Arg Pro Leu Arg
370                 375                 380
```

<210> SEQ ID NO 55
<211> LENGTH: 1227
<212> TYPE: DNA
<213> ORGANISM: Unknown
<220> FEATURE:
<223> OTHER INFORMATION: Obtained from an environmental source

<400> SEQUENCE: 55

| | | | | | |
|---|---|---|---|---|---|
| atgacacaga | cgactgcaac | tcaacgaagc | accggacagg | ccgctggcaa | gaatgccacg | 60 |
| cgacggtttc | acgtgaatgt | tccggaagcg | gaacttaccg | aactgcgacg | gcgcatcaac | 120 |
| gcgacaaggt | ttcctgaacg | ggagacggtt | aatgacgcgt | cgcagggagt | ccagctcgcg | 180 |
| acgatgcagg | cattagctcg | ctattggggg | acggaatacg | attggcgcaa | ggtcgaggcg | 240 |
| aaactgaacg | cattaccgca | gttcctgacg | gagatcgacg | gactggacat | tcatttcatc | 300 |
| cacgtccgtt | cgaaacacga | aaatgcgttg | ccgctgatcg | ttacgcacgg | atggcccggc | 360 |
| tcgatcaccg | aacagatgaa | gatcatcgat | cccctgacca | accccacggc | acacggcgga | 420 |
| agtgcatccg | acgcgttcca | tgtcgtgatt | ccgtcgatac | ccggctacgg | ttttcccggc | 480 |
| agacctgcca | cgaccggatg | ggaccccgcc | catatcgccc | cgcgcctgggt | ggtgctcatg | 540 |
| aagcgtctcg | gatacacgaa | attcgtggcg | cagggtggcg | attggggtgc | gatcatcacg | 600 |
| gagatcatgg | gagcgcaagc | gccaccggaa | ttgatgggca | ttcacaccaa | catggctaat | 660 |
| gtgataccgc | tcgacatcga | caagctggcc | ttttccggcg | ctccagcgcc | cgcgaatctc | 720 |
| tcggccgacg | agaagctcgc | ttacgaaaga | ctgagcttcg | tctatgcgaa | gggcatcggc | 780 |
| tacggattcc | agatggggtt | gagaccgcag | acgctatatg | aatcgcgga | ctcaccggtt | 840 |
| ggcctggcgg | cgtattttct | cgaccacgac | gcgcgcagtt | acgagctgat | cgcccgtgtc | 900 |
| tttgagggag | ccaatgaagg | cctcacgcgg | gacgatgtcc | ttgacaacgt | aacgctcgcg | 960 |
| tggttgacga | atacggcggt | gtcaggcggc | cgtctctatt | gggagtacat | gggtgcttcg | 1020 |
| ttcttcgccg | tcaaaggcgt | cgcggttccg | acggccgtga | gcgtcttccc | tgacgaactc | 1080 |
| tatcctgcgc | cacggagctg | ggcggagcgg | gcatatccca | agctcatcca | cttcaacaag | 1140 |
| ctccccaagg | gcggacactt | tgcggcatgg | gagcaacctc | aatatctttc | agaggaaatt | 1200 |
| cgcgcgggat | ccgctcgct | tcgctga | | | | 1227 |

<210> SEQ ID NO 56
<211> LENGTH: 408
<212> TYPE: PRT
<213> ORGANISM: Unknown
<220> FEATURE:
<223> OTHER INFORMATION: Obtained from an environmental source

<400> SEQUENCE: 56

```
Met Thr Gln Thr Thr Ala Thr Gln Arg Ser Thr Gly Gln Ala Ala Gly
1               5                   10                  15

Lys Asn Ala Thr Arg Arg Phe His Val Asn Val Pro Glu Ala Glu Leu
```

```
                    20                  25                  30
Thr Glu Leu Arg Arg Ile Asn Ala Thr Arg Phe Pro Glu Arg Glu
            35                  40                  45

Thr Val Asn Asp Ala Ser Gln Gly Val Gln Leu Ala Thr Met Gln Ala
50                  55                  60

Leu Ala Arg Tyr Trp Gly Thr Glu Tyr Asp Trp Arg Lys Val Glu Ala
65                  70                  75                  80

Lys Leu Asn Ala Leu Pro Gln Phe Leu Thr Glu Ile Asp Gly Leu Asp
                85                  90                  95

Ile His Phe Ile His Val Arg Ser Lys His Glu Asn Ala Leu Pro Leu
            100                 105                 110

Ile Val Thr His Gly Trp Pro Gly Ser Ile Thr Glu Gln Met Lys Ile
            115                 120                 125

Ile Asp Pro Leu Thr Asn Pro Thr Ala His Gly Gly Ser Ala Ser Asp
130                 135                 140

Ala Phe His Val Val Ile Pro Ser Ile Pro Gly Tyr Gly Phe Ser Gly
145                 150                 155                 160

Arg Pro Ala Thr Thr Gly Trp Asp Pro Ala His Ile Ala Arg Ala Trp
                165                 170                 175

Val Val Leu Met Lys Arg Leu Gly Tyr Thr Lys Phe Val Ala Gln Gly
            180                 185                 190

Gly Asp Trp Gly Ala Ile Ile Thr Glu Ile Met Gly Ala Gln Ala Pro
            195                 200                 205

Pro Glu Leu Met Gly Ile His Thr Asn Met Ala Asn Val Ile Pro Leu
            210                 215                 220

Asp Ile Asp Lys Leu Ala Phe Ser Gly Ala Pro Ala Pro Ala Asn Leu
225                 230                 235                 240

Ser Ala Asp Glu Lys Leu Ala Tyr Glu Arg Leu Ser Phe Val Tyr Ala
                245                 250                 255

Lys Gly Ile Gly Tyr Gly Phe Gln Met Gly Leu Arg Pro Gln Thr Leu
            260                 265                 270

Tyr Gly Ile Ala Asp Ser Pro Val Gly Leu Ala Ala Tyr Phe Leu Asp
            275                 280                 285

His Asp Ala Arg Ser Tyr Glu Leu Ile Ala Arg Val Phe Glu Gly Ala
            290                 295                 300

Asn Glu Gly Leu Thr Arg Asp Asp Val Leu Asp Asn Val Thr Leu Ala
305                 310                 315                 320

Trp Leu Thr Asn Thr Ala Val Ser Gly Arg Leu Tyr Trp Glu Tyr
                325                 330                 335

Met Gly Ala Ser Phe Phe Ala Val Lys Gly Val Ala Val Pro Thr Ala
            340                 345                 350

Val Ser Val Phe Pro Asp Glu Leu Tyr Pro Ala Pro Arg Ser Trp Ala
            355                 360                 365

Glu Arg Ala Tyr Pro Lys Leu Ile His Phe Asn Lys Leu Pro Lys Gly
            370                 375                 380

Gly His Phe Ala Ala Trp Glu Gln Pro Gln Tyr Leu Ser Glu Glu Ile
385                 390                 395                 400

Arg Ala Gly Phe Arg Ser Leu Arg
                405

<210> SEQ ID NO 57
<211> LENGTH: 984
<212> TYPE: DNA
<213> ORGANISM: Unknown
```

```
<220> FEATURE:
<223> OTHER INFORMATION: Obtained from an environmental source

<400> SEQUENCE: 57
atgaggagga atcttttgaa gaaccgcaat tttcaactga ttgagactaa cggcatccat      60
ttgcgcactg ttgtcgaagg caatggcccg ctggttattc tgctgcacgg gtggccgcag     120
tgctggtacc tatggcggca ccagatcgag ccgctggtgg cggcgggctt tcaagtggcg     180
gtgcccgacc agcgcggtta cggcggcagt gataagcccg cagagatcga agcttacaac     240
atcatcgaac tgacgaacga tgtggttggg ctggccggcg cgctcgggca cgaacgattc     300
atcgttgtcg gccacgattg gggcgcgcct gtggcatggc atacggcgct cctgcacccg     360
cagcgtgtga aagccgtcgc ggggttgagc gtgccgtaca cgcgttggaa agcacgcacg     420
ctgacgcagc aggaattta cggcgacaat ttctggtaca tggtttattt ccagcagccg     480
ggcgtggccg aagcggaact ggaagccgac attcgaaaat ctctgcggac gatttatttt     540
tcaatttccg gtgatgttcc ggcagactgg cggcccacgc gcaaaccggc gtcggccaaa     600
ttcctggacg gcatgctcga tccggggcaa aacctgccgg cgtggctgac cgaagaagat     660
ttggattatt acgtagcgca gtaccagcag agcgggtttc gcgggccgat taattggtat     720
cgcaacattg accgcaatgt tgcgctgacg ccacaacttg attcgccgga accggaatg     780
atcaggcagc ccgcattctt catcgccggg acgaaagacc ccgtgctgca attccacggc     840
ggcaaggcgc tctccgcaat ggacaaatgg atggcggacc tgcgcggcaa agtcttgatc     900
gaaggcgcgg gccactggt gcagatggag cgaccggcgg aggtgaatga agcgttactc     960
ggtttttga aggccgttgc ttga                                            984

<210> SEQ ID NO 58
<211> LENGTH: 327
<212> TYPE: PRT
<213> ORGANISM: Unknown
<220> FEATURE:
<223> OTHER INFORMATION: Obtained from an environmental source

<400> SEQUENCE: 58

Met Arg Arg Asn Leu Leu Lys Asn Arg Asn Phe Gln Leu Ile Glu Thr
  1               5                  10                  15

Asn Gly Ile His Leu Arg Thr Val Val Glu Gly Asn Gly Pro Leu Val
             20                  25                  30

Ile Leu Leu His Gly Trp Pro Gln Cys Trp Tyr Leu Trp Arg His Gln
         35                  40                  45

Ile Glu Pro Leu Val Ala Ala Gly Phe Gln Val Ala Val Pro Asp Gln
     50                  55                  60

Arg Gly Tyr Gly Gly Ser Asp Lys Pro Ala Glu Ile Glu Ala Tyr Asn
 65                  70                  75                  80

Ile Ile Glu Leu Thr Asn Asp Val Val Gly Leu Ala Gly Ala Leu Gly
                 85                  90                  95

His Glu Arg Phe Ile Val Val Gly His Asp Trp Gly Ala Pro Val Ala
            100                 105                 110

Trp His Thr Ala Leu Leu His Pro Gln Arg Val Lys Ala Val Ala Gly
        115                 120                 125

Leu Ser Val Pro Tyr Thr Arg Trp Lys Ala Arg Thr Leu Thr Gln Gln
    130                 135                 140

Glu Phe Tyr Gly Asp Asn Phe Trp Tyr Met Val Tyr Phe Gln Gln Pro
145                 150                 155                 160
```

```
Gly Val Ala Glu Ala Glu Leu Glu Ala Asp Ile Arg Lys Ser Leu Arg
                165                 170                 175

Thr Ile Tyr Phe Ser Ile Ser Gly Asp Val Pro Ala Asp Trp Arg Pro
            180                 185                 190

Thr Arg Lys Pro Ala Ser Ala Lys Phe Leu Asp Gly Met Leu Asp Pro
        195                 200                 205

Gly Gln Asn Leu Pro Ala Trp Leu Thr Glu Glu Asp Leu Asp Tyr Tyr
210                 215                 220

Val Ala Gln Tyr Gln Gln Ser Gly Phe Arg Gly Pro Ile Asn Trp Tyr
225                 230                 235                 240

Arg Asn Ile Asp Arg Asn Val Ala Leu Thr Pro Gln Leu Asp Ser Pro
                245                 250                 255

Glu Thr Gly Met Ile Arg Gln Pro Ala Phe Phe Ile Ala Gly Thr Lys
            260                 265                 270

Asp Pro Val Leu Gln Phe His Gly Gly Lys Ala Leu Ser Ala Met Asp
        275                 280                 285

Lys Trp Met Ala Asp Leu Arg Gly Lys Val Leu Ile Glu Gly Ala Gly
        290                 295                 300

His Trp Val Gln Met Glu Arg Pro Ala Glu Val Asn Glu Ala Leu Leu
305                 310                 315                 320

Gly Phe Leu Lys Ala Val Ala
                325

<210> SEQ ID NO 59
<211> LENGTH: 1020
<212> TYPE: DNA
<213> ORGANISM: Unknown
<220> FEATURE:
<223> OTHER INFORMATION: Obtained from an environmental source

<400> SEQUENCE: 59
atgagcgagt tcaagcacca attcgtccaa accaatggga tcaggatgca tgtggcggag      60
gccggcgagg gctatccggt ggttttctgc catggctttc ccgagatgtg gtactcatgg     120
cgccatcaga tgcgcgcgct ggccgaggcc ggttttcgcg ctattgcgcc ggaccagcgc     180
ggctacggcg aaaccgactg tcccgagccg ctcgaggcct accaggtgcg cgagctggtc     240
gccgacatct cgggatgct cgacgcgttg aaaatcgagc aatgcgcgat cgtcggtcat     300
gactggggcg ggttcgtcgt atggcagacc gcgatgcgcg cgccgaagcg gatagcgcga     360
gtcgcctcgc tcaacacgcc gttcatgccg atggttgc cctcgactcc ggcagtccc      420 gagcatcccc gacaggtgtg gatcacgagc cggcaaccgg cgccgatgcg ccgaccgag     480 atggcgcggc agagcgcggc gggcaatttt cattacgtgc tctatttcca gcagcccggc     540
gtggcggaag cggagttgca acgcgatatt cgcaaatcct tgcgcggttt cttctccgat     600
ccgcggccgc tgccgccgat cgagcagcgc cagccgccgg gagtgttcgg acctgcgggt     660
ggtggtatca cggaccggct gtcggcaccg catcagggtg catacatgac cgacgccgat     720
atagaagtct tcgccaaggc tttcgagcgc acgggatttc gcggcgggct cagctggtac     780
cgcaacgtcg atcgcaactg ggaagaatcg gccaatatcg tcgagcgcgt cgatcagccc     840
gcgatgatgg ttacggccga gctggacatc gtgctgtggc ccgagcagac gcttggaatg     900
gagcgctggg tgccgaatct aaagcgcgtg catataaatg ggagcggtca ttggacgcag     960
caggaaaaac ccgccgaggt taacgccgcg ctgatcgaat ttttgtctcc acttaagtag    1020

<210> SEQ ID NO 60
```

```
<211> LENGTH: 339
<212> TYPE: PRT
<213> ORGANISM: Unknown
<220> FEATURE:
<223> OTHER INFORMATION: Obtained from an environmental source

<400> SEQUENCE: 60
```

| Met | Ser | Glu | Phe | Lys | His | Gln | Phe | Val | Gln | Thr | Asn | Gly | Ile | Arg | Met |
|---|---|---|---|---|---|---|---|---|---|---|---|---|---|---|---|
| 1 | | | | 5 | | | | | 10 | | | | | 15 | |

| His | Val | Ala | Glu | Ala | Gly | Gly | Tyr | Pro | Val | Phe | Cys | His | Gly |
|---|---|---|---|---|---|---|---|---|---|---|---|---|---|
| | | 20 | | | | | 25 | | | | 30 | | |

| Phe | Pro | Glu | Met | Trp | Tyr | Ser | Trp | Arg | His | Gln | Met | Arg | Ala | Leu | Ala |
|---|---|---|---|---|---|---|---|---|---|---|---|---|---|---|---|
| | | 35 | | | | | 40 | | | | | 45 | | | |

| Glu | Ala | Gly | Phe | Arg | Ala | Ile | Ala | Pro | Asp | Gln | Arg | Gly | Tyr | Gly | Glu |
|---|---|---|---|---|---|---|---|---|---|---|---|---|---|---|---|
| | 50 | | | | | 55 | | | | | 60 | | | | |

| Thr | Asp | Cys | Pro | Glu | Pro | Leu | Glu | Ala | Tyr | Gln | Val | Arg | Glu | Leu | Val |
|---|---|---|---|---|---|---|---|---|---|---|---|---|---|---|---|
| 65 | | | | | 70 | | | | | 75 | | | | | 80 |

| Ala | Asp | Ile | Val | Gly | Met | Leu | Asp | Ala | Leu | Lys | Ile | Glu | Gln | Cys | Ala |
|---|---|---|---|---|---|---|---|---|---|---|---|---|---|---|---|
| | | | | 85 | | | | | 90 | | | | | 95 | |

| Ile | Val | Gly | His | Asp | Trp | Gly | Gly | Phe | Val | Val | Trp | Gln | Thr | Ala | Met |
|---|---|---|---|---|---|---|---|---|---|---|---|---|---|---|---|
| | | | 100 | | | | | 105 | | | | | 110 | | |

| Arg | Ala | Pro | Lys | Arg | Ile | Ala | Arg | Val | Ala | Ser | Leu | Asn | Thr | Pro | Phe |
|---|---|---|---|---|---|---|---|---|---|---|---|---|---|---|---|
| | | 115 | | | | | 120 | | | | | 125 | | | |

| Met | Pro | Arg | Trp | Leu | Pro | Ser | Thr | Pro | Gly | Ser | Pro | Glu | His | Pro | Arg |
|---|---|---|---|---|---|---|---|---|---|---|---|---|---|---|---|
| | 130 | | | | | 135 | | | | | 140 | | | | |

| Gln | Val | Trp | Ile | Thr | Ser | Arg | Gln | Pro | Ala | Pro | Met | Arg | Pro | Thr | Glu |
|---|---|---|---|---|---|---|---|---|---|---|---|---|---|---|---|
| 145 | | | | | 150 | | | | | 155 | | | | | 160 |

| Met | Ala | Arg | Gln | Ser | Ala | Ala | Gly | Asn | Phe | His | Tyr | Val | Leu | Tyr | Phe |
|---|---|---|---|---|---|---|---|---|---|---|---|---|---|---|---|
| | | | | 165 | | | | | 170 | | | | | 175 | |

| Gln | Gln | Pro | Gly | Val | Ala | Glu | Ala | Glu | Leu | Gln | Arg | Asp | Ile | Arg | Lys |
|---|---|---|---|---|---|---|---|---|---|---|---|---|---|---|---|
| | | | 180 | | | | | 185 | | | | | 190 | | |

| Ser | Leu | Arg | Gly | Phe | Phe | Ser | Asp | Pro | Arg | Pro | Leu | Pro | Ile | Glu |
|---|---|---|---|---|---|---|---|---|---|---|---|---|---|---|
| | | 195 | | | | | 200 | | | | | 205 | | |

| Gln | Arg | Gln | Pro | Pro | Gly | Val | Phe | Gly | Pro | Ala | Gly | Gly | Ile | Thr |
|---|---|---|---|---|---|---|---|---|---|---|---|---|---|---|
| | 210 | | | | | 215 | | | | | 220 | | | |

| Asp | Arg | Leu | Ser | Ala | Pro | His | Gln | Gly | Ala | Tyr | Met | Thr | Asp | Ala | Asp |
|---|---|---|---|---|---|---|---|---|---|---|---|---|---|---|---|
| 225 | | | | | 230 | | | | | 235 | | | | | 240 |

| Ile | Glu | Val | Phe | Ala | Lys | Ala | Phe | Glu | Arg | Thr | Gly | Phe | Arg | Gly | Gly |
|---|---|---|---|---|---|---|---|---|---|---|---|---|---|---|---|
| | | | 245 | | | | | 250 | | | | | 255 | | |

| Leu | Ser | Trp | Tyr | Arg | Asn | Val | Asp | Arg | Asn | Trp | Glu | Glu | Ser | Ala | Asn |
|---|---|---|---|---|---|---|---|---|---|---|---|---|---|---|---|
| | | | 260 | | | | | 265 | | | | | 270 | | |

| Ile | Val | Glu | Arg | Val | Asp | Gln | Pro | Ala | Met | Met | Val | Thr | Ala | Glu | Leu |
|---|---|---|---|---|---|---|---|---|---|---|---|---|---|---|---|
| | | 275 | | | | | 280 | | | | | 285 | | | |

| Asp | Ile | Val | Leu | Trp | Pro | Glu | Gln | Thr | Leu | Gly | Met | Glu | Arg | Trp | Val |
|---|---|---|---|---|---|---|---|---|---|---|---|---|---|---|---|
| | 290 | | | | | 295 | | | | | 300 | | | | |

| Pro | Asn | Leu | Lys | Arg | Val | His | Ile | Asn | Gly | Ser | Gly | His | Trp | Thr | Gln |
|---|---|---|---|---|---|---|---|---|---|---|---|---|---|---|---|
| 305 | | | | | 310 | | | | | 315 | | | | | 320 |

| Gln | Glu | Lys | Pro | Ala | Glu | Val | Asn | Ala | Ala | Leu | Ile | Glu | Phe | Leu | Ser |
|---|---|---|---|---|---|---|---|---|---|---|---|---|---|---|---|
| | | | | 325 | | | | | 330 | | | | | 335 | |

Pro Leu Lys

```
<210> SEQ ID NO 61
<211> LENGTH: 876
<212> TYPE: DNA
<213> ORGANISM: Unknown
<220> FEATURE:
```

-continued

<223> OTHER INFORMATION: Obtained from an environmental source

<400> SEQUENCE: 61

| | | | | | |
|---|---|---|---|---|---|
| atggccatcc | acataccgtt | gacgtacgga | gacatcggcg | acaccagtcg | gccgttggtc | 60 |
| atcgcgctgc | acggcttccc | ggacaccccg | cacacctggc | ggcacctggg | accggtcctc | 120 |
| gccgaccacg | gataccgcgt | ggcggctccg | tggctgcccg | gctacgaggc | gcccgcgacg | 180 |
| ggcccgatcg | atgtcggcac | ctatgtgcgt | caggtccgcg | cggtgcgcaa | agcgctgaaa | 240 |
| gcagacaagc | gtgcagtgct | gatcggccac | gattggggcg | cctacaccgg | atatggcgtg | 300 |
| gtgtccagcg | atccaaaagc | gttctgccgc | ttggtgacac | tggccgtgcc | gccggcgccc | 360 |
| gcactggccg | gctcgatgtt | cagctacccc | cagatcaagc | ggtcgttcta | catctggttc | 420 |
| attcagcaga | tcggactcgc | cgagaccacg | ctgctgcagc | ccggcttctg | ggagtcgctg | 480 |
| tggggcgact | ggtcaccggg | atacgatgcc | cgccaggata | tttcgtggct | gcgagaacag | 540 |
| gtgaccgccg | agacgattgc | cggagtgatc | ggcccgtatc | gtgcgatgtt | caacccggag | 600 |
| ttctcagatc | ccaatgctcg | agccgaagct | gctgccacgt | tggccgctcc | gccgataccc | 660 |
| accctgtact | tgcacggcaa | aaatgacggc | gggcttgggg | cggaattggt | agaagctgcg | 720 |
| gccgactatc | tgccggcgcc | gggatcgtcg | ttcgaaatga | tcgacggcgt | agggcacttc | 780 |
| ctgcatctcg | agaaacccga | tttgatcgcc | gggcgcattt | gctcttggct | ggacgctaac | 840 |
| tcgccgtcgc | cggccggcgg | gccagctgtg | gattga | | | 876 |

<210> SEQ ID NO 62
<211> LENGTH: 291
<212> TYPE: PRT
<213> ORGANISM: Unknown
<220> FEATURE:
<223> OTHER INFORMATION: Obtained from an environmental source

<400> SEQUENCE: 62

Met Ala Ile His Ile Pro Leu Thr Tyr Gly Asp Ile Gly Asp Thr Ser
1               5                   10                  15

Arg Pro Leu Val Ile Ala Leu His Gly Phe Pro Asp Thr Pro His Thr
            20                  25                  30

Trp Arg His Leu Gly Pro Val Leu Ala Asp His Gly Tyr Arg Val Ala
        35                  40                  45

Ala Pro Trp Leu Pro Gly Tyr Glu Ala Pro Ala Thr Gly Pro Ile Asp
    50                  55                  60

Val Gly Thr Tyr Val Arg Gln Val Arg Ala Val Arg Lys Ala Leu Lys
65                  70                  75                  80

Ala Asp Lys Arg Ala Val Leu Ile Gly His Asp Trp Gly Ala Tyr Thr
                85                  90                  95

Gly Tyr Gly Val Val Ser Ser Asp Pro Lys Ala Phe Cys Arg Leu Val
            100                 105                 110

Thr Leu Ala Val Pro Pro Ala Pro Ala Leu Ala Gly Ser Met Phe Ser
        115                 120                 125

Tyr Pro Gln Ile Lys Arg Ser Phe Tyr Ile Trp Phe Ile Gln Gln Ile
    130                 135                 140

Gly Leu Ala Glu Thr Thr Leu Leu Gln Pro Gly Phe Trp Glu Ser Leu
145                 150                 155                 160

Trp Gly Asp Trp Ser Pro Gly Tyr Asp Ala Arg Gln Asp Ile Ser Trp
                165                 170                 175

Leu Arg Glu Gln Val Thr Ala Glu Thr Ile Ala Gly Val Ile Gly Pro
            180                 185                 190

```
Tyr Arg Ala Met Phe Asn Pro Glu Phe Ser Asp Pro Asn Ala Arg Ala
        195                 200                 205

Glu Ala Ala Ala Thr Leu Ala Ala Pro Pro Ile Pro Thr Leu Tyr Leu
    210                 215                 220

His Gly Lys Asn Asp Gly Gly Leu Gly Ala Glu Leu Val Glu Ala Ala
225                 230                 235                 240

Ala Asp Tyr Leu Pro Ala Pro Gly Ser Ser Phe Glu Met Ile Asp Gly
                245                 250                 255

Val Gly His Phe Leu His Leu Glu Lys Pro Asp Leu Ile Ala Gly Arg
            260                 265                 270

Ile Cys Ser Trp Leu Asp Ala Asn Ser Pro Ser Pro Ala Gly Gly Pro
        275                 280                 285

Ala Val Asp
    290

<210> SEQ ID NO 63
<211> LENGTH: 813
<212> TYPE: DNA
<213> ORGANISM: Unknown
<220> FEATURE:
<223> OTHER INFORMATION: Obtained from an environmental source

<400> SEQUENCE: 63
atgagccggg tggaggtcga cggagtcggt atcgagtacg aggtccacgg tgcgggacgc     60
cctgtcgtgc tgctgcacgg gttccccgac accgggcggc tctggcggca tcaggtcccc    120
gcgcttgccg aggccggatt ccaggtcatc gtgcccgacc tgcgcggcta cggccgttcg    180
gacaagcccg aggccgtgga cgcctattcc attcgctgc tggccgggga cgtcatggcg     240
atcctcgccg aactggggat cggcaaggcc cacgtggcag gtcacgactg ggcgccgcc    300 ctggcctggg ccatcgcatc cttcgccccc gataacgtcg accacctggt ggtcctgtcg    360
gtgggtcacc cagcgggctt cctgcgcacg ctggagcagc gccagaagtc gtggtacatg    420
ctgctgttcc agtacgccgg catcgcggag cgctggctgt ccggggacaa ctgggcgaac    480
ttccgggcct gggccgggca tccggacgcc gatcaggtga tcgccgaact ggaggccacc    540
gggtcgctca cgcccggcct caactactac cgtgccaacg tccgccgga gagctgggcc     600 gcgccgccgc tgcaacttcc gccggtgcag gcgccgacca tgggcatctg gagcaccggg    660
gacatcgcgc tcaccgaggt acagatgacc gactcggcga agaacgtcgc gagttcttgg    720
cggtacgagc gcctcgacgg ccctggccac tggatgcaac tcgaagcccc cgatcaggtg    780
accggcctgc tgctggactt cctgccgcgc tga                                 813

<210> SEQ ID NO 64
<211> LENGTH: 270
<212> TYPE: PRT
<213> ORGANISM: Unknown
<220> FEATURE:
<223> OTHER INFORMATION: Obtained from an environmental source

<400> SEQUENCE: 64

Met Ser Arg Val Glu Val Asp Gly Val Gly Ile Glu Tyr Glu Val His
  1               5                  10                  15

Gly Ala Gly Arg Pro Val Val Leu Leu His Gly Phe Pro Asp Thr Gly
             20                  25                  30

Arg Leu Trp Arg His Gln Val Pro Ala Leu Ala Glu Ala Gly Phe Gln
         35                  40                  45
```

```
Val Ile Val Pro Asp Leu Arg Gly Tyr Gly Arg Ser Asp Lys Pro Glu
         50                  55                  60

Ala Val Asp Ala Tyr Ser Ile Pro Leu Leu Ala Gly Asp Val Met Ala
 65                  70                  75                  80

Ile Leu Ala Glu Leu Gly Ile Gly Lys Ala His Val Ala Gly His Asp
                 85                  90                  95

Trp Gly Ala Ala Leu Ala Trp Ala Ile Ala Ser Phe Ala Pro Asp Asn
                100                 105                 110

Val Asp His Leu Val Val Leu Ser Val Gly His Pro Ala Gly Phe Leu
            115                 120                 125

Arg Thr Leu Glu Gln Arg Gln Lys Ser Trp Tyr Met Leu Leu Phe Gln
        130                 135                 140

Tyr Ala Gly Ile Ala Glu Arg Trp Leu Ser Gly Asp Asn Trp Ala Asn
145                 150                 155                 160

Phe Arg Ala Trp Ala Gly His Pro Asp Ala Asp Gln Val Ile Ala Glu
                165                 170                 175

Leu Glu Ala Thr Gly Ser Leu Thr Pro Gly Leu Asn Tyr Tyr Arg Ala
            180                 185                 190

Asn Val Pro Pro Glu Ser Trp Ala Ala Pro Leu Gln Leu Pro Pro
        195                 200                 205

Val Gln Ala Pro Thr Met Gly Ile Trp Ser Thr Gly Asp Ile Ala Leu
    210                 215                 220

Thr Glu Val Gln Met Thr Asp Ser Ala Lys Asn Val Ala Ser Ser Trp
225                 230                 235                 240

Arg Tyr Glu Arg Leu Asp Gly Pro Gly His Trp Met Gln Leu Glu Ala
                245                 250                 255

Pro Asp Gln Val Thr Gly Leu Leu Leu Asp Phe Leu Pro Arg
        260                 265                 270

<210> SEQ ID NO 65
<211> LENGTH: 1206
<212> TYPE: DNA
<213> ORGANISM: Unknown
<220> FEATURE:
<223> OTHER INFORMATION: Obtained from an environmental source

<400> SEQUENCE: 65
atgaatgccg ttcccaagca acgggcact gacaacagtg ccattcgtcc gttccgcgtg      60
aatttcccgg aagccgcgct tgccgagttg cgcaagcgcg tgaacgccac catctggccc    120
gacaaggaga ccgttgccga tgagtcgcaa ggcatccagc tcgcgatgct tcagaagctc    180
gcgcgctatt gggggacgga gtacgactgg cgtccgtgcg aagcgaaact gaacgccgtg    240
ccgaatttca tcacggagat cgacggcctg gacattcact tcattcacgt ccgctcgaag    300
catgaagatg cgctgccgtt gatcgtcacg cacggctggc cgggatcggt cgtcgagcag    360
atgaagctca tcgagcccct caccaatccc acggcacatg gcggcagcgc ggccgatgcg    420
ttccacgtcg tgattccgtc gatggctggc tacggttttt cgggcaagcc gacgtccccg    480
ggctgggatt gcaccgcat ggcccgcgcg tggagtgtcc tgatgaagcg cctcgggtac    540
tcgaggtatg tggcccaggg tggggactgg ggatcgttga tttccgagca gatggggtg    600 ctcgcgcccc cggaactgct cgccatccac atcaatctgc ttttcgcggt gccgccggag    660
atcttgcagg cgctgcccag tcaccgcgca cccgccggtc tcgcggcgga cgagcagaga    720
gcgttcgaac gactcgattt cttcttcacg aacggtctca cctacgccct gcagatggca    780
aaccatccgc agaccctcta tgggattgcg gactcaccga tcggacttgc ggcgtggttc    840
```

-continued

```
ctcgagcacg acttgctgag ctaccagatg atcacgcgcg cattcgacgg acaacccgag      900
ggcctaacgc gcgatgacgt tctggacaac atcacgctca cctggctcac caatacggcg      960
atttccggag cgcgtctcta tcgggagaac aagcttgcgt tcttcgctgc gatgggcgtc     1020
aagattccgg ttgccgtgag cgcctttccc gacgaactct accagcctcc gcggagctgg     1080
atggagcgcg cgtacccgaa gctgatccac tacaacaagc tccccaaggg cggccacttt     1140
gcggcctggg agcagccgaa gctcctcgtg ggcgagttgc gcaccgcgtt caagtcgctt     1200
cgatag                                                                1206
```

<210> SEQ ID NO 66
<211> LENGTH: 401
<212> TYPE: PRT
<213> ORGANISM: Unknown
<220> FEATURE:
<223> OTHER INFORMATION: Obtained from an environmental source

<400> SEQUENCE: 66

```
Met Asn Ala Val Pro Lys Gln Thr Gly Thr Asp Asn Ser Ala Ile Arg
 1               5                  10                  15

Pro Phe Arg Val Asn Phe Pro Glu Ala Ala Leu Ala Glu Leu Arg Lys
             20                  25                  30

Arg Val Asn Ala Thr Ile Trp Pro Asp Lys Glu Thr Val Ala Asp Glu
         35                  40                  45

Ser Gln Gly Ile Gln Leu Ala Met Leu Gln Lys Leu Ala Arg Tyr Trp
     50                  55                  60

Gly Thr Glu Tyr Asp Trp Arg Pro Cys Glu Ala Lys Leu Asn Ala Val
 65                  70                  75                  80

Pro Asn Phe Ile Thr Glu Ile Asp Gly Leu Asp Ile His Phe Ile His
                 85                  90                  95

Val Arg Ser Lys His Glu Asp Ala Leu Pro Leu Ile Val Thr His Gly
            100                 105                 110

Trp Pro Gly Ser Val Val Glu Gln Met Lys Leu Ile Glu Pro Leu Thr
        115                 120                 125

Asn Pro Thr Ala His Gly Gly Ser Ala Ala Asp Ala Phe His Val Val
    130                 135                 140

Ile Pro Ser Met Ala Gly Tyr Gly Phe Ser Gly Lys Pro Thr Ser Pro
145                 150                 155                 160

Gly Trp Asp Cys Thr Arg Met Ala Arg Ala Trp Ser Val Leu Met Lys
                165                 170                 175

Arg Leu Gly Tyr Ser Arg Tyr Val Ala Gln Gly Gly Asp Trp Gly Ser
            180                 185                 190

Leu Ile Ser Glu Gln Met Gly Val Leu Ala Pro Glu Leu Leu Ala
        195                 200                 205

Ile His Ile Asn Leu Pro Phe Ala Val Pro Glu Ile Leu Gln Ala
    210                 215                 220

Leu Pro Ser His Arg Ala Pro Ala Gly Leu Ala Ala Asp Glu Gln Arg
225                 230                 235                 240

Ala Phe Glu Arg Leu Asp Phe Phe Thr Asn Gly Leu Thr Tyr Ala
                245                 250                 255

Leu Gln Met Ala Asn His Pro Gln Thr Leu Tyr Gly Ile Ala Asp Ser
            260                 265                 270

Pro Ile Gly Leu Ala Ala Trp Phe Leu Glu His Asp Leu Leu Ser Tyr
        275                 280                 285
```

-continued

```
Gln Met Ile Thr Arg Ala Phe Asp Gly Gln Pro Glu Gly Leu Thr Arg
    290                 295                 300

Asp Asp Val Leu Asp Asn Ile Thr Leu Thr Trp Leu Thr Asn Thr Ala
305                 310                 315                 320

Ile Ser Gly Ala Arg Leu Tyr Arg Glu Asn Lys Leu Ala Phe Phe Ala
                325                 330                 335

Ala Met Gly Val Lys Ile Pro Val Ala Val Ser Ala Phe Pro Asp Glu
            340                 345                 350

Leu Tyr Gln Pro Pro Arg Ser Trp Met Glu Arg Ala Tyr Pro Lys Leu
        355                 360                 365

Ile His Tyr Asn Lys Leu Pro Lys Gly Gly His Phe Ala Ala Trp Glu
    370                 375                 380

Gln Pro Lys Leu Leu Val Gly Glu Leu Arg Thr Ala Phe Lys Ser Leu
385                 390                 395                 400

Arg

<210> SEQ ID NO 67
<211> LENGTH: 1026
<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(69)

<400> SEQUENCE: 67
atgaaattcc cttcactgct cagtgccatc acaatggcac tcgccgtctc cgtgtcgacc        60
gcgttcgccg cggacaactc ggcctccggg tcatcccgcc atggcgtcgc caacgtgtcg       120
gatgcggcac tcgtcaagtc gctgccccga ttcaggaacg gctacgccga cgtcaatggc       180
gtgcgcctcc actacgttgc cggcggccgt ggcgagccac tcgtcctgct ccccggctgg       240
ccggagacct ggtggacatt ccacaagatc atgccggcgc tggccgaggg ccacaccgtc       300
atcgtcgtcg acctgcgcgg gatgggtgca tcgtccaagc ccgtcgatgg ctacgacaag       360
aagaccatgg ccagggacat ctacaccctc gtcaaatccc tgggctacga caaggtcgcc       420
atcgccggtc acgacatcgg ttcagccgtc gcgtatgcct atgcggagaa ctacccgcag       480
gccaccgaca agctggtgat gatggagttt ccgcatcccg atgaaagcct gaagtcgttc       540
ccgctcctgc ccacgcaggg cccggtgggt gacaaggtgg ttcatcgcg accttacctg        600 tggtggttcg ctctcaacca gatcaacgga ctgcccgaga actgctcgc cggtcgcatc        660 cgtgtcgaac aggattggct cttcaagtac ttcctggtag acgaaaacgc cgtggatgcg       720
cgggatcgcg ccgtgtacga gcgggcatac gacagcggcg atgcgattcg cgccagcaac       780
ggttggtacc aggcattcaa ccaggacatc gccgacaaca gggctacgg caacctggac        840 atgccggtat tggtcctggc cggcccggcc taccagtgga tgaaggcggt ggtaggtaag       900
aaagcgacca ggctgacggc actcgacgtg ccgaacagcg ccacttcgt gcaggaagaa        960 cagcccgatt tcgtcagcaa gacgatgatc gacttcctgc agaacccgga agcgtcgaac      1020
cattga                                                                  1026

<210> SEQ ID NO 68
<211> LENGTH: 341
<212> TYPE: PRT
<213> ORGANISM: Unknown
<220> FEATURE:
<223> OTHER INFORMATION: Obtained from an environmental source
```

<220> FEATURE:
<221> NAME/KEY: SIGNAL
<222> LOCATION: (1)...(23)

<400> SEQUENCE: 68

Met Lys Phe Pro Ser Leu Leu Ser Ala Ile Thr Met Ala Leu Ala Val
1               5                   10                  15

Ser Val Ser Thr Ala Phe Ala Ala Asp Asn Ser Ala Ser Gly Ser Ser
            20                  25                  30

Arg His Gly Val Ala Asn Val Ser Asp Ala Ala Leu Val Lys Ser Leu
        35                  40                  45

Pro Arg Phe Arg Asn Gly Tyr Ala Asp Val Asn Gly Val Arg Leu His
50                  55                  60

Tyr Val Ala Gly Arg Gly Glu Pro Leu Val Leu Pro Gly Trp
65                  70                  75                  80

Pro Glu Thr Trp Trp Thr Phe His Lys Ile Met Pro Ala Leu Ala Glu
            85                  90                  95

Gly His Thr Val Ile Val Val Asp Leu Arg Gly Met Gly Ala Ser Ser
            100                 105                 110

Lys Pro Val Asp Gly Tyr Asp Lys Lys Thr Met Ala Arg Asp Ile Tyr
        115                 120                 125

Thr Leu Val Lys Ser Leu Gly Tyr Asp Lys Val Ala Ile Ala Gly His
130                 135                 140

Asp Ile Gly Ser Ala Val Ala Tyr Ala Tyr Ala Glu Asn Tyr Pro Gln
145                 150                 155                 160

Ala Thr Asp Lys Leu Val Met Met Glu Phe Pro His Pro Asp Glu Ser
            165                 170                 175

Leu Lys Ser Phe Pro Leu Leu Pro Thr Gln Gly Pro Val Gly Asp Lys
        180                 185                 190

Val Gly Ser Ser Arg Pro Tyr Leu Trp Trp Phe Ala Leu Asn Gln Ile
    195                 200                 205

Asn Gly Leu Pro Glu Lys Leu Leu Ala Gly Arg Ile Arg Val Glu Gln
210                 215                 220

Asp Trp Leu Phe Lys Tyr Phe Leu Val Asp Glu Asn Ala Val Asp Ala
225                 230                 235                 240

Arg Asp Arg Ala Val Tyr Glu Arg Ala Tyr Asp Ser Gly Asp Ala Ile
            245                 250                 255

Arg Ala Ser Asn Gly Trp Tyr Gln Ala Phe Asn Gln Asp Ile Ala Asp
        260                 265                 270

Asn Lys Gly Tyr Gly Asn Leu Asp Met Pro Val Leu Val Leu Ala Gly
    275                 280                 285

Pro Ala Tyr Gln Trp Met Lys Ala Val Val Gly Lys Lys Ala Thr Arg
290                 295                 300

Leu Thr Ala Leu Asp Val Pro Asn Ser Gly His Phe Val Gln Glu Glu
305                 310                 315                 320

Gln Pro Asp Phe Val Ser Lys Thr Met Ile Asp Phe Leu Gln Asn Pro
            325                 330                 335

Glu Ala Ser Asn His
            340

<210> SEQ ID NO 69
<211> LENGTH: 1302
<212> TYPE: DNA
<213> ORGANISM: Unknown
<220> FEATURE:
<223> OTHER INFORMATION: Obtained from an environmental source

```
<400> SEQUENCE: 69
gtggctctcg caggtgcaga tcgggcagaa cacgtacatc gcaaccgagt tctaccagcc    60
gatcaccgag tcgggccgct ggttcgtcac ccctatgcg tcggccgggc agcagacacg    120
cggcgtgttc ttcggcgacg acaaggtcgc cgaataccgc atcaccagct accaggccgg    180
attcgatttc ggcgctgcga tgggcacgtg gggccaggcg aaggtcggcc ccgtctggac    240
aagagtcaac gcgcggatag acaccggctt cccacgctg ccttcggtga agagacgac    300 cgccggggtc cgggcgaacc tcttcgtcga ccagatggac aacgcctggt tccccagcga    360
cggcttcttc gcgacggggg aagcgtatgc cgcgctgacg tcgttcggat catgacgcat    420
ggctggcccg gatcggtcat cgagctgctc gagaccatcg gtccctgac cgacccgacc    480 aggtacggcg gcactcccga cgatgccttc gacgtagtgc tgccgtcctt gcctggctat    540
ggcttttcgg gcgaaccgac cgacctcggc tggaattcag gccgcatcgc ccgcgcgtgg    600
gcagtactga tgaagcgcct cggctacgca cgctatgtcg cccagggggg cgatgtggga    660
gcctccgtca cggacgcaat ggggcgccag ggaaccgagg ggctggtcgg catccatgtc    720
aacttgctct ccggggcgtt gggcatcgcc gatcgattgc cggcgacatc cgagccggaa    780
cgcgtcgcgc acaaggcgct cgcgacgttc agggcgagtg gcttcggcta cttcctggaa    840
cagtccaccc ggccccaaac gatcggctac tcactgctgg attcacccgt cgggctcgcg    900
gcctggttgc tcgaccatga cacggacagc tactacaaga tttcccgcgc gttcgtcgac    960
ggcgcgcccg tgggcaacct cacccgggag cacgtcgtcg acaacatcac cctgtactgg    1020
ctgacgggca ccggcgcgtc tgccgcccgg tggtactggg agttcggaca gtttctggcc    1080
gcagccagtg cggccggcac ggctcctccg ccggtcaagg ttcccgtcgg cttcacgacg    1140
ttccccggcg agatctgggc tgccccgcgg agctgggttg aggcggtcta ccccggcctc    1200
gcctacttca accaggtcga ccgcggcgga cactttgctg catgggaaga accggcactc    1260
ttcgtatcgg agctgcgtgc ggcgttcaaa tcgttgcggt ag                       1302

<210> SEQ ID NO 70
<211> LENGTH: 433
<212> TYPE: PRT
<213> ORGANISM: Unknown
<220> FEATURE:
<223> OTHER INFORMATION: Obtained from an environmental source

<400> SEQUENCE: 70

Met Ala Leu Ala Gly Ala Asp Arg Ala Glu His Val His Arg Asn Arg
 1               5                  10                  15

Val Leu Pro Ala Asp His Arg Val Gly Pro Leu Val Arg His Pro Leu
             20                  25                  30

Cys Val Gly Arg Ala Ala Asp Thr Arg Arg Val Leu Arg Arg Arg Gln
         35                  40                  45

Gly Arg Arg Ile Pro His His Gln Leu Pro Gly Arg Ile Arg Phe Arg
     50                  55                  60

Arg Cys Asp Gly His Val Gly Pro Gly Glu Arg Pro Arg Leu Asp
 65                  70                  75                  80

Lys Ser Gln Arg Ala Asp Arg His Arg Leu Ser His Ala Ala Phe Gly
                 85                  90                  95

Glu Arg Asp Asp Arg Arg Gly Pro Gly Glu Pro Leu Arg Arg Pro Asp
            100                 105                 110

Gly Gln Arg Leu Val Pro Gln Arg Arg Leu Leu Arg Asp Gly Gly Ser
```

```
                115                 120                 125
Val Cys Arg Ala Asp Val Val Arg Ile Met Thr His Gly Trp Pro Gly
    130                 135                 140

Ser Val Ile Glu Leu Leu Glu Thr Ile Gly Pro Leu Thr Asp Pro Thr
145                 150                 155                 160

Arg Tyr Gly Gly Thr Pro Asp Asp Ala Phe Asp Val Val Leu Pro Ser
                165                 170                 175

Leu Pro Gly Tyr Gly Phe Ser Gly Glu Pro Thr Asp Leu Gly Trp Asn
            180                 185                 190

Ser Gly Arg Ile Ala Arg Ala Trp Ala Val Leu Met Lys Arg Leu Gly
        195                 200                 205

Tyr Ala Arg Tyr Val Ala Gln Gly Gly Asp Val Gly Ala Ser Val Thr
    210                 215                 220

Asp Ala Met Gly Arg Gln Gly Thr Glu Gly Leu Val Gly Ile His Val
225                 230                 235                 240

Asn Leu Leu Ser Gly Ala Leu Gly Ile Ala Asp Arg Leu Pro Ala Thr
                245                 250                 255

Ser Glu Pro Glu Arg Val Ala His Lys Ala Leu Ala Thr Phe Arg Ala
            260                 265                 270

Ser Gly Phe Gly Tyr Phe Leu Glu Gln Ser Thr Arg Pro Gln Thr Ile
        275                 280                 285

Gly Tyr Ser Leu Leu Asp Ser Pro Val Gly Leu Ala Ala Trp Leu Leu
    290                 295                 300

Asp His Asp Thr Asp Ser Tyr Tyr Lys Ile Ser Arg Ala Phe Val Asp
305                 310                 315                 320

Gly Ala Pro Val Gly Asn Leu Thr Arg Glu His Val Val Asp Asn Ile
                325                 330                 335

Thr Leu Tyr Trp Leu Thr Gly Thr Gly Ala Ser Ala Ala Arg Trp Tyr
            340                 345                 350

Trp Glu Phe Gly Gln Phe Leu Ala Ala Ser Ala Ala Gly Thr Ala
        355                 360                 365

Pro Pro Pro Val Lys Val Pro Val Gly Phe Thr Thr Phe Pro Gly Glu
    370                 375                 380

Ile Trp Ala Ala Pro Arg Ser Trp Val Glu Ala Val Tyr Pro Gly Leu
385                 390                 395                 400

Ala Tyr Phe Asn Gln Val Asp Arg Gly Gly His Phe Ala Ala Trp Glu
                405                 410                 415

Glu Pro Ala Leu Phe Val Ser Glu Leu Arg Ala Ala Phe Lys Ser Leu
            420                 425                 430

Arg

<210> SEQ ID NO 71
<211> LENGTH: 819
<212> TYPE: DNA
<213> ORGANISM: Unknown
<220> FEATURE:
<223> OTHER INFORMATION: Obtained from an environmental source

<400> SEQUENCE: 71
atggaattga aaagcacacg tctgcaagtc aacggcacca cgctgaacgt ggtcgatgtc    60
ggccacggtg aagcggtgct cctgctgcac ggcttcccgg acacgcacac ggtatggcgc   120
aagcagatac cgccttggt ttccgccggc taccgcgtca tcgtgcccga tacgcgtggc    180
tgcggcgaga gtgagctgat gccgcaagta ggcgactacg ccatgcggca cctggtcggc   240
```

```
gatatcaagg gcatgctcga cgtgctgggc ctggacaagg tcaagctggt cgcgcacgac    300
tggggcgcgg taatcggctg gaacttcgtg atggagcacc cggagcgcgt gcagcgctat    360
gtggcactgt cggtcgggca tccgctggcg tactcgcgcg ccggacttgg ccaggcgctg    420
cgcggctact acgtgatgct gtttcagctg cgcggcattg ccgaatggct gctcaccgcc    480
ggtggctggc gcgttttttgg cctgctcacg ggttttgcgt ccgaacttcc gcagtggcgc    540
gaggtgctgc agcgtccggg ccgcctgcgc gcccacatca actactaccg cgccaacctg    600
tcgatgctgc tgcgccgcga ctacccgcgt gtgcaggtgc ccgtggtcgg tatctacagc    660
gacggcgacc gattcctgac cgaacgccag atgcaggcca gtgccgagtt ctgcgatgcg    720
ggcttccgct acgaaaaaat ggaaggcgcc aaccattggc tgcaactgga tgcaccgcag    780
cgtgccaaca tcatgatcct ggaagggctt gcagcatga                           819
```

<210> SEQ ID NO 72
<211> LENGTH: 272
<212> TYPE: PRT
<213> ORGANISM: Unknown
<220> FEATURE:
<223> OTHER INFORMATION: Obtained from an environmental source

<400> SEQUENCE: 72

```
Met Glu Leu Lys Ser Thr Arg Leu Gln Val Asn Gly Thr Thr Leu Asn
 1               5                  10                  15

Val Val Asp Val Gly His Gly Glu Ala Val Leu Leu Leu His Gly Phe
                20                  25                  30

Pro Asp Thr His Thr Val Trp Arg Lys Gln Ile Pro Ala Leu Val Ser
            35                  40                  45

Ala Gly Tyr Arg Val Ile Val Pro Asp Thr Arg Gly Cys Gly Glu Ser
        50                  55                  60

Glu Leu Met Pro Gln Val Gly Asp Tyr Ala Met Arg His Leu Val Gly
 65                 70                  75                  80

Asp Ile Lys Gly Met Leu Asp Val Leu Gly Leu Asp Lys Val Lys Leu
                85                  90                  95

Val Ala His Asp Trp Gly Ala Val Ile Gly Trp Asn Phe Val Met Glu
            100                 105                 110

His Pro Glu Arg Val Gln Arg Tyr Val Ala Leu Ser Val Gly His Pro
        115                 120                 125

Leu Ala Tyr Ser Arg Ala Gly Leu Gly Gln Ala Leu Arg Gly Tyr Tyr
    130                 135                 140

Val Met Leu Phe Gln Leu Arg Gly Ile Ala Glu Trp Leu Leu Thr Ala
145                 150                 155                 160

Gly Gly Trp Arg Val Phe Gly Leu Leu Thr Gly Phe Ala Ser Glu Leu
                165                 170                 175

Pro Gln Trp Arg Glu Val Leu Gln Arg Pro Gly Arg Leu Arg Ala His
            180                 185                 190

Ile Asn Tyr Tyr Arg Ala Asn Leu Ser Met Leu Leu Arg Arg Asp Tyr
        195                 200                 205

Pro Arg Val Gln Val Pro Val Val Gly Ile Tyr Ser Asp Gly Asp Arg
    210                 215                 220

Phe Leu Thr Glu Arg Gln Met Gln Ala Ser Ala Glu Phe Cys Asp Ala
225                 230                 235                 240

Gly Phe Arg Tyr Glu Lys Met Glu Gly Ala Asn His Trp Leu Gln Leu
                245                 250                 255

Asp Ala Pro Gln Arg Ala Asn Ile Met Ile Leu Glu Gly Leu Ala Ala
```

-continued

```
                     260              265              270
```

<210> SEQ ID NO 73
<211> LENGTH: 945
<212> TYPE: DNA
<213> ORGANISM: Unknown
<220> FEATURE:
<223> OTHER INFORMATION: Obtained from an environmental source

<400> SEQUENCE: 73

```
gtggcacccg ttcataagca cgcggcggca acggctgctc gcgtgtcgga cgcgacgctg    60
gtgaagtcgc ttcctggatt cagcaatggc tacgccgagg ttaatggcgt gcggctgcac   120
tacgtcgtcg gcggcaaagg cgagcctctg gtgctgctgc cgggctggcc tgaaacctgg   180
tggaccttcc acaagatcat gccggcgctt gccgaacact acacggtgat gcagtcgac   240
ttgcgtggca tgggtgcgtc gtcgaagccc gccgacggct acgacaagaa gaccatggcc   300
gccgatatcc acgaactcgt gaattcactt gggtacgaca aggtcagcat tgcaggccac   360
gacatcggct cggccgtggc attcgcgtat gcggcgaact atccgcaagc caccgaccgg   420
cttgtgatgc tcgaactgcc gcaccccgac gacagtctgc tgtcgtttcc gctgttgccg   480
ccgcaaggca atgttgccga caagctcggt agcgcgcgtc cgtatctgtg gtggttcgcg   540
ttcaaccaga ttcatggact ccccgaaaag ctgcttgcgg gccgcgtcgg tcttgagcag   600
gactggatct tcacttactt tttgaagaat gaaggcggga tcgacgcacg tgaccgtgcg   660
atctatgaac acgcttacaa cagcattgat gcaatccgcg caagcaacgg gtggtatcag   720
gcgttgccgc aagacatcat cgactatcgg agttacggca agctcgatat gccagttctc   780
gcgatgggcg gccccgccta cggctggatg aagaaagtcg tcgggcaaaa ggcaaccgat   840
ctgaccaccg tcgaggtgca gaacagtggt cactttgttc aggaggaaca gcccgaacgg   900
gtcgcgaagg cgatgctcga ctttctgcaa ggcgtgcacg agtga                   945
```

<210> SEQ ID NO 74
<211> LENGTH: 314
<212> TYPE: PRT
<213> ORGANISM: Unknown
<220> FEATURE:
<223> OTHER INFORMATION: Obtained from an environmental source

<400> SEQUENCE: 74

```
Met Ala Pro Val His Lys His Ala Ala Thr Ala Ala Arg Val Ser
  1               5                  10                  15

Asp Ala Thr Leu Val Lys Ser Leu Pro Gly Phe Ser Asn Gly Tyr Ala
                 20                  25                  30

Glu Val Asn Gly Val Arg Leu His Tyr Val Val Gly Gly Lys Gly Glu
             35                  40                  45

Pro Leu Val Leu Leu Pro Gly Trp Pro Glu Thr Trp Trp Thr Phe His
         50                  55                  60

Lys Ile Met Pro Ala Leu Ala Glu His Tyr Thr Val Ile Ala Val Asp
 65                  70                  75                  80

Leu Arg Gly Met Gly Ala Ser Ser Lys Pro Ala Asp Gly Tyr Asp Lys
                 85                  90                  95

Lys Thr Met Ala Ala Asp Ile His Glu Leu Val Asn Ser Leu Gly Tyr
                100                 105                 110

Asp Lys Val Ser Ile Ala Gly His Asp Ile Gly Ser Ala Val Ala Phe
            115                 120                 125

Ala Tyr Ala Ala Asn Tyr Pro Gln Ala Thr Asp Arg Leu Val Met Leu
```

-continued

```
                130                 135                 140
Glu Leu Pro His Pro Asp Asp Ser Leu Leu Ser Phe Pro Leu Leu Pro
145                 150                 155                 160

Pro Gln Gly Asn Val Ala Asp Lys Leu Gly Ser Ala Arg Pro Tyr Leu
                165                 170                 175

Trp Trp Phe Ala Phe Asn Gln Ile His Gly Leu Pro Glu Lys Leu Leu
                180                 185                 190

Ala Gly Arg Val Gly Leu Glu Gln Asp Trp Ile Phe Thr Tyr Phe Leu
                195                 200                 205

Lys Asn Glu Gly Gly Ile Asp Ala Arg Asp Arg Ala Ile Tyr Glu His
210                 215                 220

Ala Tyr Asn Ser Ile Asp Ala Ile Arg Ala Ser Asn Gly Trp Tyr Gln
225                 230                 235                 240

Ala Leu Pro Gln Asp Ile Ile Asp Tyr Arg Ser Tyr Gly Lys Leu Asp
                245                 250                 255

Met Pro Val Leu Ala Met Gly Gly Pro Ala Tyr Gly Trp Met Lys Lys
                260                 265                 270

Val Val Gly Gln Lys Ala Thr Asp Leu Thr Thr Val Glu Val Gln Asn
                275                 280                 285

Ser Gly His Phe Val Gln Glu Glu Gln Pro Glu Arg Val Ala Lys Ala
                290                 295                 300

Met Leu Asp Phe Leu Gln Gly Val His Glu
305                 310
```

<210> SEQ ID NO 75
<211> LENGTH: 963
<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(66)

<400> SEQUENCE: 75

| | | | | | | |
|---|---|---|---|---|---|---|
| atgtcgtaca | gcgcgttggc | ggcggcagtc | ggagtgctca | tggcggcgac | ccttgccgcg | 60 |
| gcccagtcgc | cgcagccggc | cggcgacgtc | ttcgatcgcg | tgaagcacgg | ctacgcgaca | 120 |
| tccgataacg | gcgtgaagat | tcactacgcc | tcgctcggcc | aggggccgct | ggtcgtcatg | 180 |
| attcacggct | tccccgattt | ctggtactcg | tggcggcacc | agatggcggc | gctcgccgat | 240 |
| cgctatcagg | tggtcgcgat | cgatcaacgc | ggctacaacc | tgagcgacaa | gccgaagggc | 300 |
| gtcgagaact | acgacgtgcg | gctgctcgtc | ggcgacgtcg | ccgccgtgat | tcgcagcctg | 360 |
| ggacgggaca | aggcgacgat | cgtcgggcac | gactggggcg | cgtcgtcgc | gtggcagttc | 420 |
| gcgctcaatc | tgccgcagat | gaccgagaac | ctgatcatcc | tcaacctgcc | gcacccgaac | 480 |
| ggcctcgcgc | gcgagctgcg | cacgaacccg | gatcagatca | gaacagcga | gtacgcgcgc | 540 |
| aatttccagg | cgaagtcgcc | gagcgatccg | accgtcttct | tcggacggcc | gatgaccgcg | 600 |
| gagaacctgt | cggggtgggt | caccgatccc | gcggcgcgcg | cgcgctacgt | cgaagcgttc | 660 |
| aagcagtccg | acttcgacgg | gatgctgaac | tactacaagc | gcaactaccc | gcgcgccgcc | 720 |
| ggccccgacg | cgcccgttcc | gcccgaaccc | cgaaggcga | agatgccggt | gctgatgttc | 780 |
| cacgggctga | aggacaccgc | gttgaacgcg | gaagcgctct | cgggcacctg | gaactggctc | 840 |
| gagaaggacc | tcacgctggt | cacggtgccg | ggcgccggcc | acttcgtgca | gcaggacgcc | 900 |
| gcggagctcg | tggcgtcgac | gatgcagtgg | tggctggcga | tgcggtatcc | cgctgcgaag | 960 | taa 963

<210> SEQ ID NO 76
<211> LENGTH: 320
<212> TYPE: PRT
<213> ORGANISM: Unknown
<220> FEATURE:
<223> OTHER INFORMATION: Obtained from an environmental source
<220> FEATURE:
<221> NAME/KEY: SIGNAL
<222> LOCATION: (1)...(22)

<400> SEQUENCE: 76

Met Ser Tyr Ser Ala Leu Ala Ala Val Gly Val Leu Met Ala Ala
1               5                   10                  15

Thr Leu Ala Ala Ala Gln Ser Pro Gln Pro Ala Gly Asp Val Phe Asp
            20                  25                  30

Arg Val Lys His Gly Tyr Ala Thr Ser Asp Asn Gly Val Lys Ile His
        35                  40                  45

Tyr Ala Ser Leu Gly Gln Gly Pro Leu Val Val Met Ile His Gly Phe
    50                  55                  60

Pro Asp Phe Trp Tyr Ser Trp Arg His Gln Met Ala Ala Leu Ala Asp
65                  70                  75                  80

Arg Tyr Gln Val Val Ala Ile Asp Gln Arg Gly Tyr Asn Leu Ser Asp
                85                  90                  95

Lys Pro Lys Gly Val Glu Asn Tyr Asp Val Arg Leu Leu Val Gly Asp
            100                 105                 110

Val Ala Ala Val Ile Arg Ser Leu Gly Arg Asp Lys Ala Thr Ile Val
        115                 120                 125

Gly His Asp Trp Gly Gly Val Val Ala Trp Gln Phe Ala Leu Asn Leu
    130                 135                 140

Pro Gln Met Thr Glu Asn Leu Ile Ile Leu Asn Leu Pro His Pro Asn
145                 150                 155                 160

Gly Leu Ala Arg Glu Leu Arg Thr Asn Pro Asp Gln Ile Lys Asn Ser
                165                 170                 175

Glu Tyr Ala Arg Asn Phe Gln Ala Lys Ser Pro Ser Asp Pro Thr Val
            180                 185                 190

Phe Phe Gly Arg Pro Met Thr Ala Glu Asn Leu Ser Gly Trp Val Thr
        195                 200                 205

Asp Pro Ala Ala Arg Ala Arg Tyr Val Glu Ala Phe Lys Gln Ser Asp
    210                 215                 220

Phe Asp Gly Met Leu Asn Tyr Tyr Lys Arg Asn Tyr Pro Arg Ala Ala
225                 230                 235                 240

Gly Pro Asp Ala Pro Val Pro Pro Glu Pro Lys Ala Lys Met Pro
                245                 250                 255

Val Leu Met Phe His Gly Leu Lys Asp Thr Ala Leu Asn Ala Glu Ala
            260                 265                 270

Leu Ser Gly Thr Trp Asn Trp Leu Glu Lys Asp Leu Thr Leu Val Thr
        275                 280                 285

Val Pro Gly Ala Gly His Phe Val Gln Gln Asp Ala Ala Glu Leu Val
    290                 295                 300

Ala Ser Thr Met Gln Trp Trp Leu Ala Met Arg Tyr Pro Ala Ala Lys
305                 310                 315                 320

<210> SEQ ID NO 77
<211> LENGTH: 1026

<212> TYPE: DNA
<213> ORGANISM: Unknown
<220> FEATURE:
<223> OTHER INFORMATION: Obtained from an environmental source
<220> FEATURE:
<221> NAME/KEY: sig_peptide
<222> LOCATION: (1)...(69)

<400> SEQUENCE: 77

| | | | | | |
|---|---|---|---|---|---|
| atgaaactcc | cttcactgct | cagtgccatc | acaatggcac | tcgccgtctc | cgtgtcgacc | 60 |
| gcgttcgccg | cggacaactc | ggcctccggg | tcatcccgcc | atgacgtcgc | caacgtgtcg | 120 |
| gatgcggcac | tcgtcaagtc | gctgcccgga | ttcaggaacg | gctacgccga | cgtcaatggc | 180 |
| gtgcgcctcc | actacgttgc | cggcggccgt | ggcgagccac | tcgtcctgct | ccccggctgg | 240 |
| ccggagacct | ggtggacatt | ccacaagatc | atgccggcgc | tggccgaggg | ccacaccgtc | 300 |
| atcgtcgtcg | acctgcgcgg | gatgggtgca | tcgtccaagc | ccgtcgatgg | ctacgacaag | 360 |
| aagaccatgg | ccagggacat | ctacaccctc | gtcaaatccc | tgggctacga | caaggtcgcc | 420 |
| atcgccggtc | acgacatcgg | ttcagccgtc | gcgtatgcct | atgcggagaa | ctacccgcag | 480 |
| gccaccgaca | agctggtgat | gatggagttt | ccgcatcccg | acgaaagcct | gaagtcgttc | 540 |
| ccgctcctgc | ccacgcagtg | cccggtgggt | gacaaggtgg | ttcatcgcg | accttacctg | 600 |
| tggtggttcg | ctctcaacca | gatcaacgga | ctgcccgaga | actgctcgc | cggtcgcatc | 660 |
| cgtgtcgaac | aggactggct | cttcaagtac | ttcctggtag | acgaaaacgc | cgtgaatgcg | 720 |
| cgggatcgcg | ccgtgtacgc | gcgggcatac | gacagcggcg | atgcgattcg | cgccagcaac | 780 |
| ggctggtacc | aggcattcaa | ccaggacatc | gccgacaaca | agggctatgg | cagcctggac | 840 |
| atgccggtat | tggtcctggc | tggccctgcc | taccagtgga | tgaaggcggt | ggtcggtaag | 900 |
| aaagcgacca | ggctgacggc | actcgacgtg | ccgaacagcg | gccacttcgt | gcaggaagaa | 960 |
| cagcccgatt | tcgtcagcaa | gacgatgatc | gacttcctgc | agaacccgga | agcgtcgaac | 1020 |
| cattga | | | | | | 1026 |

<210> SEQ ID NO 78
<211> LENGTH: 341
<212> TYPE: PRT
<213> ORGANISM: Unknown
<220> FEATURE:
<223> OTHER INFORMATION: Obtained from an environmental source
<220> FEATURE:
<221> NAME/KEY: SIGNAL
<222> LOCATION: (1)...(23)

<400> SEQUENCE: 78

Met Lys Leu Pro Ser Leu Leu Ser Ala Ile Thr Met Ala Leu Ala Val
1               5                   10                  15

Ser Val Ser Thr Ala Phe Ala Ala Asp Asn Ser Ala Ser Gly Ser Ser
                20                  25                  30

Arg His Asp Val Ala Asn Val Ser Asp Ala Ala Leu Val Lys Ser Leu
            35                  40                  45

Pro Gly Phe Arg Asn Gly Tyr Ala Asp Val Asn Gly Val Arg Leu His
        50                  55                  60

Tyr Val Ala Gly Gly Arg Gly Glu Pro Leu Val Leu Pro Gly Trp
65                  70                  75                  80

Pro Glu Thr Trp Trp Thr Phe His Lys Ile Met Pro Ala Leu Ala Glu
                85                  90                  95

Gly His Thr Val Ile Val Val Asp Leu Arg Gly Met Gly Ala Ser Ser
            100                 105                 110

```
Lys Pro Val Asp Gly Tyr Asp Lys Thr Met Ala Arg Asp Ile Tyr
            115                 120                 125
Thr Leu Val Lys Ser Leu Gly Tyr Asp Lys Val Ala Ile Ala Gly His
        130                 135                 140
Asp Ile Gly Ser Ala Val Ala Tyr Ala Tyr Ala Glu Asn Tyr Pro Gln
145                 150                 155                 160
Ala Thr Asp Lys Leu Val Met Met Glu Phe Pro His Pro Asp Glu Ser
                165                 170                 175
Leu Lys Ser Phe Pro Leu Leu Pro Thr Gln Cys Pro Val Gly Asp Lys
            180                 185                 190
Val Gly Ser Ser Arg Pro Tyr Leu Trp Trp Phe Ala Leu Asn Gln Ile
        195                 200                 205
Asn Gly Leu Pro Glu Lys Leu Leu Ala Gly Arg Ile Arg Val Glu Gln
    210                 215                 220
Asp Trp Leu Phe Lys Tyr Phe Leu Val Asp Glu Asn Ala Val Asn Ala
225                 230                 235                 240
Arg Asp Arg Ala Val Tyr Ala Arg Ala Tyr Asp Ser Gly Asp Ala Ile
                245                 250                 255
Arg Ala Ser Asn Gly Trp Tyr Gln Ala Phe Asn Gln Asp Ile Ala Asp
            260                 265                 270
Asn Lys Gly Tyr Gly Ser Leu Asp Met Pro Val Leu Val Leu Ala Gly
        275                 280                 285
Pro Ala Tyr Gln Trp Met Lys Ala Val Val Gly Lys Lys Ala Thr Arg
    290                 295                 300
Leu Thr Ala Leu Asp Val Pro Asn Ser Gly His Phe Val Gln Glu Glu
305                 310                 315                 320
Gln Pro Asp Phe Val Ser Lys Thr Met Ile Asp Phe Leu Gln Asn Pro
                325                 330                 335
Glu Ala Ser Asn His
            340

<210> SEQ ID NO 79
<211> LENGTH: 1158
<212> TYPE: DNA
<213> ORGANISM: Unknown
<220> FEATURE:
<223> OTHER INFORMATION: Obtained from an environmental source

<400> SEQUENCE: 79
atgtccgctc ccacgcccttt caagatcgaa atcccgcaga gcacgatcaa caagatcatg      60
gaacgcgtgc gcgcgttcga atggcccgat gcgccggaag gcggcggctg ggcctacggc     120
accgagcttt cgacgatgaa ggagatcgtc gagtactggc tgcacggcta cgattggtac     180
cgcgagcaag agctgatcaa tcgactgccg cacttcaaag cgcgcgtgcg cgacctcgac     240
atccatttca tccacatcaa gggctcgggc gagaagcggc ggccgctgat catcagccat     300
ggttggccag gctcgttcta cgagttcatg agcgtgatcg aaccgttggc tcagccacaa     360
aaattcggcg gctcgaagga cgatgcgttc gacattgtgg tgccctcact cccgggctac     420
ggcttttcga gtaagccggc aaagccgatg agcccgcgaa cggtcgccgg gtatttcgat     480
gagctgatga ccggaacgct tggctatacg cgttatctcg cgcaaggcgg cgactggggc     540
tcttcgatca ccggatggct cggctatgaa ggccgcggct gtcaggcgat ccacatcaac     600
atgctcggct ggcgctcgcc cggtgtcgtg ccggagaccg atgaagagaa ggccgaggcg     660
gcgaagttcg cgggctcgtt tgaggctgaa ggcgcgtact tccggctgca atcgacgaag     720
```

-continued

```
ccgttgacgc tgtcctacgg catgatggat tcgccggtcg gcgcggcggc gtggatcatc    780
gagaaattca aaggctggtc cgatctcgat gacgggcaac tcgaatccgt ctacacgaag    840
gatcagctgc tcacgaacgt gatgatctat ctcgtcacac ggacgttcgg gacggcgacg    900
tggatgtatc gcggtctctt cgaagatccg ggcggtgctc ccatccaacc aggttcacgc    960
atccgcaagc cgacggcgat cgcgcgtttc ccggtcgacc tcattccgtt cccgccccgc   1020
tcgatggtcg aaaagcacat gaacgtcgtg cgttggaccg agttcgcgcg cggcggccat   1080
ttcgccgcaa tggaacggcc gcgcgacttc atcgaagacg tccgcgcctt cggccgcgac   1140
gtgaacggcg tcttctag                                                 1158
```

<210> SEQ ID NO 80
<211> LENGTH: 385
<212> TYPE: PRT
<213> ORGANISM: Unknown
<220> FEATURE:
<223> OTHER INFORMATION: Obtained from an environmental source

<400> SEQUENCE: 80

```
Met Ser Ala Pro Thr Pro Phe Lys Ile Glu Ile Pro Gln Ser Thr Ile
  1               5                  10                  15

Asn Lys Ile Met Glu Arg Val Arg Ala Phe Glu Trp Pro Asp Ala Pro
             20                  25                  30

Glu Gly Gly Gly Trp Ala Tyr Gly Thr Glu Leu Ser Thr Met Lys Glu
         35                  40                  45

Ile Val Glu Tyr Trp Leu His Gly Tyr Asp Trp Tyr Arg Glu Gln Glu
     50                  55                  60

Leu Ile Asn Arg Leu Pro His Phe Lys Ala Arg Val Arg Asp Leu Asp
 65                  70                  75                  80

Ile His Phe Ile His Ile Lys Gly Ser Gly Glu Lys Arg Arg Pro Leu
                 85                  90                  95

Ile Ile Ser His Gly Trp Pro Gly Ser Phe Tyr Glu Phe Met Ser Val
            100                 105                 110

Ile Glu Pro Leu Ala Gln Pro Gln Lys Phe Gly Gly Ser Lys Asp Asp
        115                 120                 125

Ala Phe Asp Ile Val Val Pro Ser Leu Pro Gly Tyr Gly Phe Ser Ser
    130                 135                 140

Lys Pro Ala Lys Pro Met Ser Pro Arg Thr Val Ala Gly Tyr Phe Asp
145                 150                 155                 160

Glu Leu Met Thr Gly Thr Leu Gly Tyr Thr Arg Tyr Leu Ala Gln Gly
                165                 170                 175

Gly Asp Trp Gly Ser Ser Ile Thr Gly Trp Leu Gly Tyr Glu Gly Arg
            180                 185                 190

Gly Cys Gln Ala Ile His Ile Asn Met Leu Gly Trp Arg Ser Pro Gly
        195                 200                 205

Val Val Pro Glu Thr Asp Glu Glu Lys Ala Glu Ala Lys Phe Ala
    210                 215                 220

Gly Ser Phe Glu Ala Glu Gly Ala Tyr Phe Arg Leu Gln Ser Thr Lys
225                 230                 235                 240

Pro Leu Thr Leu Ser Tyr Gly Met Met Asp Ser Pro Val Gly Ala Ala
                245                 250                 255

Ala Trp Ile Ile Glu Lys Phe Lys Gly Trp Ser Asp Leu Asp Asp Gly
            260                 265                 270

Gln Leu Glu Ser Val Tyr Thr Lys Asp Gln Leu Leu Thr Asn Val Met
```

-continued

```
                275                 280                 285
Ile Tyr Leu Val Thr Arg Thr Phe Gly Thr Ala Thr Trp Met Tyr Arg
    290                 295                 300

Gly Leu Phe Glu Asp Pro Gly Ala Pro Ile Gln Pro Gly Ser Arg
305                 310                 315                 320

Ile Arg Lys Pro Thr Ala Ile Ala Arg Phe Pro Val Asp Leu Ile Pro
                325                 330                 335

Phe Pro Pro Arg Ser Met Val Glu Lys His Met Asn Val Val Arg Trp
                340                 345                 350

Thr Glu Phe Ala Arg Gly Gly His Phe Ala Ala Met Glu Arg Pro Arg
                355                 360                 365

Asp Phe Ile Glu Asp Val Arg Ala Phe Gly Arg Asp Val Asn Gly Val
                370                 375                 380

Phe
385

<210> SEQ ID NO 81
<211> LENGTH: 416
<212> TYPE: PRT
<213> ORGANISM: Unknown
<220> FEATURE:
<223> OTHER INFORMATION: Obtained from an environmental source

<400> SEQUENCE: 81

Ala Phe Pro Thr Val Gly Thr Ile Thr Glu Pro Ala Asn Gly Asp Lys
1               5                   10                  15

Ala Ala Leu Arg Pro Phe Arg Val His Ile Pro Glu Ala Gln Leu Val
                20                  25                  30

Asp Met Arg Arg Ile Lys Ala Thr Arg Trp Pro Asp Arg Glu Thr
                35                  40                  45

Val Pro Asp Glu Ser Gln Gly Ile Gln Leu Ala Thr Ile Gln Gly Leu
    50                  55                  60

Ala Gln Tyr Trp Ala Thr Gly Tyr Asp Trp Arg Lys Cys Glu Ala Arg
65                  70                  75                  80

Leu Asn Ser Tyr Pro Gln Phe Ile Thr Glu Ile Asp Gly Leu Asp Ile
                85                  90                  95

His Phe Ile His Val Arg Ser Lys His Ala Asp Ala Met Pro Leu Ile
                100                 105                 110

Val Thr His Gly Trp Pro Gly Ser Val Ile Glu Gln Phe Lys Ile Ile
                115                 120                 125

Asp Pro Leu Val Asn Pro Thr Ala Tyr Gly Ala Pro Ala Ser Asp Ala
                130                 135                 140

Phe His Leu Val Ile Pro Ser Leu Pro Gly Tyr Gly Phe Ser Ala Arg
145                 150                 155                 160

Pro Thr Thr Thr Gly Trp Gly Pro Glu Arg Thr Ala Arg Ala Trp Val
                165                 170                 175

Thr Leu Met Lys Arg Leu Gly Tyr Glu Arg Phe Ala Ser Gln Gly Gly
                180                 185                 190

Asp Leu Gly Gly Ile Val Thr Asn Ile Met Ala Lys Gln Ala Pro Pro
                195                 200                 205

Glu Leu Ile Gly Ile His Val Asn Phe Pro Ala Ser Val Pro Ala Glu
                210                 215                 220

Ile Leu Lys Ser Leu Ala Ala Gly Glu Ser Met Pro Ala Gly Leu Ser
225                 230                 235                 240

Asp Glu Glu Lys His Ala Tyr Glu Gln Leu Ser Ala Asn Phe Lys Lys
```

-continued

```
                245                 250                 255
Lys Arg Gly Tyr Ala Phe Glu Met Gly Thr Arg Pro Gln Thr Leu Tyr
            260                 265                 270
Gly Leu Ala Asp Ser Pro Ile Ala Leu Ala Ser Trp Leu Leu Asp His
            275                 280                 285
Gly Asp Gly Tyr Gly Gln Pro Ala Ala Leu Ser Ala Ala Val Leu
            290                 295                 300
Gly His Pro Val Asn Gly His Ser Ala Gly Ala Leu Thr Arg Asp Asp
305                 310                 315                 320
Ile Leu Asp Asp Ile Thr Leu Tyr Trp Leu Thr Asn Thr Gly Ile Ser
                325                 330                 335
Ala Ala Arg Phe Tyr Trp Glu Ser His Ala Asn Phe Phe Leu Ala Ala
            340                 345                 350
Asp Val Asn Val Pro Ala Ala Val Ser Ala Phe Pro Gly Glu Asn Tyr
            355                 360                 365
Gln Ala Pro Lys Ser Trp Thr Glu Lys Ala Tyr His Lys Leu Ile Tyr
            370                 375                 380
Phe Asn Lys Pro Glu Thr Gly Gly His Phe Ala Ala Trp Glu Pro
385                 390                 395                 400
Met Ile Phe Ala Asn Glu Val Arg Ser Gly Leu Arg Pro Leu Arg Ala
                405                 410                 415

<210> SEQ ID NO 82
<211> LENGTH: 277
<212> TYPE: PRT
<213> ORGANISM: Unknown
<220> FEATURE:
<223> OTHER INFORMATION: Obtained from an environmental source

<400> SEQUENCE: 82

Ala Asp Phe Glu Ser Arg Val Lys His Gly Tyr Ala Asp Ser Asn Gly
1               5                   10                  15
Val Lys Ile His Tyr Ala Thr Ile Gly Ser Gly Pro Leu Ile Val Met
                20                  25                  30
Ile His Gly Phe Pro Asp Phe Trp Tyr Thr Trp Arg Lys Gln Met Glu
            35                  40                  45
Gly Leu Ser Asp Lys Tyr Gln Cys Val Ala Ile Asp Gln Arg Gly Tyr
        50                  55                  60
Asn Leu Ser Asp Lys Pro Gln Gly Val Glu Asn Tyr Asp Met Ser Leu
65                  70                  75                  80
Leu Val Gly Asp Val Ile Ala Val Ile Lys His Leu Gly Lys Asp Lys
                85                  90                  95
Ala Ile Ile Val Gly His Asp Trp Gly Ala Val Ala Trp Gln Leu
            100                 105                 110
Ala Leu Asn Ala Pro Gln Tyr Val Asp Arg Leu Ile Ile Leu Asn Leu
        115                 120                 125
Pro Tyr Pro Arg Gly Ile Met Arg Glu Leu Ala His Asn Pro Lys Gln
    130                 135                 140
Gln Ala Ala Ser Ala Tyr Ala Arg Asn Phe Gln Thr Glu Gly Ala Glu
145                 150                 155                 160
Ala Met Ile Lys Pro Glu Gln Leu Ala Phe Trp Val Thr Asp Ala Glu
                165                 170                 175
Ala Lys Pro Lys Tyr Val Glu Ala Phe Gln Arg Ser Asp Ile Lys Ala
            180                 185                 190
Met Leu Asn Tyr Tyr Lys Arg Asn Tyr Pro Arg Glu Pro Tyr Gln Glu
```

195                 200                 205
Asn Thr Ser Pro Val Val Lys Thr Gln Met Pro Val Leu Met Phe His
    210                 215                 220

Gly Leu Lys Asp Thr Ala Leu Leu Ser Asp Ala Leu Asn Asn Thr Trp
225                 230                 235                 240

Asp Trp Met Gly Lys Asp Leu Thr Leu Val Thr Ile Pro Asp Ser Gly
                245                 250                 255

His Phe Val Gln Gln Asp Ala Ala Asp Leu Val Thr Arg Met Met Arg
                260                 265                 270

Ala Trp Leu Glu Arg
        275

<210> SEQ ID NO 83
<211> LENGTH: 289
<212> TYPE: PRT
<213> ORGANISM: Unknown
<220> FEATURE:
<223> OTHER INFORMATION: Obtained from an environmental source

<400> SEQUENCE: 83

Arg Asp Asp Val Phe Asp Arg Val Thr His Gly Tyr Ala Thr Ser Asp
1               5                   10                  15

Gly Gly Val Lys Ile His Tyr Ala Ser Leu Gly Gln Gly Pro Leu Val
                20                  25                  30

Val Met Ile His Gly Phe Pro Asp Phe Trp Tyr Ser Trp Arg Arg Gln
            35                  40                  45

Met Gln Ala Leu Ser Asp Arg Tyr Gln Val Val Ala Ile Asp Gln Arg
        50                  55                  60

Gly Tyr Asn Leu Ser Asp Lys Pro Lys Gly Val Asp Ala Tyr Asp Met
65                  70                  75                  80

Arg Leu Leu Val Gly Asp Val Ala Ala Val Ile Arg Ser Leu Gly Lys
                85                  90                  95

Asp Lys Ala Thr Ile Val Gly His Asp Trp Gly Gly Ile Val Ala Trp
                100                 105                 110

Asn Phe Ala Met Asn Leu Pro Gln Met Thr Glu Asn Leu Ile Ile Leu
            115                 120                 125

Asn Leu Pro His Pro Asn Gly Leu Ala Arg Glu Leu Lys Asn Asn Pro
        130                 135                 140

Asp Gln Ile Lys Asn Ser Glu Tyr Ala Arg Asn Phe Gln Thr Lys Ser
145                 150                 155                 160

Pro Ser Asp Pro Thr Val Phe Phe Gly Arg Pro Met Thr Ala Glu Asn
                165                 170                 175

Leu Ala Gly Trp Val Arg Asp Pro Glu Ala Arg Lys Arg Tyr Val Glu
                180                 185                 190

Ala Phe Gln Lys Ser Asp Phe Glu Ala Met Leu Asn Tyr Tyr Lys Arg
            195                 200                 205

Asn Tyr Pro Arg Gly Ala Gly Ala Asp Ala Pro Thr Pro Pro Leu
        210                 215                 220

Pro Lys Val Lys Met Pro Val Leu Met Phe His Gly Leu Asn Asp Thr
225                 230                 235                 240

Ala Leu Asn Ala Ser Gly Leu Asn Asp Thr Trp Gln Trp Leu Glu Lys
                245                 250                 255

Asp Leu Thr Leu Val Thr Val Pro Gly Ser Gly His Phe Val Gln Gln
                260                 265                 270

Asp Ala Ala Asp Leu Val Ala Asn Thr Met Lys Trp Trp Leu Ala Met

```
                275                 280                 285
Arg

<210> SEQ ID NO 84
<211> LENGTH: 425
<212> TYPE: PRT
<213> ORGANISM: Unknown
<220> FEATURE:
<223> OTHER INFORMATION: Obtained from an environmental source

<400> SEQUENCE: 84

Ala Gln Thr Gln Arg Ala Ser Asn Ser Phe Ala Ala Gly Ala Gly Ala
 1               5                   10                  15

Lys Thr Ala Ser Gly Glu Ala Ile Val Pro Phe Lys Ile His Val Pro
                20                  25                  30

Asp Ser Val Val Ala Asp Leu Lys Gln Arg Leu Gln Arg Ala Arg Phe
            35                  40                  45

Ala Asp Glu Ile Pro Glu Val Gly Trp Asp Tyr Gly Thr Asn Leu Ala
    50                  55                  60

Tyr Leu Lys Glu Leu Val Thr Tyr Trp Arg Asp Lys Tyr Asp Trp Arg
65                  70                  75                  80

Ala Gln Glu Arg Arg Leu Asn Gln Tyr Asp Gln Phe Lys Thr Asn Ile
                85                  90                  95

Asp Gly Leu Asp Ile His Phe Ile His Gln Arg Ser Lys Val Pro Asn
            100                 105                 110

Ala Lys Pro Leu Leu Leu Asn Gly Trp Pro Ser Ser Ile Glu Glu
        115                 120                 125

Tyr Thr Lys Val Ile Gly Pro Leu Thr Asp Pro Ala Ala His Gly Gly
    130                 135                 140

Arg Thr Thr Asp Ala Phe His Val Val Ile Pro Ser Met Pro Gly Tyr
145                 150                 155                 160

Gly Phe Ser Asp Lys Pro Arg Glu Arg Gly Tyr Asn Pro Glu Arg Met
                165                 170                 175

Ala Ser Val Trp Val Lys Leu Met Ala Arg Leu Gly Tyr Thr Arg Tyr
            180                 185                 190

Leu Thr His Gly Ser Asp Trp Gly Ile Ala Val Ala Thr His Leu Ala
        195                 200                 205

Leu Lys Asp Pro Gly His Leu Ala Ala Leu His Leu Ala Gly Cys Pro
    210                 215                 220

Gly Gly Leu Ile Gly Gln Ser Pro Ser Arg Pro Ala Gly Ala Pro Pro
225                 230                 235                 240

Pro Pro Pro Ala Pro Pro Pro Ala Ala Pro Val Ser Ala Asn Leu
                245                 250                 255

Gly Tyr Gln Glu Ile Gln Thr Thr Lys Pro Gln Thr Leu Gly His Gly
            260                 265                 270

Leu Ser Asp Ser Pro Leu Gly Leu Ala Ser Trp Ile Asp Lys Trp
        275                 280                 285

Gln Ser Trp Thr Asp His Asp Gly Asp Leu Glu Lys Val Tyr Thr Lys
    290                 295                 300

Asp Gln Leu Leu Thr Asn Val Met Ile Tyr Trp Val Thr Asn Ser Gly
305                 310                 315                 320

Ala Ser Ser Ala Arg Leu Tyr Tyr Glu Thr Arg His Val Asp Gly Arg
                325                 330                 335

Leu Leu Pro Thr Phe Phe Glu Asn Phe Leu Pro Lys Leu Pro Glu Gly
            340                 345                 350
```

-continued

Arg Val Asn Val Pro Thr Gly Cys Gly Thr Phe Pro Ser Gln Tyr Asp
            355                 360                 365

Arg Arg Asp Ile Pro Ile Ser Met Asn Thr Ala Ala Ala Arg Thr Ala
    370                 375                 380

Ala Glu Ala Arg Tyr Asn Val Val Tyr Leu Thr Ile Ser Pro His Gly
385                 390                 395                 400

Gly His Phe Pro Ala Leu Glu Gln Pro Gln Val Trp Ala Asp Asp Ile
                405                 410                 415

Arg Ala Phe Phe Arg Asp Arg Pro Leu
            420                 425

<210> SEQ ID NO 85
<211> LENGTH: 262
<212> TYPE: PRT
<213> ORGANISM: Unknown
<220> FEATURE:
<223> OTHER INFORMATION: Obtained from an environmental source

<400> SEQUENCE: 85

Leu Val Phe Leu His Gly Trp Pro Gln Ser Trp Tyr Glu Trp Arg Lys
  1               5                  10                  15

Ile Ile Pro Ala Leu Ala Glu Lys Phe Thr Val Ile Ala Pro Asp Leu
             20                  25                  30

Arg Gly Leu Gly Asp Ser Glu Arg Pro Leu Thr Gly Tyr Asp Lys Arg
         35                  40                  45

Thr Leu Ala Ser Asp Val Tyr Glu Leu Val Lys Ser Leu Gly Phe Ser
 50                  55                  60

Lys Ile Gly Leu Thr Gly His Asp Trp Gly Gly Ala Val Ala Phe Tyr
 65                  70                  75                  80

Phe Ala Tyr Asp His Pro Glu Met Val Glu Arg Leu Leu Ile Leu Asp
                 85                  90                  95

Met Val Pro Gly Tyr Gly Arg Lys Gly Ser Met Asp Leu Arg Gln
            100                 105                 110

Ala Gln Arg Tyr Trp His Ala Phe Phe His Gly Gly Met Pro Asp Leu
        115                 120                 125

Ala Glu Lys Leu Val Ser Ala Asn Val Glu Ala Tyr Leu Ser His Phe
130                 135                 140

Tyr Thr Ser Thr Thr Tyr Asn Tyr Ser Pro Asn Val Phe Ser Ala Glu
145                 150                 155                 160

Asp Ile Ala Glu Tyr Val Arg Val Tyr Ser Ala Pro Gly Ala Ile Arg
                165                 170                 175

Ala Gly Phe Gln Tyr Tyr Arg Ala Ala Leu Gln Glu Asp Leu Asp Asn
            180                 185                 190

Leu Ser Ser Cys Thr Glu Lys Leu Lys Met Pro Val Leu Ala Trp Gly
        195                 200                 205

Gly Glu Ala Phe Met Gly Asn Val Val Pro Val Trp Gln Thr Val Ala
    210                 215                 220

Glu Asn Val Gln Gly Gly Glu Leu Lys Gln Cys Gly His Phe Ile Ala
225                 230                 235                 240

Glu Glu Lys Pro Glu Phe Ala Thr Gln Gln Ala Leu Glu Phe Phe Ala
                245                 250                 255

Pro Leu Arg Gly Ala Lys
            260

<210> SEQ ID NO 86

<211> LENGTH: 280
<212> TYPE: PRT
<213> ORGANISM: Unknown
<220> FEATURE:
<223> OTHER INFORMATION: Obtained from an environmental source

<400> SEQUENCE: 86

```
Ala Glu Gly Gly Glu Phe Glu Ser Arg Val Thr His Gly Tyr Ala Asp
 1               5                  10                  15

Ser Ser Gly Val Lys Ile His Tyr Ala Ser Met Gly Lys Gly Pro Leu
            20                  25                  30

Val Val Met Val His Gly Phe Pro Asp Phe Trp Tyr Thr Trp Arg Ala
        35                  40                  45

Gln Met Glu Ala Leu Ser Asp Ser Phe Gln Cys Val Ala Ile Asp Gln
50                  55                  60

Arg Gly Tyr Asn Leu Ser Asp Lys Pro Ile Gly Val Glu Asn Tyr Gly
65                  70                  75                  80

Val Arg Leu Leu Val Gly Asp Val Ser Ala Val Ile Lys Lys Leu Gly
                85                  90                  95

Lys Glu Lys Ala Ile Leu Val Gly His Asp Trp Gly Gly Leu Val Ala
            100                 105                 110

Trp Gln Phe Ala Leu Thr Gln Pro Gln Met Thr Glu Arg Leu Ile Ile
        115                 120                 125

Leu Asn Leu Pro His Pro Arg Gly Leu Leu Arg Glu Leu Ala Gln Asn
130                 135                 140

Pro Gln Gln Gln Lys Asn Ser Gln Tyr Ala Arg Asp Phe Gln Gln Pro
145                 150                 155                 160

Glu Ala Ala Ser Lys Leu Thr Ala Glu Gln Leu Ala Phe Trp Val Lys
                165                 170                 175

Asp Ala Glu Ala Arg Thr Lys Tyr Ile Glu Ala Phe Lys Arg Ser Asp
            180                 185                 190

Phe Glu Ala Met Leu Asn Tyr Tyr Lys Arg Asn Tyr Pro Arg Glu Pro
        195                 200                 205

Tyr Thr Glu Asp Thr Ser Pro Val Val Lys Val Gln Val Pro Val Leu
    210                 215                 220

Met Ile His Gly Leu Gly Asp Thr Ala Leu Leu Pro Gly Ala Leu Asn
225                 230                 235                 240

Asn Thr Trp Asp Trp Leu Glu Lys Asp Leu Thr Leu Val Thr Ile Pro
                245                 250                 255

Gly Ala Gly His Phe Val Gln Gln Asp Ala Ala Glu Leu Val Ser Arg
            260                 265                 270

Ser Met Arg Ala Trp Leu Leu Arg
        275                 280
```

<210> SEQ ID NO 87
<211> LENGTH: 416
<212> TYPE: PRT
<213> ORGANISM: Unknown
<220> FEATURE:
<223> OTHER INFORMATION: Obtained from an environmental source

<400> SEQUENCE: 87

```
Gln Thr Gly Arg Thr Ala Ile Ala Glu Ala Ser Val Ser Ser Ser Leu
 1               5                  10                  15

Pro Ala Lys Pro Pro Ala Ala Thr Glu Asp Lys Ala Ile Arg Pro Phe
            20                  25                  30

Arg Val His Val Pro Gln Glu Ala Leu Asp Asp Leu Ser Arg Arg Leu
```

```
                    35                  40                  45
Ala Ala Thr Arg Leu Pro Asp Gln Glu Thr Val Asn Asp Arg Ser Gln
 50                  55                  60
Gly Asn Gln Leu Ala Thr Met Lys Glu Leu Val Arg Tyr Trp Gln Thr
 65                  70                  75                  80
Gly Tyr Asp Trp Arg Lys Ala Glu Gln Lys Leu Asn Ala Leu Pro Gln
                 85                  90                  95
Phe Val Thr Thr Ile Asp Gly Leu Asp Ile His Phe Ile His Val Arg
                100                 105                 110
Ser Lys His Pro Asn Ala Met Pro Leu Ile Ile Thr His Gly Trp Pro
            115                 120                 125
Gly Ser Ile Phe Glu Leu Leu Lys Val Ile Gly Pro Leu Thr Asp Pro
130                 135                 140
Thr Ala Phe Gly Ser Gly Ala Glu Asp Ala Phe Asp Val Val Ile Pro
145                 150                 155                 160
Ser Met Pro Gly Tyr Gly Phe Ser Gly Lys Pro Thr Asp Ala Gly Trp
                165                 170                 175
Asp Pro Glu His Ile Ala Arg Val Trp Ala Glu Leu Met Lys Arg Leu
            180                 185                 190
Gly Tyr Thr Arg Tyr Val Ala Gln Gly Gly Asp Trp Gly Ser Pro Val
        195                 200                 205
Ser Ser Ala Met Ala Arg Gln Ala Pro Ala Gly Leu Leu Gly Ile His
210                 215                 220
Val Asn Leu Pro Ala Ala Ile Pro Pro Asp Val Gly Arg Ala Leu Asn
225                 230                 235                 240
Ala Gly Gly Pro Ala Pro Ala Gly Leu Ser Glu Lys Glu Arg Ala Ala
                245                 250                 255
Phe Asp Ala Leu Val Thr Phe Asn Thr Lys Asn Arg Ala Tyr Ser Val
            260                 265                 270
Met Met Ala Thr Arg Pro Gln Thr Ile Gly Tyr Ala Leu Thr Asp Ser
        275                 280                 285
Pro Ala Gly Leu Ala Ala Trp Ile Tyr Asp Tyr Asn Asn Gly Glu Pro
290                 295                 300
Glu Arg Ser Leu Thr Lys Asp Glu Met Leu Asp Asp Ile Thr Leu Tyr
305                 310                 315                 320
Trp Leu Thr Asn Ser Ala Thr Ser Ala Ala Arg Leu Tyr Trp Glu Asn
                325                 330                 335
Ser Gly Arg Ser Leu Leu Ser Val Ala Ala Gln Lys Thr Ala Glu Ile
            340                 345                 350
Ser Leu Pro Val Ala Ile Thr Val Phe Pro Gly Glu Ile Tyr Arg Ala
        355                 360                 365
Pro Glu Thr Trp Ala Arg Leu Ala Tyr Arg Asn Leu Ile Tyr Phe His
    370                 375                 380
Glu Val Asp Arg Gly Gly His Phe Ala Ala Trp Glu Pro Glu Leu
385                 390                 395                 400
Phe Ser Ala Glu Leu Arg Ala Ala Phe Arg Ser Leu Gln Lys Gln Gln
                405                 410                 415
```

<210> SEQ ID NO 88
<211> LENGTH: 422
<212> TYPE: PRT
<213> ORGANISM: Unknown
<220> FEATURE:
<223> OTHER INFORMATION: Obtained from an environmental source

<400> SEQUENCE: 88

-continued

```
Gln Thr Thr Thr Asp Arg Gly Ser Ala Ile Val Ala Gln Ala Ser Ala
  1               5                  10                 15

Gln Arg Ala Ala Ala Glu Asp Pro Ser Ile Arg Pro Phe Lys Val Gln
             20                  25                  30

Ile Pro Gln Ala Ala Leu Asp Asp Leu Arg Arg Ile Asn Ala Thr
             35                  40                  45

Arg Trp Pro Asp Lys Glu Thr Val Ala Asp Glu Ser Gln Gly Ala Gln
 50                  55                  60

Leu Ala Arg Leu Gln Glu Leu Val Arg Tyr Trp Gly Ser Gly Tyr Asp
 65                  70                  75                  80

Trp Arg Lys Leu Glu Ala Lys Leu Asn Ala Leu Pro Gln Phe Thr Thr
             85                  90                  95

Thr Ile Asp Gly Val Glu Ile His Phe Ile His Val Arg Ser Arg His
             100                 105                 110

Lys Asn Ala Leu Pro Val Ile Val Thr His Gly Trp Pro Gly Ser Val
             115                 120                 125

Val Glu Gln Leu Lys Ile Ile Gly Pro Leu Thr Asp Pro Thr Ala His
 130                 135                 140

Gly Gly Ser Ala Glu Asp Ala Phe Asp Val Val Ile Pro Ser Leu Pro
145                 150                 155                 160

Gly Tyr Gly Phe Ser Gly Lys Pro Thr Gly Thr Gly Trp Asp Pro Asp
                 165                 170                 175

Arg Ile Ala Arg Ala Trp Ala Glu Leu Met Lys Arg Leu Gly Tyr Thr
             180                 185                 190

Arg Tyr Val Ala Gln Gly Gly Asp Trp Gly Ala Pro Ile Thr Ser Ala
             195                 200                 205

Met Ala Arg Gln Lys Ala Ala Gly Leu Gln Gly Ile His Val Asn Leu
 210                 215                 220

Pro Ala Thr Leu Pro Pro Glu Val Thr Ala Ala Leu Gly Thr Gly Gly
225                 230                 235                 240

Pro Ala Pro Ala Gly Leu Ser Glu Lys Glu Ser Ala Val Phe Glu Ala
                 245                 250                 255

Leu Lys Lys Tyr Gly Met Thr Gly Asn Ser Ala Tyr Phe Thr Met Met
             260                 265                 270

Thr Ala Arg Pro Gln Thr Val Gly Tyr Gly Ala Thr Asp Ser Pro Ala
             275                 280                 285

Gly Leu Ala Ala Trp Ile Leu Val His Pro Gly Phe Ala Gln Trp Arg
             290                 295                 300

Tyr Gly Ala Asp Pro Lys Gln Ser Pro Thr Lys Asp Val Leu Asp
305                 310                 315                 320

Asp Ile Thr Leu Tyr Trp Leu Thr Asn Thr Ala Ala Ser Ala Ala Arg
             325                 330                 335

Leu Tyr Trp Glu Asn Gly Ala Arg Gly Ser Val Ile Ala Ala Pro
             340                 345                 350

Gln Lys Thr Ser Glu Ile Ser Leu Pro Val Ala Ile Thr Val Phe Pro
             355                 360                 365

Asp Asp Val Tyr Arg Ala Pro Glu Ser Trp Ala Arg Arg Ala Tyr Pro
 370                 375                 380

Asn Leu Thr Tyr Phe His Glu Val Asp Lys Gly His Phe Ala Ala
385                 390                 395                 400

Trp Glu Gln Pro Glu Leu Phe Ala Ala Glu Leu Arg Ala Ala Phe Lys
                 405                 410                 415
```

```
Pro Leu Arg Gly Val Gln
        420
```

<210> SEQ ID NO 89
<211> LENGTH: 277
<212> TYPE: PRT
<213> ORGANISM: Unknown
<220> FEATURE:
<223> OTHER INFORMATION: Obtained from an environmental source

<400> SEQUENCE: 89

```
Asp Phe Glu Ala Arg Val Thr His Ala Tyr Ala Asp Ser Asn Gly Val
 1               5                  10                  15

Lys Ile His Tyr Ala Thr Ile Gly Asn Gly Pro Leu Met Val Met Ile
            20                  25                  30

His Gly Phe Pro Asp Phe Trp Tyr Ser Trp Arg Ala Gln Met Glu Ala
        35                  40                  45

Leu Ser Asp Lys Phe Gln Cys Val Ala Ile Asp Gln Arg Gly Tyr Asn
50                  55                  60

Gln Ser Asp Lys Pro Gln Gly Val Glu Asn Tyr Ser Leu Arg Phe Leu
65                  70                  75                  80

Val Gly Asp Val Ala Ala Val Ile Lys Ser Leu Gly Lys Asp Lys Ala
                85                  90                  95

Ile Ile Val Gly His Asp Trp Gly Gly Leu Val Ala Trp Gln Phe Ala
            100                 105                 110

Leu Tyr Gln Pro Gln Met Thr Glu Arg Leu Ile Ile Leu Asn Leu Pro
        115                 120                 125

His Pro Arg Gly Leu Asn Arg Glu Leu Ala Arg Asn Pro Gln Gln Gln
    130                 135                 140

Lys Asn Ser Gln Tyr Ala Arg Asp Phe Gln Gln Pro Asp Ala Ala Ser
145                 150                 155                 160

Lys Leu Thr Ala Glu Gln Leu Ala Phe Trp Val Lys Asp Pro Glu Ala
                165                 170                 175

Arg Ala Lys Tyr Ile Glu Ala Phe Lys Arg Ser Asp Phe Glu Ala Met
            180                 185                 190

Leu Asn Tyr Tyr Lys Arg Asn Tyr Pro Asn Glu Pro Tyr Thr Glu Asp
        195                 200                 205

Thr Ser Pro Leu Ala Asn Lys Val Arg Met Pro Val Leu Met Ile His
    210                 215                 220

Gly Leu Glu Asp Lys Trp Leu Leu Ser Gly Ala Leu Asn Asn Thr Trp
225                 230                 235                 240

Glu Trp Leu Asp Asn Asp Leu Thr Leu Val Thr Val Pro Arg Ala Gly
                245                 250                 255

His Phe Val Gln Gln Asp Ala Ala Glu Leu Val Ser Arg Ser Met Arg
            260                 265                 270

Ala Trp Leu Leu Arg
        275
```

<210> SEQ ID NO 90
<211> LENGTH: 318
<212> TYPE: PRT
<213> ORGANISM: Unknown
<220> FEATURE:
<223> OTHER INFORMATION: Obtained from an environmental source

<400> SEQUENCE: 90

```
Ala Asp Asn Ser Ala Ser Gly Ser Ser Arg His Gly Val Ala Asn Val
 1               5                  10                  15
```

-continued

```
Ser Asp Ala Ala Leu Val Lys Ser Leu Pro Arg Phe Arg Asn Gly Tyr
             20                  25                  30

Ala Asp Val Asn Gly Val Arg Leu His Tyr Val Ala Gly Gly Arg Gly
             35                  40                  45

Glu Pro Leu Val Leu Leu Pro Gly Trp Pro Glu Thr Trp Trp Thr Phe
 50                  55                  60

His Lys Ile Met Pro Ala Leu Ala Glu Gly His Thr Val Ile Val Val
 65                  70                  75                  80

Asp Leu Arg Gly Met Gly Ala Ser Ser Lys Pro Val Asp Gly Tyr Asp
             85                  90                  95

Lys Lys Thr Met Ala Arg Asp Ile Tyr Thr Leu Val Lys Ser Leu Gly
            100                 105                 110

Tyr Asp Lys Val Ala Ile Ala Gly His Asp Ile Gly Ser Ala Val Ala
            115                 120                 125

Tyr Ala Tyr Ala Glu Asn Tyr Pro Gln Ala Thr Asp Lys Leu Val Met
            130                 135                 140

Met Glu Phe Pro His Pro Asp Glu Ser Leu Lys Ser Phe Pro Leu Leu
145                 150                 155                 160

Pro Thr Gln Gly Pro Val Gly Asp Lys Val Gly Ser Ser Arg Pro Tyr
            165                 170                 175

Leu Trp Trp Phe Ala Leu Asn Gln Ile Asn Gly Leu Pro Glu Lys Leu
            180                 185                 190

Leu Ala Gly Arg Ile Arg Val Glu Gln Asp Trp Leu Phe Lys Tyr Phe
            195                 200                 205

Leu Val Asp Glu Asn Ala Val Asp Ala Arg Asp Arg Ala Val Tyr Glu
210                 215                 220

Arg Ala Tyr Asp Ser Gly Asp Ala Ile Arg Ala Ser Asn Gly Trp Tyr
225                 230                 235                 240

Gln Ala Phe Asn Gln Asp Ile Ala Asp Asn Lys Gly Tyr Gly Asn Leu
            245                 250                 255

Asp Met Pro Val Leu Val Leu Ala Gly Pro Ala Tyr Gln Trp Met Lys
            260                 265                 270

Ala Val Val Gly Lys Lys Ala Thr Arg Leu Thr Ala Leu Asp Val Pro
            275                 280                 285

Asn Ser Gly His Phe Val Gln Glu Glu Gln Pro Asp Phe Val Ser Lys
            290                 295                 300

Thr Met Ile Asp Phe Leu Gln Asn Pro Glu Ala Ser Asn His
305                 310                 315
```

<210> SEQ ID NO 91
<211> LENGTH: 298
<212> TYPE: PRT
<213> ORGANISM: Unknown
<220> FEATURE:
<223> OTHER INFORMATION: Obtained from an environmental source

<400> SEQUENCE: 91

```
Ser Pro Gln Pro Ala Gly Asp Val Phe Asp Arg Val Lys His Gly Tyr
 1                   5                  10                  15

Ala Thr Ser Asp Asn Gly Val Lys Ile His Tyr Ala Ser Leu Gly Gln
             20                  25                  30

Gly Pro Leu Val Val Met Ile His Gly Phe Pro Asp Phe Trp Tyr Ser
             35                  40                  45

Trp Arg His Gln Met Ala Ala Leu Ala Asp Arg Tyr Gln Val Val Ala
 50                  55                  60
```

```
Ile Asp Gln Arg Gly Tyr Asn Leu Ser Asp Lys Pro Lys Gly Val Glu
 65                  70                  75                  80

Asn Tyr Asp Val Arg Leu Val Gly Asp Val Ala Ala Val Ile Arg
             85                  90                  95

Ser Leu Gly Arg Asp Lys Ala Thr Ile Val Gly His Asp Trp Gly Gly
            100                 105                 110

Val Val Ala Trp Gln Phe Ala Leu Asn Leu Pro Gln Met Thr Glu Asn
        115                 120                 125

Leu Ile Ile Leu Asn Leu Pro His Pro Asn Gly Leu Ala Arg Glu Leu
    130                 135                 140

Arg Thr Asn Pro Asp Gln Ile Lys Asn Ser Glu Tyr Ala Arg Asn Phe
145                 150                 155                 160

Gln Ala Lys Ser Pro Ser Asp Pro Thr Val Phe Phe Gly Arg Pro Met
                165                 170                 175

Thr Ala Glu Asn Leu Ser Gly Trp Val Thr Asp Pro Ala Ala Arg Ala
            180                 185                 190

Arg Tyr Val Glu Ala Phe Lys Gln Ser Asp Phe Asp Gly Met Leu Asn
        195                 200                 205

Tyr Tyr Lys Arg Asn Tyr Pro Arg Ala Ala Gly Pro Asp Ala Pro Val
    210                 215                 220

Pro Pro Glu Pro Pro Lys Ala Lys Met Pro Val Leu Met Phe His Gly
225                 230                 235                 240

Leu Lys Asp Thr Ala Leu Asn Ala Glu Ala Leu Ser Gly Thr Trp Asn
                245                 250                 255

Trp Leu Glu Lys Asp Leu Thr Leu Val Thr Val Pro Gly Ala Gly His
            260                 265                 270

Phe Val Gln Gln Asp Ala Ala Glu Leu Val Ala Ser Thr Met Gln Trp
        275                 280                 285

Trp Leu Ala Met Arg Tyr Pro Ala Ala Lys
    290                 295

<210> SEQ ID NO 92
<211> LENGTH: 318
<212> TYPE: PRT
<213> ORGANISM: Unknown
<220> FEATURE:
<223> OTHER INFORMATION: Obtained from an environmental source

<400> SEQUENCE: 92

Ala Asp Asn Ser Ala Ser Gly Ser Ser Arg His Asp Val Ala Asn Val
  1               5                  10                  15

Ser Asp Ala Ala Leu Val Lys Ser Leu Pro Gly Phe Arg Asn Gly Tyr
             20                  25                  30

Ala Asp Val Asn Gly Val Arg Leu His Tyr Val Ala Gly Gly Arg Gly
         35                  40                  45

Glu Pro Leu Val Leu Leu Pro Gly Trp Pro Glu Thr Trp Trp Thr Phe
     50                  55                  60

His Lys Ile Met Pro Ala Leu Ala Glu Gly His Thr Val Ile Val Val
 65                  70                  75                  80

Asp Leu Arg Gly Met Gly Ala Ser Ser Lys Pro Val Asp Gly Tyr Asp
             85                  90                  95

Lys Lys Thr Met Ala Arg Asp Ile Tyr Thr Leu Val Lys Ser Leu Gly
            100                 105                 110

Tyr Asp Lys Val Ala Ile Ala Gly His Asp Ile Gly Ser Ala Val Ala
        115                 120                 125
```

-continued

```
Tyr Ala Tyr Ala Glu Asn Tyr Pro Gln Ala Thr Asp Lys Leu Val Met
        130                 135                 140

Met Glu Phe Pro His Pro Asp Glu Ser Leu Lys Ser Phe Pro Leu Leu
145                 150                 155                 160

Pro Thr Gln Cys Pro Val Gly Asp Lys Val Gly Ser Ser Arg Pro Tyr
                165                 170                 175

Leu Trp Trp Phe Ala Leu Asn Gln Ile Asn Gly Leu Pro Glu Lys Leu
            180                 185                 190

Leu Ala Gly Arg Ile Arg Val Glu Gln Asp Trp Leu Phe Lys Tyr Phe
        195                 200                 205

Leu Val Asp Glu Asn Ala Val Asn Ala Arg Asp Arg Ala Val Tyr Ala
    210                 215                 220

Arg Ala Tyr Asp Ser Gly Asp Ala Ile Arg Ala Ser Asn Gly Trp Tyr
225                 230                 235                 240

Gln Ala Phe Asn Gln Asp Ile Ala Asp Asn Lys Gly Tyr Gly Ser Leu
                245                 250                 255

Asp Met Pro Val Leu Val Leu Ala Gly Pro Ala Tyr Gln Trp Met Lys
                260                 265                 270

Ala Val Val Gly Lys Lys Ala Thr Arg Leu Thr Ala Leu Asp Val Pro
            275                 280                 285

Asn Ser Gly His Phe Val Gln Glu Glu Gln Pro Asp Phe Val Ser Lys
        290                 295                 300

Thr Met Ile Asp Phe Leu Gln Asn Pro Glu Ala Ser Asn His
305                 310                 315
```

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93
agagtttgat cctggctcag                                                    20

<210> SEQ ID NO 94
<211> LENGTH: 19
<212> TYPE: DNA
<213> ORGANISM: Artificial Sequence
<220> FEATURE:
<223> OTHER INFORMATION: primer

<400> SEQUENCE: 94
ggttaccttg ttacgactt                                                     19

EPOXIDE HYDROLASES, NUCLEIC ACIDS ENCODING THEM AND METHODS FOR MAKING AND USING THEM

CROSS-REFERENCE TO RELATED APPLICATIONS

This application is a continuation-in-part of U.S. patent application Ser. No. 10/214,473, filed Aug. 5, 2002, which claims the benefit of priority under 35 U.S.C. §119(e) of U.S. Provisional Applications Ser. No. (U.S. Ser. No.) 60/309,478, filed Aug. 3, 2001, and U.S. Ser. No. 60/393,978, filed Jul. 3, 2002. Each of the aforementioned applications are explicitly incorporated herein by reference in their entirety and for all purposes.

TECHNICAL FIELD

This invention relates to molecular and cellular biology and biochemistry. In particular, the invention is directed to polypeptides having an epoxide hydrolase activity, polynucleotides encoding the polypeptides, and methods for making and using these polynucleotides and polypeptides. The polypeptides of the invention can be used as epoxide hydrolases to catalyze the hydrolysis of epoxides and arene oxides to their corresponding diols.

BACKGROUND

Epoxide hydrolases (EH) catalyze the hydrolysis of epoxides and arene oxides to their corresponding diols. Epoxide hydrolases from microbial sources are highly versatile biocatalysts for the asymmetric hydrolysis of epoxides on a preparative scale. Besides kinetic resolution, which furnishes the corresponding vicinal diol and remaining non-hydrolyzed epoxide in nonracemic form, enantioconvergent processes are possible. These are highly attractive as they lead to the formation of a single enantiomeric diol from a racemic oxirane, see, e.g., Steinreiber (2001) Curr. Opin. Biotechnol. 12:552–558.

Microsomal epoxide hydrolases are biotransformation enzymes that catalyze the conversion of a broad array of xenobiotic epoxide substrates to more polar diol metabolites, see, e.g., Omiecinski (2000) Toxicol. Lett. 112–113:365–370. Microsomal epoxide hydrolases catalyze the addition of water to epoxides in a two-step reaction involving initial attack of an active site carboxylate on the oxirane to give an ester intermediate followed by hydrolysis of the ester. Soluble epoxide hydrolase play a role in the biosynthesis of inflammation mediators, see, e.g., Morisseau (1999) Proc. Natl. Acad. Sci. USA 96:8849–8854.

Chiral molecules, including alcohols, α-hydroxy acids and epoxides, are important for the synthesis of pharmaceuticals, agrochemicals, as well as many fine chemicals. A major challenge in modern organic chemistry is to generate such compounds in high yields, with high stereo- and regioselectivities. Enantiopure epoxides are versatile synthons for the synthesis of numerous pharmaceuticals, agrochemicals and other high value compounds.

Currently available methods have drawbacks that limit their use in industrial applications. In recent studies, epoxide hydrolases (hereinafter "EHs") have shown promise as biocatalysts for the preparation of chiral epoxides and vicinal diols. They exhibit high enantioselectivities for their substrates, and can be effectively used in the resolution of racemic epoxides prepared by chemical means. As shown in FIG. 1, the selective hydrolysis of a racemic epoxide can generate both the corresponding diols and the unreacted epoxides with high enantiomeric excess (ee) values. However, in order to fully realize the potential of EHs in industrial applications, the following significant limitations urgently need to be overcome: (1) the number of enzymes available is small; and (2) the scope of substrates is limited.

Among the available enzymes, many have selectivity for only one enantiomer limiting access to both enantiomers of a particular target. High concentrations of enzymes and low substrate concentration are required in current synthetic applications because of low catalytic efficiency particularly at high substrate/product concentrations.

As mentioned above, there is currently a need in the biotechnology and chemical industry for molecules that can optimally carry out biological or chemical processes (e.g., enzymes). For example, molecules and compounds that are utilized in both established and emerging chemical, pharmaceutical, textile, food and feed, and detergent markets must meet stringent economical and environmental standards. Expensive processes, which produce harmful byproducts and which suffer from poor or inefficient catalysis, often hamper the synthesis of polymers, pharmaceuticals, natural products and agrochemicals. Enzymes, for example, have a number of remarkable advantages, which can overcome these problems in catalysis: they act on single functional groups, they distinguish between similar functional groups on a single molecule, and they distinguish between enantiomers. Moreover, they are biodegradable and function at very low mole fractions in reaction mixtures. Because of their chemo-, regio- and stereospecificity, enzymes present a unique opportunity to optimally achieve desired selective transformations. These are often extremely difficult to duplicate chemically, especially in single-step reactions. The elimination of the need for protection groups, selectivity, the ability to carry out multi-step transformations in a single reaction vessel, along with the concomitant reduction in environmental burden, has led to the increased demand for enzymes in chemical and pharmaceutical industries.

Enzyme-based processes have been gradually replacing many conventional chemical-based methods. A current limitation to more widespread industrial use is primarily due to the relatively small number of commercially available enzymes. Only ~300 enzymes (excluding DNA modifying enzymes) are at present commercially available from the >3000 non DNA-modifying enzyme activities thus far described.

The use of enzymes for technological applications also may require performance under demanding industrial conditions. This includes activities in environments or on substrates for which the currently known arsenal of enzymes was not evolutionarily selected. However, the natural environment provides extreme conditions including, for example, extremes in temperature and pH. A number of organisms have adapted to these conditions due in part to selection for polypeptides than can withstand these extremes.

Enzymes have evolved by selective pressure to perform very specific biological functions within the milieu of a living organism, under conditions of temperature, pH and salt concentration. For the most part, the non-DNA modifying enzyme activities thus far identified have been isolated from mesophilic organisms, which represent a very small fraction of the available phylogenetic diversity. The dynamic field of biocatalysis takes on a new dimension with the help of enzymes isolated from microorganisms that thrive in extreme environments. For example, such enzymes must function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. Environmental samples obtained, for example, from extreme conditions containing organisms, polynucleotides or polypeptides (e.g., enzymes) open a new field in biocatalysis. By rapidly screening for polynucleotides encoding polypeptides of interest, the invention provides not only a source of materials for the development of biologics, therapeutics, and enzymes for industrial applications, but also provides a new materials for further processing by, for example, directed evolution and mutagenesis to develop molecules or polypeptides modified for particular activity, specificity or conditions.

In addition to the need for new enzymes for industrial use, there has been a dramatic increase in the need for bioactive compounds with novel activities. This demand has arisen largely from changes in worldwide demographics coupled with the clear and increasing trend in the number of pathogenic organisms that are resistant to currently available antibiotics. For example, while there has been a surge in demand for antibacterial drugs in emerging nations with young populations, countries with aging populations, such as the U.S., require a growing repertoire of drugs against cancer, diabetes, arthritis and other debilitating conditions. The death rate from infectious diseases has increased 58% between 1980 and 1992 and it has been estimated that the emergence of antibiotic resistant microbes has added in excess of $30 billion annually to the cost of health care in the U.S. alone. (Adams et al., *Chemical and Engineering News*, 1995; Amann et al., *Microbiological Reviews*, 59, 1995). As a response to this trend pharmaceutical companies have significantly increased their screening of microbial diversity for compounds with unique activities or specificity. Accordingly, the invention can be used to obtain and identify polynucleotides and related sequence specific information from, for example, infectious microorganisms present in the environment such as, for example, in the gut of various macroorganisms.

Identifying novel enzymes in an environmental sample is one solution to this problem. By rapidly identifying polypeptides having an activity of interest and polynucleotides encoding the polypeptide of interest the invention provides methods, compositions and sources for the development of biologics, diagnostics, therapeutics, and compositions for industrial applications.

Chiral epoxides and diols are key building blocks for the synthesis of pharmaceuticals. The epoxide group is readily transformed into a wide range of derivatives by acid or base-catalyzed ring opening reactions, while the diols similarly can be converted into a diverse range of structures. Epoxides have broad applications in areas such as anticancer agents, beta-blockers, beta agonists, antivirals, antifungals, and antibacterials. Opportunities for chiral epoxides exist in both the small synthon area, including C-3 and C-4 units, and the advanced chemical intermediate area for pharmaceuticals.

The C-3 synthons are of major significance because they are used in the processes of many pharmaceuticals and can also lead to a wide range of downstream products. Glycidols (S-(1), and R-(2)) are the leading chiral epoxides among representative C-3 synthons shown in FIG. 2. For example, R-glycidol is used as a building block for atenolol (an antihypertensive drug) and S-glycidol leads to R-glycidyl butyrate (7), an important synthon in the synthesis of oxazolidinone antibiotics. Oxazolidinones represent a relatively new class of antibiotics and currently there are over 40 at various stages of clinical development. There is also an increasing demand for both R- and S-epichlorohydrin (3,4). Among C-4 synthons, 3,4-epoxy-1-butene (8) is a small molecule with vast potential for the chemical industry. Epoxide 8 leads to the production of over 30 other chiral epoxides that are not readily available. Epoxide 10 is used in the production of saquinavir, an antiviral drug, while its diastereoisomer 11 is used in the synthesis of amprenavir, another antiviral drug (FIG. 3). The mixture of the two compounds can be prepared from phenylalanine through an alkene intermediate. Another epoxide, 12, is the building block for the synthesis of two anticancer drugs, docetaxel and paclitaxel (FIG. 4).

Chemical Asymmetric Synthesis of Epoxides and Diols

Currently available chemical methods for the asymmetric epoxidation of alkenes are the Sharpless asymmetrical epoxidation, the Jacobsen epoxidation, and the method developed by Yian Shi. The Sharpless method uses titanium-based catalysts to epoxidize a wide variety of allylic alcohols with optical yields often greater than 90%. (Johnson, R. A.; Sharpless, K. B. Catalytic asymmetric epoxidation of allylic alcohols. In *Catalytic Asymmetric Synthesis*; Ojima, I. Ed.; VCH: New York, 1993; pp. 103–158.) This methodology is compatible with a wide range of functionalities and this has led to its extensive use in synthetic chemistry. However, the Sharpless approach suffers a significant drawback as the alkenes must have hydroxyl functionality in the allylic position. In contrast to the Sharpless reaction, the asymmetric epoxidation methodology developed by Jacobsen and Katsuki, ** (Jacobsen, E. N. Asymmetric catalytic epoxidation of unfunctionalized olefins. In *Catalytic Asymmetric Synthesis*; Ojima, I. Ed.; VCH: New York, 1993; pp. 159–202; and Katsuki, T. *Coord. Chem. Rev.* 1995, 140, 189–214) which uses optically active (salen)manganese(III) complexes, does not require allylic alcohols. However, the scope of the reaction is somewhat limited due to the steric and electronic nature of the catalysts and the best substrates are cis-alkenes conjugated with aryl, acetylenic and alkenyl groups. This substrate requirement greatly limits the applicability of this method as well. Shi Yan's asymmetric epoxidation method, which uses oxiranes derived from oxone and chiral ketones, is effective for trans- and disubstituted olefins. (Zhi-Xian Wang et al., "An Efficient Catalytic Asymmetric Epoxidation Method," *J. Am. Chem. Soc.* 1997, 119, 11224–11235.) However, the use of oxone and the catalytic efficiency are two barriers that hamper its industrial application.

In the case where diols are the desired product, an alternative to epoxidation followed by hydrolysis, is the direct asymmetric dihydroxylation of alkenes. The most successful method for catalytic asymmetric dihydroxylation (AD) of alkenes to generate vicinal diols was developed by Sharpless. (Johnson, R. A.; Sharpless, K. B. Catalytic asymmetric dihydroxylation. In *Catalytic Asymmetric Synthesis*; Ojima, I. Ed.; VCH: New York, 1993; pp. 227–272.) This uses osmium-based catalysts and is applicable to a wide range of alkenes. The method, however, is not effective for some cis-alkenes. More importantly, the use of osmium which is very toxic prohibits its use for pharmaceutical production.

A different strategy of preparing chiral epoxides and diols is via hydrolytic kinetic resolution of racemic epoxides. The method currently used in industry, based on the (salen)cobalt catalysts developed by Jacobsen, is quite efficient on terminal epoxides. (Tokunaga, M.; Larrow, J. F.; Kakiuchi, F.; Jacobsen, E. N. *Science* 1997, 277, 936.) However, it is ineffective for the internal epoxides. In addition, it is not applicable for many heteroatom-containing substrates (e.g., pyridyl-type epoxides) due to interference of these atoms with the metal catalysts.

All of the methods discussed above are limited in their application to process scale chiral synthesis by problematic features that include the use of expensive metal catalysts, low substrate/catalyst ratios, and limited efficiency and productivity with varying degrees of enantioselectivities. To overcome these obstacles, attention has turned to biocatalysts. (Besse, Pl; Veschambre, H. *Tetrahedron.* 1994, 50, 8885–8927.) Direct stereospecific epoxidation of alkenes by monooxygenases (e.g. cytochromes P450s or other monooxygenases) has been reported. (Archelas, A.; Furstoss, R. *Top. Curr. Chem.* 1999, 200, 159–191.) These enzyme-catalyzed reactions often give high enantiomeric excesses, but with low yields. Epoxides may be produced indirectly from alkenes by haloperoxidases, via initial halohydrin formation and subsequent ring closure. (Besse, Pl; Veschambre, H. *Tetrahedron.* 1994, 50, 8885–8927.) Although these enzymes possess great potential for use in the synthesis of enantiopure epoxides, there are also severe limitations for their industrial applications as they all require cofactors, have complex, multi-component structures and generally are not very stable. These limitations pose significant challenges for both the discovery of these enzymes and the development of large-scale industrial biocatalytic applications.

The clear potential demonstrated by the microbial EHs has prompted researchers to explore their use in preparative scale synthesis of epoxides and diols. Shown in Scheme 8 are representative examples in which multi-grams of epoxides and/or diols were made with high ee values. (Choi, et al., *Appl. Microbiol. Biotechnol.* 1999, 53, 7–11; Guerard, et al., *J. Eur. J. Org. Chem.* 1999, 3399–3402; Goswami, et al., *Tetrahedron: Asymmetry* 1999, 10, 3167–3175; Cleij, M.; Archelas, A.; Furstoss, R. *Tetrahedron: Asymmetry* 1998, 9, 1839–1842; and Genzel, Y.; Archelas, A.; Broxterman, Q. B.; Furstoss, R. *Tetrahedron: Asymmetry* 2000, 11, 3041–3044.) However, several obstacles must be overcome before a broad industrial platform for EH catalyzed synthesis of epoxides and diols can be realized. First, the number of enzymes available is still small and those that have shown promise in synthetic applications are even more rare. Current discovery of new EHs through screening available strains is hampered by limited culture collections and the lack of powerful screening assays. Secondly, the available enzymes have limited substrate scope and are selective for only one enantiomer as their substrate. For example, *A. niger* EH prefers styrene-oxide types of substrates, and hydrolyzes R-enantiomers in all the transformations in FIG. 5. Lastly, in most of these preparations, high concentrations of enzymes (either whole cells or crude extract) and rather low substrate concentrations had to be used because of the enzymes' low catalytic efficiency.

Novel EHs need to be discovered to offer complementary enantioselectivity (for example, those that recognize S-enantiomers). EHs suitable for large-scale preparation of different types of epoxides also need to be discovered. Equally important is to improve the stereoselectivity and activity of the existing and new EHs using protein engineering technologies.

SUMMARY

The invention provides isolated or recombinant nucleic acids comprising a nucleic acid sequence having at least 50% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the nucleic acid encodes at least one polypeptide having an epoxide hydrolase activity, and the sequence identities are determined by analysis with a sequence comparison algorithm or by a visual inspection.

In alternative aspects, the isolated or recombinant nucleic acids comprise a nucleic acid sequence having at least 50%, 55%, 60%, 65%, 70%, 75%, 80%, 85%, 90%, 95%, 98%, 99%, or more sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 50, 100, 150, 200, 250, 300, 350, 400, 450, 500, 550, 600, 650, 700, 750, 800, 850, 900, 950, 1000, 1050, 1100, 1200, 1300, 1400, or more residues, a nucleic acid sequence having at least 60%, 65%, 70%, 75%, 80%, 85%, 90%, 95%, 98%, 99%, or more sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 50, 100, 150, 200, 250, 300, 350, 400, 450, 500, 550, 600, 650, 700, 750, 800, 850, 900, 950, 1000, 1050, 1100, 1200, 1300, 1400, or more residues, or, a nucleic acid sequence having at least 70%, 75%, 80%, 85%, 90%, 95%, 98%, 99%, or more sequence identity to SEQ ID NO:25, or SEQ ID NO:37 over a region of at least about 100, 150, 200, 250, 300, 350, 400, 450, 500, 550, 600, 650, 700, 750, 800, 850, 900, 950, 1000, 1050, 1100, 1200, 1300, 1400, or more residues.

In one aspect, the isolated or recombinant nucleic acid comprises a nucleic acid sequence having at least 99% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues.

In one aspect, the isolated or recombinant nucleic acid comprises a nucleic acid having a sequence as set forth in SEQ ID NO:1, a nucleic acid having a sequence as set forth in SEQ ID NO:3, a nucleic acid having a sequence as set forth in SEQ ID NO:5, a nucleic acid having a sequence as set forth in SEQ ID NO:7, a nucleic acid having a sequence as set forth in SEQ ID NO:9, a nucleic acid having a sequence as set forth in SEQ ID NO:11, a nucleic acid having a sequence as set forth in SEQ ID NO:13, a nucleic acid having a sequence as set forth in SEQ ID NO:15, a nucleic acid having a sequence as set forth in SEQ ID NO:17, a nucleic acid having a sequence as set forth in SEQ ID NO:19, a nucleic acid having a sequence as set forth in SEQ ID NO:21, a nucleic acid having a sequence as set forth in SEQ ID NO:23, a nucleic acid having a sequence as set forth in SEQ ID NO:25, a nucleic acid having a sequence as set forth in SEQ ID NO:27, a nucleic acid having a sequence as set forth in SEQ ID NO:29, a nucleic acid having a sequence as set forth in SEQ ID NO:31, a nucleic acid having a sequence as set forth in SEQ ID NO:33, a nucleic acid having a sequence as set forth in SEQ ID NO:35, a nucleic acid having a sequence as set forth in SEQ ID NO:37, a nucleic acid having a sequence as set forth in SEQ ID NO:39, a nucleic acid having a sequence as set forth in SEQ ID NO:41, a nucleic acid having a sequence as set forth in SEQ ID NO:43, a nucleic acid having a sequence as set forth in SEQ ID NO:45, a nucleic acid having a sequence as set forth in SEQ ID NO:47, a nucleic acid having a sequence as set forth in SEQ ID NO:49, a nucleic acid having a sequence as set forth in SEQ ID NO:51, a nucleic acid having a sequence as set forth in SEQ ID NO:53, a nucleic acid having a sequence as set forth in SEQ ID NO:55, a nucleic acid having a sequence as set forth in SEQ ID NO:57, a nucleic acid having a sequence as set forth in SEQ ID NO:59, a nucleic acid having a sequence as set forth in SEQ ID NO:61, a nucleic acid having a sequence as set forth in SEQ ID NO:63, a nucleic acid having a sequence as set forth in SEQ ID NO:65, a nucleic acid having a sequence as set forth in SEQ ID NO:67, a nucleic acid having a sequence as set forth in SEQ ID NO:69, a nucleic acid having a sequence as set forth in SEQ ID NO:71, a nucleic acid having a sequence as set forth in SEQ ID NO:73, a nucleic acid having a sequence as set forth in SEQ ID NO:75, a nucleic acid having a sequence as set forth in SEQ ID NO:77, or a nucleic acid having a sequence as set forth in SEQ ID NO:79.

In one aspect, the nucleic acid sequence encodes a polypeptide comprising a polypeptide having a sequence as set forth in SEQ ID NO:2, a polypeptide having a sequence as set forth in SEQ ID NO:4, a polypeptide having a sequence as set forth in SEQ ID NO:6, a polypeptide having a sequence as set forth in SEQ ID NO:8, a polypeptide having a sequence as set forth in SEQ ID NO:10, a polypeptide having a sequence as set forth in SEQ ID NO:12, a polypeptide having a sequence as set forth in SEQ ID NO:14, a polypeptide having a sequence as set forth in SEQ ID NO:16, a polypeptide having a sequence as set forth in SEQ ID NO:18, a polypeptide having a sequence as set forth in SEQ ID NO:20, a polypeptide having a sequence as set forth in SEQ ID NO:22, a polypeptide having a sequence as set forth in SEQ ID NO:24, a polypeptide having a sequence as set forth in SEQ ID NO:26, a polypeptide having a sequence as set forth in SEQ ID NO:28, a polypeptide having a sequence as set forth in SEQ ID NO:30, a polypeptide having a sequence as set forth in SEQ ID NO:32, a polypeptide having a sequence as set forth in SEQ ID NO:34, a polypeptide having a sequence as set forth in SEQ ID NO:36, a polypeptide having a sequence as set forth in SEQ ID NO:38, a polypeptide having a sequence as set forth in SEQ ID NO:40, a polypeptide having a sequence as set forth in SEQ ID NO:42, a polypeptide having a sequence as set forth in SEQ ID NO:44, a polypeptide having a sequence as set forth in SEQ ID NO:46, a polypeptide having a sequence as set forth in SEQ ID NO:48, a polypeptide having a sequence as set forth in SEQ ID NO:50, a polypeptide having a sequence as set forth in SEQ ID NO:52, a polypeptide having a sequence as set forth in SEQ ID NO:54, a polypeptide having a sequence as set forth in SEQ ID NO:56, a polypeptide having a sequence as set forth in SEQ ID NO:58, a polypeptide having a sequence as set forth in SEQ ID NO:60, a polypeptide having a sequence as set forth in SEQ ID NO:62, a polypeptide having a sequence as set forth in SEQ ID NO:64, a polypeptide having a sequence as set forth in SEQ ID NO:66, a polypeptide having a sequence as set forth in SEQ ID NO:68, a polypeptide having a sequence as set forth in SEQ ID NO:70, a polypeptide having a sequence as set forth in SEQ ID NO:72, a polypeptide having a sequence as set forth in SEQ ID NO:74, a polypeptide having a sequence as set forth in SEQ ID NO:76, a polypeptide having a sequence as set forth in SEQ ID NO:78, or a polypeptide having a sequence as set forth in SEQ ID NO:80.

In one aspect, the sequence comparison algorithm is a BLAST version 2.2.2 algorithm where a filtering setting is set to blastall-p blastp-d "nr pataa" -F F, and all other options are set to default.

In one aspect, the epoxide hydrolase activity comprises catalyzing the addition of water to an oxirane compound. The epoxide hydrolase activity can further comprise formation of a corresponding diol. The epoxide hydrolase activity can further comprise formation of an enantiomerically enriched epoxide. The oxirane compound can comprise an epoxide or arene oxide. The oxirane compound or the corresponding diol can be optically active. In one aspect, the oxirane compound or the corresponding diol is enantiomerically pure. The epoxide hydrolase activity can be enantioselective.

In one aspect, the epoxide hydrolase activity is thermostable. The polypeptide can retain an epoxide hydrolase activity under conditions comprising a temperature range of between about 37° C. to about 70° C. In one aspect, the epoxide hydrolase activity is thermotolerant. The polypeptide can retain an epoxide hydrolase activity after exposure to a temperature in the range from greater than 37° C. to about 90° C. In one aspect, the polypeptide retains an epoxide hydrolase activity after exposure to a temperature in the range from greater than 37° C. to about 50° C.

The invention provides an isolated or recombinant nucleic acid, wherein the nucleic acid comprises a sequence that hybridizes under stringent conditions to a nucleic acid comprising a sequence as set forth in SEQ ID NO:1, a sequence as set forth in SEQ ID NO:3, a sequence as set forth in SEQ ID NO:5, a sequence as set forth in SEQ ID NO:7, a sequence as set forth in SEQ ID NO:9, a sequence as set forth in SEQ ID NO:11, a sequence as set forth in SEQ ID NO:13, a sequence as set forth in SEQ ID NO:15, a sequence as set forth in SEQ ID NO:17, a sequence as set forth in SEQ ID NO:19, a sequence as set forth in SEQ ID NO:21, a sequence as set forth in SEQ ID NO:23, a sequence as set forth in SEQ ID NO:25, a sequence as set forth in SEQ ID NO:27, a sequence as set forth in SEQ ID NO:29, a sequence as set forth in SEQ ID NO:31, a sequence as set forth in SEQ ID NO:33, a sequence as set forth in SEQ ID NO:35, a sequence as set forth in SEQ ID NO:37, a sequence as set forth in SEQ ID NO:39, a sequence as set forth in SEQ ID NO:41, a sequence as set forth in SEQ ID NO:43, a sequence as set forth in SEQ ID NO:45, a sequence as set forth in SEQ ID NO:47, a sequence as set forth in SEQ ID NO:49, a sequence as set forth in SEQ ID NO:51, a sequence as set forth in SEQ ID NO:53, a sequence as set forth in SEQ ID NO:55, a sequence as set forth in SEQ ID NO:57, a sequence as set forth in SEQ ID NO:59, a sequence as set forth in SEQ ID NO:61, a sequence as set forth in SEQ ID NO:63, a sequence as set forth in SEQ ID NO:65, a sequence as set forth in SEQ ID NO:67, a sequence as set forth in SEQ ID NO:69, a sequence as set forth in SEQ ID NO:71, a sequence as set forth in SEQ ID NO:73, a sequence as set forth in SEQ ID NO:75, a sequence as set forth in SEQ ID NO:77, or a sequence as set forth in SEQ ID NO:79, wherein the nucleic acid encodes a polypeptide having an epoxide hydrolase activity. In alternative aspects, the nucleic acid is at least about 100, 150, 200, 250, 300, 350, 400, 450, 500, 550, 600, 650, 700, 750, 800, 850, 900, 950, 1000, 1050, 1100, 1200, 1300, 1400, or more residues, or, the full length of the gene or transcript. In one aspect, the stringent conditions include a wash step comprising a wash in 0.2×SSC at a temperature of about 65° C. for about 15 minutes.

The invention provides a nucleic acid probe for identifying a nucleic acid encoding a polypeptide with an epoxide hydrolase activity, wherein the probe comprises at least 10 consecutive bases of a sequence as set forth in SEQ ID NO:1, a sequence as set forth in SEQ ID NO:3, a sequence as set forth in SEQ ID NO:5, a sequence as set forth in SEQ ID NO:7, a sequence as set forth in SEQ ID NO:9, a sequence as set forth in SEQ ID NO:11, a sequence as set forth in SEQ ID NO:13, a sequence as set forth in SEQ ID NO:15, a sequence as set forth in SEQ ID NO:17, a sequence as set forth in SEQ ID NO:19, a sequence as set forth in SEQ ID NO:21, a sequence as set forth in SEQ ID NO:23, a sequence as set forth in SEQ ID NO:25, a sequence as set forth in SEQ ID NO:27, a sequence as set forth in SEQ ID NO:29, a sequence as set forth in SEQ ID NO:31, a sequence as set forth in SEQ ID NO:33, a sequence as set forth in SEQ ID NO:35, a sequence as set forth in SEQ ID NO:37, a sequence as set forth in SEQ ID NO:39, a sequence as set forth in SEQ ID NO:41, a sequence as set forth in SEQ ID NO:43, a sequence as set forth in SEQ ID NO:45, a sequence as set forth in SEQ ID NO:47, a sequence as set forth in SEQ ID NO:49, a sequence as set forth in SEQ ID NO:51, a sequence as set forth in SEQ ID NO:53, a sequence as set forth in SEQ ID NO:55, a sequence as set forth in SEQ ID NO:57, a sequence as set forth in SEQ ID NO:59, a sequence as set forth in SEQ ID NO:61, a sequence as set forth in SEQ ID NO:63, a sequence as set forth in SEQ ID NO:65, a sequence as set forth in SEQ ID NO:67, a sequence as set forth in SEQ ID NO:69, a sequence as set forth in SEQ ID NO:71, a sequence as set forth in SEQ ID NO:73, a sequence as set forth in SEQ ID NO:75, a sequence as set forth in SEQ ID NO:77, or a sequence as set forth in SEQ ID NO:79, wherein the probe identifies the nucleic acid by binding or hybridization. In alternative aspects, the probe comprises an oligonucleotide comprising at least about 10 to 50, about 20 to 60, about 30 to 70, about 40 to 80, or about 60 to 100 consecutive bases of a sequence of the invention.

The invention provides nucleic acid probes for identifying a nucleic acid encoding a polypeptide having an epoxide hydrolase activity, wherein the probe can comprise a nucleic acid of the invention, e.g., a nucleic acid sequence having at least 50% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the sequence identities are determined by analysis with a sequence comparison algorithm or by visual inspection. In alternative aspects, the probe comprises an oligonucleotide comprising at least about 10 to 50, about 20 to 60, about 30 to 70, about 40 to 80, or about 60 to 100 consecutive bases of a nucleic acid of the invention, e.g., a nucleic acid sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof.

The probe can comprise a nucleic acid sequence having at least 90%, 91%, 92%, 93%, 94%, 95%, 96%, 97%, 98%, 99%, or more sequence identity to a region of at least about 50, 100, 150, 200, 250, 300, 350, 400, 450, 500, 550, 600, 650, 700, 750, 800, 850, 900, 950, 1000, 1050, 1100, 1200, 1300, 1400, or more residues of a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof.

The invention provides an amplification primer sequence pair for amplifying a nucleic acid encoding a polypeptide having a epoxide hydrolase activity, wherein the primer pair is capable of amplifying a nucleic acid of the invention, e.g., a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof. In one aspect, each member of the amplification primer sequence pair comprises an oligonucleotide comprising at least about 10 to 50 consecutive bases of the sequence.

The invention provides methods of amplifying a nucleic acid encoding a polypeptide having an epoxide hydrolase activity comprising amplification of a template nucleic acid with an amplification primer sequence pair capable of amplifying a nucleic acid of the invention, e.g., a nucleic acid sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof.

The invention provides expression cassettes comprising a nucleic acid of the invention, e.g., a nucleic acid sequence having at least 50% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the sequence identities are determined by analysis with a sequence comparison algorithm or by a visual inspection; or, a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof.

The invention provides vectors comprising a nucleic acid of the invention, e.g., a nucleic acid sequence having at least 50% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the sequence identities are determined by analysis with a sequence comparison algorithm or by a visual inspection; or, a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof.

The invention provides cloning vehicles comprising a vector of the invention, wherein the cloning vehicle comprises a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cells comprising a vector, wherein the vector comprises a nucleic acid of the invention, e.g., a sequence having at least 50% sequence identity to SEQ ID NO:1, SEQ ID NO:3, SEQ ID NO:5, SEQ ID NO:7, SEQ ID NO:1, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the sequence identities are determined by analysis with a sequence comparison algorithm or by a visual inspection; or, a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof.

The invention provides transformed cells comprising a nucleic acid of the invention, e.g., a nucleic acid sequence having at least 50% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the sequence identities are determined by analysis with a sequence comparison algorithm or by a visual inspection; or, a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof. In one aspect, the cell is a bacterial cell, a mammalian cell, a fungal cell, a yeast cell, an insect cell or a plant cell.

The invention provides transgenic non-human animals comprising a nucleic acid of the invention, e.g., a nucleic acid sequence having at least 50% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the sequence identities are determined by analysis with a sequence comparison algorithm or by a visual inspection; or, a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof. The transgenic non-human animal can be a mouse or a rat.

The invention provides transgenic plants comprising a nucleic acid of the invention, e.g., a nucleic acid sequence having at least 50% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the sequence identities are determined by analysis with a sequence comparison algorithm or by a visual inspection; or, a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof. The plant can be a corn plant, a potato plant, a tomato plant, a wheat plant, an oilseed plant, a rapeseed plant, a soybean plant or a tobacco plant.

The invention provides transgenic seeds comprising a nucleic acid of the invention, e.g., a nucleic acid sequence having at least 50% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the sequence identities are determined by analysis with a sequence comparison algorithm or by a visual inspection; or, a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof. The transgenic seed can be a corn seed, a wheat kernel, an oilseed, a rapeseed, a soybean seed, a palm kernel, a sunflower seed, a sesame seed, a peanut or a tobacco plant seed.

The invention provides antisense oligonucleotides comprising a nucleic acid of the invention, e.g., a nucleic acid sequence complementary to or capable of hybridizing under stringent conditions to a nucleic acid sequence having at least 50% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the sequence identities are determined by analysis with a sequence comparison algorithm or by a visual inspection; or, a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof. The antisense oligonucleotide can be between about 10 to 50, about 20 to 60, about 30 to 70, about 40 to 80, or about 60 to 100 bases in length.

The invention provides methods of inhibiting the translation of an epoxide hydrolase message in a cell comprising administering to the cell or expressing in the cell an antisense oligonucleotide comprising a nucleic acid of the invention, e.g., a nucleic acid sequence complementary to or capable of hybridizing under stringent conditions to a nucleic acid comprising a nucleic acid sequence having at least 50% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the sequence identities are determined by analysis with a sequence comparison algorithm or by a visual inspection; or, a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof, a sequence as set forth in SEQ ID NO:57, or a subsequence thereof, a sequence as set forth in SEQ ID NO:59, or a subsequence thereof, a sequence as set forth in SEQ ID NO:61, or a subsequence thereof, a sequence as set forth in SEQ ID NO:63, or a subsequence thereof, a sequence as set forth in SEQ ID NO:65, or a subsequence thereof, a sequence as set forth in SEQ ID NO:67, or a subsequence thereof, a sequence as set forth in SEQ ID NO:69, or a subsequence thereof, SEQ ID NO:71, or a subsequence thereof, SEQ ID NO:73, or a subsequence thereof, SEQ ID NO:75, or a subsequence thereof, SEQ ID NO:77, or a subsequence thereof, SEQ ID NO:79, or a subsequence thereof.

The invention provides isolated or recombinant polypeptides comprising an amino acid sequence having at least 50% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:32, SEQ ID NO:34, SEQ ID NO:36, SEQ ID NO:42, SEQ ID NO:44, SEQ ID NO:46, SEQ ID NO:48, SEQ ID NO:54, SEQ ID NO:58, SEQ ID NO:60, SEQ ID NO:62, SEQ ID NO:64, SEQ ID NO:68, SEQ ID NO:70, SEQ ID NO:72, SEQ ID NO:74, SEQ ID NO:76, SEQ ID NO:78, or SEQ ID NO:80 over a region of at least about 100 residues, an amino acid sequence having at least 60% identity to SEQ ID NO:10, SEQ ID NO:24, SEQ ID NO:28, SEQ ID NO:30, SEQ ID NO:40, SEQ ID NO:50, SEQ ID NO:52, SEQ ID NO:56, or SEQ ID NO:66 over a region of at least about 100 residues, an amino acid sequence having at least 70 identity to SEQ ID NO:26, or SEQ ID NO:38 over a region of at least about 100 residues, or a polypeptide encoded by nucleic acid of the invention, e.g., a nucleic acid comprising (i) a nucleic acid sequence having at least 50% sequence identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:31, SEQ ID NO:33, SEQ ID NO:35, SEQ ID NO:41, SEQ ID NO:43, SEQ ID NO:45, SEQ ID NO:47, SEQ ID NO:53, SEQ ID NO:57, SEQ ID NO:59, SEQ ID NO:61, SEQ ID NO:63, SEQ ID NO:67, SEQ ID NO:69, SEQ ID NO:71, SEQ ID NO:73, SEQ ID NO:75, SEQ ID NO:77, or SEQ ID NO:79 over a region of at least about 100 residues, a nucleic acid sequence having at least 60% sequence identity to SEQ ID NO:9, SEQ ID NO:23, SEQ ID NO:27, SEQ ID NO:29, SEQ ID NO:39, SEQ ID NO:49, SEQ ID NO:51, SEQ ID NO:55, or SEQ ID NO:65 over a region of at least about 100 residues, or a nucleic acid sequence having at least 70% sequence identity to SEQ ID NO:25, or SEQ ID NO:37 over a region of at least about 100 residues, wherein the sequence identities are determined by analysis with a sequence comparison algorithm or by a visual inspection; or, (ii) a nucleic acid that hybridizes under stringent conditions to a nucleic acid of the invention.

In one aspect, the polypeptide has an epoxide hydrolase activity. The epoxide hydrolase activity can comprise catalyzing the addition of water to an oxirane compound. The epoxide hydrolase activity can further comprise formation of a corresponding diol. The epoxide hydrolase activity can further comprise formation of an enantiomerically enriched epoxide. The oxirane compound can comprise an epoxide or arene oxide. The oxirane compound or the corresponding diol can be optically active.

In one aspect, the oxirane compound or the corresponding diol is enantiomerically pure. The epoxide hydrolase activity can be enantioselective. The epoxide hydrolase activity can comprise hydrolyzing a mono-substituted, 2,2-disubstituted, 2,3-disubstituted, trisubstituted epoxide or a styrene-oxide.

In one aspect, the epoxide hydrolase activity is thermostable. The polypeptide can retain an epoxide hydrolase activity under conditions comprising a temperature range of between about 37° C. to about 70° C. The epoxide hydrolase activity can be thermotolerant. The polypeptide can retain an epoxide hydrolase activity after exposure to a temperature in the range from greater than 37° C. to about 90° C. The polypeptide can retain an epoxide hydrolase activity after exposure to a temperature in the range from greater than 37° C. to about 50° C.

In alternative aspects, the polypeptide comprises an amino acid sequence having at least 50%, 55%, 60%, 65%, 70%, 75%, 80%, 85%, 90%, 95%, 98%, 99%, or more identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:32, SEQ ID NO:34, SEQ ID NO:36, SEQ ID NO:42, SEQ ID NO:44, SEQ ID NO:46, SEQ ID NO:48, SEQ ID NO:54, SEQ ID NO:58, SEQ ID NO:60, SEQ ID NO:62, SEQ ID NO:64, SEQ ID NO:68, SEQ ID NO:70, SEQ ID NO:72, SEQ ID NO:74, SEQ ID NO:76, SEQ ID NO:78, or SEQ ID NO:80 over a region of at least about 50, 100, 150, 200, 250, 300, 350, 400, 450, 500, 550, 600, 650, 700, 750, 800, 850, 900, 950, 1000 or more residues, an amino acid sequence having at least 60%, 65%, 70%, 75%, 80%, 85%, 90%, 95%, 98%, 99%, or more identity to SEQ ID NO:10, SEQ ID NO:24, SEQ ID NO:28, SEQ ID NO:30, SEQ ID NO:40, SEQ ID NO:50, SEQ ID NO:52, SEQ ID NO:56, or SEQ ID NO:66 over a region of at least about 50, 100, 150, 200, 250, 300, 350, 400, 450, 500, or more residues, or an amino acid sequence having at least about 70%, 75%, 80%, 85%, 90%, 95%, 98%, 99%, or more identity to SEQ ID NO:26, or SEQ ID NO:38 over a region of at least about 50, 100, 150, 200, 250, 300, 350, 400, 450, 500, 550, 600, 650, 700, 750, 800, 850, 900, 950, 1000 or more residues.

The invention provides isolated or recombinant polypeptides, wherein the polypeptide comprises an amino acid sequence as set forth in SEQ ID NO:2, an amino acid sequence as set forth in SEQ ID NO:4, an amino acid sequence as set forth in SEQ ID NO:6, an amino acid sequence as set forth in SEQ ID NO:8, an amino acid sequence as set forth in SEQ ID NO:10, an amino acid sequence as set forth in SEQ ID NO:12, an amino acid sequence as set forth in SEQ ID NO:14, an amino acid sequence as set forth in SEQ ID NO:16, an amino acid sequence as set forth in SEQ ID NO:18, an amino acid sequence as set forth in SEQ ID NO:20, an amino acid sequence as set forth in SEQ ID NO:22, an amino acid sequence as set forth in SEQ ID NO:24, an amino acid sequence as set forth in SEQ ID NO:26, an amino acid sequence as set forth in SEQ ID NO:28, an amino acid sequence as set forth in SEQ ID NO:30, an amino acid sequence as set forth in SEQ ID NO:32, an amino acid sequence as set forth in SEQ ID NO:34, an amino acid sequence as set forth in SEQ ID NO:36, an amino acid sequence as set forth in SEQ ID NO:38, an amino acid sequence as set forth in SEQ ID NO:40, an amino acid sequence as set forth in SEQ ID NO:42, an amino acid sequence as set forth in SEQ ID NO:44, an amino acid sequence as set forth in SEQ ID NO:46, an amino acid sequence as set forth in SEQ ID NO:48, an amino acid sequence as set forth in SEQ ID NO:50, an amino acid sequence as set forth in SEQ ID NO:52, an amino acid sequence as set forth in SEQ ID NO:54, an amino acid sequence as set forth in SEQ ID NO:56, an amino acid sequence as set forth in SEQ ID NO:58, an amino acid sequence as set forth in SEQ ID NO:60, an amino acid sequence as set forth in SEQ ID NO:62, an amino acid sequence as set forth in SEQ ID NO:64, an amino acid sequence as set forth in SEQ ID NO:66, an amino acid sequence as set forth in SEQ ID NO:68, an amino acid sequence as set forth in SEQ ID NO:70, an amino acid sequence as set forth in SEQ ID NO:72, an amino acid sequence as set forth in SEQ ID NO:74, an amino acid sequence as set forth in SEQ ID NO:76, an amino acid sequence as set forth in SEQ ID NO:78, or an amino acid sequence as set forth in SEQ ID NO:80, or a subsequence thereof.

In one aspect, the isolated or recombinant polypeptide comprising the polypeptide of the invention lacks a signal sequence.

In one aspect, the epoxide hydrolase activity comprises a specific activity at about 37° C. in the range from about 100 to about 1000 units per milligram of protein. In another aspect, the epoxide hydrolase activity comprises a specific activity from about 500 to about 1200 units per milligram of protein. Alternatively, the epoxide hydrolase activity comprises a specific activity at 37° C. in the range from about 500 to about 1000 units per milligram of protein. In one aspect, the epoxide hydrolase activity comprises a specific activity at 37° C. in the range from about 750 to about 1000 units per milligram of protein.

The invention provides the isolated or recombinant polypeptide, wherein the thermotolerance comprises retention of at least half of the specific activity of the epoxide hydrolase at 37° C. after being heated to the elevated temperature. In one aspect, the thermotolerance comprises retention of specific activity at 37° C. in the range from about 500 to about 1200 units per milligram of protein after being heated to the elevated temperature.

The invention provides the polypeptide of the invention, wherein the polypeptide comprises at least one glycosylation site. In one aspect, glycosylation can be an N-linked glycosylation. In one aspect, the epoxide hydrolase is glycosylated after being expressed in a P. pastoris or a S. pombe.

In one aspect, the polypeptide can retain an epoxide hydrolase activity under conditions comprising about pH 4.5 or pH 5. Alternatively, the polypeptide can retain an epoxide hydrolase activity under conditions comprising about pH 9.0, pH 9.5, or pH 10.

The invention provides protein preparations comprising a polypeptide of the invention, wherein the protein preparation comprises a liquid, a solid or a gel.

The invention provides heterodimers comprising a polypeptide of the invention and a second domain. In one aspect, the second domain is a polypeptide and the heterodimer is a fusion protein. In one aspect, the second domain can be an epitope or a tag.

The invention provides immobilized polypeptide having an epoxide hydrolase activity, wherein the polypeptide comprises a polypeptide of the invention or a polypeptide encoded by a nucleic acid of the invention or a polypeptide comprising a polypeptide of the invention and a second domain. The polypeptide can be immobilized on a cell, a metal, a resin, a polymer, a ceramic, a glass, a microelectrode, a graphitic particle, a bead, a gel, a plate, an array or a capillary tube.

The invention provides arrays comprising an immobilized polypeptide, wherein the polypeptide comprises a polypeptide of the invention or a polypeptide encoded by a nucleic acid of the invention or a polypeptide comprising a polypeptide of the invention and a second domain.

The invention provides arrays comprising an immobilized nucleic acid of the invention. The invention provides arrays comprising an antibody of the invention.

The invention provides isolated or recombinant antibodies that specifically binds to a polypeptide of the invention or to a polypeptide encoded by a nucleic acid of the invention. The antibody can be a monoclonal or a polyclonal antibody. The invention provides hybridomas comprising an antibody that specifically binds to a polypeptide of the invention or to a polypeptide encoded by a nucleic acid of the invention.

The invention provides methods of isolating or identifying a polypeptide with epoxide hydrolase activity comprising the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying a polypeptide having an epoxide hydrolase activity.

The invention provides methods of making an anti-epoxide hydrolase antibody comprising administering to a non-human animal a nucleic acid of the invention, or a polypeptide of the invention, in an amount sufficient to generate a humoral immune response, thereby making an anti-epoxide hydrolase antibody.

The invention provides methods of producing a recombinant polypeptide comprising the steps of: (a) providing a nucleic acid of the invention operably linked to a promoter; and (b) expressing the nucleic acid of step (a) under conditions that allow expression of the polypeptide, thereby producing a recombinant polypeptide. In one aspect, the method can further comprise transforming a host cell with the nucleic acid of step (a) followed by expressing the nucleic acid of step (a), thereby producing a recombinant polypeptide in a transformed cell.

The invention provides methods for identifying a polypeptide having an epoxide hydrolase activity comprising the following steps: (a) providing a polypeptide of the invention or a polypeptide encoded by a nucleic acid of the invention; (b) providing an epoxide hydrolase substrate; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide having an epoxide hydrolase activity. In one aspect, the substrate can be an epoxide.

The invention provides methods for identifying an epoxide hydrolase substrate comprising the following steps: (a) providing a polypeptide of the invention or a polypeptide encoded by a nucleic acid of the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as an epoxide hydrolase substrate.

The invention provides methods of determining whether a test compound specifically binds to a polypeptide comprising the following steps: (a) expressing a nucleic acid or a vector comprising the nucleic acid under conditions permissive for translation of the nucleic acid to a polypeptide, wherein the nucleic acid comprises a nucleic acid of the invention, or, providing a polypeptide of the invention; (b) providing a test compound; (c) contacting the polypeptide with the test compound; and (d) determining whether the test compound of step (b) specifically binds to the polypeptide.

The invention provides methods for identifying a modulator of an epoxide hydrolase activity comprising the following steps: (a) providing a polypeptide of the invention or a polypeptide encoded by a nucleic acid of the invention; (b) providing a test compound; (c) contacting the polypeptide of step (a) with the test compound of step (b) and measuring an activity of the epoxide hydrolase, wherein a change in the epoxide hydrolase activity measured in the presence of the test compound compared to the activity in the absence of the test compound provides a determination that the test compound modulates the epoxide hydrolase activity. In one aspect, the epoxide hydrolase activity is measured by providing an epoxide hydrolase substrate and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of the epoxide hydrolase activity. An increase in the amount of the substrate or a decrease in the amount of the reaction product with the test compound as compared to the amount of substrate or reaction product without the test compound identifies the test compound as an inhibitor of the epoxide hydrolase activity.

The invention provides computer systems comprising a processor and a data storage device wherein said data storage device has stored thereon a polypeptide sequence or a nucleic acid sequence, wherein the polypeptide sequence comprises a polypeptide of the invention, or subsequence thereof, and the nucleic acid comprises a nucleic acid of the invention. In one aspect, the computer system can further comprise a sequence comparison algorithm and a data storage device having at least one reference sequence stored thereon. In one aspect, the sequence comparison algorithm comprises a computer program that indicates polymorphisms. In another aspect, the computer system can further comprise an identifier that identifies one or more features in said sequence.

The invention provides computer readable media having stored thereon a polypeptide sequence or a nucleic acid sequence, wherein the polypeptide sequence comprises a polypeptide of the invention, or subsequence thereof, and the nucleic acid comprises a nucleic acid of the invention, or subsequence thereof.

The invention provides methods for identifying a feature in a sequence comprising the steps of: (a) reading the sequence using a computer program which identifies one or more features in a sequence, wherein the sequence comprises a polypeptide sequence or a nucleic acid sequence, wherein the polypeptide sequence comprises a polypeptide of the invention or subsequence thereof, and the nucleic acid comprises a nucleic acid of the invention or subsequence thereof; and (b) identifying one or more features in the sequence with the computer program.

The invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence, wherein the polypeptide sequence comprises a polypeptide of the invention, or subsequence thereof, and the nucleic acid comprises a nucleic acid of the invention or subsequence thereof; and (b) determining differences between the first sequence and the second sequence with the computer program. In one aspect, the step of determining differences between the first sequence and the second sequence further comprises the step of identifying polymorphisms. In one aspect, the method can further comprise an identifier that identifies one or more features in a sequence. In another aspect, the method can further comprise reading the first sequence using a computer program and identifying one or more features in the sequence.

The invention provides methods for isolating or recovering a nucleic acid encoding a polypeptide with an epoxide hydrolase activity from an environmental sample comprising the steps of: (a) providing an amplification primer sequence pair for amplifying a nucleic acid encoding a polypeptide with an epoxide hydrolase activity, wherein the primer pair is capable of amplifying SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, or a subsequence thereof; (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide with an epoxide hydrolase activity from an environmental sample. In one aspect, one and each member of the amplification primer sequence pair comprises an oligonucleotide comprising at least about 10 to 50 consecutive bases of a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or a subsequence thereof.

The invention provides methods for isolating or recovering a nucleic acid encoding a polypeptide with a epoxide hydrolase activity from an environmental sample comprising the steps of: (a) providing a polynucleotide probe comprising a nucleic acid of the invention, or a subsequence thereof; (b) isolating a nucleic acid from the environmental sample or treating the environmental sample such that nucleic acid in the sample is accessible for hybridization to a polynucleotide probe of step (a); (c) combining the isolated nucleic acid or the treated environmental sample of step (b) with the polynucleotide probe of step (a); and (d) isolating a nucleic acid that specifically hybridizes with the polynucleotide probe of step (a), thereby isolating or recovering a nucleic acid encoding a polypeptide with an epoxide hydrolase activity from an environmental sample. In one aspect, the environmental sample comprises a water sample, a liquid sample, a soil sample, an air sample or a biological sample. The biological sample can be derived from a bacterial cell, a protozoan cell, an insect cell, a yeast cell, a plant cell, a fungal cell or a mammalian cell.

The invention provides methods of generating a variant of a nucleic acid encoding a polypeptide with an epoxide hydrolase activity comprising the steps of: (a) providing a template nucleic acid comprising a nucleic acid of the invention; and (b) modifying, deleting or adding one or more nucleotides in the template sequence, or a combination thereof, to generate a variant of the template nucleic acid. In one aspect, the method can further comprise expressing the variant nucleic acid to generate a variant epoxide hydrolase polypeptide.

In one aspect, the modifications, additions or deletions are introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis™ (GSSM™), synthetic ligation reassembly (SLR) and a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until an epoxide hydrolase having an altered or different activity or an altered or different stability from that of a polypeptide encoded by the template nucleic acid is produced. In one aspect, the variant epoxide hydrolase polypeptide can be thermotolerant, and retains some activity after being exposed to an elevated temperature. In another aspect, the variant epoxide hydrolase polypeptide has increased glycosylation as compared to the epoxide hydrolase encoded by a template nucleic acid. Alternatively, the variant epoxide hydrolase polypeptide has an epoxide hydrolase activity under a high temperature, wherein the epoxide hydrolase. encoded by the template nucleic acid is not active under the high temperature. In one aspect, the method is iteratively repeated until an epoxide hydrolase coding sequence having an altered codon usage from that of the template nucleic acid is produced. In another aspect, the method is iteratively repeated until an epoxide hydrolase gene having higher or lower level of message expression or stability from that of the template nucleic acid is produced.

The invention provides methods for modifying codons in a nucleic acid encoding a polypeptide with a epoxide hydrolase activity to increase its expression in a host cell, the method comprising the following steps: (a) providing a nucleic acid encoding a polypeptide with a epoxide hydrolase activity comprising a nucleic acid of the invention; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding an epoxide hydrolase polypeptide, the method comprising the following steps: (a) providing a nucleic acid encoding a polypeptide with an epoxide hydrolase activity comprising a nucleic acid of the invention; and, (b) identifying a codon in the nucleic acid of step (a) and replacing it with a different codon encoding the same amino acid as the replaced codon, thereby modifying codons in a nucleic acid encoding an epoxide hydrolase.

The invention provides methods for modifying codons in a nucleic acid encoding a epoxide hydrolase polypeptide to increase its expression in a host cell, the method comprising the following steps: (a) providing a nucleic acid encoding an epoxide hydrolase polypeptide comprising a nucleic acid of the invention; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having an epoxide hydrolase activity to decrease its expression in a host cell, the method comprising the following steps: (a) providing a nucleic acid encoding an epoxide hydrolase polypeptide comprising a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In one aspect, the host cell can be a bacterial cell, a fungal cell, an insect cell, a yeast cell, a plant cell or a mammalian cell.

The invention provides methods for producing a library of nucleic acids encoding a plurality of modified epoxide hydrolase active sites or substrate binding sites, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or a subsequence thereof, and the nucleic acid encodes a epoxide hydrolase active site or an epoxide hydrolase substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified epoxide hydrolase active sites or substrate binding sites. In one aspect, the method can further comprise mutagenizing the first nucleic acid of step (a) by a method comprising an optimized directed evolution system, Gene Site Saturation Mutagenesis™ (GSSM™), a synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, or a combination thereof. In another aspect, the method can further comprise mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising the following steps: (a) providing a plurality of biosynthetic enzymes capable of synthesizing or modifying a small molecule, wherein one of the enzymes comprises an epoxide hydrolase enzyme encoded by a nucleic acid comprising a nucleic acid of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions.

The invention provides methods for modifying a small molecule comprising the following steps: (a) providing an epoxide hydrolase enzyme, wherein the enzyme comprises a polypeptide of the invention, or, is encoded by a nucleic acid of the invention; (b) providing a small molecule; and (c) reacting the enzyme of step (a) with the small molecule of step (b) under conditions that facilitate an enzymatic reaction catalyzed by the epoxide hydrolase enzyme, thereby modifying a small molecule by an epoxide hydrolase enzymatic reaction. In one aspect, the method can further comprise a plurality of small molecule substrates for the enzyme of step (a), thereby generating a library of modified small molecules produced by at least one enzymatic reaction catalyzed by the epoxide hydrolase enzyme. In one aspect, the method can further comprise a plurality of additional enzymes under conditions that facilitate a plurality of biocatalytic reactions by the enzymes to form a library of modified small molecules produced by the plurality of enzymatic reactions. In one aspect, the method can comprise the step of testing the library to determine if a particular modified small molecule which exhibits a desired activity is present within the library. The step of testing the library can comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of an epoxide hydrolase enzyme comprising the steps of: (a) providing an epoxide hydrolase enzyme, wherein the enzyme comprises a polypeptide of the invention, or, is encoded by a nucleic acid of the invention; and (b) deleting a plurality of amino acid residues from the sequence of step (a) and testing the remaining subsequence for an epoxide hydrolase activity, thereby determining a functional fragment of an epoxide hydrolase enzyme. In one aspect, the epoxide hydrolase activity can be measured by providing an epoxide hydrolase substrate and detecting a decrease in the amount of the substrate or an increase in the amount of a reaction product.

The invention provides methods for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In one aspect, the genetic composition of the cell is modified by a method comprising deletion of a sequence or modification of a sequence in the cell, or, knocking out the expression of a gene. In one aspect, the method can further comprise selecting a cell comprising a newly engineered phenotype. In one aspect, the method can further comprise culturing the selected cell, thereby generating a new cell strain comprising a newly engineered phenotype.

The invention provides methods for hydrolyzing an epoxide comprising the following steps: (a) providing a polypeptide having an epoxide hydrolase activity, wherein the polypeptide comprises a polypeptide of the invention, or, a polypeptide encoded by a nucleic acid of the invention; (b) providing a composition comprising an epoxide; and (c) contacting the polypeptide of step (a) with the composition of step (b) under conditions wherein the polypeptide hydrolyzes the epoxide. In one aspect, the epoxide is mono-substituted, 2,2-disubstituted, 2,3-disubstituted, trisubstituted, or a styrene oxide.

The invention provides methods for producing a chiral diol comprising the following steps: (a) providing a polypeptide having an epoxide hydrolase activity, wherein the polypeptide comprises a polypeptide of the invention, or, a polypeptide encoded by a nucleic acid of the invention; (b) providing a composition comprising a chiral epoxide; and (c) contacting the polypeptide of step (a) with the composition of step (b) under conditions wherein the polypeptide catalyzes the conversion of the chiral epoxide to the chiral diol.

The invention provides methods for producing a chiral epoxide comprising the following steps: (a) providing a polypeptide having an epoxide hydrolase activity, wherein the polypeptide a polypeptide of the invention, or, a polypeptide encoded by a nucleic acid of the invention, wherein the epoxide hydrolase activity is enantioselective or enantiospecific; (b) providing a composition comprising a racemic mixture of chiral epoxides; (c) combining the polypeptide of step (a) with the composition of step (b) under conditions wherein the enantioselective or enantiospecific polypeptide converts the epoxide substrate of the specific chirality to a diol, thereby leading to accumulation of the unreacted epoxide of the opposite chirality.

The invention provides methods of increasing thermotolerance or thermostability of an epoxide hydrolase polypeptide, the method comprising glycosylating an epoxide hydrolase polypeptide, wherein the polypeptide comprises at least thirty contiguous amino acids of a polypeptide of the invention, or a polypeptide encoded by a nucleic acid of the invention, thereby increasing the thermotolerance or thermostability of the epoxide hydrolase polypeptide. In one aspect, the epoxide hydrolase specific activity is thermostable or thermotolerant at a temperature in the range from greater than about 37° C. to about 90° C.

The invention provides methods for overexpressing a recombinant epoxide hydrolase polypeptide in a cell comprising expressing a vector comprising a nucleic acid comprising a nucleic acid sequence at least 50% sequence identity to a nucleic acid of the invention over a region of at least about 100 residues, wherein the sequence identities are determined by analysis with a sequence comparison algorithm or by visual inspection, wherein overexpression is effected by use of a high activity promoter, a dicistronic vector or by gene amplification of the vector.

The invention provides growth-based methods for selecting a cell comprising a nucleic acid encoding an epoxide hydrolase comprising the following steps: (a) providing a plurality of cells, wherein the cells lack a composition essential for growth; (b) providing a precursor or substrate, wherein the precursor or substrate is capable of being converted by an epoxide hydrolase to a composition essential for growth of the cells; (c) growing the cells in a medium lacking a carbon source essential for growth and adding the precursor or substrate of step (b); and, (d) screening the cells for growth, wherein the cells in the growth stimulated clone are identified as comprising the nucleic acid encoding an epoxide hydrolase capable of converting the precursor or substrate to the composition essential for growth, thereby selecting a cell comprising a nucleic acid encoding an epoxide hydrolase.

The invention provides growth-based methods for selecting a nucleic acid encoding an epoxide hydrolase comprising the following steps: (a) providing a nucleic acid encoding a polypeptide; (b) providing a precursor or substrate, wherein the precursor or substrate is capable of being converted by an epoxide hydrolase to a composition essential for growth of the cell; (c) providing a plurality of cells, wherein the cells cannot make the composition of step (b); (d) inserting the nucleic acid into the cells and growing the cells under conditions wherein the nucleic acid is expressed and its encoded polypeptide is translated, and the cells are grown in a medium lacking the carbon source essential for growth, and adding the precursor or substrate of step (b); and, (e) screening the cells for growth, wherein the nucleic acid in the growth stimulated clone is identified as encoding an epoxide hydrolase capable of converting the precursor or substrate to the composition comprising essential for growth, thereby selecting a nucleic acid encoding an epoxide hydrolase.

The invention provides methods for identifying a nucleic acid encoding an epoxide hydrolase comprising the following steps: (a) providing a nucleic acid library; (b) providing a precursor or substrate, wherein the precursor or substrate is capable of being converted by an epoxide hydrolase to a composition essential for growth of the cells; (c) providing a plurality of cells, wherein the cells cannot make the composition of step (b); (d) inserting in a cell a member of the gene library and culturing the cells in a medium lacking the composition essential for growth; (e) adding the precursor or substrate of step (b) to the culture; (f) selecting a growing cell and identifying the inserted library member of step (d), wherein the cell is capable of growth by enzymatic conversion of the precursor to the composition essential for growth, and the enzyme is encoded by the library member, thereby identifying a nucleic acid encoding an epoxide hydrolase.

In one aspect, the precursor or substrate comprises glycidol or propylene oxide. In one aspect, the composition essential for growth comprises glycerol or propane diol. In one aspect, the precursor or substrate comprises a pure enantiomer or a racemic mixture. The composition essential for growth can comprise a pure enantiomer or a racemic mixture. In one aspect, the nucleic acid is a member of a gene library. In one aspect, the library can be obtained from a mixed population of organisms. The mixed population of organisms is derived from a soil sample, a water sample or an air sample. In one aspect, the cells comprise *E. coli* fucA-disrupted mutant.

The invention provides methods for identifying an epoxide hydrolase comprising the following steps: (a) providing a polypeptide; (b) providing a precursor or substrate, wherein the precursor or substrate is capable of being converted by an epoxide hydrolase to a composition essential for growth of the cells; (c) providing a plurality of cells, wherein the cells cannot make the composition of step (b); (d) inserting the polypeptide into the cells and culturing the cells, and the cells are grown in a medium lacking the composition essential for growth, and adding the precursor or substrate of step (b); and, (e) screening the cells for growth, wherein the polypeptide in the growth stimulated clone is identified as being an epoxide hydrolase capable of converting the precursor or substrate to a composition essential for growth of the cells, thereby identifying an epoxide hydrolase.

The invention provides methods for identifying an epoxide hydrolase comprising the following steps: (a) providing a polypeptide library; (b) providing a precursor or substrate, wherein the precursor or substrate is capable of being converted by an epoxide hydrolase to a composition essential for growth of the cells; (c) providing a plurality of cells, wherein the cells cannot make the composition of step (b); (d) inserting in a cell a member of the polypeptide library and culturing the cells in a medium lacking the composition essential for growth; (d) adding the polypeptide library of step (a) and the precursor or substrate of step (b) to the cells of step (c); and (f) selecting a growing cell and identifying the inserted polypeptide of step (d), wherein the cell is capable of growth by enzymatic conversion of the precursor to the composition essential for growth, thereby identifying an epoxide hydrolase. In one aspect, the library is obtained from a mixed population of organisms.

The invention provides direct activity assay methods for screening for a polypeptide having an epoxide hydrolase activity comprising the following steps: (a) providing a plurality of polypeptides; (b) providing a precursor or substrate covalently linked to a fluorophore, wherein the precursor or substrate is capable of being converted by an epoxide hydrolase to a diol, wherein the fluorophore can generate a fluorescent signal when free; (c) combining the polypeptides of step (a) with the precursor or substrate of step (b) under conditions wherein the polypeptides can convert the precursor or substrate to a diol linked to the fluorophore; (d) converting the diol linked to the fluorophore of step (c) to a free fluorophore; (e) measuring the fluorescence quantum yield; and (f) screening the polypeptides for epoxide hydrolase activity, wherein the polypeptide is identified as having an epoxide hydrolase activity capable of converting the precursor or substrate to the diol as detected by an increase in the fluorescence quantum yield due to formation of the free fluorophore, thereby selecting a polypeptide having an epoxide hydrolase activity. In one aspect, the conversion of the diol linked to the fluorophore to free fluorophore further comprises the following steps: (a) subjecting the diol linked to the fluorophore of step to periodate oxidation resulting in the formation of an aldehyde linked to the fluorophore; (b) subjecting the aldehyde of step (a) to a BSA-catalyzed β-elimination resulting in the formation of the free fluorophore. In one aspect, the fluorophore can be umbellipherone.

The invention provides direct activity calorimetric methods for screening for a polypeptide having an epoxide hydrolase activity comprising the following steps: (a) providing a plurality of polypeptides; (b) providing a precursor or substrate, wherein the precursor or substrate is capable of being converted by an epoxide hydrolase to a diol, (c) providing a chemical, wherein the chemical is capable of reaction with the precursor or substrate forming a product capable of absorbance at a visible wavelength, wherein the chemical is not reactive with the diol; (d) combining the polypeptide of step (a) with the precursor or substrate of step (b) under conditions wherein the polypeptide can convert the precursor or substrate to the diol; (e) measuring a decrease of light absorbance at the wavelength characteristic for absorbance of the product linked to the precursor or substrate; and (f) screening the polypeptides for epoxide hydrolase activity, wherein the polypeptide is identified as having an epoxide hydrolase activity capable of converting the precursor or substrate to the diol as detected by a decrease in the absorbance at the characteristic wavelength due to formation of the diol, thereby selecting a polypeptide having an epoxide hydrolase activity. In one aspect, the chemical, which is capable of reaction with the precursor or substrate forming a product capable of absorbance at a visible wavelength, is 4-(p-nitrobenzyl)-pyridine.

The invention provides in vitro growth selection screens using epoxides as precursors to discover nucleic acids encoding epoxide hydrolases that produce a diol product comprising the following steps: (a) providing a nucleic acid library; (b) providing a precursor, wherein the precursor is capable of being converted to a diol; (c) providing an in vitro transcription/translation system lacking the diol; (d) adding to the in vitro transcription/translation system a member of the nucleic acid library; (e) adding the precursor of step (b); and (f) selecting a sample producing the diol and identifying the inserted nucleic acid of step (d), wherein selecting the sample comprising the precursor selects a nucleic acid encoding a corresponding epoxide hydrolase.

The invention provides in vitro growth selection screens using epoxides as precursors to discover epoxide hydrolases that produce a diol comprising the following steps: (a) providing a polypeptide library; (b) providing a precursor, wherein the precursor is capable of being converted to a diol; (c) providing an in vitro transcription/translation system lacking the diol; (d) adding to the in vitro transcription/translation system a member of the polypeptide library; (e) adding the precursor of step (b); and (f) selecting a sample producing the diol and identifying the added polypeptide of step (d), wherein selecting the sample comprising the diol selects a corresponding epoxide hydrolase.

DESCRIPTION OF DRAWINGS

FIG. 6 is a chart summary of exemplary reactions that can be used with the epoxide hydrolases of the invention.

FIG. 7 is a schematic representation of an exemplary reaction where an epoxide hydrolase of the invention is used in the desymmetrization of meso-epoxides.

Like reference symbols in the various drawings indicate like elements.

DETAILED DESCRIPTION

Figure 1:
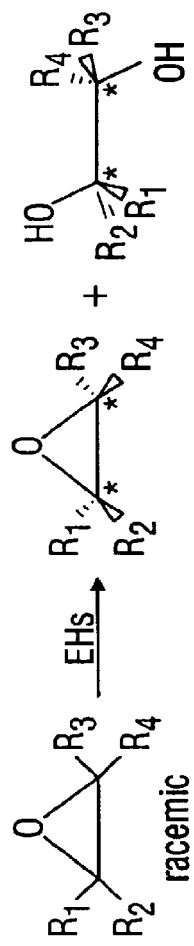
FIG. 1 is a schematic representation of the selective hydrolysis of a racemic epoxide generating the corresponding diol and the unreacted epoxides with high enantiomeric excess (ee) values.
Figure 2:
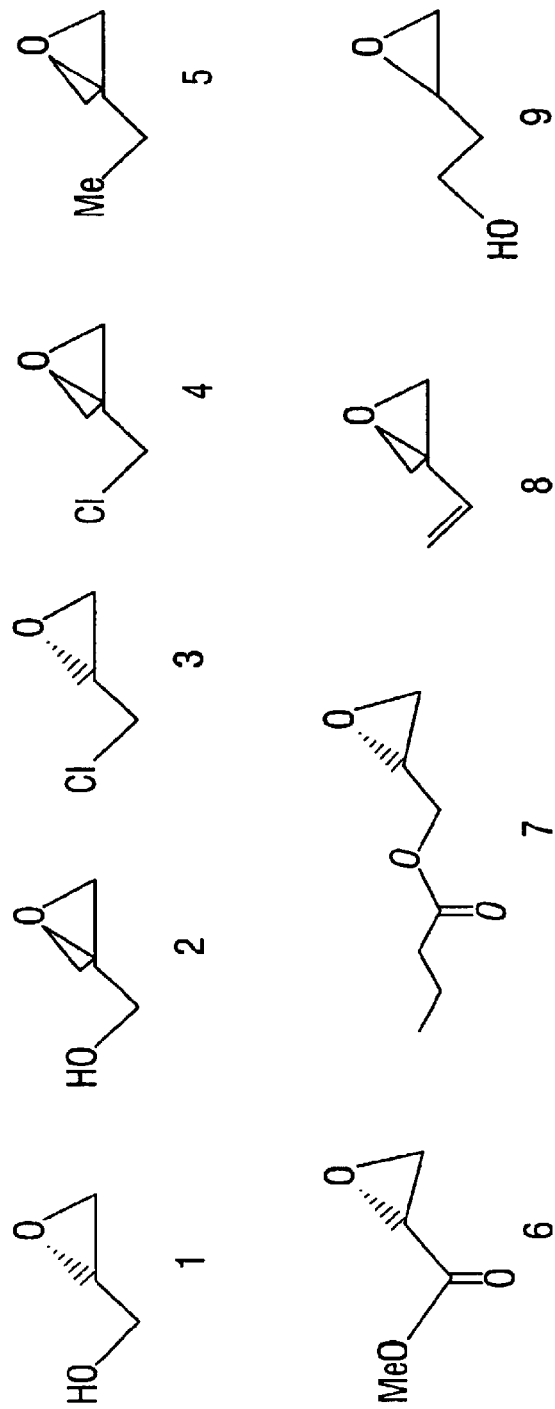
FIG. 2 is a schematic representation of glycidols, (S-(1), and R-(2)), the leading chiral epoxides among representative C-3 synthons.
Figure 3:
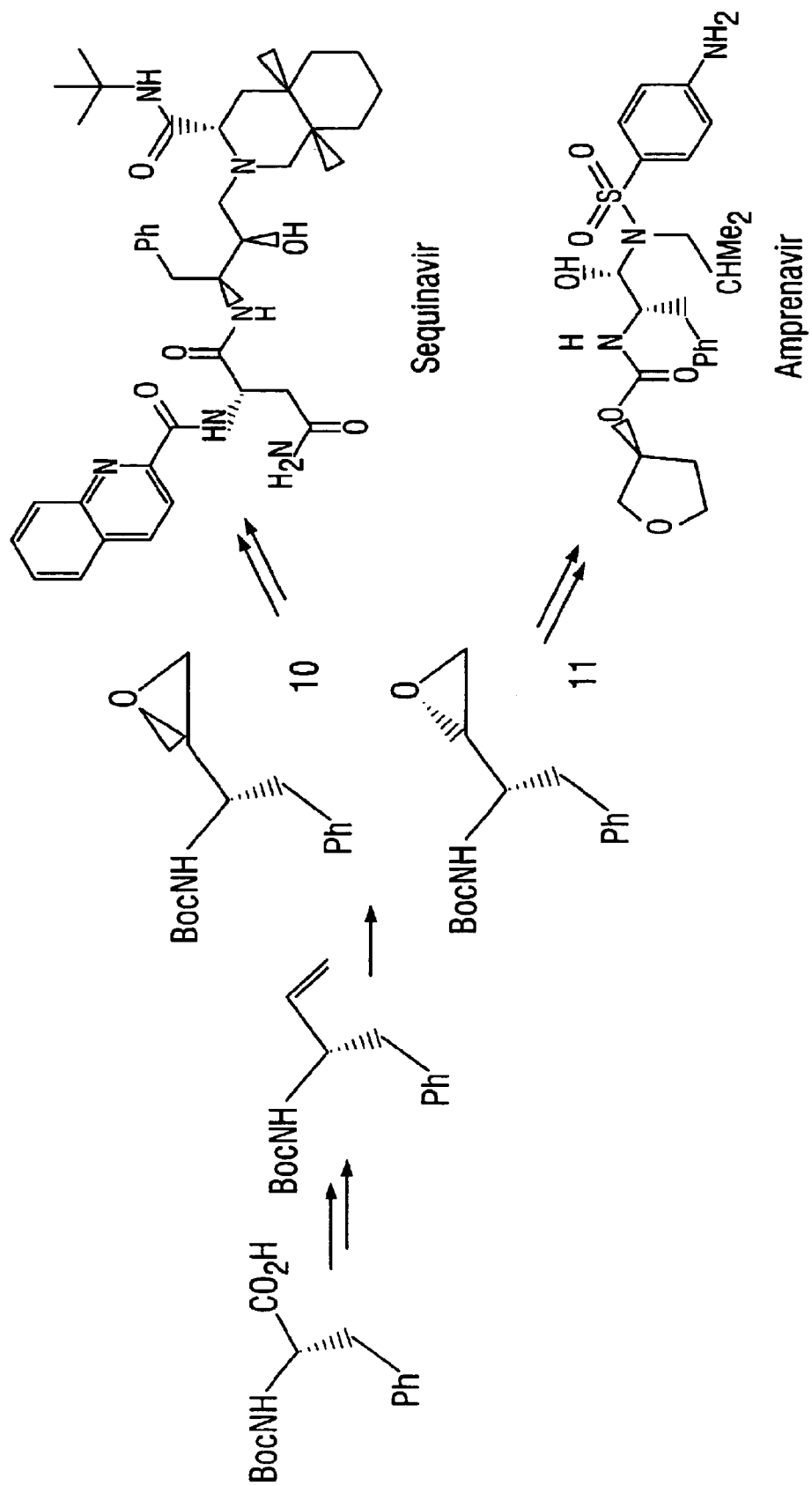
FIG. 3 is a schematic representation of the production of saquinavir, an antiviral drug and the synthesis of amprenavir, another antiviral drug.
Figure 4:
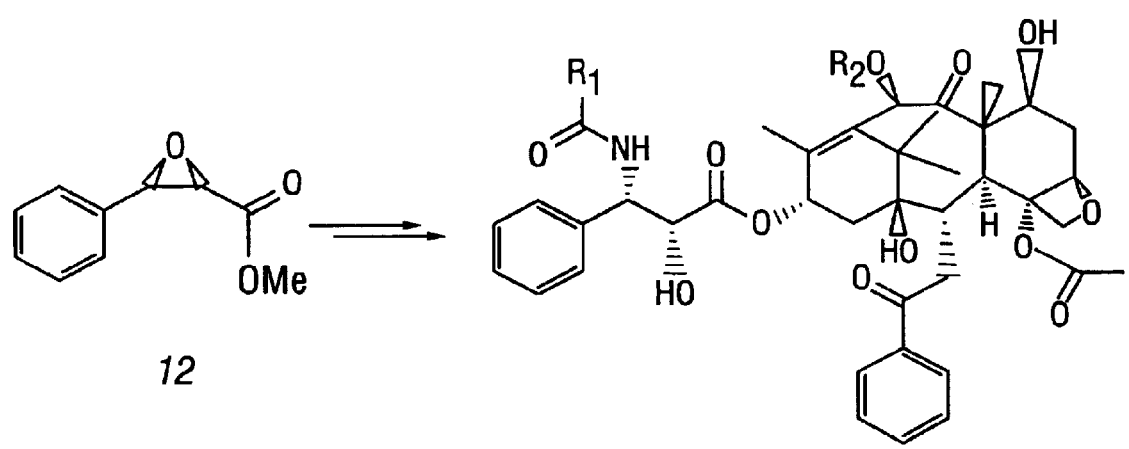
FIG. 4 is a schematic representation of the synthesis of two anticancer drugs, docetaxel and paclitaxel.
Figure 5:
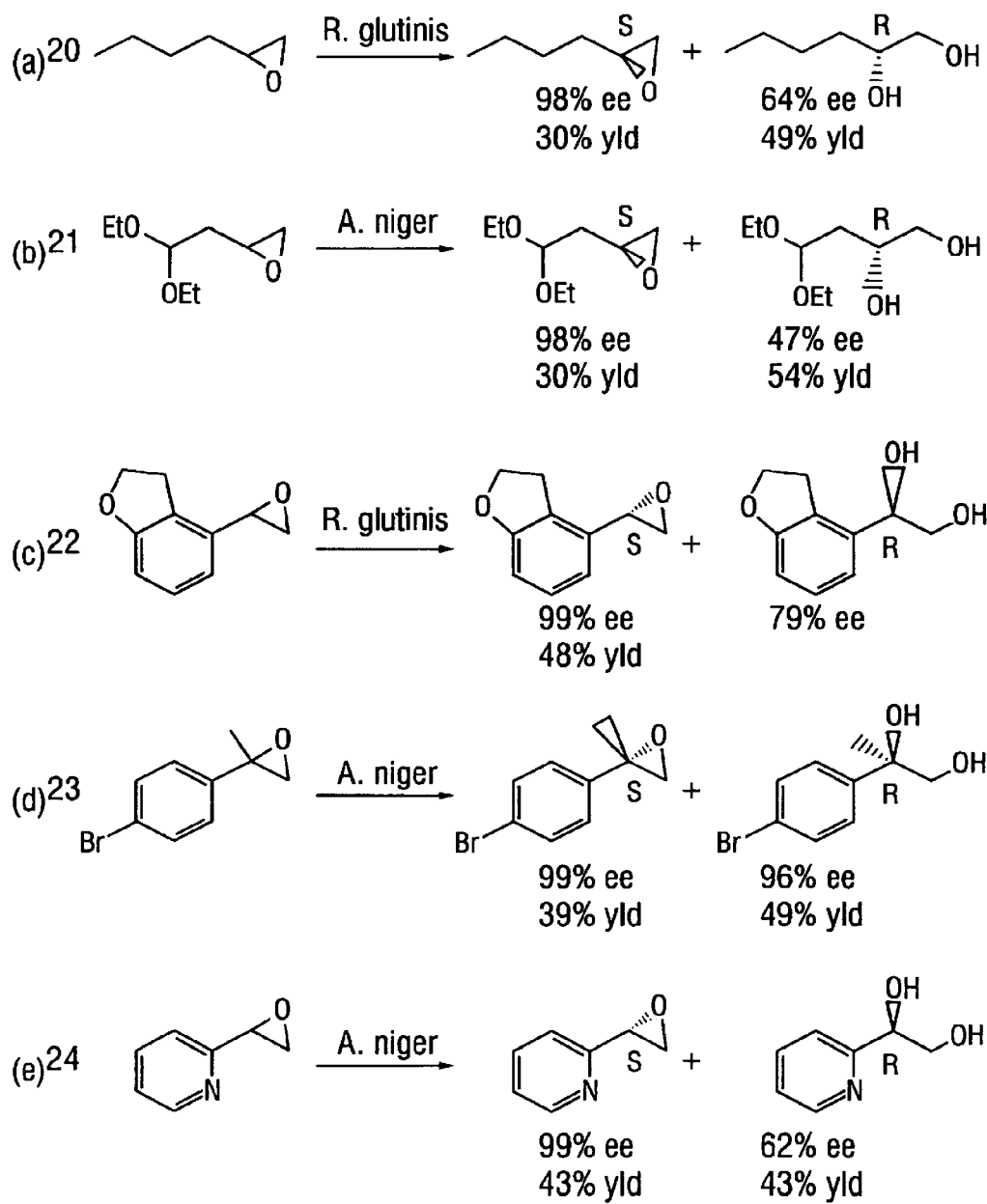
FIG. 5 is a schematic representation of hydrolysis of styrene-oxide types of substrates by *A. niger* epoxide hydrolase hydrolyzing R-enantiomers in all transformations.

The invention provides polypeptides having epoxide hydrolase activity, polynucleotides encoding the polypeptides, and methods for making and using these polynucleotides and polypeptides. The polypeptides of the invention can be used as epoxide hydrolases to catalyze the hydrolysis of epoxides and arene oxides to their corresponding diols. Epoxide hydrolases of the invention can be hydrolytic enzymes to catalyze the opening of an epoxide ring to convert a substrate to a corresponding diol. Epoxide hydrolases of the invention can be highly regio- and enantioselective, allowing the preparation of pure enantiomers. The polypeptides of the invention can be used to hydrolyze hazardous epoxide compounds generated through peroxidation in living organisms, and, to eliminate the high chemical reactivity of epoxide compounds.

The invention provides epoxide hydrolases (EHs) from wide varieties of biodiversity sources such as enzyme or gene libraries. The invention provides methods to rapidly select or screen enzymes and genes to obtain suitable EHs. The invention provides methods to access untapped biodiversity and to rapidly screen for sequences and activities of interest utilizing recombinant DNA technology. This invention combines the benefits associated with the ability to rapidly screen natural compounds with the flexibility and reproducibility afforded with working with the genetic material of organisms.

The invention provides method to synthesize useful chiral epoxides using the enzymes of the present invention. The invention provides useful chiral epoxides and their derivatives produced using the EHs of the present invention.

The epoxide hydrolases of the invention are highly versatile biocatalysts for the asymmetric hydrolysis of epoxides on a preparative scale. Besides kinetic resolution, which furnishes the corresponding vicinal diol and remaining non-hydrolyzed epoxide in nonracemic form, the epoxide hydrolases of the invention are used in enantioconvergent processes for the generation of a single enantiomeric diol from a racemic oxirane. The epoxide hydrolases of the invention can be used in the hydrolysis of highly substituted epoxides, e.g., highly substituted 2,2- and 2,3-disubstituted epoxides. The epoxide hydrolases of the invention can be used in any method known in the art, see, e.g., Orru (1999) Curr. Opin. Chem. Biol. 3:16–21.

The polypeptides of the invention can be used as epoxide hydrolases in Sharpless epoxidation, Katsuki-Jacobsen reactions, Shi Epoxidation and Jacobsen hydrolytic kinetic resolution reactions (see FIG. 6).

The invention provides methods for using epoxide hydrolases of the invention to provide stereospecific reaction products. The polypeptides of the invention can be used in the desymmetrization of meso-epoxides. In one aspect, the conversion of substrate to either R,R or S,S-product was with greater than 97% ee, and, in one aspect, 99% conversion. FIG. 7 is a schematic of an exemplary reaction where an epoxide hydrolase of the invention is used in the desymmetrization of meso-epoxides.

In one aspect the invention provides epoxide hydrolases to produce styrene glycol, and corresponding methods. The epoxide hydrolases are reacted with styrene oxide to produce styrene glycols.

The invention provides methods for enzymatic separation of epoxide-enantiomer mixtures. The invention provides methods for protecting a cell against oxidants, e.g., in an immunotoxic reaction, comprising introducing around or into the cell an antioxidizing agent comprising an epoxide hydrolase. The invention provides epoxide hydrolase inhibitors (e.g., an antisense or ribozyme nucleic acid, or an antibody, of the invention) to ameliorate an immunological disorder, e.g., a T cell mediated disorder, and corresponding methods of ameliorating an immunological disorder, e.g., a T cell mediated disorder. The invention provides epoxide hydrolases to treat peroxisomal disorders, and corresponding methods of ameliorating a peroxisomal disorder. The invention provides epoxide hydrolases to treat dysfunction, damage or diseases of the respiratory system and corresponding methods of ameliorating dysfunction, damage or diseases of the respiratory system. The invention provides reagents for forensic analyses, e.g., as chromosome markers or tissue or organ specific markers, comprising epoxide hydrolases of the invention. The invention provides epoxide hydrolases to develop novel pest control, e.g., insect, agents, and, compositions comprising epoxide hydrolase inhibitors (e.g., an antisense or ribozyme nucleic acid, or an antibody, of the invention) for use in pest control.

The invention provides epoxide hydrolases to hydrolyze leukotrienes, and corresponding methods, e.g., their use as anti-inflammatory reagents. Thus, the invention provides pharmaceutical compositions comprising one or more epoxide hydrolases of the invention to act as anti-inflammatory reagents by hydrolyzing leukotrienes and other inflammation-causing compositions. Alternatively, inflammation can be treated by inhibition of epoxide hydrolases using compositions comprising epoxide hydrolase inhibitors (e.g., an antisense or ribozyme nucleic acid, or an antibody, of the invention) to inhibit inflammation mediates by poly-unsaturated lipid metabolites. The invention provides epoxide hydrolases and methods to evaluate the cytotoxicity of a compound by measuring the expression of epoxide hydrolase in a cell.

The polypeptides of the invention can be made or used as epoxide hydrolases in any known method, protocol or industrial use, as described, e.g., in U.S. Pat. Nos. 6,387,668; 6,379,938; 6,372,469; 6,372,469; 5,635,369; 6,174,695, describing use of epoxide hydrolase inhibitors to inhibit inflammation mediated by poly-unsaturated lipid metabolites; U.S. Pat. No. 5,759,765, describing epoxide hydrolases and methods to evaluate the cytotoxicity of a compound by measuring the expression of epoxide hydrolase in a cell; and, WO 01/46476, describing use of epoxide hydrolases to provide stereospecific reaction products; WO 01/07623, WO 00/68394, WO 00/37619, describing methods for enzymatic separation of epoxide-enantiomer mixtures; WO 99/06059, describing a method for protecting a cell against immunotoxicity comprising introducing into the cell an antioxidizing agent comprising an epoxide hydrolase; WO 00/23060, describing use of epoxide hydrolase inhibitors to ameliorate an immunological disorder, e.g., a T cell mediated disorder; WO 00/29846, describing use of epoxide hydrolases in treating peroxisomal disorders; WO 99/64627, describing use of epoxide hydrolases to treat dysfunction, damage or diseases of the respiratory system; WO 01/42451, describing use of epoxide hydrolases in reagents for forensic analyses, e.g., as chromosome markers or tissue or organ specific markers; U.S. Pat. Nos. 6,153,397, 6,143,542, 6,037,160, and WO 99/32153, describing use of epoxide hydrolase inhibitors in pest control; JP 20217597, describing use of epoxide hydrolases to produce styrene glycol by reaction with styrene oxides; WO 00/50577, describing the use of epoxide hydrolases to hydrolyze leukotrienes and to act as anti-inflammatory reagents.

Definitions

The term "epoxide hydrolase" encompasses enzymes catalyzing the cofactor independent hydrolysis of oxirane compounds, for example, epoxides, to their corresponding diols by addition of a water molecule. The term also includes epoxide hydrolases capable of hydrolyzing peptide bonds at high temperatures, low temperatures, alkaline pHs and at acidic pHs. An epoxide hydrolase activity includes an epoxide hydrolase regioselective activity, i.e., when two possible carbons of the substrate are attacked. An epoxide hydrolase activity also comprises an enantioselective epoxide hydrolase activity, i.e., a preference of the enzyme for the substrates of certain chirality. An epoxide hydrolase activity comprises an epoxide hydrolase activity, which is not stereo selective.

An "epoxide hydrolase variant" has an amino acid sequence which is derived from the amino acid sequence of a "precursor epoxide hydrolase". The precursor epoxide hydrolases include naturally-occurring epoxide hydrolases and recombinant epoxide hydrolases. The amino acid sequence of the epoxide hydrolase variant is "derived" from the precursor epoxide hydrolase amino acid sequence by the substitution, deletion or insertion of one or more amino acids of the precursor amino acid sequence. Such modification is of the "precursor DNA sequence" which encodes the amino acid sequence of the precursor epoxide hydrolase rather than manipulation of the precursor epoxide hydrolase enzyme per se. Suitable methods for such manipulation of the precursor DNA sequence include methods disclosed herein, as well as methods known to those skilled in the art The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267–273; Yarmush (1992) J. Biochem. Biophys. Methods 25:85–97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544–546), which consists of a VH domain; and (vi) an isolated complementarity determining region (CDR). Single chain antibodies are also included by reference in the term "antibody."

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

As used herein, the terms "computer," "computer program" and "processor" are used in their broadest general contexts and incorporate all such devices, as described in detail, below.

The term "expression cassette" as used herein refers to a nucleotide sequence which is capable of affecting expression of a structural gene (i.e., a protein coding sequence, such as an epoxide hydrolase polypeptide of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. "Operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

"Plasmids" can be commercially available, publicly available on an unrestricted basis, or can be constructed from available plasmids in accord with published procedures. Equivalent plasmids to those described herein are known in the art and will be apparent to the ordinarily skilled artisan.

The term "gene" means a nucleic acid sequence comprising a segment of DNA involved in producing a transcription product (e.g., a message), which in turn is translated to produce a polypeptide chain, or regulates gene transcription, reproduction or stability. Genes can include, inter alia, regions preceding and following the coding region, such as leader and trailer, promoters and enhancers, as well as, where applicable, intervening sequences (introns) between individual coding segments (exons).

The phrases "nucleic acid" or "nucleic acid sequence" as used herein refer to an oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189–197; Strauss-Soukup (1997) Biochemistry 36:8692–8698; Samstag (1996) Antisense Nucleic Acid Drug Dev 6:153–156.

"Amino acid" or "amino acid sequence" as used herein refer to an oligopeptide, peptide, polypeptide, or protein sequence, or to a fragment, portion, or subunit of any of these, and to naturally occurring or synthetic molecules.

The terms "polypeptide" and "protein" as used herein, refer to amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

As used herein, the term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

As used herein, the term "recombinant" means that the nucleic acid is adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert of interest. In one aspect, the enriched nucleic acids represent 15%, 20%, 30%, 40%, 50%, 60%, 70%, 80%, 90% or more of the number of nucleic acid inserts in the population of recombinant backbone molecules. "Recombinant" polypeptides or proteins refer to polypeptides or proteins produced by recombinant DNA techniques; e.g., produced from cells transformed by an exogenous DNA construct encoding the desired polypeptide or protein. "Synthetic" polypeptides or protein are those prepared by chemical synthesis, as described in further detail, below.

A promoter sequence is "operably linked to" a coding sequence when RNA polymerase which initiates transcription at the promoter will transcribe the coding sequence into mRNA, as discussed further, below.

"Oligonucleotide" refers to either a single stranded polydeoxynucleotide or two complementary polydeoxynucleotide strands which may be chemically synthesized.

Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Hybridization" refers to the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

The term "variant" refers to polynucleotides or polypeptides of the invention modified at one or more base pairs, codons, introns, exons, or amino acid residues (respectively) yet still retain the biological activity of an epoxide hydrolase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof. Techniques for producing variant epoxide hydrolase having activity at a pH or temperature, for example, that is different from a wild-type epoxide hydrolase, are included herein.

The term "saturation mutagenesis" or "GSSM" includes a method that uses degenerate oligonucleotide primers to introduce point mutations into a polynucleotide, as described in detail, below.

The term "optimized directed evolution system" or "optimized directed evolution" includes a method for reassembling fragments of related nucleic acid sequences, e.g., related genes, and explained in detail, below.

The term "synthetic ligation reassembly" or "SLR" includes a method of ligating oligonucleotide fragments in a non-stochastic fashion, and explained in detail, below.

Generating and Manipulating Nucleic Acids

The invention provides nucleic acids, including expression cassettes such as expression vectors, encoding the polypeptides of the invention. The invention also includes methods for discovering new epoxide hydrolase sequences using the nucleic acids of the invention. Also provided are methods for modifying the nucleic acids of the invention by, e.g., synthetic ligation reassembly, optimized directed evolution system and/or saturation mutagenesis.

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

General Techniques

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333–335; yeast artificial chromosomes (YAC); bacterial artificial chromosomes (BAC); P1 artificial chromosomes, see, e.g., Woon (1998) Genomics 50:306–316; P1-derived vectors (PACs), see, e.g., Kern (1997) Biotechniques 23:120–124; cosmids, recombinant viruses, phages or plasmids.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787–1797; Dobeli (1998) Protein Expr. Purif 12:404–414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441–53.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing a polypeptide in bacteria include the E. coli lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Expression Vectors and Cloning Vehicles

The invention provides expression vectors and cloning vehicles comprising nucleic acids of the invention, e.g., sequences encoding the proteins of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, Aspergillus and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSV-LSV40 (Pharmacia). However, any other plasmid or other vector may be used so long as they are replicable and viable in the host. Low copy number or high copy number vectors may be employed with the present invention.

The expression vector may comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli, and the S. cerevisiae TRP1 gene. Promoter regions can be selected from any desired gene using chloramphenicol transferase (CAT) vectors or other vectors with selectable markers.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

A DNA sequence may be inserted into a vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector may be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

Host Cells and Transformed Cells

The invention also provides a transformed cell comprising a nucleic acid sequence of the invention, e.g., a sequence encoding a polypeptide of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include E. coli, Streptomyces, Bacillus subtilis, Salmonella typhimurium and various species within the genera Pseudomonas, Streptomyces, and Staphylococcus. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Amplification of Nucleic Acids

In practicing the invention, nucleic acids encoding the polypeptides of the invention, or modified nucleic acids, can be reproduced by, e.g., amplification. The invention provides amplification primer sequence pairs for amplifying nucleic acids encoding epoxide hydrolase polypeptides, where the primer pairs are capable of amplifying nucleic acid sequences including the exemplary SEQ ID NO:1, or a subsequence thereof; a sequence as set forth in SEQ ID NO:3, or a subsequence thereof; a sequence as set forth in SEQ ID NO:5, or a subsequence thereof; and, a sequence as set forth in SEQ ID NO:7, or a subsequence thereof, a sequence as set forth in SEQ ID NO:9, or a subsequence thereof One of skill in the art can design amplification primer sequence pairs for any part of or the full length of these sequences; for example:

The exemplary SEQ ID NO:1 is atgtcaaaca acgctcccca atcctcgtcg cgccgccatt tcgtcggcgt ggccgctgcg 60
gcgctcgcga caggctcgct gagccggctc gcctttgcca acgcattccc gactgtcggc 120
acgatcacgg aacccgccaa tggcgacaag gcagcgctgc gcccgttccg cgttcacatt 180
cctgaagcgc agctcgtcga catgcggcgg cgcatcaagg cgacgcgctg gccggaccgc 240
gaaaccgtgc ccgacgaatc gcagggtatt cagctcgcca ccatccaggg actgcccaa 300 tactgggcga ccggatacga ctggcgtaaa tgcgaggcgc gactgaattc gtatccgcaa 360
ttcatcacgg agatcgacgg actcgatatc catttcatcc atgtgcgctc gaagcacgcc 420
gacgccatgc cgttgatcgt cacgcatgga tggcccgggt cggtcatcga acagttcaag 480
atcatcgatc cgctcgtcaa tccgaccgcg tacggcgcgc cggcatcgga tgccttccat 540
ctcgtgattc cctctttgcc cggttacggc ttttcggcca gaccgaccac gacgggatgg 600
ggaccggagc gcaccgcacg cgcgtgggtc accttgatga aacgcctcgg ctatgagcgt 660
tttgcttcgc agggcggcga tctcggcggg atcgtcacga acatcatggc caaacaggcg 720
ccgcccgaac tgatcggcat tcatgtgaac ttccctgcct ccgttccagc ggagattctg 780
aagtcgctgg ctgccggtga atcgatgccc gccggattat cggacgagga aaagcacgcg 840
tatgagcagt tgagtgccaa cttcaagaag aagcgcggct acgcattcga aatgggcacg 900
cgcccgcaga cgctttacgg actcgccgac tcacccatcg cgctggcttc ctgctactc 960 gaccacggcg acggctacgg ccagcccgcg gctgcgctga gcgcggccgt ccttggtcac 1020 ccccgtcaacg gtcactcagc aggcgcgctg acgcgagacg acatactcga cgacatcacg 1080
ctttactggc tgaccaacac cggtatctcg gcagcgcgtt tctactggga gtcgcatgcg 1140
aacttctttc tcgcagccga cgtcaatgtg cctgctgccg tgagcgcatt tcccggagaa 1200
aattaccagg cgccgaagag ctggacggaa aaggcctatc acaagctgat ttacttcaac 1260
aagcccgaaa cgggcggcca cttcgcggca tgggaagagc cgatgatctt cgcgaatgaa 1320
gtgcgctcgg ggttaaggcc cttgcgcgcg tga

Thus, an exemplary amplification primer sequence pair is residues 1 to 21 of SEQ ID NO:1 and the complementary strand of the last 21 residues of SEQ ID NO:1.

The exemplary SEQ ID NO:1 encodes a polypeptide having the sequence

Met Ser Asn Asn Ala Pro Gln Ser Ser Ser Arg Arg His Phe Val Gly Val Ala Ala Ala Ala Leu Ala Thr Gly Ser Leu Ser Arg Leu Ala Phe Ala Asn Ala Phe Pro Thr Val Gly Thr Ile Thr Glu Pro Ala Asn Gly Asp Lys Ala Ala Leu Arg Pro Phe Arg Val His Ile Pro Glu Ala Gln Leu Val Asp Met Arg Arg Arg Ile Lys Ala Thr Arg Trp Pro Asp Arg Glu Thr Val Pro Asp Glu Ser Gln Gly Ile Gln Leu Ala Thr Ile Gln Gly Leu Ala Gln Tyr Trp Ala Thr Gly Tyr Asp Trp Arg Lys Cys Glu Ala Arg Leu Asn Ser Tyr Pro Gln Phe Ile Thr Glu Ile Asp Gly Leu Asp Ile His Phe Ile His Val Arg Ser Lys His Ala Asp Ala Met Pro Leu Ile Val Thr His Gly Trp Pro Gly Ser Val Ile Glu Gln Phe Lys Ile Ile Asp Pro Leu Val Asn Pro Thr Ala Tyr Gly Ala Pro Ala Ser Asp Ala Phe His Leu Val Ile Pro Ser Leu Pro Gly Tyr Gly Phe Ser Ala Arg Pro Thr Thr Thr Gly Trp Gly Pro Glu Arg Thr Ala Arg Ala Trp Val Thr Leu Met Lys Arg Leu Gly Tyr Glu Arg Phe Ala Ser Gln Gly Gly Asp Leu Gly Gly Ile Val Thr Asn Ile Met Ala Lys Gln Ala Pro Pro Glu Leu Ile Gly Ile His Val Asn Phe Pro Ala Ser Val Pro Ala Glu Ile Leu Lys Ser Leu Ala Ala Gly Glu Ser Met Pro Ala Gly Leu Ser Asp Glu Glu Lys His Ala Tyr Glu Gln Leu Ser Ala Asn Phe Lys Lys Lys Arg Gly Tyr Ala Phe Glu Met Gly Thr Arg Pro Gln Thr Leu Tyr Gly Leu Ala Asp Ser Pro Ile Ala Leu Ala Ser Trp Leu Leu Asp His Gly Asp Gly Tyr Gly Gln Pro Ala Ala Ala Leu Ser Ala Ala Val Leu Gly His Pro Val Asn Gly His Ser Ala Gly Ala Leu Thr Arg Asp Asp Ile Leu Asp Asp Ile Thr Leu Tyr Trp Leu Thr Asn Thr Gly Ile Ser Ala Ala Arg Phe Tyr Trp Glu Ser His Ala Asn Phe Phe Leu Ala Ala Asp Val Asn Val Pro Ala Ala Val Ser Ala Phe Pro Gly Glu Asn Tyr Gln Ala Pro Lys Ser Trp Thr Glu Lys Ala Tyr His Lys Leu Ile Tyr Phe Asn Lys Pro Glu Thr Gly Gly His Phe Ala Ala Trp Glu Glu Pro Met Ile Phe Ala Asn Glu Val Arg Ser Gly Leu Arg Pro Leu Arg Ala (SEQ ID NO:2)

The exemplary SEQ ID NO:3 is atgcgggtgc agctgtccga ggtgaacctc gacgtcgagg tgagcgggga ggggccggcc 60
gtgctgctcg tgcacggctt ccccgacagc catcgtctgt ggcgtcatca ggtcgcggcg 120
ctgaacgacg ccggtttcac cacggtcgcg cccaccctgc ggggcttcgg cgcctcggac 180
cgccccgagg gcggccccgc ggcgtaccac ccgggcaggc acgtcgccga cctggtcgag 240
ctcctggcgc acctcgacct cgaccgggtc catctggtgg gccacgactg gggttcgggc 300
atcgcgcagg ccctgaccca gttctacccg gaccgggtgc ggagcctgag catcctgtcc 360
gtcggccatc tggcgtcgat ccggtcggcg ggctgggagc agaagcagcg gtcctggtac 420
atgcttctgt tccagctggc cggggtggcc gaggactggc tggcgcggga cgacttcgcg 480
aacatgcggg agatgctggg cgagcacccg gacgccgagt ccgcgatcga ggcgctgcgc 540
gcgcccggag cgctgacggc cgcgctggac atctaccgcg cgggcctgcc gcctgaggtg 600
ctgttcggcg cggacgcgcc ggcggtgccg ctgccggagt cggtcccggt gctgggcctg 660
tggtcgaccg gcgaccgttc cctcaccgag cgctcgatgg cggggacggc cgagtacgtc 720
gccgggccgt ggcgctacga gcgcgtcgag gacgcgggcc actggctgca gctcgaccag 780
ccggagaggg tcaacgaact gctgctctcc ttcctcaagg agaacggcta g 831

Thus, an exemplary amplification primer sequence pair is residues 1 to 21 of SEQ ID NO:3 and the complementary strand of the last 21 residues of SEQ ID NO:3.

The exemplary SEQ ID NO:3 encodes a polypeptide having the sequence

Met Arg Val Gln Leu Ser Glu Val Asn Leu Asp Val Glu Val Ser Gly Glu Gly Pro Ala Val Leu Leu Val His Gly Phe Pro Asp Ser His Arg Leu Trp Arg His Gln Val Ala Ala Leu Asn Asp Ala Gly Phe Thr Thr Val Ala Pro Thr Leu Arg Gly Phe Gly Ala Ser Asp Arg Pro Glu Gly Gly Pro Ala Ala Tyr His Pro Gly Arg His Val Ala Asp Leu Val Glu Leu Leu Ala His Leu Asp Leu Asp Arg Val His Leu Val Gly His Asp Trp Gly Ser Gly Ile Ala Gln Ala Leu Thr Gln Phe Tyr Pro Asp Arg Val Arg Ser Leu Ser Ile Leu Ser Val Gly His Leu Ala Ser Ile Arg Ser Ala Gly Trp Glu Gln Lys Gln Arg Ser Trp Tyr Met Leu Leu Phe Gln Leu Ala Gly Val Ala Glu Asp Trp Leu Ala Arg Asp Asp Phe Ala Asn Met Arg Glu Met Leu Gly Glu His Pro Asp Ala Glu Ser Ala Ile Glu Ala Leu Arg Ala Pro Gly Ala Leu Thr Ala Ala Leu Asp Ile Tyr Arg Ala Gly Leu Pro Pro Glu Val Leu Phe Gly Ala Asp Ala Pro Ala Val Pro Leu Pro Glu Ser Val Pro Val Leu Gly Leu Trp Ser Thr Gly Asp Arg Phe Leu Thr Glu Arg Ser Met Ala Gly Thr Ala Glu Tyr Val Ala Gly Pro Trp Arg Tyr Glu Arg Val Glu Asp Ala Gly His Trp Leu Gln Leu Asp Gln Pro Glu Arg Val Asn Glu Leu Leu Leu Ser Phe Leu Lys Glu Asn Gly (SEQ ID NO:4)

The exemplary SEQ ID NO:5 is atgaggccaa cctccacacc cgagggcccc ggctccgtct ccggggcacc caacctcccg 60
gaggggttcg ccgacaccft caccagcagg tacgtcgacg ccggtgagct gcgtctccat 120
gcagttaccg gcggcgaagg cccgcccctg ctcctcgtcc acgggtggcc cgagacctgg 180
tacgcctggc ggatggtgat gccggcgttg gccgagcact tcgaggtgat cgcggtcgac 240
cagcgcgggg tcgggctgtc cgacaagccc gaggacggat acgacagcac aagcctgcc 300 aacgacctcg tcggactgat ggacgcgctc ggccatgagc ggttcgcact gtatggaacc 360
gacactggaa tgccgatcgc ctatgcactg gctgcggacc agccggaccg aatcgaccgt 420
ttgatcgtct cggaggcccc gcttcccggc gtgactccct caccacctttt gctcctcccg 480 ccccaactca ctgccaagtt ctggcacctg atgttcaacc agctccccgc cgaggtgaac 540
gaggcgctcg tcaggggggcg ggaggacatc ttcttcgggg cggagttcga cgcctctgcc 600
gggacgaaga agctgccagc cgacatcgtg aggtactaca tcgatacggt cgcgaccgac 660
cccgaccatc tgccgcggag cttcgggttc taccgggcga tcccgaccac gatcgcgcag 720
aacgagcagc ggaagacacg gcgtctgccc atgcccgttc tgcgatcgg cggggaggag 780 agcggtggag aagggccggg gaacgcgatg aagctcgtcg cagacgacgt gcagaccctg 840
gtcctcgcgg gcagcggcca ctgggtcgcc gagcaggcgc ctcacgcgct gctggcggcg 900
ctgagcgagt tcctggctcc ctacctcgag gaagcgactg cacaggtagg agcggcccgc 960 tga

Thus, an exemplary amplification primer sequence pair is residues 1 to 21 of SEQ ID NO:5 and the complementary strand of the last 21 residues of SEQ ID NO:5.

The exemplary SEQ ID NO:5 encodes a polypeptide having the sequence

Met Arg Pro Thr Ser Thr Pro Glu Gly Pro Gly Ser Val Ser Gly Ala Pro Asn Leu Pro Glu Gly Phe Ala Asp Thr Phe Thr Ser Arg Tyr Val Asp Ala Gly Glu Leu Arg Leu His Ala Val Thr Gly Gly Glu Gly Pro Pro Leu Leu Leu Val His Gly Trp Pro Glu Thr Trp Tyr Ala Trp Arg Met Val Met Pro Ala

Leu Ala Glu His Phe Glu Val Ile Ala Val Asp Gln Arg Gly
Val Gly Leu Ser Asp Lys Pro Glu Asp Gly Tyr Asp Ser Thr
Ser Leu Ala Asn Asp Leu Val Gly Leu Met Asp Ala Leu
Gly His Glu Arg Phe Ala Leu Tyr Gly Thr Asp Thr Gly
Met Pro Ile Ala Tyr Ala Leu Ala Ala Asp Gln Pro Asp Arg
Ile Asp Arg Leu Ile Val Ser Glu Ala Pro Leu Pro Gly Val
Thr Pro Ser Pro Pro Leu Leu Leu Pro Pro Gln Leu Thr Ala
Lys Phe Trp His Leu Met Phe Asn Gln Leu Pro Ala Glu
Val Asn Glu Ala Leu Val Arg Gly Arg Glu Asp Ile Phe Phe
Gly Ala Glu Phe Asp Ala Ser Ala Gly Thr Lys Lys Leu Pro
Ala Asp Ile Val Arg Tyr Tyr Ile Asp Thr Val Ala Thr Asp
Pro Asp His Leu Arg Gly Ser Phe Gly Phe Tyr Arg Ala Ile
Pro Thr Thr Ile Ala Gln Asn Glu Gln Arg Lys Thr Arg Arg
Leu Pro Met Pro Val Leu Ala Ile Gly Gly Glu Glu Ser Gly
Gly Glu Gly Pro Gly Asn Ala Met Lys Leu Val Ala Asp
Asp Val Gln Thr Leu Val Leu Ala Gly Ser Gly His Trp Val
Ala Glu Gln Ala Pro His Ala Leu Leu Ala Ala Leu Ser Glu
Phe Leu Ala Pro Tyr Leu Glu Glu Ala Thr Ala Gln Val Gly
Ala Ala Arg (SEQ ID NO:6)

The exemplary SEQ ID NO:7 is
atgtcgcccc gttcgattcc tgctctggct ctactgctct gttcgactgt ctc-
cgctttg 60
gccgccgatt tcgaatcgcg cgtgaagcat ggctacgccg actccaacgg
cgtgaagatt 120
cactacgcca cgatcggcag cgggccgctg atcgtgatga tccacggctt
ccccgacttc 180
tggtacacgt ggcgcaagca gatggagggt ttgtcggaca agtaccaatg
cgtggccatc 240
gaccagcgcg gctataacct cagcgacaag ccgcagggcg tcgagaacta
cgacatgagc 300
ctgctggtgg gcgacgtcat cgccgtgatc aagcacctgg gcaaagacaa
ggccatcatc 360
gtcggtcacg actggggcgg ggcggtcgca tggcagctgg ctctgaacgc
gccccagtat 420
gtcgaccgcc taatcattct taacctccca taccccgcgcg gcatcatgcg
cgagctggct 480
cacaacccca agcaacaagc cgccagcgcc tacgcccgca attttcagac
tgagggcgcg 540
gaagccatga tcaagccgga gcaactggcc ttctgggtca ccgatgccga
ggccaagccg 600
aaatacgtgg aggcctttca gcgctcggac atcaaggcca tgctgaacta cta-
caagcgc 660
aactacccgc gagagccgta tcaggaaaac acctcgccgg tggtgaagac
gcagatgccc 720
gtgctcatgt tccacggtct caaagacacc gcgctgctct ccgacgcgct caa-
caacacc 780
tgggactgga tgggcaaaga cctcaccctg gtgaccatcc ctgattccgg
ccacttcgtg 840
cagcaagatg cagccgacct ggtgacgcgg atgatgcggg cgtggctgga
acgttga 897

Thus, an exemplary amplification primer sequence pair is residues 1 to 21 of SEQ ID NO:7 and the complementary strand of the last 21 residues of SEQ ID NO:7.

The exemplary SEQ ID NO:7 encodes a polypeptide having the sequence

Met Ser Pro Arg Ser Ile Pro Ala Leu Ala Leu Leu Leu Cys
Ser Thr Val Ser Ala Leu Ala Ala Asp Phe Glu Ser Arg Val
Lys His Gly Tyr Ala Asp Ser Asn Gly Val Lys Ile His Tyr
Ala Thr Ile Gly Ser Gly Pro Leu Ile Val Met Ile His Gly
Phe Pro Asp Phe Trp Tyr Thr Trp Arg Lys Gln Met Glu
Gly Leu Ser Asp Lys Tyr Gln Cys Val Ala Ile Asp Gln Arg
Gly Tyr Asn Leu Ser Asp Lys Pro Gln Gly Val Glu Asn
Tyr Asp Met Ser Leu Leu Val Gly Asp Val Ile Ala Val Ile
Lys His Leu Gly Lys Asp Lys Ala Ile Ile Val Gly His Asp
Trp Gly Gly Ala Val Ala Trp Gln Leu Ala Leu Asn Ala Pro
Gln Tyr Val Asp Arg Leu Ile Ile Leu Asn Leu Pro Tyr Pro
Arg Gly Ile Met Arg Glu Leu Ala His Asn Pro Lys Gln Gln
Ala Ala Ser Ala Tyr Ala Arg Asn Phe Gln Thr Glu Gly Ala
Glu Ala Met Ile Lys Pro Glu Gln Leu Ala Phe Trp Val Thr
Asp Ala Glu Ala Lys Pro Lys Tyr Val Glu Ala Phe Gln Arg
Ser Asp Ile Lys Ala Met Leu Asn Tyr Tyr Lys Arg Asn Tyr
Pro Arg Glu Pro Tyr Gln Glu Asn Thr Ser Pro Val Val Lys
Thr Gln Met Pro Val Leu Met Phe His Gly Leu Lys Asp
Thr Ala Leu Leu Ser Asp Ala Leu Asn Asn Thr Trp Asp
Trp Met Gly Lys Asp Leu Thr Leu Val Thr Ile Pro Asp Ser
Gly His Phe Val Gln Gln Asp Ala Ala Asp Leu Val Thr Arg
Met Met Arg Ala Trp Leu Glu Arg (SEQ ID NO:8)

The exemplary SEQ ID NO:9 is
atgagtgtcg ttacagaaca cactgacaag accgctattc gtccgttcaa gat-
caatgtg 60
ccggaggcgg acctgaagga tttgcacagg cgcatccagg cgaccaagtt
tcccgaacgc 120
gagacggttc cggatgccac gcagggcgtg cagcttgcca cggttcaggc
cctcgcgcag 180
tattgggcga aagactacaa ctggcacaag tgtgagtcga ggctgaatgc act-
gccgcag 240
ttcatgaccg agattgaggg gctcgacatt catttcattc acgttcgttc gaag-
catccg 300
aacgcgctgc cggtcatcgt gacgcacggc tggccaggat cgatcgtcga
gcagttgaag 360
atcatcgatc cgctgacgaa tcgacggcg catggtggaa gcgcatcgga
cgccttcgac 420
gtggtggtcc cgtccatgcc cggctatgga tactcggca gcctaccgc cgc-
cgggtgg 480
aatcccgttc gcatcgcgcg tgcctgggtt gtgctgatga agcgcctggg tta-
cacgaag 540
ttcgtagccc aaggtggtga ctggggcgca gtcgtcgtcg acatgatggg
gctacaagca 600
cctcctgagt tgctaggtat ccacaccaac atgcctggca tctttccgac cga-
cattgac 660
caggcggctt tcggcggcgc accgacgcca ggagggtttt cacccgacga
gaaagttgct 720
tacgagcgtg tgcgcttcgt ctatcaaaag ggagtcgcct acggtttcca
gatgggctt 780
cgaccgcaga cactgtacgc aatcggggac tcaccggttg ggctcgcggc
ctatttcctt 840
gatcacgacg cccggagcta tgagctgatc gcacgcgtct ttcaaggaca
ggccgaaggc 900
ctcacgcgcg atgacatcct ggacaacgtc acgatcacgt ggttgacgaa
caccgccgtc 960
tctgcgctc gcctctattg ggagtattgg ggcaaagggt cgtacttcag cgc-
caagggc 1020
gtctccatcc cggttgccgt gagcgtgttc cctgacgaac tctatcccgc
ccccagagc 1080
tggacagagc gcgcctatcc gaaactgatg tacttcaaga agcacaacaa
gggcgggcac 1140
ttcgcggcat gggaacagcc acaactcttg tctgaggacc tgcgcgaggg
cttccgatcg 1200
ttgcggtag 1209

Thus, an exemplary amplification primer sequence pair is residues 1 to 21 of SEQ ID NO:9 and the complementary strand of the last 21 residues of SEQ ID NO:9.

The exemplary SEQ ID NO:9 encodes a polypeptide having the sequence

Met Ser Val Val Thr Glu His Thr Asp Lys Thr Ala Iie Arg Pro
Phe Lys Ile Asn Val Pro Glu Ala Asp Leu Lys Asp Leu His
Arg Arg Ile Gln Ala Thr Lys Phe Pro Glu Arg Glu Thr Val
Pro Asp Ala Thr Gln Gly Val Gln Leu Ala Thr Val Gln Ala
Leu Ala Gln Tyr Trp Ala Lys Asp Tyr Asn Trp His Lys Cys
Glu Ser Arg Leu Asn Ala Leu Pro Gln Phe Met Thr Glu
Ile Glu Gly Leu Asp Ile His Phe Ile His Val Arg Ser Lys
His Pro Asn Ala Leu Pro Val Ile Val Thr His Gly Trp Pro
Gly Ser Ile Val Glu Gln Leu Lys Ile Ile Asp Pro Leu Thr
Asn Pro Thr Ala His Gly Gly Ser Ala Ser Asp Ala Phe Asp

Val Val Val Pro Ser Met Pro Gly Tyr Gly Tyr Ser Gly Lys
Pro Thr Ala Ala Gly Trp Asn Pro Val Arg Ile Ala Arg Ala
Trp Val Val Val Leu Met Lys Arg Leu Gly Tyr Thr Lys Phe Val
Ala Gln Gly Gly Asp Trp Gly Ala Val Val Val Asp Met
Met Gly Leu Gln Ala Pro Pro Glu Leu Leu Gly Ile His Thr
Asn Met Pro Gly Ile Phe Pro Thr Asp Ile Asp Gln Ala Ala
Phe Gly Gly Ala Pro Thr Pro Gly Gly Phe Ser Pro Asp Glu
Lys Val Ala Tyr Glu Arg Val Arg Phe Val Tyr Gln Lys Gly
Val Ala Tyr Gly Phe Gln Met Gly Leu Arg Pro Gln Thr
Leu Tyr Ala Ile Gly Asp Ser Pro Val Gly Leu Ala Ala Tyr
Phe Leu Asp His Asp Ala Arg Ser Tyr Glu Leu Ile Ala Arg
Val Phe Gln Gly Gln Ala Glu Gly Leu Thr Arg Asp Asp
Ile Leu Asp Asn Val Thr Ile Thr Trp Leu Thr Asn Thr Ala
Val Ser Gly Ala Arg Leu Tyr Trp Glu Tyr Trp Gly Lys Gly
Ser Tyr Phe Ser Ala Lys Gly Val Ser Ile Pro Val Ala Val
Ser Val Phe Pro Asp Glu Leu Tyr Pro Ala Pro Gln Ser Trp
Thr Glu Arg Ala Tyr Pro Lys Leu Met Tyr Phe Lys Lys His
Asn Lys Gly Gly His Phe Ala Ala Trp Glu Gln Pro Gln
Leu Leu Ser Glu Asp Leu Arg Glu Gly Phe Arg Ser Leu
Arg (SEQ ID NO:10)

The exemplary SEQ ID NO:11 is atgagcaaca cacacgtcgc cgccgggacg gagatccgcc ccttcaccgt
cgaggtcgcc 60
caagacgagt tggacgacct cagccgtcgc atctcggcga cgcgctggcc
cgaggaggag 120
accgtcgagg atcagtcgca gggcgtgccg ctggcgacga tgcaggagct
cgtccgctac 180
tggggctccg agtacgactt cggaaggctg gaggcacggt tgaacgcctt
ccctcagttc 240
atcaccgaga tcgacggcct cgacatccac ttcatccacg ttcgctcgcc
ggaggagaac 300
gcgctgccga tcatcctcac gcacggctgg ccggggctcgt tcatcgagat gct-
gaacgtg 360
atcgggccac tgtccgaccc gaccgcgcac ggcggcgacg cggaggacgc
gttcgacgtc 420
gtggttccgt ccatcccggg ctacgggttc tcggggaagc cgagcgcgac
cgggtgggac 480
ccggttcaca tcgcgcgcgc gtggatcgcc ctgatggagc gcctcggccc
tgaccgctac 540
gtcgcgcagg gcggcgactg gggcgcgcag atcacggatg tgatgggtgc
ggaggcgccg 600
ccggaactgg cggggatccc gggcttttac accaagacgg gcttcggcac
gcaggtcgcc 660
gaagggaagg aagtgaaaga gttcgagggc gagcaatata tactcgagcg
cgggattcgc 720
gccgacctct cgatcgtcaa gggatggaag gccgacgaga ccggcaatct
catgttccgc 780
aagacaacgc gaaacttcaa cctgccggct gcgacctgcg ggaaggtgtg
cctcgccgag 840
gtggaagaga tcgtcccggt cgggctcgct gatcccgact gcatccacct
gccctcgatc 900
tatgtgaacc ggttgatcga tggctcgccc tacgagaaga agatcgagtt ccg-
gaccgtc 960
cgtcagcacg aggcggcatg a 981

Thus, an exemplary amplification primer sequence pair is residues 1 to 21 of SEQ ID NO:11 and the complementary strand of the last 21 residues of SEQ ID NO:11.

The exemplary SEQ ID NO:11 encodes a polypeptide having the sequence

Met Ser Asn Thr His Val Ala Ala Gly Thr Glu Ile Arg Pro
Phe Thr Val Glu Val Ala Gln Asp Glu Leu Asp Asp Leu
Ser Arg Arg Ile Ser Ala Thr Arg Trp Pro Glu Glu Glu Thr
Val Glu Asp Gln Ser Gln Gly Val Pro Leu Ala Thr Met Gln
Glu Leu Val Arg Tyr Trp Gly Ser Glu Tyr Asp Phe Gly Arg
Leu Glu Ala Arg Leu Asn Ala Phe Pro Gln Phe Ile Thr Glu
Ile Asp Gly Leu Asp Ile His Phe Ile His Val Arg Ser Pro
Glu Glu Asn Ala Leu Pro Ile Ile Leu Thr His Gly Trp Pro

Gly Ser Phe Ile Glu Met Leu Asn Val Ile Gly Pro Leu Ser
Asp Pro Thr Ala His Gly Gly Asp Ala Glu Asp Ala Phe
Asp Val Val Val Pro Ser Ile Pro Gly Tyr Gly Phe Ser Gly
Lys Pro Ser Ala Thr Gly Trp Asp Pro Val His Ile Ala Arg
Ala Trp Ile Ala Leu Met Glu Arg Leu Gly Pro Asp Arg Tyr
Val Ala Gln Gly Gly Asp Trp Gly Ala Gln Ile Thr Asp Val
Met Gly Ala Glu Ala Pro Pro Glu Leu Ala Gly Ile Pro Gly
Phe Tyr Thr Lys Thr Gly Phe Gly Thr Gln Val Ala Glu Gly
Lys Glu Val Lys Glu Phe Glu Gly Glu Gln Tyr Ile Leu Glu
Arg Gly Ile Arg Ala Asp Leu Ser Ile Val Lys Gly Trp Lys
Ala Asp Glu Thr Gly Asn Leu Met Phe Arg Lys Thr Thr
Arg Asn Phe Asn Leu Pro Ala Ala Thr Cys Gly Lys Val
Cys Leu Ala Glu Val Glu Glu Ile Val Pro Val Gly Ser Leu
Asp Pro Asp Cys Ile His Leu Pro Ser Ile Tyr Val Asn Arg
Leu Ile Asp Gly Ser Pro Tyr Glu Lys Lys Ile Glu Phe Arg
Thr Val Arg Gln His Glu Ala Ala (SEQ ID NO:12)

The exemplary SEQ ID NO:13 is atgatttcgc tcttcgcccc cggaatcctc gccatcgcgc tcggcagcgc
gcaggcgccg 60
cgcgacgatg tgttcgatcg cgtgacgcac ggttacgcga cgtcggatgg
cggcgtgaag 120
atccactacg cgtcgctcgg ccaggggccg ctcgtggtga tgatccacgg
cttcccggat 180
ttctggtact cgtggcggcg ccagatgcaa gcgttgtcgg atcgctatca
ggtggtcgcc 240
atcgatcagc gcggctacaa cctgagcgac aagcccaagg gcgtcgacgc
ctacgacatg 300
cgcctgctcg tcggcgacgt cgccgctgtg atccgcagcc tcggcaaaga
caaagccacg 360
atcgtcggcc acgactgggg cggcatcgtc gcatggaact tcgcgatgaa
cctgccccag 420
atgaccgaga acctgatcat cctgaacctg ccgcatccga acggccttgc
ccgggagctc 480
aagaacaatc ccgatcagat caagaacagt gagtacgcgc gcaacttcca
gaccaagtcg 540
ccgtccgatc cgaccgtgtt cttcggcagg ccgatgacgg cggagaacct
ggcgggctgg 600
gtccgcgatc ccgaggcgcg caagcggtac gtcgaggcgt tccagaagtc
cgatttcgag 660
gcgatgctga actactacaa gcggaactac ccgcgcggcg cgggcgcgga
cgcgccgacg 720
ccgccgccgc tcccgaaggt gaagatgccg gtgctgatgt ttcacgggct
caacgacacc 780
gcgttgaacg cgtcgggact gaacgacacg tggcagtggc tggagaagga
tctgacgctc 840
gtcacggttc cgggctcggg acacttcgtg cagcaggatg cggccgacct
cgtcgccaac 900
acgatgaagt ggtggctcgc gatgcgttga Thus, an exemplary amplification primer sequence pair is residues 1 to 21 of SEQ ID NO:13 and the complementary strand of the last 21 residues of SEQ ID NO:13.

The exemplary SEQ ID NO:13 encodes a polypeptide having the sequence

Met Ile Ser Leu Phe Ala Pro Gly Ile Leu Ala Ile Ala Leu Gly
Ser Ala Gln Ala Pro Arg Asp Asp Val Phe Asp Arg Val Thr
His Gly Tyr Ala Thr Ser Asp Gly Gly Val Lys Ile His Tyr
Ala Ser Leu Gly Gln Gly Pro Leu Val Val Met Ile His Gly
Phe Pro Asp Phe Trp Tyr Ser Trp Arg Arg Gln Met Gln Ala
Leu Ser Asp Arg Tyr Gln Val Val Ala Ile Asp Gln Arg Gly
Tyr Asn Leu Ser Asp Lys Pro Lys Gly Val Asp Ala Tyr Asp
Met Arg Leu Leu Val Gly Asp Val Ala Ala Val Ile Arg Ser
Leu Gly Lys Asp Lys Ala Thr Ile Val Gly His Asp Trp Gly
Gly Ile Val Ala Trp Asn Phe Ala Met Asn Leu Pro Gln Met
Thr Glu Asn Leu Ile Ile Leu Asn Leu Pro His Pro Asn Gly
Leu Ala Arg Glu Leu Lys Asn Asn Pro Asp Gln Ile Lys
Asn Ser Glu Tyr Ala Arg Asn Phe Gln Thr Lys Ser Pro Ser
Asp Pro Thr Val Phe Phe Gly Arg Pro Met Thr Ala Glu

Asn Leu Ala Gly Trp Val Arg Asp Pro Glu Ala Arg Lys
Arg Tyr Val Glu Ala Phe Gln Lys Ser Asp Phe Glu Ala
Met Leu Asn Tyr Tyr Lys Arg Asn Tyr Pro Arg Gly Ala
Gly Ala Asp Ala Pro Thr Pro Pro Pro Leu Pro Lys Val Lys
Met Pro Val Leu Met Phe His Gly Leu Asn Asp Thr Ala
Leu Asn Ala Ser Gly Leu Asn Asp Thr Trp Gln Trp Leu
Glu Lys Asp Leu Thr Leu Val Thr Val Pro Gly Ser Gly His
Phe Val Gln Gln Asp Ala Ala Asp Leu Val Ala Asn Thr
Met Lys Trp Leu Ala Met Arg (SEQ ID NO:14)

The exemplary SEQ ID NO:15 is gtgagagcag gtagggttcg ggcgcgcggg atcgagttcg cgacgctgga ggagggcaac 60
ggtccgctcg tctctgcct gcacgggttc ccgatcatc cccgctcgtt ccgcaccag 120
ctgccggcgc tcgcgaaggc cggattccgc gcggtcgcgc ccgcgctccg tggctacgcg 180
ccgaccgggc cggcccccga cggccgctat cagtcggcgg cgctcgccat ggatgccgtc 240
gcgctgatcg aggcactcgg ttacgacgac gcggtcgtct tcgggcacga ctggggcgcg 300
accgccgcct acggcgccgc gctcgccgca ccgcagcggg tccgcaagct cgtcaccgcc 360
gcggtgccgt acggcccgca ggtggtcggc tcgttcatga ccagctacga ccagcagcgc 420
cggtcctggt acatgttctt ctttcagacg ccgttcgccg acgccgccgt cgcgcacgac 480
gacttcgcgt tcctcgagcg gctgtggcgc gattggtcgc cgggctggaa gtacccaccc 540
gaagagatgg ccgcgctcaa agagacgttc cgccagcccg gcgtgctgga ggccgcactc 600
ggctactacc gcgccgcctt caatccggcg ctgcaggacc ccgagctcgc ggcgttgcag 660
ggccggatga tgacggaccc gatcgaggtg ccgggcctga tgctgcacgg cgccgccgac 720
ggttgcatgg gcgctgagct cgtcgagggg atggcggcgc tcttcccgcg cggcctccgc 780
gtcgaaatcg tcccgggaac gggccactc ctgcaccagg aagcccccga tcggatcaat 840
ccgatcgtcc tcgacttcct gcggtcgtag 870

Thus, an exemplary amplification primer sequence pair is residues 1 to 21 of SEQ ID NO:15 and the complementary strand of the last 21 residues of SEQ ID NO:15.

The exemplary SEQ ID NO:15 encodes a polypeptide having the sequence

Met Arg Ala Gly Arg Val Arg Ala Arg Gly Ile Glu Phe Ala
Thr Leu Glu Glu Gly Asn Gly Pro Leu Val Leu Cys Leu
His Gly Phe Pro Asp His Pro Arg Ser Phe Arg His Gln Leu
Pro Ala Leu Ala Lys Ala Gly Phe Arg Ala Val Ala Pro Ala
Leu Arg Gly Tyr Ala Pro Thr Gly Pro Ala Pro Asp Gly Arg
Tyr Gln Ser Ala Ala Leu Ala Met Asp Ala Val Ala Leu Ile
Glu Ala Leu Gly Tyr Asp Asp Ala Val Val Phe Gly His Asp
Trp Gly Ala Thr Ala Ala Tyr Gly Ala Ala Leu Ala Ala Pro
Gln Arg Val Arg Lys Leu Val Thr Ala Ala Val Pro Tyr Gly
Pro Gln Val Val Gly Ser Phe Met Thr Ser Tyr Asp Gln Gln
Arg Arg Ser Trp Tyr Met Phe Phe Phe Gln Thr Pro Phe
Ala Asp Ala Ala Val Ala His Asp Asp Phe Ala Phe Leu
Glu Arg Leu Trp Arg Asp Trp Ser Pro Gly Trp Lys Tyr Pro
Pro Glu Glu Met Ala Ala Leu Lys Glu Thr Phe Arg Gln
Pro Gly Val Leu Glu Ala Ala Leu Gly Tyr Tyr Arg Ala Ala
Phe Asn Pro Ala Leu Gln Asp Pro Glu Leu Ala Ala Leu
Gln Gly Arg Met Met Thr Asp Pro Ile Glu Val Pro Gly Leu
Met Leu His Gly Ala Ala Asp Gly Cys Met Gly Ala Glu
Leu Val Glu Gly Met Ala Ala Leu Phe Pro Arg Gly Leu
Arg Val Glu Ile Val Pro Gly Thr Gly His Phe Leu His Gln
Glu Ala Pro Asp Arg Ile Asn Pro Ile Val Leu Asp Phe Leu
Arg Ser (SEQ ID NO:16)

The exemplary SEQ ID NO:17 is atggcgaggg tcaatcgacg gttgacggtt ttcggactcg tagtcgcgct gtcggtcgtg 60
ggcgcacggg cggctcagac ccagcgtgcg tcgaactcct tcgctgcagg cgcgggcgcg 120
aagactgcct caggcgaagc gatcgtgcct ttcaagatcc atgttcccga ctct-gtcgtg 180
gccgacctga agcagcggct ccagcgcgcc cggtttgcgg acgagattcc cgaggtggga 240
tgggactatg gcacgaacct ggctatctc aaggagctcg tgacgtactg gcgc-gacaag 300
tacgactggc gggctcagga gcggcgcctc aaccagtacg accaattcaa gacgaacatc 360
gacgggctcg acatccactt cattcatcaa cgatcgaagg tgccgaacgc caagcccctc 420
ctgctgctga acgggtggcc gagctcgatc gaggagtaca cgaaggtcat cggtcctctc 480
actgacccgg ccgcccacgg cggccgcacc accgacgcct ttcacgtcgt catcccgtcg 540
atgccgggct acggcttctc ggacaaaccg cgegagcgcg gctacaaccc cgagcgcatg 600
gcaagcgtat gggtgaagct gatggcgcgc ctcggataca cgcgttacct gacgcatggc 660
agcgattggg gaatcgcggt agccacgcac ctcgccctga agacccggg gcatctggcg 720
gcgcttcatc ttgcgggctg cccgggcggc ctgatcgggc agtctccgtc acggcccgca 780
ggcgcgcccc cgccgccacc agccccccg cctccagccg cgccagtctc cgcgaatctg 840
gggtatcagg aaatacaaac gaccaagccg cagacactcg gccacgggct gagtgattca 900
ccctggggc tcgcgtcgtg gattatcgac aagtggcagt ctggaccga tcac-gatggc 960
gatctcgaga aggtctacac caaagaccag ctgctgacga atgtcatgat ttactgggtc 1020
accaactcag gggcgtcttc ggctcgcttg tactacgaga cgagacatgt ggatggacgg 1080
ctgctgccga cctttttcga gaactttctt ccgaagcttc ccgagggccg cgt-caacgtt 1140
ccaaccggat gcgggacgtt tccctcgcag tacgatcgcc gegacattcc gat-cagcatg 1200
aacactgcag cagcacgcac ggctgctgag gcccgctaca acgtggtcta tctgacgatt 1260
tgccacacg gaggccactt tcggcgctc gagcagccgc aggtctgggc cgacgacatt 1320
cgagcgttct tccgcgatcg gccactgtaa 1350

Thus, an exemplary amplification primer sequence pair is residues 1 to 21 of SEQ ID NO:17 and the complementary strand of the last 21 residues of SEQ ID NO:17.

The exemplary SEQ ID NO:17 encodes a polypeptide having the sequence

Met Ala Arg Val Asn Arg Arg Leu Thr Val Phe Gly Leu Val
Val Ala Leu Ser Val Val Gly Ala Arg Ala Ala Gln Thr Gln
Arg Ala Ser Asn Ser Phe Ala Ala Gly Ala Gly Ala Lys Thr
Ala Ser Gly Glu Ala Ile Val Pro Phe Lys Ile His Val Pro
Asp Ser Val Val Ala Asp Leu Lys Gln Arg Leu Gln Arg
Ala Arg Phe Ala Asp Glu Ile Pro Glu Val Gly Trp Asp Tyr
Gly Thr Asn Leu Ala Tyr Leu Lys Glu Leu Val Thr Tyr Trp
Arg Asp Lys Tyr Asp Trp Arg Ala Gln Glu Arg Arg Leu
Asn Gln Tyr Asp Gln Phe Lys Thr Asn Ile Asp Gly Leu
Asp Ile His Phe Ile His Gln Arg Ser Lys Val Pro Asn Ala
Lys Pro Leu Leu Leu Asn Gly Trp Pro Ser Ser Ile Glu
Glu Tyr Thr Lys Val Ile Gly Pro Leu Thr Asp Pro Ala Ala
His Gly Gly Arg Thr Thr Asp Ala Phe His Val Val Ile Pro
Ser Met Pro Gly Tyr Gly Phe Ser Asp Lys Pro Arg Gln Arg
Gly Tyr Asn Pro Glu Arg Met Ala Ser Val Trp Val Lys Leu
Met Ala Arg Leu Gly Tyr Thr Arg Tyr Leu Thr His Gly
Ser Asp Trp Gly Ile Ala Val Ala Thr His Leu Ala Leu Lys

Asp Pro Gly His Leu Ala Ala Leu His Leu Ala Gly Cys
Pro Gly Gly Leu Ile Gly Gln Ser Pro Ser Arg Pro Ala Gly
Ala Pro Pro Pro Pro Pro Ala Pro Pro Pro Pro Ala Ala Pro
Val Ser Ala Asn Leu Gly Tyr Gln Gln Ile Gln Thr Thr Lys
Pro Gln Thr Leu Gly His Gly Leu Ser Asp Ser Pro Leu
Gly Leu Ala Ser Trp Ile Ile Asp Lys Trp Gln Ser Trp Thr
Asp His Asp Gly Asp Leu Glu Lys Val Tyr Thr Lys Asp
Gln Leu Leu Thr Asn Val Met Ile Tyr Trp Val Thr Asn Ser
Gly Ala Ser Ser Ala Arg Leu Tyr Tyr Glu Thr Arg His Val
Asp Gly Arg Leu Leu Pro Thr Phe Phe Glu Asn Phe Leu
Pro Lys Leu Pro Glu Gly Arg Val Asn Val Pro Thr Gly Cys
Gly Thr Phe Pro Ser Gln Tyr Asp Arg Arg Asp Ile Pro Ile
Ser Met Asn Thr Ala Ala Ala Arg Thr Ala Ala Glu Ala Arg
Tyr Asn Val Val Tyr Leu Thr Ile Ser Pro His Gly Gly His
Phe Pro Ala Leu Glu Gln Pro Gln Val Trp Ala Asp Asp Ile
Arg Ala Phe Phe Arg Asp Arg Pro Leu (SEQ ID NO:18)

The exemplary SEQ ID NO:19 is atgagcgaag taaaacatcg cgaggtagat acgaacggta tccgcatgca
catcgctgaa 60 agcgggacgg gcccgttggt gttgctgtgc catggttttc ccgaatcttg gtat-
tcgtgg 120 cgccaccagt tggatgcggt cgcagaagct ggattccacg tggttgcacc tga-
catgcga 180 ggttatggcc taactgagag tccagaagaa atcgaccggt acaccctcct
ccatttggtc 240 ggggatatgg tcggcctgct ggacgctctt ggggaggaga gggcggtgat
tgctgggcac 300 gattggggtg ctccggtcgc gtggcacgcc gctcttctac gccccgatcg
cttccgcggt 360 gtgatcggct tgagcgtgcc cttcacgccg cggcggcctg cacgccccac
cagcatgatg 420 cctcagacgg aagacgcgtt gttctatcaa ctttacttcc aatctccagg cgt-
tgcggaa 480 gcggagttcg agcgcgacgt tcgtctaagc atccgaagcc tcctctactc
cgcttccggg 540 gatgctccac gttgggaaaa ccgtgaaggg gctcgagagg aagttggtat
ggtaccgcgc 600 cgaggtggct tactttcgcg gttgatgaac cctgcctcgt tgccgccttg gat-
caccgag 660 gcggacgtgg acttctacgt gagcgagttc acgcgcacgg gatttcgcgg
gccactgaac 720 tggtaccgca atatcgaccg caactgggaa ctcctagcac ccatggcggc
aacgacagtg 780 tcagtcccgg ggctgtacat cgcaggcgac cgcgatctcg ttttggcttt
tcgtgggatg 840 gaccagatca tcgccagcct gtccaagttt gtaccgcggc ttcagggaac
agtcgtgctc 900 ccaggttgcg gtcattggac ccagcaggaa cgggcccgag aggtcacgaa
ggccatgatt 960 gacttcgccc ggcgacttta g 981

Thus, an exemplary amplification primer sequence pair is
residues 1 to 21 of SEQ ID NO:19 and the complementary
strand of the last 21 residues of SEQ ID NO:19.

The exemplary SEQ ID NO:19 encodes a polypeptide
having the sequence

Met Ser Glu Val Lys His Arg Glu Val Asp Thr Asn Gly Ile
Arg Met His Ile Ala Glu Ser Gly Thr Gly Pro Leu Val Leu
Leu Cys His Gly Phe Pro Glu Ser Trp Tyr Ser Trp Arg His
Gln Leu Asp Ala Val Ala Glu Ala Gly Phe His Val Val Ala
Pro Asp Met Arg Gly Tyr Gly Leu Thr Glu Ser Pro Glu
Glu Ile Asp Arg Tyr Thr Leu Leu His Leu Val Gly Asp Met
Val Gly Leu Leu Asp Ala Leu Gly Glu Glu Arg Ala Val
Ile Ala Gly His Asp Trp Gly Ala Pro Val Ala Trp His Ala
Ala Leu Leu Arg Pro Asp Arg Pro Arg Gly Val Ile Gly Leu
Ser Val Pro Phe Thr Pro Arg Arg Pro Ala Arg Pro Thr Ser
Met Met Pro Gln Thr Glu Asp Ala Leu Phe Tyr Gln Leu
Tyr Phe Gln Ser Pro Gly Val Ala Glu Ala Glu Phe Glu Arg

Asp Val Arg Leu Ser Ile Arg Ser Leu Leu Tyr Ser Ala Ser
Gly Asp Ala Pro Arg Trp Glu Asn Arg Glu Gly Ala Arg
Glu Glu Val Gly Met Val Pro Arg Arg Gly Gly Leu Leu
Ser Arg Leu Met Asn Pro Ala Ser Leu Pro Pro Trp Ile Thr
Glu Ala Asp Val Asp Phe Tyr Val Ser Glu Phe Thr Arg Thr
Gly Phe Arg Gly Pro Leu Asn Trp Tyr Arg Asn Ile Asp Arg
Asn Trp Glu Leu Leu Ala Pro Met Ala Ala Thr Thr Val Ser
Val Pro Gly Leu Tyr Ile Ala Gly Asp Arg Asp Leu Val Leu
Ala Phe Arg Gly Met Asp Gln Ile Ile Ala Ser Leu Ser Lys
Phe Val Pro Arg Leu Gln Gly Thr Val Val Leu Pro Gly Cys
Gly His Trp Thr Gln Gln Glu Arg Ala Arg Glu Val Thr Lys
Ala Met Ile Asp Phe Ala Arg Arg Leu (SEQ ID NO:20)

The exemplary SEQ ID NO:21 is gtgagagtag aggcagacgg cgtcgggatc tcgtacgagg tgaccggaca
gggacggccg 60 gtgatcctgc tgcacggctt cccagactcg ggacggcttt ggcgcaacca ggt-
gccggct 120 ttggctgagg ccggcttcca ggtgatcgtc cctgacctgc gcgggtacgg
gcagtccgat 180 aagccagagg ccgtcgatgc gtactcccct ccggccctgg ccggggacgt
catggcggta 240 ctggctgatg cgggcgtcga tcgggcccac gtcgtgggcc acgactgggg
tgcggcgctc 300 ggctgggtgc tggcctcgct cgtgcccgac cgggtcgatc acctcgccgt tct-
gtcggtc 360 ggccatcccg cgaccttccg caggacgctg gcacagaacg agaagtcctg
gtacatgctt 420 ctcttccagt tcgcgggcat cgccgagcac tggctcagcg acaacgactg
ggccaacttc 480 cgcgcctggg cgcggcaccc tgacaccgac gcagtcatca gcgacctcga
ggcgaccaag 540 tccctgacgc ctgcgctgaa ctggtatcgc gccaatgtcc cgcccgagtc ctg-
gaccgcg 600 cctccgctgg ctcttcctgc cgtgcccgcg cccgtgatgg ggatctggag cac-
cggcgac 660 atagccctga ccgagaagca gatgacggac tcgcaggaga acgtcagcgg
cccgtggcgg 720 tacgagcgga tcgatggccc tggccactgg atgcagctcg aggctccgga
gacgatcagc 780 cgcctgctcc tcgactttct ccctgcctag 810

Thus, an exemplary amplification primer sequence pair is
residues 1 to 21 of SEQ ID NO:21 and the complementary
strand of the last 21 residues of SEQ ID NO:21.

The exemplary SEQ ID NO:21 encodes a polypeptide
having the sequence

Met Arg Val Glu Ala Asp Gly Val Gly Ile Ser Tyr Glu Val
Thr Gly Gln Gly Arg Pro Val Ile Leu Leu His Gly Phe Pro
Asp Ser Gly Arg Leu Trp Arg Asn Gln Val Pro Ala Leu
Ala Glu Ala Gly Phe Gln Val Ile Val Pro Asp Leu Arg Gly
Tyr Gly Gln Ser Asp Lys Pro Glu Ala Val Asp Ala Tyr Ser
Leu Pro Ala Leu Ala Gly Asp Val Met Ala Val Leu Ala
Asp Ala Gly Val Asp Arg Ala His Val Val Gly His Asp Trp
Gly Ala Ala Leu Gly Trp Val Leu Ala Ser Leu Val Pro Asp
Arg Val Asp His Leu Ala Val Leu Ser Val Gly His Pro Ala
Thr Phe Arg Arg Thr Leu Ala Gln Asn Glu Lys Ser Trp Tyr
Met Leu Leu Phe Gln Phe Ala Gly Ile Ala Glu His Trp Leu
Ser Asp Asn Asp Trp Ala Asn Phe Arg Ala Trp Ala Arg His
Pro Asp Thr Asp Ala Val Ile Ser Asp Leu Glu Ala Thr Lys
Ser Leu Thr Pro Ala Leu Asn Trp Tyr Arg Ala Asn Val Pro
Pro Glu Ser Trp Thr Ala Pro Pro Leu Ala Leu Pro Ala Val
Pro Ala Pro Val Met Gly Ile Trp Ser Thr Gly Asp Ile Ala
Leu Thr Glu Lys Gln Met Thr Asp Ser Gln Glu Asn Val
Ser Gly Pro Trp Arg Tyr Glu Arg Ile Asp Gly Pro Gly His
Trp Met Gln Leu Glu Ala Pro Glu Thr Ile Ser Arg Leu Leu
Leu Asp Phe Leu Pro Ala (SEQ ID NO:22)

The exemplary SEQ ID NO:23 is
atgacccega cegttgcgac aaaaaccagc gaccagcaga cagcggagaa
gacagcgatt 60
cggccgtttc gcatcaacgt tcccgacgcg gaactgaccg acctgcgcag
gcgcgtcagc 120
gcgacgaggt ggcccgaacg cgagacggtt ccggatcaaa cgcagggcgt
gcagctcgcg 180
acggttcaac agcttgcgcg ttattgggcg accgagtacg actggcgtaa
gtgcgaggcg 240
aggctgaatg ccctgccgca gttcatcacg gagatcgatg gcctggatat 300
ccacttcatt
cacgtgcgct cgaagcacga tcgcgcgttg ccgctcatcg tcacgcacgg
atggcctggc 360
tccatcgtcg agcagctgaa gatcatcgat ccgctcacca atcccacggc
ccatggcggc 420
accgcgtccg acgccttcga cgtcgtgatc ccgtcgatgc ccggctacgg
gtgttcaggc 480
cggccgtcga ccaccggctg ggacgtcgca cacatcgcgc gcgcgtgggt
ggtgctcatg 540
aaacgcctcg gctactcgaa gttcgcggcg cagggtggcg attggggcgc
gattgtggtc 600
gatcagatgg gcgtccaggc ggctccggaa ttgatcggca ttcacaccaa
catgcctggt 660
atctttcccg cggacatcga tcaggcggcg tttgccggga agccggcgcc
atcgggtctg 720
tcagccgacg agaaagttgc gtacgagcgc ttgctgttcg tgtatcaaaa
gggaatcggg 780
tacggatatc agatgggact gcgaccgcag acgctgtacg gaatcgccga
ttcacccgtc 840
ggcctggcgg cgtattttct cgatcacgac gcgcgcagtc tcgatctgat
ctcgcgcgtc 900
ttcgcggag cgtccgaggg cctctcacgc gatgacgtcc tcgacaacgt
cacgatcgcc 960
tggttgacga acacgggggt gtccggcggc cgtctctact gggagaacta
tggcaagctc 1020
ggattcttca atgtcaaagg cgtatcgatc ccggtggccg tgagcgtgtt 35
ccccgacgag 1080
ctctatccag cgcccgcggag ctggacggag aaggcgtatc cgaaactgat
ccacttcaac 1140
aaggtcgaca agggcggaca cttcgcggcc ttcgagcagc cgaagctctt
gtccgacgag 1200
attcgcacgg gtctgaagtc tctgcgcacc tga 1233

Thus, an exemplary amplification primer sequence pair is residues 1 to 21 of SEQ ID NO:23 and the complementary strand of the last 21 residues of SEQ ID NO:23.

The exemplary SEQ ID NO:23 encodes a polypeptide having the sequence

Met Thr Pro Thr Val Ala Thr Lys Thr Ser Asp Gln Gln Thr
Ala Glu Lys Thr Ala Ile Arg Pro Phe Arg Ile Asn Val Pro
Asp Ala Glu Leu Thr Asp Leu Arg Arg Arg Val Ser Ala
Thr Arg Trp Pro Glu Arg Glu Thr Val Pro Asp Gln Thr Gln
Gly Val Gln Leu Ala Thr Val Gln Gln Leu Ala Arg Tyr Trp
Ala Thr Glu Tyr Asp Trp Arg Lys Cys Glu Ala Arg Leu
Asn Ala Leu Pro Gln Phe Ile Thr Glu Ile Asp Gly Leu Asp
Ile His Phe Ile His Val Arg Ser Lys His Asp Arg Ala Leu
Pro Leu Ile Val Thr His Gly Trp Pro Gly Ser Ile Val Glu
Gln Leu Lys Ile Ile Asp Pro Leu Thr Asn Pro Thr Ala His
Gly Gly Thr Ala Ser Asp Ala Phe Asp Val Val Ile Pro Ser
Met Pro Gly Tyr Gly Cys Ser Gly Arg Pro Ser Thr Thr Gly
Trp Asp Val Ala His Ile Ala Arg Ala Trp Val Val Leu Met
Lys Arg Leu Gly Tyr Ser Lys Phe Ala Ala Gln Gly Gly
Asp Trp Gly Ala Ile Val Val Asp Gln Met Gly Val Gln Ala
Ala Pro Glu Leu Ile Gly Ile His Thr Asn Met Pro Gly Ile
Phe Pro Ala Asp Ile Asp Gln Ala Ala Phe Ala Gly Lys Pro
Ala Pro Ser Gly Leu Ser Ala Asp Glu Lys Val Ala Tyr Glu
Arg Leu Leu Phe Val Tyr Gln Lys Gly Ile Gly Tyr Gly Tyr
Gln Met Gly Leu Arg Pro Gln Thr Leu Tyr Gly Ile Ala Asp
Ser Pro Val Gly Leu Ala Ala Tyr Phe Leu Asp His Asp Ala
Arg Ser Leu Asp Leu Ile Ser Arg Val Phe Ala Gly Ala Ser
Glu Gly Leu Ser Arg Asp Asp Val Leu Asp Asn Val Thr
Ile Ala Trp Leu Thr Asn Thr Gly Val Ser Gly Gly Arg Leu
Tyr Trp Glu Asn Tyr Gly Lys Leu Gly Phe Phe Asn Val
Lys Gly Val Ser Ile Pro Val Ala Val Ser Val Phe Pro Asp
Glu Leu Tyr Pro Ala Pro Arg Ser Trp Thr Glu Lys Ala Tyr
Pro Lys Leu Ile His Phe Asn Lys Val Asp Lys Gly Gly His
Phe Ala Ala Phe Glu Gln Pro Lys Leu Leu Ser Asp Glu
Ile Arg Thr Gly Leu Lys Ser Leu Arg Thr (SEQ ID NO:24)

The exemplary SEQ ID NO:25 is
atgtccgaac cctggaagca tcacgccaaa gttgtcaacg gctttcgtat gcac-
tatgtc 60
attgccggtt ccggctaccc actcgtattt ctgcatggct ggccccagag ttg-
gtatgag 120
tggcgaaaga tcattccggc actcgctgag aagttcacgg taattgcccc
ggacctacgc 180
ggattgggag attctgaacg tcctctcaca gggtatgata aacgtaccct ggc-
ctcagat 240
gtgtacgagt tggtgaaatc cctgggcttc agcaaaattg gctcactgg ccat-
gactgg 300
ggtggtgccg tagcgttcta ctttgcttac gatcatccag agatggtcga acgct-
tgctg 360
attctcgaca tggtgccagg ttacgggcgc aaaggtgggt caatggacct
tcgccaagca 420
cagcgctatt ggcacgcgtt ctttcacggt ggcatgccag acttagctga
aaagctggtc 480
agcgccaacg tcgaagccta cttaagccat ttctacactt cgaccacgta caac-
tacagt 540
ccaaatgtgt tcagtgcaga agatatagcc gaatacgtgc gcgtatattc
cgctccaggg 600
gcgatccgtg ccggggtttca atactatcgt gctgcgttgc aagaagacct tga-
caacctc 660
agcagctgca cagaaaaact gaaaatgcct gtgctcgcat ggggaggcga 35
agcattcatg 720
ggcaacgttg taccggtgtg gcagacggtc gccgagaacg tacaaggagg
cgagctcaag 780
cagtgtggcc acttcatcgc ggaggagaaa cctgagttcg ccactcaaca
agcgctgaa 840
tttttcgcgc cgctccgggg agcaaagtag 870

Thus, an exemplary amplification primer sequence pair is residues 1 to 21 of SEQ ID NO:25 and the complementary strand of the last 21 residues of SEQ ID NO:25.

The exemplary SEQ ID NO:25 encodes a polypeptide having the sequence

Met Ser Glu Pro Trp Lys His His Ala Lys Val Val Asn Gly
Phe Arg Met His Tyr Val Ile Ala Gly Ser Gly Tyr Pro Leu
Val Phe Leu His Gly Trp Pro Gln Ser Trp Tyr Glu Trp Arg
Lys Ile Ile Pro Ala Leu Ala Glu Lys Phe Thr Val Ile Ala
Pro Asp Leu Arg Gly Leu Gly Asp Ser Glu Arg Pro Leu
Thr Gly Tyr Asp Lys Arg Thr Leu Ala Ser Asp Val Tyr Glu
Leu Val Lys Ser Leu Gly Phe Ser Lys Ile Gly Leu Thr Gly
His Asp Trp Gly Gly Ala Val Ala Phe Tyr Phe Ala Tyr Asp
His Pro Glu Met Val Glu Arg Leu Leu Ile Leu Asp Met
Val Pro Gly Tyr Gly Arg Lys Gly Gly Ser Met Asp Leu
Arg Gln Ala Gln Arg Tyr Trp His Ala Phe Phe His Gly Gly
Met Pro Asp Leu Ala Glu Lys Leu Val Ser Ala Asn Val Glu
Ala Tyr Leu Ser His Phe Tyr Thr Ser Thr Thr Tyr Asn Tyr
Ser Pro Asn Val Phe Ser Ala Glu Asp Ile Ala Glu Tyr Val
Arg Val Tyr Ser Ala Pro Gly Ala Ile Arg Ala Gly Phe Gln
Tyr Tyr Arg Ala Ala Leu Gln Glu Asp Leu Asp Asn Leu
Ser Ser Cys Thr Glu Lys Leu Lys Met Pro Val Leu Ala Trp
Gly Gly Glu Ala Phe Met Gly Asn Val Val Pro Val Trp Gln
Thr Val Ala Glu Asn Val Gln Gly Gly Glu Leu Lys Gln
Cys Gly His Phe Ile Ala Glu Glu Lys Pro Glu Phe Ala Thr
Gln Gln Ala Leu Glu Phe Phe Ala Pro Leu Arg Gly Ala
Lys (SEQ ID NO:26)

The exemplary SEQ ID NO:27 is
atgacacgcg actcactcca actcgccgcc gtcgcgttgg ccatggtgct cgccggcgcc 60
ttcgcgattc ccgggtgggc gcaaaccacc gtcggcagcg atgcctcgat ccgtcccttc 120
aagatccaag tgccgcaagc ctcgctcgac gacctgcgcc ggcgtattgc ggcaacgcgc 180
tggcccgaca aggagaccgt cgacaacgca tcccagggcg cgcagcttgc gcagatgcag 240
gagctcgtga ggtactgggg cacgagctac gactggcgca aggccgaggc gaagctcaac 300
gcgttgccgc aattcacgac caacatcgac ggcgtcgaca ttcatttcat ccacgtgcgc 360
tcgcgtcatc ccaatgcgct gcccgtcatc attacgcacg gctggcccgg atcggtgatc 420
gagcagctca agctcatcga tccgctcacg gatccgaccg cgcacggcgg cagcgccgac 480
gacgcgttcg acgtcgtcat tccgtcggtg ccgggctacg ggttttccgg caagccgacc 540
ggcaccgggt gggatccgga tcgcatcgcg cgcgcgtggg cggagctcat gaaacgcctc 600
ggctacacac gttatgtcgc gcaaggcggc gactggggct cgccgatctc gagcgcgatg 660
gcgcggcagg gagcgccggg gttgctcggt attcacatca acctgcctgc gacggtgccg 720
ccggaagcag ccgccgcgct cggggggtggc ccgctgccgg cagggcttc cgacaaggaa 780
cgcgccgcga tcgacacgct catggcttat gccaaggccg gcaacgcctc gtacttcacg 840
atgttgacgg cgcgcccgca aaccgtcggt tacggcgcga acgactcgcc gacgggcctt 900
gcggcctgga tcctcgtgca tccgggtttc aggcaatggt cgtacggcgt cgatccgacg 960
gagtcgccga gcaaggacga cgtgctcgac gacatcacgc tgtattggct caccgggacc 1020
gcgacctcgg ccggccggt gtactgggag aacggcgcgc gcggcagcgt catcgtcgc 1080
gccgcgcaga agaccggcga gatctcgctt ccggtcgcga tcacggtgtt tcccgacgac 1140
gtctatcgcg cgccggagac ctgggcgcgg cgcgcgtacc gcaacctcgt ctacttccac 1200
gaagtggaca agggcggaca tttcgcagcg tgggaacagc ccgagctgtt cagcgccgag 1260
ctgcgcgctg cgttcaggcc gctgcgcgag gcgcactga 1299

Thus, an exemplary amplification primer sequence pair is residues 1 to 21 of SEQ ID NO:27 and the complementary strand of the last 21 residues of SEQ ID NO:27.

The exemplary SEQ ID NO:27 encodes a polypeptide having the sequence

Met Thr Arg Asp Ser Leu Gln Leu Ala Ala Val Ala Leu Ala Met Val Leu Ala Gly Ala Phe Ala Ile Pro Gly Trp Ala Gln Thr Thr Val Gly Ser Asp Ala Ser Ile Arg Pro Phe Lys Ile Gln Val Pro Gln Ala Ser Leu Asp Asp Leu Arg Arg Arg Ile Ala Ala Thr Arg Trp Pro Asp Lys Glu Thr Val Asp Asn Ala Ser Gln Gly Ala Gln Leu Ala Gln Met Gln Glu Leu Val Arg Tyr Trp Gly Thr Ser Tyr Asp Trp Arg Lys Ala Glu Ala Lys Leu Asn Ala Leu Pro Gln Phe Thr Thr Asn Ile Asp Gly Val Asp Ile His Phe Ile His Val Arg Ser Arg His Pro Asn Ala Leu Pro Val Ile Ile Thr His Gly Trp Pro Gly Ser Val Ile Glu Gln Leu Lys Leu Ile Asp Pro Leu Thr Asp Pro Thr Ala His Gly Gly Ser Ala Asp Asp Ala Phe Asp Val Val Ile Pro Ser Val Pro Gly Tyr Gly Phe Ser Gly Lys Pro Thr Gly Thr Gly Trp Asp Pro Asp Arg Ile Ala Arg Ala Trp Ala Glu Leu Met Lys Arg Leu Gly Tyr Thr Arg Tyr Val Ala Gln Gly Gly Asp Trp Gly Ser Pro Ile Ser Ser Ala Met Ala Arg Gln Gly Ala Pro Gly Leu Leu Gly Ile His Ile Asn Leu Pro Ala Thr Val Pro Pro Glu Ala Ala Ala Ala Leu Gly Gly Gly Pro Leu Pro Ala Gly Leu Ser Asp Lys Glu Arg Ala Ala Ile Asp Thr Leu Met Ala Tyr Ala Lys Ala Gly Asn Ala Ser Tyr Phe Thr Met Leu Thr Ala Arg Pro Gln Thr Val Gly Tyr Gly Ala Asn Asp Ser Pro Thr Gly Leu Ala Ala Trp Ile Leu Val His Pro Gly Phe Arg Gln Trp Ser Tyr Gly Val Asp Pro Thr Glu Ser Pro Ser Lys Asp Asp Val Leu Asp Asp Ile Thr Leu Tyr Trp Leu Thr Gly Thr Ala Thr Ser Ala Gly Arg Leu Tyr Trp Glu Asn Gly Ala Arg Gly Ser Val Ile Val Ala Ala Ala Gln Lys Thr Gly Glu Ile Ser Leu Pro Val Ala Ile Thr Val Phe Pro Asp Asp Val Tyr Arg Ala Pro Glu Thr Trp Ala Arg Arg Ala Tyr Arg Asn Leu Val Tyr Phe His Glu Val Asp Lys Gly Gly His Phe Ala Ala Trp Glu Gln Pro Glu Leu Phe Ser Ala Glu Leu Arg Ala Ala Phe Arg Pro Leu Arg Glu Ala His (SEQ ID NO:28)

The exemplary SEQ ID NO:29 is
atgcatgaga taaagcatcg cgttgtcgaa acgaatggca tccgcatgca cgtcgctgag 60
tgcggggtgg gtccgcttgt gctcctgtgt cacgggtttc ccgagtgttg gtattcgtgg 120
cgccatcagt tgccggccct cgcggaagct ggattccacg tcgtcgcgcc tgacatgcga 180
ggctacggcg agacagaccg gccacaggaa atcgaggagt acacgctcct gcatttagtt 240
ggtgacatga taggtctgct cgacgttttg ggtgcagaaa gcgcggtgat cgccggccac 300
gattggggtg ccccggtggc gtggcattct gcgcttctac gcccagatcg gttccgcgcc 360
gtcatcggct tgagcgtacc gttcaggccg agactccccg tgcgcccgac tagcgtcatg 420
cctcagaccg acgacgcgct cttctaccag ctttacttcc aaacttcagg catcgccgag 480
gcggagttcg agcgcgacgt ccggctgagc atccgcagcc tcctctattc ggcttcgggc 540
gatcgccgc gtcgcgataa caccggaatg cctggtggcg aagtcggaat ggtgccacgc 600
caaggtggtt tcctctcgcg cctgataaat cccgcatcgc taccccactg gctcaccgac 660
gcggacgtag acttctacgt gaaggagttc acgcgcacag gatttcgcgg cggtctgaac 720
tggtaccgca acatcgaccg caattgggag ctcttggcgc ccttcactgc ggcgcgtgtg 780
tccgtccccg cactctttgt cgccggcgac cgcgatctcg tagtcgcctt tcgtgggatg 840
gaccaactca tccccaatct ggcgaagttt gtcccgcagc tccttggcac cctcatgctc 900
ccaggctgcg gccactggac ccaacaggaa tgtccgcgcg aggtcaatga cgccatgctc 960
gatttccttc gtcggctgta g 981

Thus, an exemplary amplification primer sequence pair is residues 1 to 21 of SEQ ID NO:29 and the complementary strand of the last 21 residues of SEQ ID NO:29.

The exemplary SEQ ID NO:29 encodes a polypeptide having the sequence

Met His Glu Ile Lys His Arg Val Val Glu Thr Asn Gly Ile Arg Met His Val Ala Glu Cys Gly Val Gly Pro Leu Val Leu Leu Cys His Gly Phe Pro Glu Cys Trp Tyr Ser Trp Arg His Gln Leu Pro Ala Leu Ala Glu Ala Gly Phe His Val Val Ala Pro Asp Met Arg Gly Tyr Gly Glu Thr Asp Arg Pro Gln Glu Ile Glu Glu Tyr Thr Leu Leu His Leu Val Gly Asp Met Ile Gly Leu Leu Asp Val Leu Gly Ala Glu Ser Ala Val Ile Ala Gly His Asp Trp Gly Ala Pro Val Ala Trp His Ser Ala Leu Leu Arg Pro Asp Arg Phe Arg Ala Val Ile Gly Leu Ser Val Pro Phe Arg Pro Arg Leu Pro Val Arg Pro Thr Ser Val Met Pro Gln Thr Asp Asp Ala Leu Phe Tyr Gln Leu Tyr Phe Gln Thr Ser Gly Ile Ala Glu Ala Glu Phe Glu Arg Asp Val Arg Leu Ser Ile Arg Ser Leu Leu Tyr Ser Ala Ser Gly Asp Ala Pro Arg Arg Asp Asn Thr Gly Met Pro Gly Gly

Glu Val Gly Met Val Pro Arg Gln Gly Gly Phe Leu Ser
Arg Leu Ile Asn Pro Ala Ser Leu Pro His Trp Leu Thr Asp
Ala Asp Val Asp Phe Tyr Val Lys Glu Phe Thr Arg Thr Gly
Phe Arg Gly Gly Leu Asn Trp Tyr Arg Asn Ile Asp Arg
Asn Trp Glu Leu Leu Ala Pro Phe Thr Ala Ala Arg Val Ser
Val Pro Ala Leu Phe Val Ala Gly Asp Arg Asp Leu Val Val
Ala Phe Arg Gly Met Asp Gln Leu Ile Pro Asn Leu Ala
Lys Phe Val Pro Gln Leu Leu Gly Thr Leu Met Leu Pro
Gly Cys Gly His Trp Thr Gln Gln Glu Cys Pro Arg Glu
Val Asn Asp Ala Met Leu Asp Phe Leu Arg Arg Leu (SEQ ID NO:30)

The exemplary SEQ ID NO:31 is
atgaagcgta tggttctaaa aacagcaatc gccctgcttg cgtcggatgc agc-
cgagggt 60
ggcgagttcg agtcgcgggt gacgcatggt tacgccgatt cttcgggggt
aaaaatccac 120
tatgccagca tgggcaaggg tccactggta gtgatggtcc acggtttccc
cgatttctgg 180
tacacctggc gggcacaaat ggaagcactt tccgattcgt tccaatgtgt tgc-
catcgac 240
caacgcggat acaatttgag cgacaagccc atcggcgtcg agaactacgg
cgtccgcctg 300
ttggtcggag acgtttcggc ggtgataaaa aagctgggca aagaaaaggc
gatcctggtt 360
ggacatgact ggggcgggct ggttgcctgg caattcgcgc tcacccaacc
gcaaatgacc 420
gagcggctca tcattctgaa tttgccgcat cctcggggcc tgctgcgcga gttg-
gcccag 480
aatccgcaac agcagaagaa cagccagtat gcacgggact ttcagcaacc
cgaggccgcc 540
tcgaaattga cggccgagca gcttgccttc tgggtgaaag atgcggaggc
ccggaccaag 600
tacatcgaag cgttcaaacg ctcgattt gaggcgatgc tcaactatta
caagcgcaac 660
tacccgcgcg agccttacac cgaggatact tcgccagtgg taaaggtgca
ggtgcctgtt 720
cttatgattc atgggttagg cgacacggct ttgctgcccg gcgcgctcaa caa-
cacgtgg 780
gattggttgg agaaagattt gacgctggtc acgattcctg gcgccggcca
cttcgttcaa 840
caggacgcg ctgaattggt gtcgcgctcg atgagagcat ggttgctgcg ctga 894

Thus, an exemplary amplification primer sequence pair is residues 1 to 21 of SEQ ID NO:31 and the complementary strand of the last 21 residues of SEQ ID NO:31.

The exemplary SEQ ID NO:31 encodes a polypeptide having the sequence

Met Lys Arg Met Val Leu Lys Thr Ala Ile Ala Leu Leu Ala
Ser Asp Ala Ala Glu Gly Gly Glu Phe Glu Ser Arg Val Thr
His Gly Tyr Ala Asp Ser Ser Gly Val Lys Ile His Tyr Ala
Ser Met Gly Lys Gly Pro Leu Val Val Met Val His Gly Phe
Pro Asp Phe Trp Tyr Thr Trp Arg Ala Gln Met Glu Ala
Leu Ser Asp Ser Phe Gln Cys Val Ala Ile Asp Gln Arg Gly
Tyr Asn Leu Ser Asp Lys Pro Ile Gly Val Glu Asn Tyr Gly
Val Arg Leu Leu Val Gly Asp Val Ser Ala Val Ile Lys Lys
Leu Gly Lys Glu Lys Ala Ile Leu Val Gly His Asp Trp Gly
Gly Leu Val Ala Trp Gln Phe Ala Leu Thr Gln Pro Gln
Met Thr Glu Arg Leu Ile Ile Leu Asn Leu Pro His Pro Arg
Gly Leu Leu Arg Glu Leu Ala Gln Asn Pro Gln Gln Gln
Lys Asn Ser Gln Tyr Ala Arg Asp Phe Gln Gln Pro Glu Ala
Ala Ser Lys Leu Thr Ala Glu Gln Leu Ala Phe Trp Val Lys
Asp Ala Glu Ala Arg Thr Lys Tyr Ile Glu Ala Phe Lys Arg
Ser Asp Phe Glu Ala Met Leu Asn Tyr Tyr Lys Arg Asn
Tyr Pro Arg Glu Pro Tyr Thr Glu Asp Thr Ser Pro Val Val
Lys Val Gln Val Pro Val Leu Met Ile His Gly Leu Gly Asp
Thr Ala Leu Leu Pro Gly Ala Leu Asn Asn Thr Trp Asp
Trp Leu Glu Lys Asp Leu Thr Leu Val Thr Ile Pro Gly Ala
Gly His Phe Val Gln Gln Asp Ala Ala Glu Leu Val Ser Arg
Ser Met Arg Ala Trp Leu Leu Arg (SEQ ID NO:32)

The exemplary SEQ ID NO:33 is
atgcagctcg aaaaagcgca gtacatgccc gccttagcgt catcgcacac ttg-
gcgcagc 60
tttcttcgct acataacagt cgccgtgcttt ttgggcattt tcctgctcgg cgctca-
gagc 120
tacgcccaga ccggtaggac cgccatcgcg gaggcctccg tcagcagctc
gcttcctgcg 180
aagccgcctg cagcgaccga agataaggcg atccgtcctt tccgcgtcca
cgtcccacaa 240
gaggcgctcg acgacctcag ccgtcgcctc gcggcgacgc gcttgcctga
ccaggagacc 300
gtcaacgatc gatcgcaggg caatcagttg gcaacgatga aggaactcgt
gcggtattgg 360
cagacaggct acgactggcg caaggcggag cagaaactga acgcattgcc
gcagtttgtt 420
acgacgatag acggcctaga catccatttc atccacgtcc gctcgaaaca
tcccaacgcg 480
atgccactca ttatcacgca cggctggcct ggatcgatat ttgaattact aaag-
gttatc 540
ggcccgctta ccgatccgac ggcgttcggc agcggcgcgg aagatgcctt
cgacgtcgtg 600
atcccgtcga tgcctggcta tggcttctcc ggcaagccga cggacgccgg
ttgggacccc 660
gaacacatcg cgcgagtctg ggcggagctg atgaagcgcc tcggatacac
ccgctacgtc 720
gcccagggcg gcgactgggg ctcccccgtc tccagcgcga tggcgcgcca
ggcgccggcg 780
ggactgctcg gcatccacgt caacttgccg gcggctatac cgcccgacgt
gggcagggcg 840
ctcaacgccg gcgggcccgc gccggcggga ctctccgaga aggagcgcgc
ggcgtttgac 900
gcgctcgtca cgttcaacac gaagaacagg gcctactcgg tgatgatggc
cacgcggccg 960
cagacgatag gctacgcctt gacggattct ccggcggggc ttgcggcctg
gatatatgac 1020
tacaacaacg gcgagcccga gcgctcactg accaaagacg agatgctgga
cgacatcacg 1080
ctgtactggc tgacgaacag cgccgacctcg gcggcgcggc tgtactggga
gaacagcgga 1140
cgaagccttc tttctgtggc cgcgcagaag accgccgaga tctcgctccc
agtggccatc 1200
acggtatttc cgggagagat ctatcgagcc ccggagacgt gggcccggct
cgcctatcgc 1260
aacctgatct actttcacga ggtcgacagg ggcggacact tcgcggcctg
ggaagagccg 1320
gagcttttct ccgccgagtt gcgcgccgcc ttcagatcac ttcagaaaca
gcaatga 1377

Thus, an exemplary amplification primer sequence pair is residues 1 to 21 of SEQ ID NO:33 and the complementary strand of the last 21 residues of SEQ ID NO:33.

The exemplary SEQ ID NO:33 encodes a polypeptide having the sequence

Met Gln Leu Glu Lys Ala Gln Tyr Met Pro Ala Leu Ala Ser
Ser His Thr Trp Arg Ser Phe Leu Arg Tyr Ile Thr Val Ala
Cys Phe Leu Gly Ile Phe Leu Leu Gly Ala Gln Ser Tyr Ala
Gln Thr Gly Arg Thr Ala Ile Ala Glu Ala Ser Val Ser Ser
Ser Leu Pro Ala Lys Pro Pro Ala Ala Thr Glu Asp Lys Ala
Ile Arg Pro Phe Arg Val His Val Pro Gln Glu Ala Leu Asp
Asp Leu Ser Arg Arg Leu Ala Ala Thr Arg Leu Pro Asp
Gln Glu Thr Val Asn Asp Arg Ser Gln Gly Asn Gln Leu
Ala Thr Met Lys Glu Leu Val Arg Tyr Trp Gln Thr Gly Tyr
Asp Trp Arg Lys Ala Gly Gln Lys Leu Asn Ala Leu Pro
Gln Phe Val Thr Thr Ile Asp Gly Leu Asp Ile His Phe Ile
His Val Arg Ser Lys His Pro Asn Ala Met Pro Leu Ile Ile
Thr His Gly Trp Pro Gly Ser Ile Phe Glu Leu Leu Lys Val

Ile Gly Pro Leu Thr Asp Pro Thr Ala Phe Gly Ser Gly Ala
Glu Asp Ala Phe Asp Val Val Ile Pro Ser Met Pro Gly Tyr
Gly Phe Ser Gly Lys Pro Thr Asp Ala Gly Trp Asp Pro Glu
His Ile Ala Arg Val Trp Ala Glu Leu Met Lys Arg Leu Gly
Tyr Thr Arg Tyr Val Ala Gln Gly Gly Asp Trp Gly Ser Pro
Val Ser Ser Ala Met Ala Arg Gln Ala Pro Ala Gly Leu Leu
Gly Ile His Val Asn Leu Pro Ala Ala Ile Pro Pro Asp Val
Gly Arg Ala Leu Asn Ala Gly Gly Pro Ala Pro Ala Gly
Leu Ser Glu Lys Glu Arg Ala Ala Phe Asp Ala Leu Val Thr
Phe Asn Thr Lys Asn Arg Ala Tyr Ser Val Met Met Ala Thr
Arg Pro Gln Thr Ile Gly Tyr Ala Leu Thr Asp Ser Pro Ala
Gly Leu Ala Ala Trp Ile Tyr Asp Tyr Asn Asn Gly Glu Pro
Glu Arg Ser Leu Thr Lys Asp Glu Met Leu Asp Asp Ile
Thr Leu Tyr Trp Leu Thr Asn Ser Ala Thr Ser Ala Ala Arg
Leu Tyr Trp Glu Asn Ser Gly Arg Ser Leu Leu Ser Val Ala
Ala Gln Lys Thr Ala Glu Ile Ser Leu Pro Val Ala Ile Thr
Val Phe Pro Gly Glu Ile Tyr Arg Ala Pro Glu Thr Trp Ala
Arg Leu Ala Tyr Arg Asn Leu Ile Tyr Phe His Glu Val Asp
Arg Gly Gly His Phe Ala Ala Trp Glu Glu Pro Glu Leu
Phe Ser Ala Glu Leu Arg Ala Ala Phe Arg Ser Leu Gln Lys
Gln Gln (SEQ ID NO:34)

The exemplary SEQ ID NO:35 is atgaacttca ataccgtcga ggtcacaggc cttaagatct tctaccgcga ggc-
cgggaac 60
ccgtcaaagc cggccatcgt cctgctgcac gggttccctt cgtcctcgta
ctcattccac 120
gatctcattc cgctcctgtc ggatcgtttt catgtcattg cgccggacta ccccg-
gcatg 180
gggtacagcg aagcgccacc cacgggcgca atgcgcccga ctttcgacga
tatggtgaag 240
gccatggaca catttatcgc ccaatgtgcc cctgggccgg tcatcttgta cat-
gcatgac 300
atcggcggcc ccatcggctt gcgaatcgcg gcggcacacc cggagaggat
cgcgggcctg 360
atctttcaga acttcacgat ttcgatggag ggttggaacc cggagcgtct caag-
gtctac 420
gagcggcttg gcggtccgga aaccccggag aatctggccg aaaccgagca
attcgcaacc 480
gtagaacgca gtgcgttct tcataagagg ggcgcgcatc ggcccgaggc
cctgaatccg 540
gacagttggg cgattgatgc ctatgccttc tcgatcccgg ccagccgcgc ctt-
tatgtcg 600
agcttgttta tgaatgtcac cagcaacatt ccgcactatc cggaatggca
ggcatatctg 660
aaagaccggc agccgagatc gctgatcgtg tgggggcaaa atgacccggt
tttctcgccg 720
gcagctccgg aaaccgtcaa gaggctcttg ccggcggcga gggttcattc
tttcaacggc 780
ggacacttcg tgctcgacga atacgccgaa ccgatcgccg cggcgatcat
cgagacgttt 840
gccggagaca agaaatga 858

Thus, an exemplary amplification primer sequence pair is residues 1 to 21 of SEQ ID NO:35 and the complementary strand of the last 21 residues of SEQ ID NO:35.

The exemplary SEQ ID NO:35 encodes a polypeptide having the sequence

Met Asn Phe Asn Thr Val Glu Val Thr Gly Leu Lys Ile Phe
Tyr Arg Glu Ala Gly Asn Pro Ser Lys Pro Ala Ile Val Leu
Leu His Gly Phe Pro Ser Ser Ser Tyr Ser Phe His Asp Leu
Ile Pro Leu Leu Ser Asp Arg Phe His Val Ile Ala Pro Asp
Tyr Pro Gly Met Gly Tyr Ser Glu Ala Pro Pro Thr Gly Ala
Met Arg Pro Thr Phe Asp Asp Met Val Lys Ala Met Asp
Thr Phe Ile Ala Gln Cys Ala Pro Gly Pro Val Ile Leu Tyr
Met His Asp Ile Gly Gly Pro Ile Gly Leu Arg Ile Ala Ala
Ala His Pro Glu Arg Ile Ala Gly Leu Ile Phe Gln Asn Phe
Thr Ile Ser Met Glu Gly Trp Asn Pro Glu Arg Leu Lys Val
Tyr Glu Arg Leu Gly Gly Pro Glu Thr Pro Glu Asn Leu

Ala Glu Thr Glu Gln Phe Ala Thr Val Glu Arg Ser Ala Phe
Leu His Lys Arg Gly Ala His Arg Pro Glu Ala Leu Asn
Pro Asp Ser Trp Ala Ile Asp Ala Tyr Ala Phe Ser Ile Pro
Ala Ser Arg Ala Phe Met Ser Ser Leu Phe Met Asn Val Thr
Ser Asn Ile Pro His Tyr Pro Glu Trp Gln Ala Tyr Leu Lys
Asp Arg Gln Pro Arg Ser Leu Ile Val Trp Gly Gln Asn Asp
Pro Val Phe Ser Pro Ala Ala Pro Glu Thr Val Lys Arg Leu
Leu Pro Ala Ala Arg Val His Ser Phe Asn Gly Gly His Phe
Val Leu Asp Glu Tyr Ala Glu Pro Ile Ala Ala Ala Ile Ile
Glu Thr Phe Ala Gly Asp Lys Lys (SEQ ID NO:26)

The exemplary SEQ ID NO:37 is atgacccaga cgacaacccg ccctgccatc cgctccttcg aggtctcctt
tcccgatgaa 60
gcactcgcgg acctccgccg gcgcttagca gcgacgcgct ggccggagaa
agagaccgtc 120
gccgacaact cacaaggcgt cccgctggtc aacatgcagc agctggcccg
ctactgggcg 180
gccgaatacg actggcgcaa gacggaggcg aagctcaacg ccttgcccca
attcctgact 240
gaaatcgacg ggctgggcat tcacttcatt cacgtccgct cgcgccatga
gaacgccctg 300
ccgatcatca tcacgcacgg ctggccgggc tcgattatcg agcagctcaa gat-
catcgag 360
ccgctcacca acccgaccgc ctctggcggt agcgccgaag acgccttcca
cgtggtcatc 420
ccttcgctgc ccggctatgg cttttccggc aagccggcgg cgccgggctg
gaacccaatc 480
accatcgcaa ctgcctggac cacactgatg aaacgccttg gctactcccg
cttcgtcgcc 540
cagggcggcg actggggcaa cgccgtatcg gagatcatgg ccttgcaggc
tcctcccgaa 600
ctggtcggca tccacaccaa catggcggcc accgttccgg ccaacgtcgc
gaaggcgctc 660
gcattccacg agggcccgcc ttccggcctt tcgcccgaag agtcctccgc ctg-
gagccag 720
ctggactact tttacaagaa gggcctgggc tacgccctgg agatgaatac ccg-
gccccag 780
accctgtacg ggctggcgga ttcgccggtt ggcctggccg cctggatgct
cgaccacgac 840
attcgcagcc aggagctaat cgcccgcgtc tttgacggac agtcggaggg
cctatctaaa 900
gaggacgtga tcgagaacgt cacccctcac tggctgacga gcaccgcgat
ttcctcggcg 960
cgcctctact gggataccgc tcaacttggc ggtggcgggt ttttcgacgt
ccgaggtatc 1020
aagattccgg tcgccgtcag cgccttcccg gatgagatct acacgccgcc
ccgcagttgg 1080
gccgaggcgg cctacccgaa gctcatccat tacaaccggc tcgacaaagg
cggccacttc 1140
gccgctggg aacaaccgca gctcttctcg tccgagctgc gcgcagcatt
tagaactttg 1200
cgctag 1206

Thus, an exemplary amplification primer sequence pair is residues 1 to 21 of SEQ ID NO:37 and the complementary strand of the last 21 residues of SEQ ID NO:37.

The exemplary SEQ ID NO:37 encodes a polypeptide having the sequence

Met Thr Gln Thr Thr Thr Arg Pro Ala Ile Arg Ser Phe Glu
Val Ser Phe Pro Asp Glu Ala Leu Ala Asp Leu Arg Arg
Arg Leu Ala Ala Thr Arg Trp Pro Glu Lys Glu Thr Val Ala
Asp Asn Ser Gln Gly Val Pro Leu Val Asn Met Gln Gln
Leu Ala Arg Tyr Trp Ala Ala Glu Tyr Asp Trp Arg Lys Thr
Glu Ala Lys Leu Asn Ala Leu Pro Gln Phe Leu Thr Glu
Ile Asp Gly Leu Gly Ile His Phe Ile His Val Arg Ser Arg
His Glu Asn Ala Leu Pro Ile Ile Ile Thr His Gly Trp Pro
Gly Ser Ile Ile Glu Gln Leu Lys Ile Ile Glu Pro Leu Thr
Asn Pro Thr Ala Ser Gly Gly Ser Ala Glu Asp Ala Phe His

Val Val Ile Pro Ser Leu Pro Gly Tyr Gly Phe Ser Gly Lys
Pro Ala Ala Pro Gly Trp Asn Pro Ile Thr Ile Ala Thr Ala
Trp Thr Thr Leu Met Lys Arg Leu Gly Tyr Ser Arg Phe
Val Ala Gln Gly Gly Asp Trp Gly Asn Ala Val Ser Glu Ile
Met Ala Leu Gln Ala Pro Pro Glu Leu Val Gly Ile His Thr
Asn Met Ala Ala Thr Val Pro Ala Asn Val Ala Lys Ala Leu
Ala Phe His Glu Gly Pro Pro Ser Gly Leu Ser Pro Glu Glu
Ser Ser Ala Trp Ser Gln Leu Asp Tyr Phe Tyr Lys Lys Gly
Leu Gly Tyr Ala Leu Glu Met Asn Thr Arg Pro Gln Thr
Leu Tyr Gly Leu Ala Asp Ser Pro Val Gly Leu Ala Ala Trp
Met Leu Asp His Asp Ile Arg Ser Gln Glu Leu Ile Ala Arg
Val Phe Asp Gly Gln Ser Gly Gly Leu Ser Lys Glu Asp
Val Ile Glu Asn Val Thr Leu Tyr Trp Leu Thr Ser Thr Ala
Ile Ser Ser Ala Arg Leu Tyr Trp Asp Thr Ala Gln Leu Gly
Gly Gly Gly Phe Phe Asp Val Arg Gly Ile Lys Ile Pro Val
Ala Val Ser Ala Phe Pro Asp Glu Ile Tyr Thr Pro Pro Arg
Ser Trp Ala Glu Ala Ala Tyr Pro Lys Leu Ile His Tyr Asn
Arg Leu Asp Lys Gly Gly His Phe Ala Ala Trp Glu Gln
Pro Gln Leu Phe Ser Ser Glu Leu Arg Ala Ala Phe Arg Thr
Leu Arg (SEQ ID NO:38)

The exemplary SEQ ID NO:39 is atgacctcag agaaactgca gtacccggcg agaactcaaa cgacccgcct
tagcgccgcc 60
gcggcggccg ggcttgcctc gggacttctc gtcttctctt gcccgaatta cggc-
cagacc 120
accaccgatc gtgggagcgc gatcgtcgcc caggcgtctg cgcagcgcgc
ggcagcggaa 180
gatccatcga tccgcccctt caaggtgcaa ataccgcaag ccgcgctcga
cgacctgcgc 240
cggcgcatca acgccacgcg ctggcccgac aaggagaccg tcgccgacga
gtcgcagggt 300
gcgcagttgg cgaggctcca ggagctggtt cgctactggg gcagcggcta
cgactggcgc 360
aagctggaag cgaagctgaa tgccctgccg caattcacga cgaccatcga
cggtgtcgag 420
attcacttca tccacgtccg ctctcgtcac aagaatgcgc tcccggtgat cgt- 35
cacccac 480
gggtggccgg gatccgtcgt cgagcaactc aagatcatcg gcccgctcac
ggatccaacc 540
gcccatggcg gcagcgccga ggatgctttc gacgtcgtga tcccgtccct
gccaggttac 600
ggcttctccg gcaagccaac cggtaccggc tgggaccccg accgaatcgc
gcgagcctgg 660
gcggagctga tgaagcgcct cgggtacacc cgctacgtcg cccagggcgg
cgactgggt 720
gccccatca cgagcgcgat ggcacgccag aaagcggcgg gattgcaggg 45
tatccacgtc 780
aacctgcccg caacgctgcc gcccgaggtg actgcagcgc tcggcaccgg
cgggcctgcg 840
ccggcgggac tctccgagaa ggaaagcgca gtgttcgagg cactgaagaa
gtacggcatg 900
acggggaact cggcctactt cacgatgatg acggcgcggc cgcagacggt
cggctatggc 960
gcgacggact caccggccgg cctcgcggca tggatcctcg tgcatccagg
cttcgcccag 1020
tggagatacg gcgccgatcc aaagcagtcg ccgactaagg acgacgtgct 55
cgacgacatc 1080
acgctgtact ggctgacgaa caccgcggcg tcggcggcgc ggctgtactg
ggagaacggc 1140
gcacgaggca gcgtcattgc cgccgcgccg cagaaaacct ccgaaatctc
gctgcccgtg 1200
gccattacgg ttttcccgga cgacgtctat cgagccccgg agtcatgggc ccg-
gcgggca 1260
taccccaacc tgacctattt ccacgaggtc gacaagggcg gacatttcgc
cgcgtgggag 1320
cagccggaac tcttcgcggc cgagctgcgc gccgcgttca agccacttcg
gggggtgcaa 1380
tga 1383

Thus, an exemplary amplification primer sequence pair is residues 1 to 21 of SEQ ID NO:39 and the complementary strand of the last 21 residues of SEQ ID NO:39.

The exemplary SEQ ID NO:39 encodes a polypeptide having the sequence

Met Thr Ser Glu Lys Leu Gln Tyr Pro Ala Arg Thr Gln Thr
Thr Arg Leu Ser Ala Ala Ala Ala Ala Gly Leu Ala Ser Gly
Leu Leu Val Phe Ser Cys Pro Asn Tyr Gly Gln Thr Thr Thr
Asp Arg Gly Ser Ala Ile Val Ala Gln Ala Ser Ala Gln Arg
Ala Ala Ala Glu Asp Pro Ser Ile Arg Pro Phe Lys Val Gln
Ile Pro Gln Ala Ala Leu Asp Asp Leu Arg Arg Arg Ile Asn
Ala Thr Arg Trp Pro Asp Lys Glu Thr Val Ala Asp Glu Ser
Gln Gly Ala Gln Leu Ala Arg Leu Gln Glu Leu Val Arg
Tyr Trp Gly Ser Gly Tyr Asp Trp Arg Lys Leu Glu Ala Lys
Leu Asn Ala Leu Pro Gln Phe Thr Thr Thr Ile Asp Gly Val
Glu Ile His Phe Ile His Val Arg Ser Arg His Lys Asn Ala
Leu Pro Val Ile Val Thr His Gly Trp Pro Gly Ser Val Val
Glu Gln Leu Lys Ile Ile Gly Pro Leu Thr Asp Pro Thr Ala
His Gly Gly Ser Ala Glu Asp Ala Phe Asp Val Val Ile Pro
Ser Leu Pro Gly Tyr Gly Phe Ser Gly Lys Pro Thr Gly Thr
Gly Trp Asp Pro Asp Arg Ile Ala Arg Ala Trp Ala Glu Leu
Met Lys Arg Leu Gly Tyr Thr Arg Tyr Val Ala Gln Gly
Gly Asp Trp Gly Ala Pro Ile Thr Ser Ala Met Ala Arg Gln
Lys Ala Ala Gly Leu Gln Gly Ile His Val Asn Leu Pro Ala
Thr Leu Pro Pro Glu Val Thr Ala Ala Leu Gly Thr Gly Gly
Pro Ala Pro Ala Gly Leu Ser Glu Lys Glu Ser Ala Val Phe
Glu Ala Leu Lys Lys Tyr Gly Met Thr Gly Asn Ser Ala Tyr
Phe Thr Met Met Thr Ala Arg Pro Gln Thr Val Gly Tyr
Gly Ala Thr Asp Ser Pro Ala Gly Leu Ala Ala Trp Ile Leu
Val His Pro Gly Phe Ala Gln Trp Arg Tyr Gly Ala Asp Pro
Lys Gln Ser Pro Thr Lys Asp Asp Val Leu Asp Asp Ile Thr
Leu Tyr Trp Leu Thr Asn Thr Ala Ala Ser Ala Ala Arg Leu
Tyr Trp Glu Asn Gly Ala Arg Gly Ser Val Ile Ala Ala Ala
Pro Gln Lys Thr Ser Glu Ile Ser Leu Pro Val Ala Ile Thr
Val Phe Pro Asp Asp Val Tyr Arg Ala Pro Glu Ser Trp Ala
Arg Arg Ala Tyr Pro Asn Leu Thr Tyr Phe His Glu Val Asp
Lys Gly Gly His Phe Ala Ala Trp Glu Gln Pro Glu Leu
Phe Ala Ala Glu Leu Arg Ala Ala Phe Lys Pro Leu Arg
Gly Val Gln (SEQ ID NO:30)

Determining the Degree of Sequence Identity

The invention provides nucleic acids and polypeptides having at least 99%, 98%, 97%, 96%, 95%, 90%, 85%, 80%, 75%, 70%, 65%, 60%, 55% or 50% sequence identity (homology) to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80. In alternative aspects, the sequence identify can be over a region of at least about 5, 10, 20, 30, 40, 50, 100, 150, 200, 250, 300, 350, 400, 450, 500, 550, 600, 650, 700, 750, 800, 850, 900, 950, 1000, or more, consecutive residues, or the full length of the nucleic acid or polypeptide.

The extent of sequence identity (homology) may be determined using any computer program and associated parameters, including those described herein, such as BLAST 2.2.2. or FASTA version 3.0t78, with the default parameters.

Homologous sequences also include RNA sequences in which uridines replace the thymines in the nucleic acid sequences. The homologous sequences may be obtained using any of the procedures described herein or may result from the correction of a sequencing error. It will be appreciated that the nucleic acid sequences as set forth herein can be represented in the traditional single character format (see, e.g., Stryer, Lubert. Biochemistry, 3rd Ed., W. H Freeman & Co., New York) or in any other format which records the identity of the nucleotides in a sequence.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444–2448, 1988; Altschul et al., J. Mol. Biol. 215(3):403–410, 1990; Thompson et al., Nucleic Acids Res. 22(2):4673–4680, 1994; Higgins et al., Methods Enzymol. 266:383–402, 1996; Altschul et al., J. Mol. Biol. 215(3):403–410, 1990; Altschul et al., Nature Genetics 3:266–272, 1993).

Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (an exemplary sequence SEQ ID NO:1, SEQ ID NO:2, SEQ ID NO:3, SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80) to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, continuous residues ranging anywhere from 20 to the full length of exemplary sequences SEQ ID NO:1, SEQ ID NO:3, SEQ ID NO:5, SEQ ID NO:7, SEQ ID NO:9, SEQ ID NO:10, SEQ ID NO:1, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80 are compared to a reference sequence of the same number of contiguous positions after the two sequences are optimally aligned. If the reference sequence has the requisite sequence identity to SEQ ID NO:1, SEQ ID NO:3, SEQ ID NO:5, SEQ ID NO:7, SEQ ID NO:9, e.g., 50%, 55%, 60%, 65%, 70%, 75%, 80%, 90% or 95% sequence identity to SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, that sequence is within the scope of the invention. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). Several genomes have been sequenced, e.g., *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Databases containing genomic information annotated with some functional information are maintained by different organization, and are accessible via the internet.

BLAST, BLAST 2. BLASTBLAST 2.2.2 algorithms are also used to practice the invention. They are described, e.g., in Altschul (1977) Nuc. Acids Res. 25:3389–3402; Altschul (1990) J. Mol. Biol. 215:403–410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443–1445, 1992; Henikoff and Henikoff, Proteins 17:49–61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used, default options to blastp. There are about 38 setting options in the BLAST 2.2.2 program. In this exemplary aspect of the invention, all default values are used except for the default filtering setting (i.e., all parameters set to default except filtering which is set to OFF); in its place a "-F F" setting is used, which disables filtering. Use of default filtering often results in Karlin-Altschul violations due to short length of sequence.

The default values used in this exemplary aspect of the invention include:
"Filter for low complexity: ON
Word Size: 3
Matrix: Blosum62
Gap Costs: Existence: 11
Extension: 1"

Other default settings are: filter for low complexity OFF, word size of 3 for protein, BLOSUM62 matrix, gap existence penalty of -11 and a gap extension penalty of -1.

An exemplary NCBI BLAST 2.2.2 program setting is set forth in Example 1, below. Note that the "-W" option defaults to 0. This means that, if not set, the word size defaults to 3 for proteins and 11 for nucleotides.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

The epoxide hydrolase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The epoxide hydrolase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Many secreted and membrane bound proteins are synthesized in a precursor form. This precursor molecule contains a NH2-terminal extension of amino acids and is generally referred to as signal or leader peptide. This additional peptide sequence assists the protein in traversing the cell membrane. There is great variability as to the length and the sequence of these peptides. This variability can be observed when the same protein is considered obtained from different species (intraspecies) but also when different proteins are considered from the same species (interspecies).

In spite of the observed variation there are some general structural characteristics which must be satisfied in order for these peptides to be correctly processed and to correctly perform their function in membrane transport. Signal peptides have a basic N-terminal region followed by a central hydrophobic core which is of sufficient length to span the membrane.

Exemplary signal peptides which can direct the secretion of the encoded proteins include amino acids 1–34 of SEQ ID NO:2, amino acids 1–21 of SEQ ID NO:8, amino acids 1–20 of SEQ ID NO:14, amino acids 1–24 of SEQ ID NO:18, amino acids 1–27 of SEQ ID NO:26, amino acids 1–17 of SEQ ID NO:32, amino acids 1–42 of SEQ ID NO:34, amino acids 1–38 of SEQ ID NO:40, amino acids 1–28 of SEQ ID NO:48, amino acids 1–23 of SEQ ID NO:68, amino acids 1–22 of SEQ ID NO:76 and amino acids 1–23 of SEQ ID NO:78.

Exemplary nucleic acid sequences that encode signal peptides which direct the secretion of the encoded proteins include nucleotides 1–102 of SEQ ID NO:1, nucleotides 1–63 of SEQ ID NO:7, nucleotides 1–60 of SEQ ID NO:13, nucleotides 1–72 of SEQ ID NO:17, nucleotides 1–81 of SEQ ID NO:25, nucleotides 1–51 of SEQ ID NO:31, nucleotides 1–123 of SEQ ID NO:33, nucleotides 1–114 of SEQ ID NO:39, nucleotides 1–63 of SEQ ID NO:47, nucleotides 1–69 of SEQ ID NO:67, nucleotides 1–66 of SEQ ID NO:75 and nucleotides 1–69 of SEQ ID NO:77.

Computer Systems and Computer Program Products

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 8:
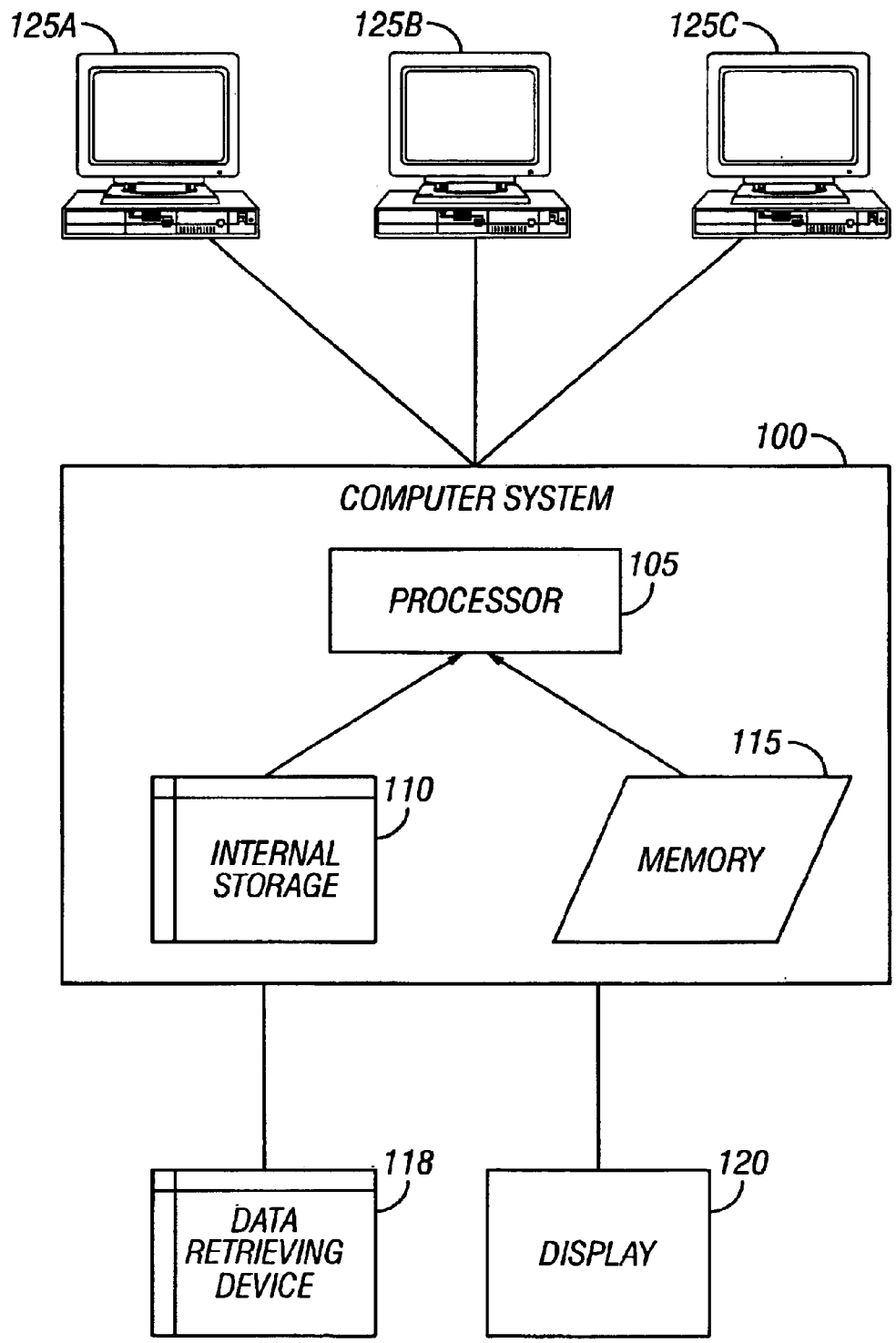
FIG. 8 is a block diagram of a computer system.

Aspects of the invention include systems (e.g., internet based systems), particularly computer systems, which store and manipulate the sequences and sequence information described herein. One example of a computer system 100 is illustrated in block diagram form in FIG. 8. As used herein, "a computer system" refers to the hardware components, software components, and data storage components used to analyze a nucleotide or polypeptide sequence of the invention. The computer system 100 can include a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines. The computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one aspect, the computer system 100 includes a processor 105 connected to a bus which is connected to a main memory 115 (preferably implemented as RAM) and one or more internal data storage devices 110, such as a hard drive and/or other computer readable media having data recorded thereon. The computer system 100 can further include one or more data retrieving device 118 for reading the data stored on the internal data storage devices 110. The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device. The computer system 100 includes a display 120 which is used to display output to a computer user. It should also be noted that the computer system 100 can be linked to other computer systems 125a–c in a network or wide area network to provide centralized access to the computer system 100. Software for accessing and processing the nucleotide or amino acid sequences of the invention can reside in main memory 115 during execution. In some aspects, the computer system 100 may further comprise a sequence comparison algorithm for comparing a nucleic acid sequence of the invention. The algorithm and sequence (s) can be stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of the invention stored on a computer readable medium to reference sequences stored on a computer readable medium to identify homologies or structural motifs.

Figure 9:
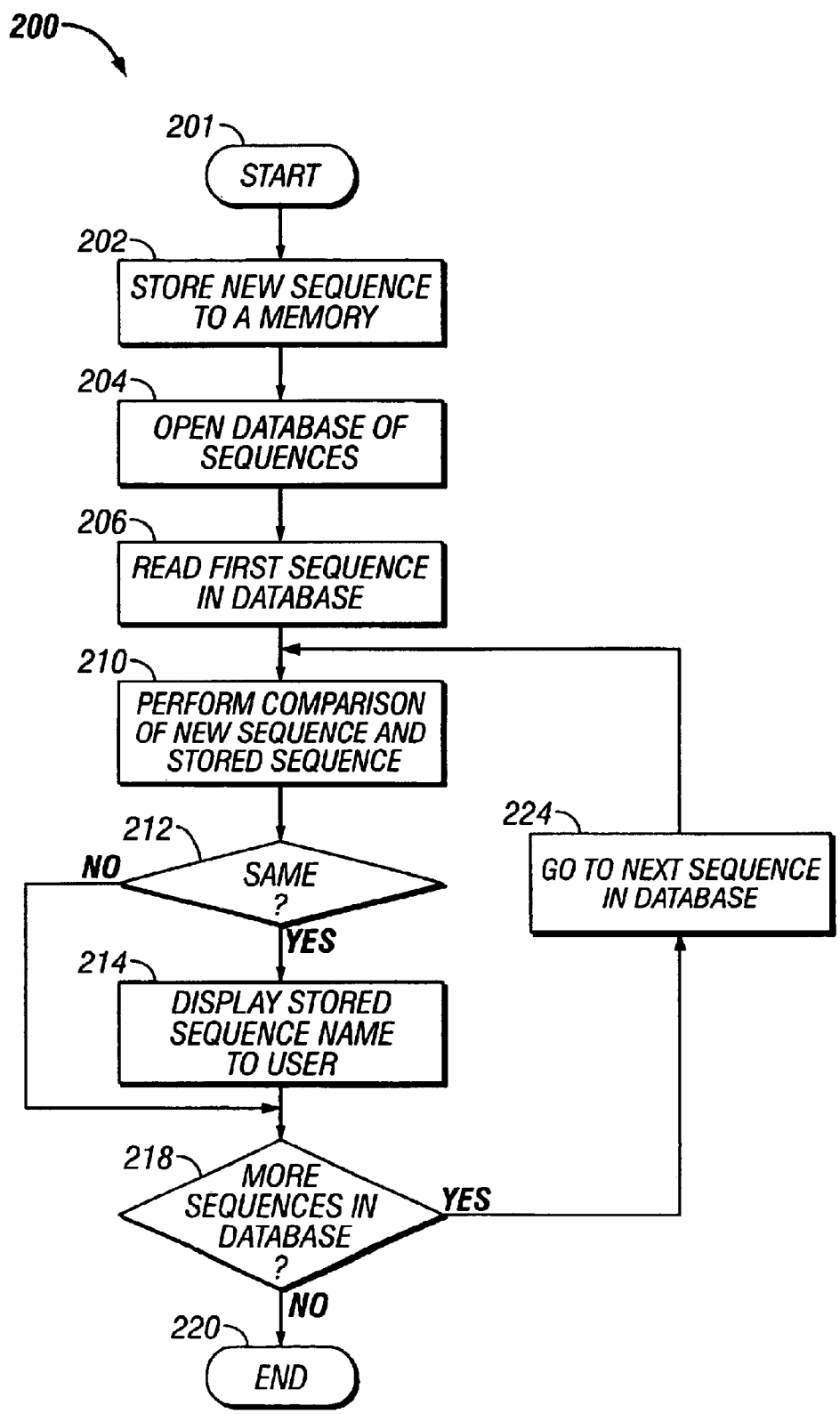
FIG. 9 is a flow diagram illustrating one aspect of a process for comparing a new nucleotide or protein sequence with a database of sequences in order to determine the homology levels between the new sequence and the sequences in the database.
Figure 10:
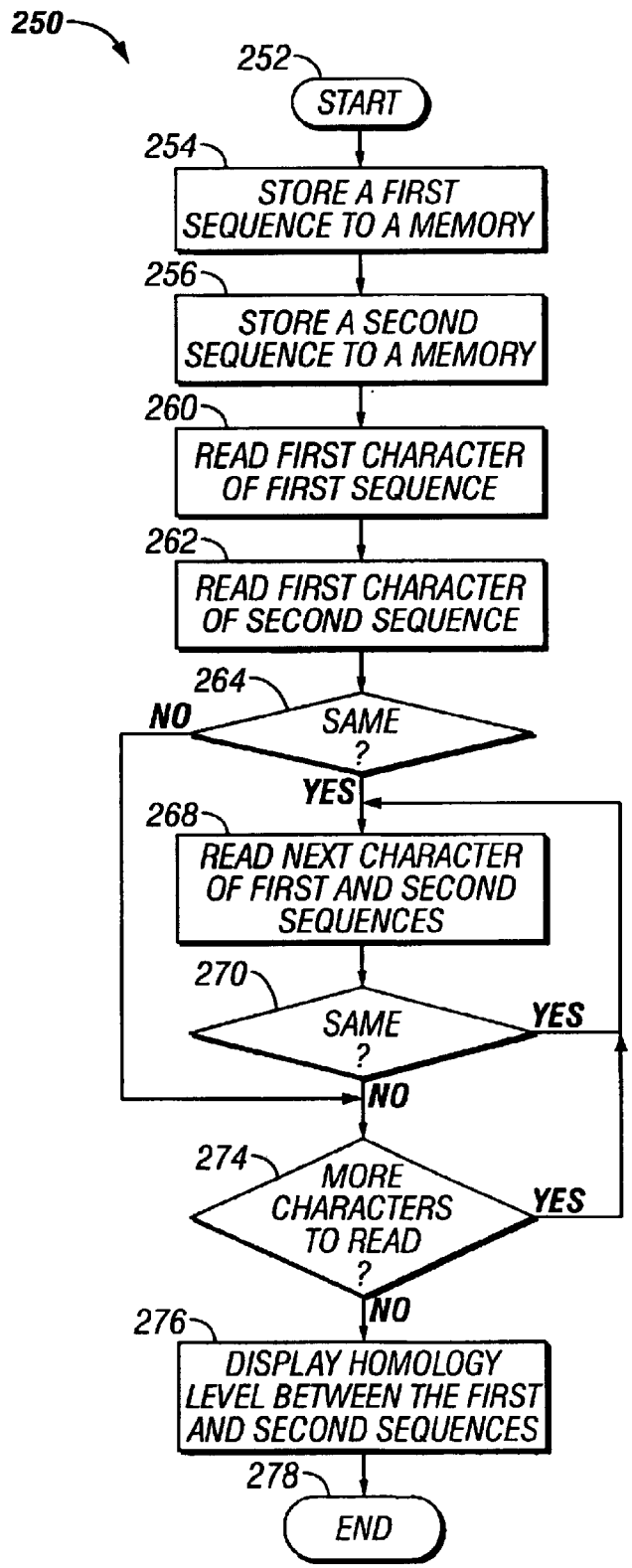
FIG. 10 is a flow diagram illustrating one aspect of a process in a computer for determining whether two sequences are homologous.

The parameters used with the above algorithms may be adapted depending on the sequence length and degree of homology studied. In some aspects, the parameters may be the default parameters used by the algorithms in the absence of instructions from the user. FIG. 9 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GEN-BANK that is available through the Internet. The process 200 begins at a start state 201 and then moves to a state 202 wherein the new sequence to be compared is stored to a memory in a computer system 100. As discussed above, the memory could be any type of memory, including RAM or an internal storage device. The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system. Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200. If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database. It should be noted that if a determination had been made at the decision state 212 that the sequences were not homologous, then the process 200 would move immediately to the decision state 218 in order to determine if any other sequences were available in the database for comparison. Accordingly, one aspect of the invention is a computer system comprising a processor, a data storage device having stored thereon a nucleic acid sequence of the invention and a sequence comparer for conducting the comparison. The sequence comparer may indicate a homology level between the sequences compared or identify structural motifs, or it may identify structural motifs in sequences which are compared to these nucleic acid codes and polypeptide codes. FIG. 10 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it can be a single letter amino acid code so that the first and sequence sequences can be easily compared. A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read. If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with an every character in a second sequence, the homology level would be 100%.

Alternatively, the computer program can compare a reference sequence to a sequence of the invention to determine whether the sequences differ at one or more positions. The program can record the length and identity of inserted, deleted or substituted nucleotides or amino acid residues with respect to the sequence of either the reference or the invention. The computer program may be a program which determines whether a reference sequence contains a single nucleotide polymorphism (SNP) with respect to a sequence of the invention, or, whether a sequence of the invention comprises a SNP of a known sequence. Thus, in some aspects, the computer program is a program which identifies SNPs. The method may be implemented by the computer systems described above and the method illustrated in FIG. 10. The method can be performed by reading a sequence of the invention and the reference sequences through the use of the computer program and identifying differences with the computer program.

Figure 11:
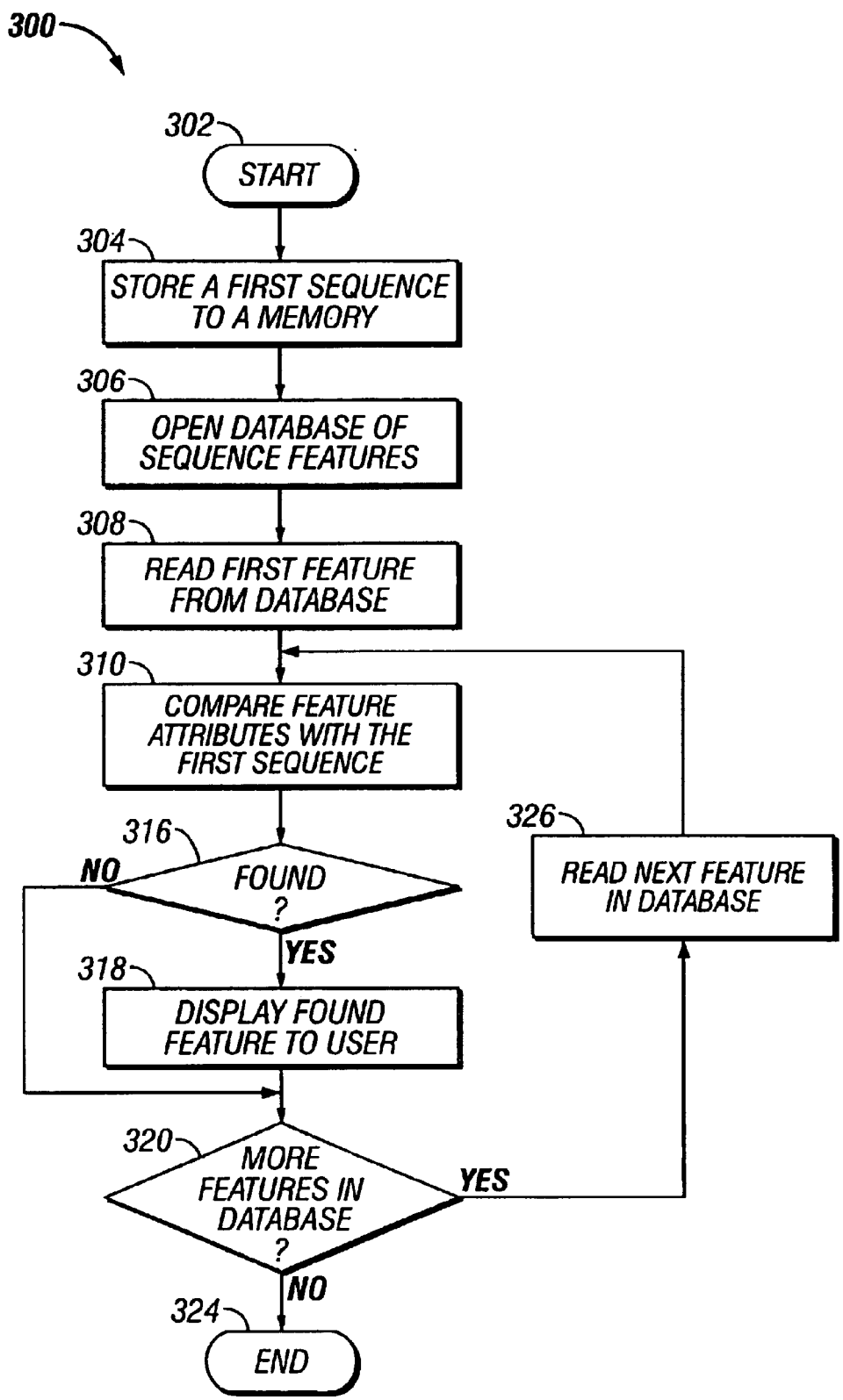
FIG. 11 is a flow diagram illustrating one aspect of an identifier process 300 for detecting the presence of a feature in a sequence.

In other aspects the computer based system comprises an identifier for identifying features within a nucleic acid or polypeptide of the invention. An "identifier" refers to one or more programs which identifies certain features within a nucleic acid sequence. For example, an identifier may comprise a program which identifies an open reading frame (ORF) in a nucleic acid sequence. FIG. 11 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art. Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user. The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. If the feature attribute is not found in the first sequence at the decision state 316, the process 300 moves directly to the decision state 320 in order to determine if any more features exist in the database. Thus, in one aspect, the invention provides a computer program that identifies open reading frames (ORFs).

A polypeptide or nucleic acid sequence of the invention may be stored and manipulated in a variety of data processor programs in a variety of formats. For example, a sequence can be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence of the invention. The programs and databases used to practice the invention include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237–245, 1990), Catalyst (Molecular Simulations Inc.), Catalyst/SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

The term "signal peptide" as used herein refers to a N-terminal amino acid sequence which, when associated with a polypeptide, permits the export of the target polypeptide from the cell and cleavage of the signal peptide. The signal peptide accesses the general protein secretion pathway. The signal peptides include, but are not limited to, a sequence of 15–24 amino acids that are able to be direct export of polypeptides from the cell using the cell's dedicated transport system. Signal peptide sequences can share similarity on their primary structure and can contain a conserved processing site of glycine-glycine residues or glycine-alanine residues at positions-2 and -1 of the processing site.

Exemplary nucleic acid sequences encoding signal peptides which direct the secretion of the encoded proteins include nucleotides 1–102 of SEQ ID NO:1, nucleotides 1–63 of SEQ ID NO:7, nucleotides 1–60 of SEQ ID NO:13, nucleotides 1–72 of SEQ ID NO:17, nucleotides 1–81 of SEQ ID NO:25, nucleotides 1–51 of SEQ ID NO:31, nucleotides 1–123 of SEQ ID NO:33, nucleotides 1–114 of SEQ ID NO:39, nucleotides 1–63 of SEQ ID NO:47, nucleotides 1–69 of SEQ ID NO:67, nucleotides 1–66 of SEQ ID NO:75 and nucleotides 1–69 of SEQ ID NO:77.

Exemplary signal peptides which direct the secretion of the encoded proteins include amino acids 1–34 of SEQ ID NO:2, amino acids 1–21 of SEQ ID NO:8, amino acids 1–20 of SEQ ID NO:14, amino acids 1–24 of SEQ ID NO:18, amino acids 1–27 of SEQ ID NO:26, amino acids 1–17 of SEQ ID NO:32, amino acids 1–42 of SEQ ID NO:34, amino acids 1–38 of SEQ ID NO:40, amino acids 1–28 of SEQ ID NO:48, amino acids 1–23 of SEQ ID NO:68, amino acids 1–22 of SEQ ID NO:76 and amino acids 1–23 of SEQ ID NO:78.

Exemplary mature polypeptides (e.g., polypeptides lacking a signal sequence) of the invention include SEQ ID NO:81 (amino acids 35–450 of SEQ ID NO:2), SEQ ID NO:82 (amino acids 22–298 of SEQ ID NO:8), SEQ ID NO:83 (amino acids 21–309 of SEQ ID NO:14), SEQ ID NO:84 (amino acids 25–449 of SEQ ID NO:18), SEQ ID NO:85 (amino acids 28–289 of SEQ ID NO:26), SEQ ID NO:86 (amino acids 18–297 of SEQ ID NO:32), SEQ ID NO:87 (amino acids 43–458 of SEQ ID NO:34), SEQ ID NO:88 (amino acids 39–460 of SEQ ID NO:40), SEQ ID NO:89 (amino acids 22–298 of SEQ ID NO:48), SEQ ID NO:90 (amino acids 24–341 of SEQ ID NO:68), SEQ ID NO:91 (amino acids 23–320 of SEQ ID NO:76), SEQ ID NO:92 (amino acids 24–341 of SEQ ID NO:78).

In another embodiment, a nucleic acid molecule includes a nucleotide sequence encoding a protein having an amino acid sequence sufficiently homologous to the amino acid sequence of SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91 or SEQ ID NO:92. In a preferred embodiment, a nucleic acid molecule includes a nucleotide sequence encoding a protein having an amino acid sequence at least 50%, 55%, 60%, 65%, 70%, 75%, 80%, 81%, 85%, 90%, 95%, 98% or more homologous to an amino acid sequence including SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91 or SEQ ID NO:92 (e.g., the entire amino acid sequence of SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91 or SEQ ID NO:92).

Nucleic acid molecules corresponding to natural allelic variants and homologues of the cDNAs of the invention can be isolated based on their homology to the nucleic acids disclosed herein using the cDNAs disclosed herein, or a portion thereof, as a hybridization probe according to standard hybridization techniques under stringent hybridization conditions.

In addition to naturally-occurring allelic variants of the epoxide hydrolase sequences that may exist in the population, the skilled artisan will further appreciate that changes can be introduced by mutation into the nucleotide sequences encoding the amino acid sequence of SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91 or SEQ ID NO:92, thereby leading to changes in the amino acid sequence of the encoded proteins, without altering the functional ability of the proteins. For example, nucleotide substitutions leading to amino acid substitutions at "non-essential" amino acid residues can be made in the sequence encoding the amino acid sequence of SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91 or SEQ ID NO:92. A "non-essential" amino acid residue is a residue that can be altered from the wild-type sequence of SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91 or SEQ ID NO:92 (e.g., the sequence of SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91 or SEQ ID NO:92) without altering the biological activity, whereas an "essential" amino acid residue is required for biological activity. For example, amino acid residues that are conserved among the proteins of the present invention, are predicted to be particularly unamenable to alteration. Furthermore, additional amino acid residues that are conserved between the proteins of the present invention and other family members are not likely to be amenable to alteration.

Accordingly, another aspect of the invention pertains to nucleic acid molecules encoding proteins that contain changes in amino acid residues that are not essential for activity. Such proteins differ in amino acid sequence from SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91 or SEQ ID NO:92, yet retain biological activity. In one embodiment, the isolated nucleic acid molecule comprises a nucleotide sequence encoding a protein, wherein the protein comprises an amino acid sequence at least about 41%, 42%, 45%, 50%, 55%, 59%, 60%, 65%, 70%, 75%, 80%, 81%, 85%, 90%, 95%, 98% or more homologous to the amino acid sequence of SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91 or SEQ ID NO:92 (e.g., the entire amino acid sequence of SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91 or SEQ ID NO:92).

Hybridization of Nucleic Acids

The invention provides isolated or recombinant nucleic acids that hybridize under stringent conditions to an exemplary sequence of the invention, e.g., SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80 The stringent conditions can be highly stringent conditions, medium stringent conditions, low stringent conditions, including the high and reduced stringency conditions described herein. In alternative embodiments, nucleic acids of the invention as defined by their ability to hybridize under stringent conditions can be between about five residues and the full length of a sequence of the invention; e.g., they can be at least 5, 10, 15, 20, 25, 30, 35, 40, 50, 55, 60, 65, 70, 75, 80, 90, 100, 150, 200, 250, 300, 350, 400 residues in length. Nucleic acids shorter than full length are also included. These nucleic acids are useful as, e.g., hybridization probes, labeling probes, PCR oligonucleotide probes, iRNA, antisense or sequences encoding antibody binding peptides (epitopes), motifs, active sites and the like.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/ml polyriboadenylic acid. Approximately $2\times10^7$ cpm (specific activity $4-9\times10^8$ cpm/ug) of $^{32}P$ end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at $T_m-10°$ C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas:

For probes between 14 and 70 nucleotides in length the melting temperature ($T_m$) is calculated using the formula: $T_m=81.5+16.6(\log [Na+])+0.41(\text{fraction } G+C)-(600/N)$ where N is the length of the probe.

If the hybridization is carried out in a solution containing formamide, the melting temperature may be calculated using the equation: $T_m=81.5+16.6(\log [Na+])+0.41 (\text{fraction } G+C)-(0.63\% \text{ formamide})-(600/N)$ where N is the length of the probe.

Prehybridization may be carried out in 6×SSC, 5× Denhardt's reagent, 0.5% SDS, 100 μg denatured fragmented salmon sperm DNA or 6×SSC, 5× Denhardt's reagent, 0.5% SDS, 100 μg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the $T_m$. For shorter probes, such as oligonucleotide probes, the hybridization may be conducted at 5–10° C., below the $T_m$. Typically, for hybridizations in 6×SSC, the hybridization is conducted at approximately 68° C. Usually, for hybridizations in 50% formamide containing solutions, the hybridization is conducted at approximately 42° C.

All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a $Na^+$ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 97%, at least 95%, at least 90%, at least 85%, at least 80%, at least 75%, at least 70%, at least 65%, at least 60%, at least 55%, or at least 50% homology to a nucleic acid sequence of the invention, or fragments comprising at least about 10, 15, 20, 25, 30, 35, 40, 50, 75, 100, 150, 200, 300, 400, or 500 consecutive bases thereof, and the sequences complementary thereto. Homology can be measured using an alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of the invention or the sequences complementary thereto.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism.

In one aspect, nucleic acid sequences of the invention are used as probes to identify and isolate related nucleic acids.

In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH2PO4, pH 7.0, 5.0 mM Na2EDTA, 0.5% SDS, 10× Denhardt's, and 0.5 mg/ml polyriboadenylic acid. Approximately $2 \times 10^7$ cpm (specific activity $4-9 \times 10^8$ cpm/ug) of 32P end-labeled oligonucleotide probe are then added to the solution. After 12–16 hours of incubation, the membrane is washed for 30 minutes at room temperature (RT) in 1×SET (150 mM NaCl, 20 mM Tris hydrochloride, pH 7.8, 1 mM Na2EDTA) containing 0.5% SDS, followed by a 30 minute wash in fresh 1×SET at Tm–10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+0.41(fraction G+C)−(600/N) where N is the length of the probe. If the hybridization is carried out in a solution containing formamide, the melting temperature may be calculated using the equation: Tm=81.5+16.6(log [Na+])+0.41(fraction G+C)−(0.63% formamide)−(600/N) where N is the length of the probe. Prehybridization may be carried out in 6×SSC, 5× Denhardt's reagent, 0.5% SDS, 100 µg denatured fragmented salmon sperm DNA or 6×SSC, 5× Denhardt's reagent, 0.5% SDS, 100 µg denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 5–10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a $Na^+$ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods of the invention can be used to isolate nucleic acids having a sequence with at least about 99%, 98%, 97%, at least 95%, at least 90%, at least 85%, at least 80%, at least 75%, at least 70%, at least 65%, at least 60%, at least 55%, or at least 50% homology to a nucleic acid sequence of the invention comprising at least about 10, 15, 20, 25, 30, 35, 40, 50, 75, 100, 150, 200, 250, 300, 350, 400, 500, 550, 600, 650, 700, 750, 800, 850, 900, 950, 1000, or more consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to a nucleic acid of the invention.

Additionally, the probes and methods of the invention may be used to isolate nucleic acids which encode polypeptides having at least about 99%, at least 95%, at least 90%, at least 85%, at least 80%, at least 75%, at least 70%, at least 65%, at least 60%, at least 55%, or at least 50% sequence identity (homology) to a polypeptide of the invention comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters, or a BLAST 2.2.2 program with exemplary settings as set forth herein).

Oligonucleotides Probes and Methods for Using Them

The invention also provides nucleic acid probes for identifying nucleic acids encoding a polypeptide with epoxide hydrolase activity. In one aspect, the probe comprises at least 10 consecutive bases of a sequence as set forth in an exemplary sequence of the invention. Alternatively, a probe of the invention can be at least about 5, 6, 7, 8 or 9 to about 40, about 10 to 50, about 20 to 60 about 30 to 70, consecutive bases of a sequence of the invention. The probes identify a nucleic acid by binding or hybridization. The probes can be used in arrays of the invention, see discussion below, including, e.g., capillary arrays. The probes of the invention can also be used to isolate other nucleic acids or polypeptides.

The probes of the invention can be used to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences present in the sample. Where necessary, conditions which permit the probe to specifically hybridize to complementary sequences may be determined by placing the probe in contact with complementary sequences from samples known to contain the complementary sequence, as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids (see discussion on specific hybridization conditions).

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product. Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel and Sambrook.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). In one aspect, the probes comprise oligonucleotides. In one aspect, the amplification reaction may comprise a PCR reaction. PCR protocols are described in Ausubel and Sambrook (see discussion on amplification reactions). In such-procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism. In one aspect, nucleic acid sequences of the invention are used as probes to identify and isolate related nucleic acids.

In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH2PO4, pH 7.0, 5.0 mM Na2EDTA, 0.5% SDS, 10× Denhardt's, and 0.5 mg/ml polyriboadenylic acid. Approximately $2 \times 10^7$ cpm (specific activity $4-9 \times 10^8$ cpm/ug) of 32P end-labeled oligonucleotide probe are then added to the solution. After 12–16 hours of incubation, the membrane is washed for 30 minutes at room temperature (RT) in 1×SET (150 mM NaCl, 20 mM Tris hydrochloride, pH 7.8, 1 mM Na2EDTA) containing 0.5% SDS, followed by a 30 minute wash in fresh 1×SET at Tm−10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+0.41(fraction G+C)−(600/N) where N is the length of the probe. If the hybridization is carried out in a solution containing formamide, the melting temperature may be calculated using the equation: Tm=81.5+16.6(log [Na+])+0.41 (fraction G+C)−(0.63% formamide)−(600/N) where N is the length of the probe. Prehybridization may be carried out in 6×SSC, 5× Denhardt's reagent, 0.5% SDS, 100 μg denatured fragmented salmon sperm DNA or 6×SSC, 5× Denhardt's reagent, 0.5% SDS, 100 μg denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 5–10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods of the invention can be used to isolate nucleic acids having a sequence with at least about 99%, 98%, 97%, at least 95%, at least 90%, at least 85%, at least 80%, at least 75%, at least 70%, at least 65%, at least 60%, at least 55%, or at least 50% homology to a nucleic acid sequence of the invention comprising at least about 10, 15, 20, 25, 30, 35, 40, 50, 75, 100, 150, 200, 250, 300, 350, 400, 500, 550, 600, 650, 700, 750, 800, 850, 900, 950, 1000, or more consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to a nucleic acid of the invention.

Additionally, the probes and methods of the invention may be used to isolate nucleic acids which encode polypeptides having at least about 99%, at least 95%, at least 90%, at least 85%, at least 80%, at least 75%, at least 70%, at least 65%, at least 60%, at least 55%, or at least 50% sequence identity (homology) to a polypeptide of the invention comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters, or a BLAST 2.2.2 program with exemplary settings as set forth herein).

Inhibiting Expression of Epoxide Hydrolase

The invention further provides for nucleic acids complementary to (e.g., antisense sequences to) the nucleic acid sequences of the invention. Antisense sequences are capable of inhibiting the transport, splicing or transcription of epoxide hydrolase-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind epoxide hydrolase gene or message, in either case preventing or inhibiting the production or function of epoxide hydrolase. The association can be through sequence specific hybridization. Another useful class of inhibitors includes oligonucleotides which cause inactivation or cleavage of epoxide hydrolase message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

Antisense Oligonucleotides

The invention provides antisense oligonucleotides capable of binding epoxide hydrolase message which can inhibit proteolytic activity by targeting mRNA. Strategies for designing antisense oligonucleotides are well described in the scientific and patent literature, and the skilled artisan can design such epoxide hydrolase oligonucleotides using the novel reagents of the invention. For example, gene walking/RNA mapping protocols to screen for effective antisense oligonucleotides are well known in the art, see, e.g., Ho (2000) Methods Enzymol. 314:168–183, describing an RNA mapping assay, which is based on standard molecular techniques to provide an easy and reliable method for potent antisense sequence selection. See also Smith (2000) Eur. J. Pharm. Sci. 11:191–198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189☐1197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense epoxide hydrolase sequences of the invention (see, e.g., Gold (1995) J. of Biol. Chem. 270:13581–13584).

Inhibitory Ribozymes

The invention provides for with ribozymes capable of binding epoxide hydrolase message which can inhibit proteolytic activity by targeting mRNA. Strategies for designing ribozymes and selecting the epoxide hydrolase-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary basepairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule can be formed in a hammerhead motif, but may also be formed in the motif of a hairpin, hepatitis delta virus, group I intron or RnaseP-like RNA (in association with an RNA guide sequence). Examples of such hammerhead motifs are described by Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

Modification of Nucleic Acids

The invention provides methods of generating variants of the nucleic acids of the invention, e.g., those encoding an epoxide hydrolase enzyme. These methods can be repeated or used in various combinations to generate epoxide hydrolase enzymes having an altered or different activity or an altered or different stability from that of an epoxide hydrolase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

A nucleic acid of the invention can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467–5471; or, combinatorial multiple cassette mutagenesis, see, e.g., Crameri (1995) Biotechniques 18:194–196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis™ (GSSM™), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1–4; Ness (1999) Nature Biotechnology 17:893–896; Chang (1999) "Evolution of a cytokine using DNA family shuffling" Nature Biotechnology 17:793–797; Minshull (1999) "Protein evolution by molecular breeding" Current Opinion in Chemical Biology 3:284–290; Christians (1999) "Directed evolution of thymidine kinase for AZT phosphorylation using DNA family shuffling" Nature Biotechnology 17:259–264; Crameri (1998) "DNA shuffling of a family of genes from diverse species accelerates directed evolution" Nature 391:288–291; Crameri (1997) "Molecular evolution of an arsenate detoxification pathway by DNA shuffling," Nature Biotechnology 15:436–438; Zhang (1997) "Directed evolution of an effective fucosidase from a galactosidase by DNA shuffling and screening" Proc. Natl. Acad. Sci. USA 94:4504–4509; Patten et al. (1997) "Applications of DNA Shuffling to Pharmaceuticals and Vaccines" Current Opinion in Biotechnology 8:724–733; Crameri et al. (1996) "Construction and evolution of antibody-phage libraries by DNA shuffling" Nature Medicine 2:100–103; Gates et al. (1996) "Affinity selective isolation of ligands from peptide libraries through display on a lac repressor 'headpiece dimer'" Journal of Molecular Biology 255:373–386; Stemmer (1996) "Sexual PCR and Assembly PCR" In: The Encyclopedia of Molecular Biology. VCH Publishers, New York. pp.447–457; Crameri and Stemmer (1995) "Combinatorial multiple cassette mutagenesis creates all the permutations of mutant and wildtype cassettes" BioTechniques 18:194–195;

Stemmer et al. (1995) "Single-step assembly of a gene and entire plasmid form large numbers of oligodeoxyribonucleotides" Gene, 164:49–53; Stemmer (1995) "The Evolution of Molecular Computation" Science 270: 1510; Stemmer (1995) "Searching Sequence Space" Bio/Technology 13:549–553; Stemmer (1994) "Rapid evolution of a protein in vitro by DNA shuffling" Nature 370:389–391; and Stemmer (1994) "DNA shuffling by random fragmentation and reassembly: In vitro recombination for molecular evolution." Proc. Natl. Acad. Sci. USA 91:10747–10751.

Mutational methods of generating diversity include, for example, site-directed mutagenesis (Ling et al. (1997) "Approaches to DNA mutagenesis: an overview" Anal Biochem. 254(2): 157–178; Dale et al. (1996) "Oligonucleotide-directed random mutagenesis using the phosphorothioate method" Methods Mol. Biol. 57:369–374; Smith (1985) "In vitro mutagenesis" Ann. Rev. Genet. 19:423–462; Botstein & Shortle (1985) "Strategies and applications of in vitro mutagenesis" Science 229:1193–1201; Carter (1986) "Site-directed mutagenesis" Biochem. J. 237:1–7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488–492; Kunkel et al. (1987) "Rapid and efficient site-specific mutagenesis without phenotypic selection" Methods in Enzymol. 154, 367–382; and Bass et al. (1988) "Mutant Trp repressors with new DNA-binding specificities" Science 242:240–245); oligonucleotide-directed mutagenesis (Methods in Enzymol. 100: 468–500 (1983); Methods in Enzymol. 154: 329–350 (1987); Zoller & Smith (1982) "Oligonucleotide-directed mutagenesis using M13-derived vectors: an efficient and general procedure for the production of point mutations in any DNA fragment" Nucleic Acids Res. 10:6487–6500; Zoller & Smith (1983) "Oligonucleotide-directed mutagenesis of DNA fragments cloned into M13 vectors" Methods in Enzymol. 100:468–500; and Zoller & Smith (1987) Oligonucleotide-directed mutagenesis: a simple method using two oligonucleotide primers and a single-stranded DNA template" Methods in Enzymol. 154:329–350); phosphorothioate-modified DNA mutagenesis (Taylor et al. (1985) "The use of phosphorothioate-modified DNA in restriction enzyme reactions to prepare nicked DNA" Nucl. Acids Res. 13: 8749–8764; Taylor et al. (1985) "The rapid generation of oligonucleotide-directed mutations at high frequency using phosphorothioate-modified DNA" Nucl. Acids Res. 13: 8765–8787 (1985); Nakamaye (1986) "Inhibition of restriction endonuclease Nci I cleavage by phosphorothioate groups and its application to oligonucleotide-directed mutagenesis" Nucl. Acids Res. 14: 9679–9698; Sayers et al. (1988) "Y-T Exonucleases in phosphorothioate-based oligonucleotide-directed mutagenesis" Nucl. Acids Res. 16:791–802; and Sayers et al. (1988) "Strand specific cleavage of phosphorothioate-containing DNA by reaction with restriction endonucleases in the presence of ethidium bromide" Nucl. Acids Res. 16: 803–814); mutagenesis using gapped duplex DNA (Kramer et al. (1984) "The gapped duplex DNA approach to oligonucleotide-directed mutation construction" Nucl. Acids Res. 12: 9441–9456; Kramer & Fritz (1987) Methods in Enzymol. "Oligonucleotide-directed construction of mutations via gapped duplex DNA" 154:350–367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987–6999).

Additional protocols used in the methods of the invention include point mismatch repair (Kramer (1984) "Point Mismatch Repair" Cell 38:879–887), mutagenesis using repair-deficient host strains (Carter et al. (1985) "Improved oligonucleotide site-directed mutagenesis using M13 vectors" Nucl. Acids Res. 13: 4431–4443; and Carter (1987) "Improved oligonucleotide-directed mutagenesis using M13 vectors" Methods in Enzymol. 154: 382–403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415–423), mutagenesis by total gene synthesis (Nambiar et al. (1984) "Total synthesis and cloning of a gene coding for the ribonuclease S protein" Science 223: 1299–1301; Sakamar and Khorana (1988) "Total synthesis and expression of a gene for the a-subunit of bovine rod outer segment guanine nucleotide-binding protein (transducin)" Nucl. Acids Res. 14: 6361–6372; Wells et al. (1985) "Cassette mutagenesis: an efficient method for generation of multiple mutations at defined sites" Gene 34:315–323; and Grundstrom et al. (1985) "Oligonucleotide-directed mutagenesis by microscale 'shot-gun' gene synthesis" Nucl. Acids Res. 13: 3305–3316), double-strand break repair (Mandecki (1986); Arnold (1993) "Protein engineering for unusual environments" Current Opinion in Biotechnology 4:450–455. "Oligonucleotide-directed double-strand break repair in plasmids of *Escherichia coli*: a method for site-specific mutagenesis" Proc. Natl. Acad. Sci. USA, 83:7177–7181). Additional details on many of the above methods can be found in Methods in Enzymology Volume 154, which also describes useful controls for trouble-shooting problems with various mutagenesis methods. See also U.S. Pat. Nos. 5,605, 793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library ImLmunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Certain U.S. applications provide additional details regarding various diversity generating methods, including "SHUFFLING OF CODON ALTERED GENES" by Patten et al. filed Sep. 28, 1999, (U.S. Ser. No. 09/407,800); "EVOLUTION OF WHOLE CELLS AND ORGANISMS BY RECURSIVE SEQUENCE RECOMBINATION" by del Cardayre et al., filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549).

Non-stochastic, or "directed evolution," methods include, e.g., saturation mutagenesis (GSSM), synthetic ligation reassembly (SLR), or a combination thereof are used to modify the nucleic acids of the invention to generate epoxide hydrolase with new or altered properties (e.g., activity under highly acidic or alkaline conditions, high temperatures, and the like). Polypeptides encoded by the modified nucleic acids can be screened for an activity before testing for proteolytic or other activity. Any testing modality or protocol can be used, e.g., using a capillary array platform. See, e.g., U.S. Pat. Nos. 6,361,974; 6,280,926; 5,939,250.

Saturation Mutagenesis, or, GSSM™

In one aspect of the invention, non-stochastic gene modification, a "directed evolution process," is used to generate epoxide hydrolases with new or altered properties. Variations of this method have been termed "Gene Site Saturation Mutagenesis™ (GSSM™)," "site-saturation mutagenesis," "saturation mutagenesis" or simply "GSSM." It can be used in combination with other mutagenization processes. See, e.g., U.S. Pat. Nos. 6,171,820; 6,238,884. In one aspect, GSSM comprises providing a template polynucleotide and a plurality of oligonucleotides, wherein each oligonucleotide comprises a sequence homologous to the template polynucleotide, thereby targeting a specific sequence of the template polynucleotide, and a sequence that is a variant of the homologous gene; generating progeny polynucleotides comprising non-stochastic sequence variations by replicating the template polynucleotide with the oligonucleotides, thereby generating polynucleotides comprising homologous gene sequence variations.

In one aspect, codon primers containing a degenerate N,N,G/T sequence are used to introduce point mutations into a polynucleotide, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position×100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., epoxide hydrolases) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., E. coli host, using, e.g., an expression vector) and subjected to expression screening. When an individual progeny polypeptide is identified by screening to display a favorable change in property (when compared to the parental polypeptide, such as increased proteolytic activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In another aspect, site-saturation mutagenesis can be used together with another stochastic or non-stochastic means to vary sequence, e.g., synthetic ligation reassembly (see below), shuffling, chimerization, recombination and other mutagenizing processes and mutagenizing agents. This invention provides for the use of any mutagenizing process (es), including saturation mutagenesis, in an iterative manner.

Synthetic Ligation Reassembly (SLR)

The invention provides a non-stochastic gene modification system termed "synthetic ligation reassembly," or simply "SLR," a "directed evolution process," to generate epoxide hydrolases with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. patent application Ser. No. (U.S. Ser. No.) 09/332,835 entitled "Synthetic Ligation Reassembly in Directed Evolution" and filed on Jun. 14, 1999 ("U.S. Ser. No. 09/332, 835"). In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over 10100 different chimeras. SLR can be used to generate libraries comprised of over 101000 different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled. In one aspect of this method, the sequences of a plurality of parental nucleic acid templates are aligned in order to select one or more demarcation points. The demarcation points can be located at an area of homology, and are comprised of one or more nucleotides. These demarcation points are preferably shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more preferably a serviceable demarcation points is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another aspect, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

In another aspect, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g. by mutagenesis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

In one aspect, a nucleic acid building block is used to introduce an intron. Thus, functional introns are introduced into a man-made gene manufactured according to the methods described herein. The artificially introduced intron(s) can be functional in a host cells for gene splicing much in the way that naturally-occurring introns serve functionally in gene splicing.

Optimized Directed Evolution System

The invention provides a non-stochastic gene modification system termed "optimized directed evolution system" to generate epoxide hydrolases with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, 1013 chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate 1013 chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. Additional information can also be found, e.g., in U.S. Ser. No. 09/332,835; U.S. Pat. No. 6,361,974. The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a 1/3 chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate 1013 chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. See also U.S. Ser. No. 09/332,835.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a 1/3 chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. One can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events.

Determining Crossover Events

Aspects of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is preferably performed in MATLABa (The Mathworks, Natick, Mass.) a programming language and development environment for technical computing.

Iterative Processes

In practicing the invention, these processes can be iteratively repeated. For example a nucleic acid (or, the nucleic acid) responsible for an altered epoxide hydrolase phenotype is identified, re-isolated, again modified, re-tested for activity. This process can be iteratively repeated until a desired phenotype is engineered. For example, an entire biochemical anabolic or catabolic pathway can be engineered into a cell, including proteolytic activity.

Similarly, if it is determined that a particular oligonucleotide has no affect at all on the desired trait (e.g., a new epoxide hydrolase phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In vivo shuffling of molecules is use in methods of the invention that provide variants of polypeptides of the invention, e.g., antibodies, epoxide hydrolases, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In one aspect, the invention provides a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

Producing Sequence Variants

The invention also provides methods of making sequence variants of the nucleic acid and epoxide hydrolase sequences of the invention or isolating epoxide hydrolases using the nucleic acids and polypeptides of the invention. In one aspect, the invention provides for variants of an epoxide hydrolase gene of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11–15, 1989) and Caldwell, R. C. & Joyce G. F., PCR Methods Applic., 2:28–33, 1992. Briefly, in such procedures, nucleic acids to be mutagenized are mixed with PCR primers, reaction buffer, MgCl2, MnCl2, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM MnCl2, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241:53–57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747–10751. Briefly, in such procedures a plurality of nucleic acids to be recombined are digested with DNase to generate fragments having an average size of 50–200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10–30 ng/:1 in a solution of 0.2 mM of each dNTP, 2.2 mM MgCl2, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50–55° C. for 30 seconds, 72° C. for 30 seconds (30–45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described, e.g., in PCT Publication No. WO 91/16427.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, e.g., in Arkin (1992) Proc. Natl. Acad. Sci. USA 89:7811–7815.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, e.g., in Delegrave (1993) Biotechnology Res. 11:1548–1552. Random and site-directed mutagenesis are described, e.g., in Arnold (1993) Current Opinion in Biotechnology 4:450–455.

In some aspects, the variants are created using shuffling procedures wherein portions of a plurality of nucleic acids which encode distinct polypeptides are fused together to create chimeric nucleic acid sequences which encode chimeric polypeptides as described in, e.g., U.S. Pat. Nos. 5,965,408; 5,939,250.

The invention also provides variants of polypeptides of the invention comprising sequences in which one or more of the amino acid residues (e.g., of an exemplary polypeptide, such as SEQ ID NO:2) are substituted with a conserved or non-conserved amino acid residue (e.g., a conserved amino acid residue) and such substituted amino acid residue may or may not be one encoded by the genetic code. Conservative substitutions are those that substitute a given amino acid in a polypeptide by another amino acid of like characteristics. Thus, polypeptides of the invention include those with conservative substitutions of sequences of the invention, e.g., the exemplary SEQ ID NO:2, including but not limited to the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. Other variants are those in which one or more of the amino acid residues of the polypeptides of the invention includes a substituent group.

Other variants within the scope of the invention are those in which the polypeptide is associated with another compound, such as a compound to increase the half-life of the polypeptide, for example, polyethylene glycol.

Additional variants within the scope of the invention are those in which additional amino acids are fused to the polypeptide, such as a leader sequence, a secretory sequence, a proprotein sequence or a sequence which facilitates purification, enrichment, or stabilization of the polypeptide.

In some aspects, the variants, fragments, derivatives and analogs of the polypeptides of the invention retain the same biological function or activity as the exemplary polypeptides, e.g., a proteolytic activity, as described herein. In other aspects, the variant, fragment, derivative, or analog includes a proprotein, such that the variant, fragment, derivative, or analog can be activated by cleavage of the proprotein portion to produce an active polypeptide.

Optimizing Codons to Achieve High Levels of Protein Expression in Host Cells

The invention provides methods for modifying epoxide hydrolase-encoding nucleic acids to modify codon usage. In one aspect, the invention provides methods for modifying codons in a nucleic acid encoding an epoxide hydrolase to increase or decrease its expression in a host cell. The invention also provides nucleic acids encoding an epoxide hydrolase modified to increase its expression in a host cell, epoxide hydrolase so modified, and methods of making the modified epoxide hydrolases. The method comprises identifying a "non-preferred" or a "less preferred" codon in epoxide hydrolase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli* and *Pseudomonas fluorescens*; gram positive bacteria, such as *Streptomyces diversa, Lactobacillus gasseri, Lactococcus lactis, Lactococcus cremoris, Bacillus subtilis*. Exemplary host cells also include eukaryotic organisms, e.g., various yeast, such as *Saccharomyces* sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding an epoxide hydrolase isolated from a bacterial cell are modified such that the nucleic acid is optimally expressed in a bacterial cell different from the bacteria from which the epoxide hydrolase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113–118; Hale (1998) Protein Expr. Purif. 12:185–188; Narum (2001) Infect. Immun. 69:7250–7253. See also Narum (2001) Infect. Immun. 69:7250–7253, describing optimizing codons in mouse systems; Outchkourov (2002) Protein Expr. Purif. 24:18–24, describing optimizing codons in yeast; Feng (2000) Biochemistry 39:15399–15409, describing optimizing codons in *E. coli*; Humphreys (2000) Protein Expr. Purif. 20:252–264, describing optimizing codon usage that affects secretion in *E. coli*.

Transgenic Non-Human Animals

The invention provides transgenic non-human animals comprising a nucleic acid, a polypeptide (e.g., epoxide hydrolase), an expression cassette or vector or a transfected or transformed cell of the invention. The transgenic non-human animals can be, e.g., goats, rabbits, sheep, pigs, cows, rats and mice, comprising the nucleic acids of the invention. These animals can be used, e.g., as in vivo models to study epoxide hydrolase activity, or, as models to screen for modulators of epoxide hydrolase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147–157, describing the production of recombinant proteins in the milk of transgenic dairy animals; Baguisi (1999) Nat. Biotechnol. 17:456–461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express or to be unable to express an epoxide hydrolase.

Polypeptides and Peptides

The invention provides isolated or recombinant polypeptides having a sequence identity to an exemplary sequence of the invention, e.g., SEQ ID NO:2; SEQ ID NO:4; SEQ ID NO:6; SEQ ID NO:8, SEQ ID NO:10, SEQ ID NO:12, SEQ ID NO:14, SEQ ID NO:16, SEQ ID NO:18, SEQ ID NO:20; SEQ ID NO:22; SEQ ID NO:22; SEQ ID NO:26; SEQ ID NO:28, SEQ ID NO:30, SEQ ID NO:32, SEQ ID NO:34, SEQ ID NO:36; SEQ ID NO:38, SEQ ID NO:40, SEQ ID NO:42, SEQ ID NO:44, SEQ ID NO:46, SEQ ID NO:48, SEQ ID NO:50; SEQ ID NO:52; SEQ ID NO:54; SEQ ID NO:56; SEQ ID NO:58, SEQ ID NO:60; SEQ ID NO:62, SEQ ID NO:64, SEQ ID NO:66, SEQ ID NO:68, SEQ ID NO:70; SEQ ID NO:72; SEQ ID NO:74; SEQ ID NO:76; SEQ ID NO:78, SEQ ID NO:80. As discussed above, the identity can be over the full length of the polypeptide, or, the identity can be over a region of at least about 50, 60, 70, 80, 90, 100, 150, 200, 250, 300, 350, 400, 450, 500, 550, 600, 650, 700 or more residues. Polypeptides of the invention can also be shorter than the full length of exemplary polypeptides (e.g., SEQ ID NO:2; SEQ ID NO:4; SEQ ID NO:6; SEQ ID NO:8, SEQ ID NO:10, SEQ ID NO:12, SEQ ID NO:14, SEQ ID NO:16; SEQ ID NO:18, SEQ ID NO:20; SEQ ID NO:22; SEQ ID NO:22; SEQ ID NO:26; SEQ ID NO:28, SEQ ID NO:30, SEQ ID NO:32, SEQ ID NO:34, SEQ ID NO:36; SEQ ID NO:38, SEQ ID NO:40, SEQ ID NO:42, SEQ ID NO:44, SEQ ID NO:46, SEQ ID NO:48, SEQ ID NO:50; SEQ ID NO:52; SEQ ID NO:54; SEQ ID NO:56; SEQ ID NO:58, SEQ ID NO:60; SEQ ID NO:62, SEQ ID NO:64, SEQ ID NO:66, SEQ ID NO:68, SEQ ID NO:70; SEQ ID NO:72; SEQ ID NO:74; SEQ ID NO:76; SEQ ID NO:78, SEQ ID NO:80). In alternative aspects, the invention provides polypeptides (peptides, fragments) ranging in size between about 5 and the full length of a polypeptide, e.g., an enzyme, such as an epoxide hydrolase; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary epoxide hydrolase of the invention. Peptides of the invention can be useful as, e.g., labeling probes, antigens, toleragens, motifs, epoxide hydrolase active sites.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215–223; Horn (1980) Nucleic Acids Res. Symp. Ser. 225–232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3–13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has an epoxide hydrolase activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH2- for —C(=O)—NH—), aminomethylene (CH2-NH), ethylene, olefin (CH=CH), ether (CH2-O), thioether (CH2-S), tetrazole (CN4-), thiazole, retroamide, thioamide, or ester (see, e.g., Spatola (1983) in Chemistry and Biochemistry of Amino Acids, Peptides and Proteins, Vol. 7, pp 267–357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxy-biphenylphenylalanine; D- or L-2-indole (alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3 (2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids omithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W. H. Freeman and Company, New York (1993); Posttranslational Covalent Modification of Proteins, B. C. Johnson, Ed., Academic Press, New York, pp. 1–12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149–2154, 1963) (See also Stewart, J. M. and Young, J. D., Solid Phase Peptide Synthesis, 2nd Ed., Pierce Chemical Co., Rockford, Ill., pp. 11–12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

Epoxide Hydrolases

Epoxide hydrolases show promise as appealing tools for the synthesis of enantiopure epoxides via the hydrolytic kinetic resolution of racemic epoxides. Some of the attractive features of this potentially useful enzyme class are outlined below.

EHs are ubiquitous in nature. EHs have been found in all mammalian species tested, with the mammalian liver microsomal epoxide hydrolase (mEH) being the best studied. (Armstrong, R. N. Drug Metab. Rev. 1999, 31, 71–86.) Most mammalian EHs are involved in the detoxification of epoxides, while a few are engaged in the biosynthesis of hormones. Although mammalian EHs have been known for decades, most studies were focused on their biological role and mechanism. In a few cases where their use for organic synthesis was investigated, it was found that several substrates, could be efficiently processed by epoxide hydrolases leading to enantiomerically enriched—epoxides (the unreacted enantiomer) and/or to the corresponding vicinal diols. (Archer, I. V. J. Tetrahedron 1997, 53, 15617–15662.) The observed intrinsic enantioselectivity of these enzymes demonstrated the potential of EHs as biocatalysts for the synthesis of chiral epoxides and diols. However, their use on a preparative scale was not feasible due to the difficulty of obtaining large quantities of enzymes through overexpression.

In the last ten years, a number of EHs have been found from various bacteria, yeast, and fungi. (Svaving, J.; de Bont, J. A. M. Enz. Microbiol. Technol. 1998, 22, 19–26.) Examples of bacterial EHs include those isolated from *Agrobacterium radiobacter, Rhodococcus* sp., *Corynebacterium* sp., *Mycobacterium paraffinicum, Nocardia* sp., *Pseudomonas* NRRL B-2994, and some *Streptomyces* strains. Fungal EHs were also found in *Aspergillus niger, Helminthosporum sativum, Diploida gossypina, Beauveria sulfurescens*, and some *Fursarium* strains. The best-known yeast EH is *Rhodotorula glutinis* enzyme. Almost all of these enzymes were discovered during the screening of available strains with various epoxide substrates, and only a handful of them were further investigated at the genetic level. Some of these enzymes showing good enantioselectivity and potentially being readily available through fermentation. However, in order to be used for large-scale industrial production of epoxides, the scope of substrates recognized by microbial epoxide hydrolases need to be expanded and discovery of novel EHs should offer a viable solution.

EHs are cofactor-free, 'easy-to-use' catalysts. Biochemical studies have shown that EHs, like other well-recognized hydrolytic enzymes such as lipases and esterases, require neither prosthetic groups nor metal ions for activity. Current proposed mechanism by which EHs operate also bears similarity to that of esterases in that a covalent adduct is formed between the enzyme active site and the substrate during the catalytic cycle. Site-directed mutagenesis studies and structural data of a bacterial enzyme (*A. radiobacter*) suggested an active site Asp as the nucleophile. (Nardini, M.; Ridder, I. S.; Rozeboon, H. J.; Kalk, K. H.; Rink, R.; Janssen, D. B.; Dijkstra, B. W. J. Biol. Chem. 1999, 274, 14579–14596.)

Figure 12:
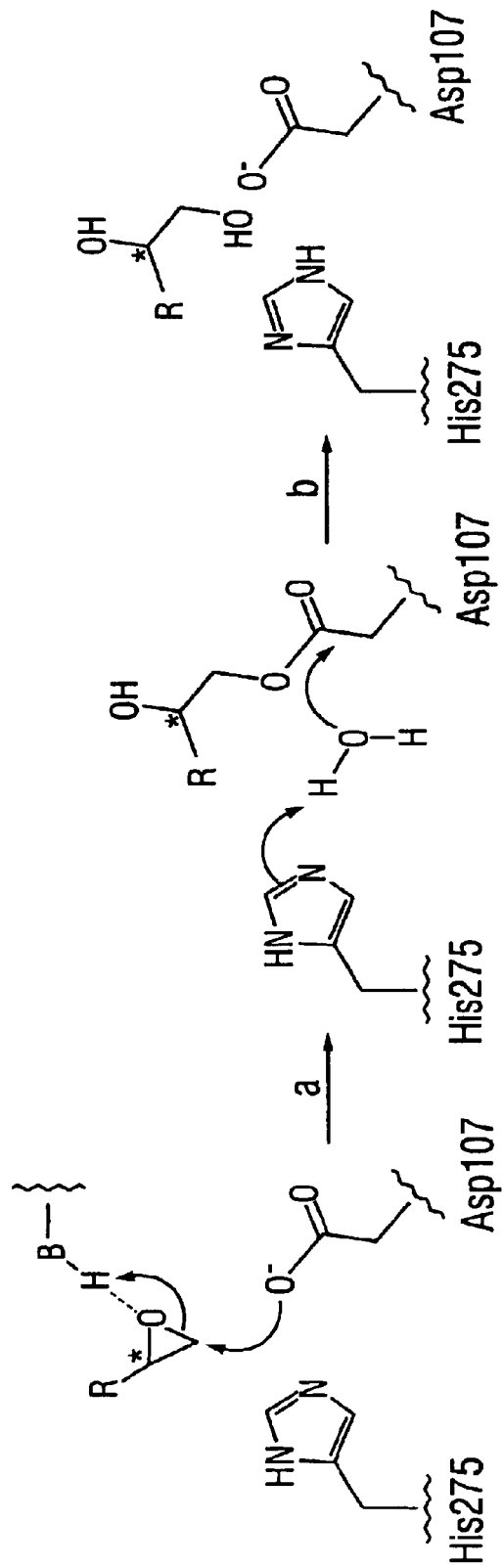
FIG. 12 is an illustration of the mechanism of *A. radiobacter* epoxide hydrolase.

FIG. 12 illustrates the mechanism of *A. radiobacter* epoxide hydrolase. The catalytic mechanism involves two distinct steps. The first step (a) is an SN2 nucleophilic attack by an Asp 107 carboxylate oxygen on the least hindered carbon atom of the epoxide, resulting in a covalent ester intermediate. In the second step (b), the ester intermediate is hydrolyzed by a water molecule that is activated by the Asp246-His275 pair. In comparison to ester hydrolysis where there is no stereochemical concern, epoxide hydrolysis has important stereochemical consequences: the regioselectivity (two possible carbons being attacked) and the inversion of absolute configuration at the attacked carbon. Therefore, both the regioselectivity and enantioselectivity need to be taken into consideration when analyzing epoxide hydrolase-catalyzed reactions.

EHs often exhibit high enantioselectivity as well as high activity toward certain categories of epoxide substrates.

Figure 13:
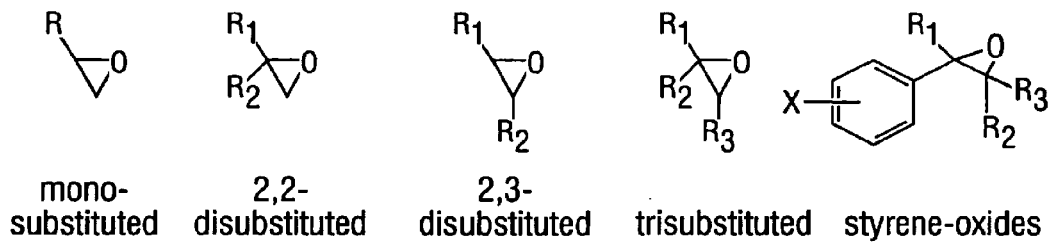
FIG. 13 is an illustration of the types of epoxide substrates.

Studies on different EHs have provided considerable amounts of information regarding their stereoselectivity on different epoxide substrates. (Orru, R. V. A.; Faber, F. Curr. Opin. Chem. Biol. 1999, 3, 16–21.) In general, epoxide substrates can be divided into five types: mono-substituted, 2,2-disubstituted, 2,3-disubstituted, trisubstituted, and styrene-oxides (FIG. 13). The known EHs have been shown to have different stereoselectivities to different types of substrates.

Most bacterial and fungal epoxide hydrolases studied were not very stereoselective for monosubstituted epoxides. These molecules, which represent rather flexible and less bulky molecules, may make chiral recognition a difficult task. However, some enzymes found from red yeasts, such as *Rhodotorula glutinis* strain CIMW 147, exhibited excellent selectivity. (Weijers, C. A. G. M.; Botes, A. L.; van Dyk, M. S.; de Bont, J. A. M. Tetrahedron: Asymmetry 1998, 9, 467–473.) The majority of these enzymes have selectivity for the R-epoxides as their substrates.

For the sterically more bulky 2,2-disubstituted substrates, good enantioselectivity is exhibited by some bacterial enzymes, in particular those from *Rhodococcus* (strains NCIMB 11216, DSM 43338) and closely related *Nocardia* sp. (strains H8, TB1, EH1). (Orru, R. V. A.; Archelas, A.; Furstoss, R.; Faber, K. Adv. Biochem. Eng. Biotechnol. 1998, 63, 145–167.) In several cases, the regioselectivity has been determined to be absolute (i.e. attack occurred exclusively at the less hindered unsubstituted oxirane carbon atom). Interestingly, most bacterial epoxide hydrolases were selective for the S-enantiomers.

Figure 14:
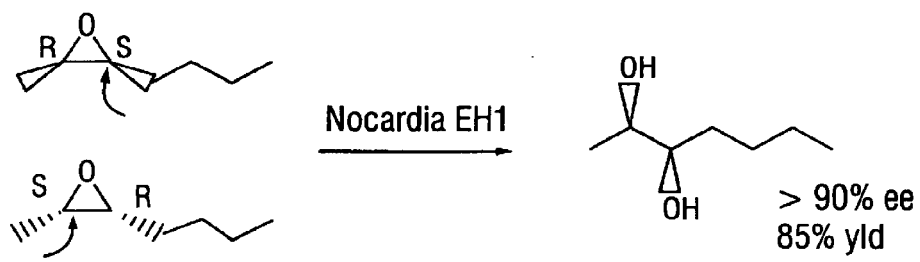
FIG. 14 is an illustration of the enantioconvergent hydrolysis of cis-2,3-epoxyheptane to 2R,3R-2,3-dihydroxyheptane catalyzed by *Norcardia* EH1.

Mixed regioselectivities are common for the hydrolysis of 2,3-disubstituted substrates, in which ring-opening occurs at both positions of the oxirane ring at various ratios. This is likely due to the fact that both reaction centers have similar steric effects. Interestingly, significant applications may be found in two scenarios. In the cases where R1 and R2 are identical, the substrates are meso compounds. Epoxide hydrolases-catalyzed desymmetrization can lead to a single enantiomeric diol product with 100% yield. In some other cases, it has been shown that the hydrolysis proceeded in an enantioconvergent manner, leading to only one stercoisomeric diol as the sole product. This potentially can be useful for the synthesis of enantiopure vicinal diols. For example, *Norcardia* EH1 catalyzed the enantioconvergent hydrolysis of cis-2,3-epoxyheptane to 2R,3R-2,3-dihydroxyheptane with good yield and enantiomeric excess (FIG. 14). (Kroutil, W.; Mischitz, M.; Plachota, P.; Faber, K. Tetrahedron Lett. 1996, 37, 8379–8382.) The 2S,3R-enantiomer reacted 10-fold faster than the 2R,3S-enantiomer but hydrolysis of both enantiomers occurred via attack at the S-centers, leading exclusively to the 2R,3R-diol product.

Only limited data are available on the enzymatic hydrolysis of trisubstituted epoxides. In a few cases, bacterial and yeast EHs showed good enantioselectivity for these bulky substrates. (Weijers, C. A. G. M. Tetrahedron: Asymmetry 1997, 8, 639–647; and Archer, I. V. J.; Leak, D. J.; Widdowson, D. A. Tetrahedron Lett. 1996, 37, 8819–8822.) More enzymes for these substrates may be available as novel EHs continue to be discovered.

Styrene-oxides are viewed as a special group of substrates because the benzylic carbon of these substrates provides stability to the carbocation nature of the transition state of the reaction. As a result, this group of substrates usually exhibits poor regioselectivity if the benzylic carbon is also sterically hindered. However, excellent enantioselectivity was observed in the reactions catalyzed by enzymes from red yeasts such as *Rhodotorula glutinis* strain CIMW 147, and in particular the fungal epoxide hydrolases, such as the enzyme from *Aspergillus niger*. (Weijers, C. A. G. M. Tetrahedron: Asymmetry 1997, 8, 639–647; and Archelas, A.; Furstoss, R. Curr. Opin. Chem. Biol. 2001, 5, 112–119.) In the latter case, very good regioselectivity was also obtained for the synthesis of diols.

A review of the data available to date indicates that EHs with high stereoselectivity exist for almost all types of epoxides, although there seems to be a correlation between certain microbial sources and the substitutional pattern of various types of epoxide substrates. For instance, yeast EHs work best with mono-substituted oxiranes, while fungal EHs show highest enantioselectivity with styrene-oxide substrates. Bacterial enzymes are the catalysts of choice for 2,2- and 2,3-disubstituted epoxides. However, since only a small number of enzymes have been discovered and studied, this correlation may be a result of the biased data set. Nonetheless, the high stereoselectivity and activity exhibited by the microbial EHs on certain epoxide substrates strongly suggest that these enzymes may be the tools chemists are looking for to prepare enantiopure epoxides and vicinal diols.

Chiral epoxides and diols have important applications in anti-cancer, antivirals, antifungals, antibacterials, and other pharmaceuticals. In the preparation of these important compounds, epoxide hydrolases have shown great promise. As a kinetic resolution method with a limit of 50% yield, epoxide hydrolase-mediated syntheses are not expected to completely replace the current chemical asymmetric epoxidation. However, industrial applications of epoxide hydrolases can be envisioned in the following capacities: to replace chemical methods as "cleaner" catalysts in certain transformations; to be the choice of catalysts where the chemical methods are limited; to prepare certain diols in an enantioconvergent manner where the yields are not limited to 50%; to be used in combination with other asymmetric epoxidation methods to improve overall ee value by hydrolyzing a minor epoxide enantiomer.

As used herein, the bioactivity of interest is activity as a catalyst for the modification of epoxides. As used herein, biomolecule refers to epoxide hydrolases.

Preferably, the first step of the efforts for discovering these enzymes involves developing sensitive, high throughput methods for the discovery of catalysts for the modification of epoxides. A combination of optimized assays and screening hosts can be applied to demonstrate that biocatalysts can be obtained from environmental gene libraries. The host strain libraries and environmental gene libraries can be built using the technologies described in U.S. Pat. No. 5,958,672, U.S. Pat. No. 6,001,574 and U.S. Pat. No. 5,763,239.

Hybrid Epoxide Hydrolases and Peptide Libraries

In one aspect, the invention provides hybrid epoxide hydrolases and fusion proteins, including peptide libraries, comprising sequences of the invention. The peptide libraries comprising sequences of the invention are used to isolate peptide inhibitors of targets (e.g., receptors, enzymes) and to identify formal binding partners of targets (e.g., ligands, such as cytokines, hormones and the like).

The field of biomolecule screening for biologically and therapeutically relevant compounds is rapidly growing. Relevant biomolecules that have been the focus of such screening include chemical libraries, nucleic acid libraries and peptide libraries, in search of molecules that either inhibit or augment the biological activity of identified target molecules. With particular regard to peptide libraries, the isolation of peptide inhibitors of targets and the identification of formal binding partners of targets has been a key focus. Screening of combinatorial libraries of potential drugs on therapeutically relevant target cells is a rapidly growing and important field. However, one particular problem with peptide libraries is the difficulty assessing whether any particular peptide has been expressed, and at what level, prior to determining whether the peptide has a biological effect. Thus, in order to express and subsequently screen functional peptides in cells, the peptides need to be expressed in sufficient quantities to overcome catabolic mechanisms such as proteolysis and transport out of the cytoplasm into endosomes.

In one aspect, the fusion proteins of the invention (e.g., the peptide moiety) are conformationally stabilized (relative to linear peptides) to allow a higher binding affinity for their cellular targets. The present invention provides fusions of epoxide hydrolases of the invention and other peptides, including known and random peptides, that are fused in such a manner that the structure of the epoxide hydrolases is not significantly perturbed and the peptide is metabolically or structurally conformationally stabilized. This allows the creation of a peptide library that is easily monitored, both for its presence within cells and its quantity.

Amino acid sequence variants of the invention can be characterized by the predetermined nature of the variation, a feature that sets them apart from naturally occurring allelic or interspecies variation of the epoxide hydrolase amino acid sequence. In one aspect, the variants of the invention exhibit the same qualitative biological activity as the naturally occurring analogue, although variants can also be selected which have modified characteristics. While the site or region for introducing an amino acid sequence variation is predetermined, the mutation per se need not be predetermined. For example, in order to optimize the performance of a mutation at a given site, random mutagenesis may be conducted at the target codon or region and the expressed epoxide hydrolase variants screened for the optimal combination of desired activity. Techniques for making substitution mutations at predetermined sites in DNA having a known sequence are well known, for example, M13 primer mutagenesis and PCR mutagenesis. Screening of the mutants is done using assays of proteolytic activities. In alternative aspects, amino acid substitutions can be single residues; insertions can be on the order of from about 1 to 20 amino acids, although considerably larger insertions may be tolerated. Deletions can range from about 1 to about 20 residues, although in some cases deletions may be much larger. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

The invention provides epoxide hydrolases where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. The variants can exhibit the same qualitative biological activity (i.e. proteolytic activity) although variants can be selected to modify the characteristics of the epoxide hydrolases as needed.

In one aspect, epoxide hydrolases of the invention comprise epitopes or purification tags, signal sequences or other fusion sequences, etc. In one aspect, the epoxide hydrolases of the invention can be fused to a random peptide to form a fusion polypeptide. By "fused" or "operably linked" herein is meant that the random peptide and the epoxide hydrolase are linked together, in such a manner as to minimize the disruption to the stability of the epoxide hydrolase structure (i.e. it can retain proteolytic activity) or maintains a Tm of at least 42° C. The fusion polypeptide (or fusion polynucleotide encoding the fusion polypeptide) can comprise further components as well, including multiple peptides at multiple loops.

In one aspect, the peptides and nucleic acids encoding them are randomized, either fully randomized or they are biased in their randomization, e.g. in nucleotide/residue frequency generally or per position. "Randomized" means that each nucleic acid and peptide consists of essentially random nucleotides and amino acids, respectively. In one aspect, the nucleic acids which give rise to the peptides can be chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response. Thus, the invention provides an interaction library large enough so that at least one of its members will have a structure that gives it affinity for some molecule, protein, or other factor whose activity is necessary for completion of a signaling pathway.

In one aspect, a peptide library of the invention is fully randomized, with no sequence preferences or constants at any position. In another aspect, the library is biased, that is, some positions within the sequence are either held constant, or are selected from a limited number of possibilities. For example, in one aspect, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc. For example, individual residues may be fixed in the random peptide sequence of the insert to create a structural bias. In an alternative aspect, the random libraries can be biased to a particular secondary structure by including an appropriate number of residues (beyond the glycine linkers) which prefer the particular secondary structure.

In one aspect, the bias is towards peptides that interact with known classes of molecules. For example, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from wasps, can be limited to a short peptide region with death-inducing apoptotic or G protein inducing functions. Thus, a number of molecules or protein domains are suitable as starting points for the generation of biased randomized peptides. A large number of small molecule domains are known, that confer a common function, structure or affinity. In addition, areas of weak amino acid homology may have strong structural homology. Exemplary molecules, domains, and/or corresponding consensus sequences used in the invention (e.g., incorporated into fusion proteins of the invention) include SH-2 domains, SH-3 domains, Pleckstrin, death domains, epoxide hydrolase cleavage/recognition sites, enzyme inhibitors, enzyme substrates, Traf, etc. Similarly, there are a number of known nucleic acid binding proteins containing domains suitable for use in the invention, e.g., leucine zipper consensus sequences.

The invention provides a variety of expression vectors comprising nucleic acids of the invention, including those encoding a fusion protein. The expression vectors may be either self-replicating extra chromosomal vectors or vectors which integrate into a host genome. Generally, these expression vectors include transcriptional and translational regulatory nucleic acid operably linked to the nucleic acid encoding the fusion protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site.

Transcriptional and translational regulatory sequences used in the expression cassettes and vectors of the invention include, but are not limited to, promoter sequences, ribosomal binding sites, transcriptional start and stop sequences, translational start and stop sequences, and enhancer or activator sequences. In one aspect, the regulatory sequences include a promoter and transcriptional start and stop sequences. Promoter sequences encode either constitutive or inducible promoters. The promoters may be either naturally occurring promoters or hybrid promoters. Hybrid promoters, which combine elements of more than one promoter, are also known in the art, and are useful in the present invention. In one aspect, the promoters are strong promoters, allowing high expression in cells, particularly mammalian cells, such as the CMV promoter, particularly in combination with a Tet regulatory element.

In addition, the expression vector may comprise additional elements. In one exemplification, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In one aspect, the nucleic acids or vectors of the invention are introduced into the cells for screening, thus, the nucleic acids enter the cells in a manner suitable for subsequent expression of the nucleic acid. The method of introduction is largely dictated by the targeted cell type. Exemplary methods include CaPO4 precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

Expression vectors of the invention may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

Screening Methodologies and "On-Line" Monitoring Devices

In practicing the methods of the invention, a variety of apparatus and methodologies can be used to in conjunction with the polypeptides and nucleic acids of the invention, e.g., to screen polypeptides for epoxide hydrolase reactivity, to screen compounds as potential modulators of activity (e.g., potentiation or inhibition of enzyme activity), for antibodies that bind to a polypeptide of the invention, for nucleic acids that hybridize to a nucleic acid of the invention, and the like.

Immobilized Enzyme Solid Supports

The epoxide hydrolase enzymes, fragments thereof and nucleic acids that encode the enzymes and fragments can be affixed to a solid support. This is often economical and efficient in the use of epoxide hydrolases in industrial processes. For example, a consortium or cocktail of epoxide hydrolase enzymes (or active fragments thereof), which are used in a specific chemical reaction, can be attached to a solid support and dunked into a process vat. The enzymatic reaction can occur. Then, the solid support can be taken out of the vat, along with the enzymes affixed thereto, for repeated use. In one embodiment of the invention, an isolated nucleic acid of the invention is affixed to a solid support. In another embodiment of the invention, the solid support is selected from the group of a gel, a resin, a polymer, a ceramic, a glass, a microelectrode and any combination thereof.

For example, solid supports useful in this invention include gels. Some examples of gels include Sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextran-agarose, poly(Carbamoyl Sulfonate) hydrogel, BSA-PEG hydrogel, phosphorylated polyvinyl alcohol (PVA), monoaminoethyl-N-aminoethyl (MANA), amino, or any combination thereof.

Another solid support useful in the present invention are resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50, polyvinyl, polyacrylic, polymethacrylate, or any combination thereof. another type of solid support useful in the present invention is ceramic. Some examples include non-porous ceramic, porous ceramic, $SiO_2$, $Al_2O_3$. Another type of solid support useful in the present invention is glass. Some examples include non-porous glass, porous glass, aminopropyl glass or any combination thereof. Another type of solid support that can be used is a microelectrode. An example is a polyethyleneimine-coated magnetite. Graphitic particles can be used as a solid support. Another example of a solid support is a cell, such as a red blood cell.

Methods of Immobilization

There are many methods that would be known to one of skill in the art for immobilizing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N, O. Kaplan. Volume 136; and Immobilization of Enzymes and Cells. 1997. Humana Press. Edited by G. F. Bickerstaff. Series: Methods in Biotechnology, Edited by J. M. Walker.

Capillary Arrays

Capillary arrays, such as the GIGAMATRIX™, Diversa Corporation, San Diego, Calif., can be used to in the methods of the invention. Nucleic acids or polypeptides of the invention can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample.

A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube.

The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a micro titer plate having about 100,000 or more individual capillaries bound together.

Arrays, or "Biochips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of an epoxide hydrolase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171–R174; Schummer (1997) Biotechniques 23:1087–1092; Kern (1997) Biotechniques 23:120–124; Solinas-Toldo (1997) Genes, Chromosomes & Cancer 20:399–407; Bowtell (1999) Nature Genetics Supp. 21:25–32. See also published U.S. patent applications Nos. 20010018642; 20010019827; 20010016322; 20010014449; 20010014448; 20010012537; 20010008765.

Antibodies and Antibody-Based Screening Methods

The invention provides isolated or recombinant antibodies that specifically bind to an epoxide hydrolase of the invention. These antibodies can be used to isolate, identify or quantify the fluorescent polypeptides of the invention or related polypeptides. These antibodies can be used to isolate other polypeptides within the scope the invention or other related epoxide hydrolases.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62–70; Katz (1997) Annu. Rev. Biophys. Biomol. Struct. 26:27–45.

Polypeptides or peptides can be used to generate antibodies which bind specifically to the polypeptides of the invention. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77–96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides from other organisms and samples. In such techniques, polypeptides from the organism are contacted with the antibody and those polypeptides which specifically bind the antibody are detected. Any of the procedures described above may be used to detect antibody binding.

Kits

The invention provides kits comprising the compositions, e.g., nucleic acids, expression cassettes, vectors, cells, polypeptides (e.g., epoxide hydrolases) and/or antibodies of the invention. The kits also can contain instructional material teaching the methodologies and industrial uses of the invention, as described herein.

Measuring Metabolic Parameters

The methods of the invention provide whole cell evolution, or whole cell engineering, of a cell to develop a new cell strain having a new phenotype by modifying the genetic composition of the cell, where the genetic composition is modified by addition to the cell of a nucleic acid. To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line." Metabolic parameters can be monitored using the fluorescent polypeptides of the invention.

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:

identity of all pathway substrates, products and intermediary metabolites identity of all the chemical reactions interconverting the pathway metabolites, the stoichiometry of the pathway reactions, identity of all the enzymes catalyzing the reactions, the enzyme reaction kinetics, the regulatory interactions between pathway components, e.g. allosteric interactions, enzyme-enzyme interactions etc, intracellular compartmentalization of enzymes or any other supramolecular organization of the enzymes, and, the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript or generating new transcripts in a cell. This increased or decreased expression can be traced by use of a fluorescent polypeptide of the invention. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114:313–318; Xia (2001) Transplantation 72:907–914).

In one aspect of the invention, the engineered phenotype is generated by knocking out expression of a homologous gene. The gene's coding sequence or one or more transcriptional control elements can be knocked out, e.g., promoters enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide or generating new polypeptides in a cell. This increased or decreased expression can be traced by use of an epoxide hydrolase of the invention. Polypeptides, peptides and amino acids also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

Assay Development

Several assay methods for obtaining EHs can be used. These assay methods include growth-based assays, direct activity-based assays and sequence-based assays. Preferably, to successfully obtain a range of EHs with desirable characteristics, all three of these assay methods may be used complementarily.

Growth-Based Assays.

The most direct and high throughput growth-based selection method for identifying enzymes that are capable of catalyzing the modification of epoxides. EHs may be discovered if they convert an epoxide substrate to a diol that can be utilized by host bacteria as a carbon source. When the library cells are grown in minimal media supplemented with this epoxide as the sole carbon source, only those clones harboring active epoxide hydrolases will be able to produce the corresponding diol and to utilize it as a carbon source for growth and proliferation. Over time, these clones will dominate the microbial population, and thus can be readily isolated.

Figure 15:
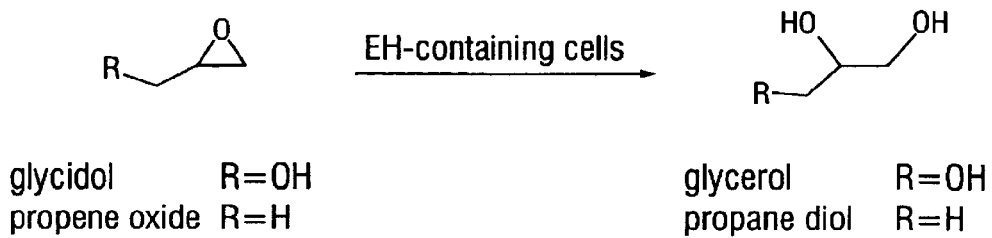
FIG. 15 is an illustration of glycidol and propylene oxide used as selection substrates.

Two epoxides, glycidol and propylene oxide (FIG. 15), will be used as selection substrates initially because their corresponding vicinal diols, glycerol, propane diol, are known to support the growth of *E. coli* or its mutants as sole carbon sources. (Maloy, S. R.; Nunn, W. D. J. Bacteriol. 1982, 149, 173–180; and Hacking, A. J.; Lin, E. C. C. J. Bacteriol. 1976, 126, 1166–1172.) These will be used as a racemic mixture and as pure enantiomers. Note that both of these epoxides are important chiral synthons in the fine chemical and pharmaceutical industries.

Appropriate hosts need to be used for the selection experiments. For example, an *E. coli* fucA-disrupted mutant that can use propane diol as carbon source is required for propylene oxide selection. (Hacking, A. J.; Lin, E. C. C. J. Bacteriol. 1976, 126, 1166–1172.) These hosts can be generated via targeted mutation of certain genes or transposon (Tn) mutagenesis in a random fashion. The latter strategy is more attractive because it is more convenient and extremely powerful. Tn is introduced into *E. coli* hosts through electroporation, where in vivo transposition leads to random Tn insertion in genomic DNA. This results in an *E. coli* insertion library suitable for screening for desired mutants, such as those that can utilize propane diol as carbon source. Several insertion libraries of different *E. coli* hosts will be used to screen for propane diol-utilizing mutants. Specifically, the library cells will be plated out on agar plates containing minimal medium with propane diol as the sole carbon source. Upon incubation, propane diol-utilizing clones can be identified because only they will grow and form colonies on the plates.

The use of these two simple epoxides as discovery substrates can be expected to yield a variety of EHs with different specificities; for example a variety of EHs with optimal specificities on more complex epoxides can still be discovered if they have weak activity on glycidol or propylene oxide. Ultimately the generality of this discovery technique will depend on the sensitivity of the selection. Additional epoxide substrates for selection may also be identified if *E. coli* mutants capable of growing on other vicinal diols are discovered from the Tn insertion libraries. Screening for these diol-utilizing mutants will be carried out using protocols described above.

Epoxides are known to be toxic to microbes due to alkylation of proteins and nucleic acids. The effect of different concentrations of glycidol on the growth of an *E. coli* host was evaluated. The results showed that *E. coli* can tolerate up to 0.05% of glycidol (v/v). This concentration may be high enough for selection as the cells were able to grow with 0.025% glycerol provided extracellularly in the media as the sole carbon source. If necessary, however, *E. coli* mutants bearing higher glycidol tolerance may be discovered by screening libraries of mutagenized hosts including the Tn insertion libraries mentioned above.

Also, a positive control clone has been developed that has epoxide hydrolase activity. Having such a control is useful because it can be used to guide and evaluate the assay development for both the selection and screening. An epoxide hydrolase from *A. radiobacter*, whose nucleotide sequence was reported, can be readily cloned and expressed in *E. coli*. (Arand, M.; Oesch, F. Biochem. J. 1999, 344, 273–280.) Primers have been designed and synthesized for the amplification and cloning of this gene. In addition, as described below, an active epoxide hydrolase that may be used as the positive control has been identified.

Sequence Based Assays

A complementary approach to the activity-based discovery of epoxide hydrolases is sequence-based discovery of epoxide hydrolases followed by assessment of their substrate specificities in secondary assays. Using sequence-based methods is a valuable strategy for discovering particular classes of enzymes. Considerable amounts of sequence and structural information are available on EHs, rendering the development of sequenced-based discovery possible.

Since this method is not based on activity, it is complementary to other activity based-methods. In addition, it can be extremely high throughput. Both the prokaryotic and eukaryotic EHs belong to the a,b-hydrolase fold superfamily and share low, but significant sequence homology. (Nardini, M.; Ridder, I. S.; Rozeboon, H. J.; Kalk, K. H.; Rink, R.; Janssen, D. B.; Dijkstra, B. W. J. Biol. Chem. 1999, 274, 14579–14596; Argiridadi, et. al, Proc. Natl. Acad. Sci. USA 1999, 96, 10637–10642; and Zou, J.; et al., Structure 2000, 8, 111–122.) Bacterial EHs, however, have higher sequence similarity. Alignments of the nucleotide sequences of bacterial EHs will allow the identification of conserved sequences. Primers will be designed based on these regions. These primers will be used to generate PCR products from DNA libraries. The products will be gel-separated, purified, and subjected for sequence analysis. The full-length sequences of positive hits can be retrieved by southern blotting. The activities of these hits will then be investigated using fluorogenic or chromogenic assays. One limitation of the sequence-based approach compared to activity-based methods is that it is limited to the discovery of genes that share homology to existing genes. However, as new EH genes are discovered and a sequence database of EHs is built up, the sequence-based approach becomes increasingly powerful as more sequences can be used in probe design.

Bioinformatic analysis of a DNA database resulted in a total of 6 putative epoxide hydrolase genes as well as 3 partial open reading frame (ORFs) that bear homology to *A. radiobacter* and other epoxide hydrolases. Based on the conserved nucleotide sequences extracted from these ORFs, degenerate primers have been designed and used for screening a gene library known to contain one of these genes. This screening did result in the finding of the known gene as was expected. Another PCR product (~200 bp) was also obtained and upon sequencing, the partial ORF showed strong sequence homology to other known EHs. This unexpected result thus indicates that the sequence-based strategy is capable of discovering novel EHs.

Fluorescence Based Assays

Fluorogenic and chromogenic assays have been used to great effect in high-throughput screening for enzyme characterization and discovery. Fluorogenic assays have been commonly used for many hydrolytic enzymes in which the substrates release a fluorescent signal upon the hydrolysis reaction. These assays are activity-based like the selection method, but they can be used for more diverse substrates than the selection experiments. The limitation, however, is that they have lower throughput than the selection assays.

Figure 16:
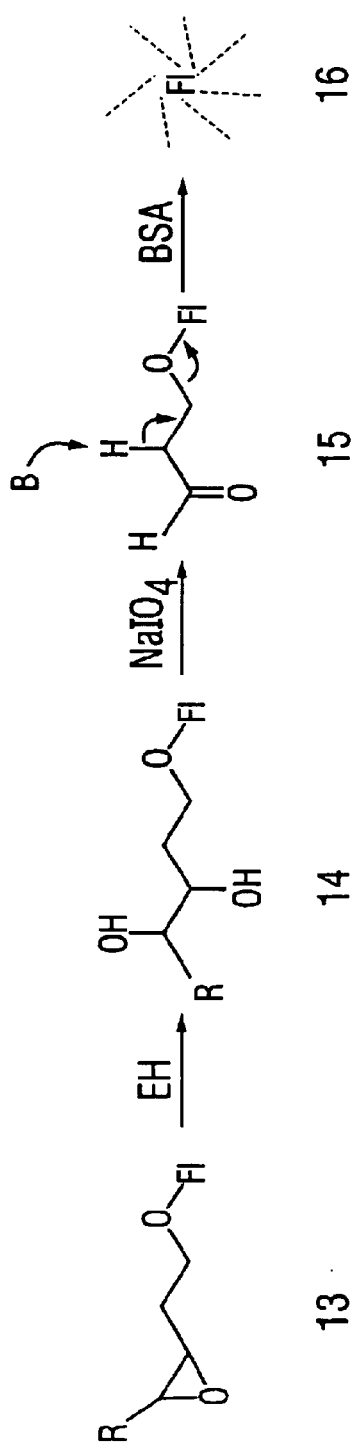
FIG. 16 is an illustration of a high-throughput screening method based on a periodate-coupled fluorogenic assay for an epoxide hydrolase.

A periodate-coupled fluorogenic assay for EHs reported in literature has been modified and developed into a high throughput screening method. (Badalassi, F.; Wahler, D.; Klein, G.; Crotti, P.; Reymond, J.-L. Angew. Chem. Int. Ed. 2000, 39, 4067–4070.) As shown in FIG. 16, the epoxide substrate (13) used in this assay contains a masked fluorophore that can generate strong fluorescence when released. Following the EH-catalyzed hydrolysis of 13, periodate is added to oxidize the vicinal diol product (14) to generate a carbonyl-containing intermediate (15). Under basic conditions, 15 can undergo a b-elimination reaction catalyzed by bovine serum albumin (BSA) to release a fluorescent product (16) such as umbelliferone.

The assay is carried out in a 1536-well format. Clones from gene libraries are distributed into individual wells, preferably 5 clones per well for the primary screening. These clones are allowed to grow for 24–48 hrs before substrate 19 is added. After 2 hours of incubation, sodium periodate and BSA are added to promote the b-elimination reaction. The fluorescence level in each well is measured to identify preliminary hits. These hits can be reconfirmed by running a second round of assays. Robotic systems have been developed to automate all the liquid handling and fluorescence measurement processes.

Figure 17:
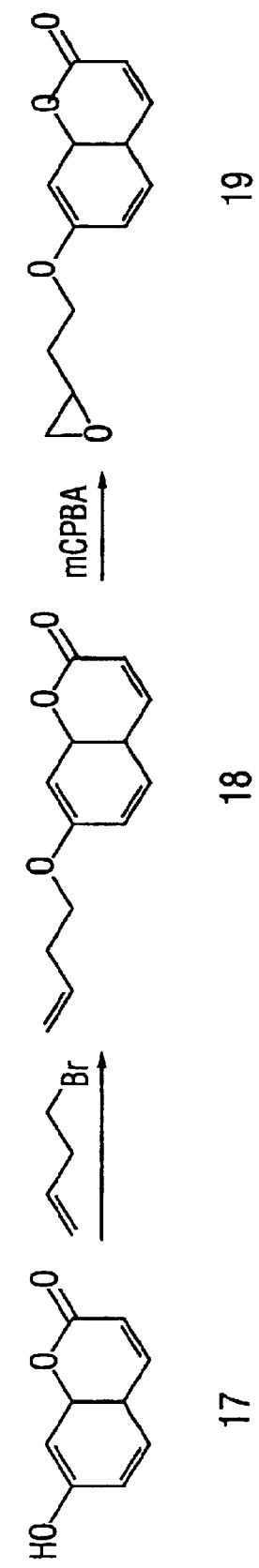
FIG. 17 is an illustration of the synthesis of the substrates for a periodate-coupled fluorogenic assay for an epoxide hydrolase.

The first substrate for this assay development, 19, has been synthesized according to FIG. 17. Coupling of umbelliferone (17) with 4-bromo-1-butene in the presence of potassium carbonate at 50° C. yielded olefin 18, which was subjected to an epoxidation reaction using meta-chloroperbenzoic acid (mCPBA). The resulting epoxide 19 was used to detect epoxide hydrolase activity of the 6 clones mentioned above. These clones contain putative epoxide hydrolase genes. One of them was found to be active for 19. This showed that the assay is useful.

Colorimetric Assay

A colorimetric assay can be extremely useful in high throughput screening if a sensitive color change is involved and the assay can be performed in solid agar format. Screening on solid agar offers extremely high throughput, while a color change allows easy identification of hits. A colorimetric assay that uses 4-(p-nitrobenzyl)-pyridine (20) to detect epoxide substrates can be employed. In the liquid-based assay (see Scheme 12), epoxides react with 20 to generate an adduct (21) which can tautomerize to a highly conjugated compound 22. 22 exhibits a blue color (Imax= 560 nm). Hydrolyzed epoxides (e.g., diols) are not reactive with 20, and thus observation of a decrease in absorbance at 560 nm is indicative of epoxide hydrolysis. In the solid assay, colonies grown on agar plates were transferred to filter paper preincubated with epoxides. Epoxide hydrolase activity was detected by the formation of colorless halos on the blue filter paper. This assay has the potential to be converted to a HTP screen. The disadvantage of this assay is that it detects the disappearance of the substrate instead of the appearance of the products. The advantage, however, is that it targets substrates directly, not their derivatives. Therefore, even if its relative low sensitivity proves to be a problem for HTP screening, it may be used for secondary screening of primary hits detected from other discovery methods.

The colorimetric assay was tested on the positive epoxide hydrolase clone mentioned above using three epoxides: styrene oxide, epichlorohydrin, and glycidol. All three epoxides were found to be substrates, with epichlorohydrin showing the highest activity.

These screening methods can be used to discover a wide range of novel epoxide hydrolases, thereby creating a toolbox of synthetically useful biocatalysts. Optionally, where necessary, evolution technologies, which are discussed below, may be used to optimize the properties of the enzymes.

In a more preferred embodiment, the assays developed will be applied to screen the environmental gene libraries for the presence of microbial enzymes with the necessary activities and substrate specificities. Positive hits from these screens may then be sequenced and the genes subcloned into expression vectors. The expressed recombinant enzymes can then be characterized with respect to activity and substrate selectivities. Should the identified enzymes require enhancement of one or more of their properties (e.g. pH and temperature optima, thermostability, thermotolerance, substrate specificity etc.) they can be optimized using GSSM™ (Gene Site Saturation Mutagenesis), Gene Reassembly™ and other technologies discussed below. These epoxide hydrolases may be used in the chemo-enzymatic synthesis of specific fine chemicals and high value precursors to pharmaceuticals and agrochemicals. The optimized enzymes developed using a method of the present invention may be applied in the development of a commercially viable synthesis route to one or more target compounds. Specifically, the epoxide hydrolases can be used as key intermediates in the synthesis of fine chemicals and enantiomeric pharmaceuticals having the desired purities.

In one aspect, the environmental gene libraries are constructed using DNA isolated from a wide variety of microenvironments around the world. Application of an appropriate discovery method then allows enzymes to be extracted from these libraries according to function, enzyme class or a specific combination of the two. In contrast to traditional discovery programs, the preferred discovery method ensures capture of genes from uncultivated microbes and facilitates screening in well-defined, domesticated laboratory hosts. This expression cloning method results in simultaneous capture of enzyme activities and the corresponding genetic information.

A discovery method involves: isolating and fractionating nucleic acids from nature or other suitable sources; constructing environmental gene libraries; screening the genes in the environmental libraries to discover the desired genes encoding the desired enzymes using the methods described below; optimizing the desired genes to optimize the activity of the desired enzymes using the evolution technologies described in U.S. Pat. No. 5,830,696, U.S. Pat. No. 5,939,250 and U.S. Pat. No. 5,965,408, which are incorporated herein by reference; sequencing the optimized genes; overexpressing the sequenced genes in suitable host strains; producing a large number of the suitable strains containing the optimized genes by fermentation and obtaining the desired enzymes, optionally contained in host strains, after purification.

Newly cloned or discovered enzymes can then be further customized by using the evolution technologies described in U.S. Pat. No. 5,830,696, U.S. Pat. No. 5,939,250 and U.S. Pat. No. 5,965,408 and a combinatorial evolution technology described below.

The screening step in one aspect of the present invention may be carried out by one or more of expression and sequence-based screening methods including single cell activity screens, microtiter plate-based activity screens, sequence-based screening and growth selection methods. These methods may all be applied to the discovery of epoxide hydrolases utilizing the assays described above.

Figure 18:
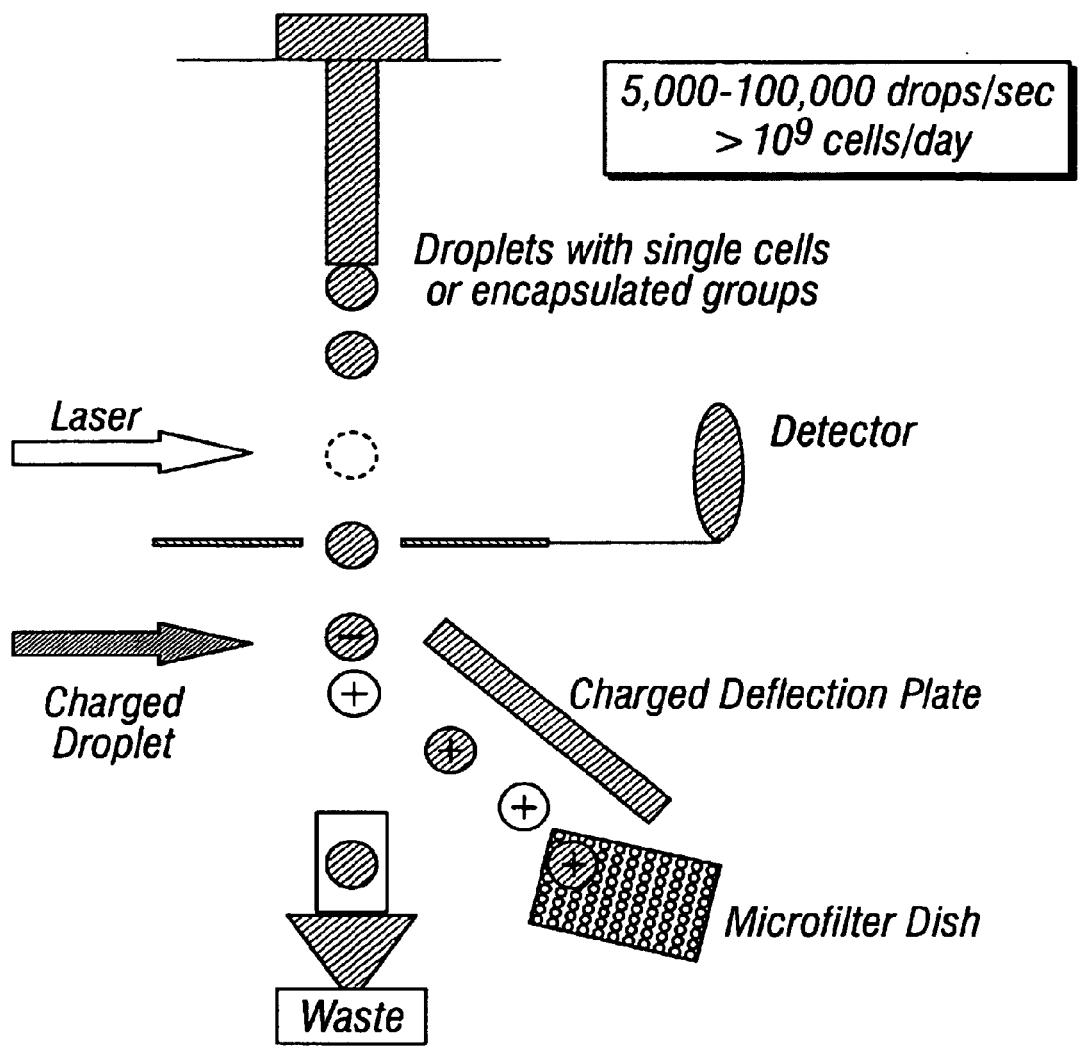
FIG. 18 is an illustration of Fluorescence Activated Cell Sorting (FACS) for ultra high throughput single cell activity and sequence screening.

Single cell activity screening method is a method derived from Fluorescence Activated Cell Sorting (FACS) by substantially modifying the FACS platform for expression and sequence hybridization-based screening of environmental libraries (FIG. 18). In the case of expression screening, fluorescent substrates are soaked into clone libraries and when a clone expresses a gene product that is capable of cleaving the substrate, the fluorescence quantum yield increases. Alternatively, FACS-hybridization cloning methodology permits the recovery of recombinant clones based on sequence homology. This single cell activity screening method allows screening rates of 50,000 clones per second and a daily screening rate of up to 109 clones.

The growth selection method can be one of the most powerful methods for enzyme discovery. In this method the substrate of choice acts as a nutrient source for the host cells only when those cells contain the enzyme activity of interest, allowing them to grow selectively. Genetic manipulation of cell lines may be involved in this growth selection method. The substrate used in this method may also be custom synthesized.

Figure 19:
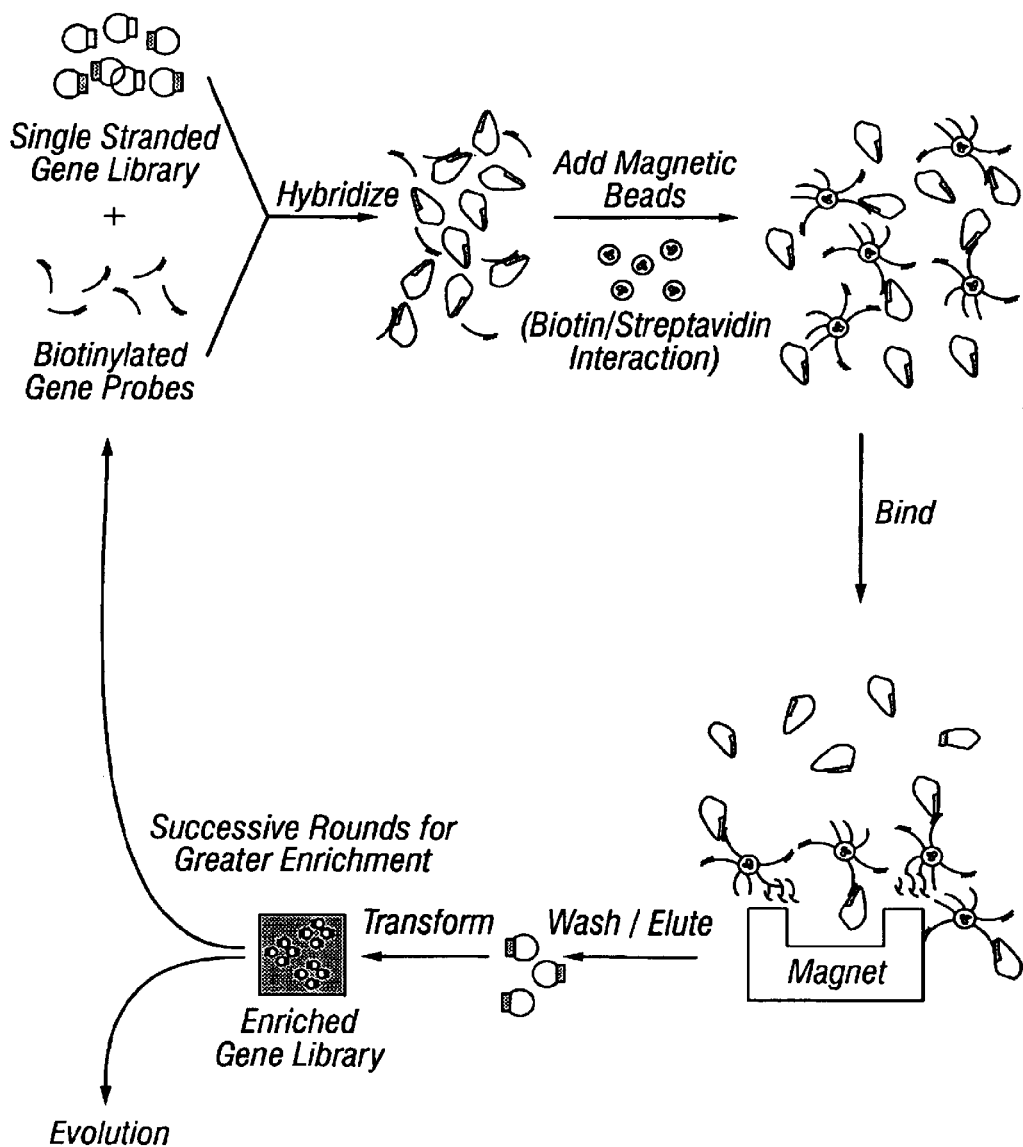
FIG. 19 is an illustration of environmental library biopanning for sequence-based discovery.

In another aspect, sequence-based discovery methods may be powerful and complementary alternatives to expression cloning. Both solution phase and FACS-based formats can be used for ultra high throughput DNA hybridization-based discovery techniques, such as environmental biopanning, which facilitate screening of the large and complex environmental gene libraries. In the solution based environmental biopanning technique, inserts from mega libraries are rendered single stranded and combined in solution with arrays of biotinylated hybridization probes known as hooks (FIG. 19). Library clones containing related sequences hybridize to the hooks and are captured on streptavidin coated magnetic beads. The eluted sequence-enriched DNA inserts are then either subjected to another cycle of biopanning or back-cloned into lambda. In this way enrichment is achieved greater than 1000-fold for sequences of interest. The FACS-based biopanning approach further facilitates the enzyme identification process by allowing for amplification-free biopanning of both small and large insert clones.

Laboratory evolution of enzymes can be used to further improve, customize or refine the properties of the enzymes. These laboratory evolution technologies include Gene Site Saturation Mutagenesis (GSSM™) and GeneReassembly™, where multiple natural genes can be combined to create a combinatorial evolution library. If necessary, these technologies can be applied to the epoxide hydrolases discovered using the enzyme discovery method to further optimize these epoxide hydrolases for characteristics such as thermostability, specific activity or stereospecificity.

In one aspect, the present invention provides rapid screening of libraries derived from more than one organism, such as a mixed population of organisms from, for example, an environmental sample or an uncultivated population of organisms or a cultivated population of organisms.

In one aspect, gene libraries are generated by obtaining nucleic acids from a mixed population of organisms and cloning the nucleic acids into a suitable vector for transforming a plurality of clones to generate a gene library. The gene library thus contains gene or gene fragments present in organisms of the mixed population. The gene library can be an expression library, in which case the library can be screened for an expressed polypeptide having a desired activity. Alternatively, the gene library can be screened for sequences of interest by, for example, PCR or hybridization screening. In one embodiment, nucleic acids from isolates of a sample containing a mixed population of organism are pooled and the pooled nucleic acids are used to generate a gene library.

By "isolates" is meant that a particular species, genus, family, order, or class of organisms is obtained or derived from a sample having more than one organism or from a mixed population of organisms. Nucleic acids from these isolated populations can then be used to generate a gene library. Isolates can be obtained from by selectively filtering or culturing a sample containing more than one organism or a mixed population of organisms. For example, isolates of bacteria can be obtained by filtering the sample through a filter, which excludes organisms based on size or by culturing the sample on media that allows from selective growth or selective inhibition of certain populations of organisms.

An "enriched population" is a population of organisms wherein the percentage of organisms belonging to a particular species, genus, family, order or class of organisms is increased with respect to the population as a whole. For example, selective growth or inhibition media can increase the overall number of organisms. One can enrich for prokaryotic organisms with respect to the total number of organisms in the population. Similarly, a particular species, genus, family, order or class of organisms can be enriched by growing a mixed population on a selective media that inhibits or promotes the growth of a subpopulation within the mixed population.

In another aspect, nucleic acids from a plurality (e.g., two or more) of isolates from a mixed population of organisms are used to generate a plurality of gene libraries containing a plurality of clones, and the gene libraries from at least two isolates are then pooled to obtain a "pooled isolate library."

Once gene libraries are generated, the clones are screened to detect a bioactivity, in this case activity as a catalyst for the modification of epoxides or a biomolecule of interest (e.g., an EH). Such screening techniques include, for example, contacting a clone, clonal population, or population of nucleic acid sequences with a substrate or substrates having a detectable molecule that provides a detectable signal upon interaction with the bioactivity or biomolecule of interest. The substrate can be an enzymatic substrate, a bioactive molecule, an oligonucleotide, and the like.

In one aspect, gene libraries are generated, clones are either exposed to a chromagenic or fluorogenic substrate or substrate(s) of interest, or hybridized to a labeled probe (e.g., an oligonucleotide having a detectable molecule) having a sequence corresponding to a sequence of interest and positive clones are identified by a detectable signal (e.g., fluorescence emission).

In one aspect, expression libraries generated from a mixed population of organisms are screened for an activity of interest. Specifically, expression libraries are generated, clones are exposed to the substrate or substrate(s) of interest, and positive clone are identified and isolated. The present invention does not require cells to survive. The cells only need to be viable long enough to produce the molecule to be detected, and can thereafter be either viable or nonviable cells, so long as the expressed biomolecule (e.g., an enzyme) remains active.

In certain aspect, the invention provides an approach that combines direct cloning of genes encoding novel or desired bioactivities from environmental samples with a high-throughput screening system designed for the rapid discovery of new molecules, for example, enzymes. The approach is based on the construction of environmental "expression libraries" which can represent the collective genomes of numerous naturally occurring microorganisms archived in cloning vectors that can be propagated in *E. coli* or other suitable host cells. Because the cloned DNA can be initially extracted directly from environmental samples or from isolates of the environmental samples, the libraries are not limited to the small fraction of prokaryotes that can be grown in pure culture. Additionally, a normalization of the environmental DNA present in these samples could allow a more equal representation of the DNA from all of the species present in a sample. Normalization techniques (described below) can dramatically increase the efficiency of finding interesting genes from minor constituents of the sample that may be under-represented by several orders of magnitude compared to the dominant species in the sample. Normalization can occur in any of the foregoing embodiments following obtaining nucleic acids from the sample or isolate (s).

In another aspect, the invention provides a high-throughput capillary array system for screening that allows one to assess an enormous number of clones to identify and recover cells encoding useful enzymes, as well as other biomolecules (e.g., ligands). In particular, the capillary array-based techniques described herein can be used to screen, identify and recover proteins having a desired bioactivity or other ligands having a desired binding affinity. For example, binding assays may be conducted by using an appropriate substrate or other marker that emits a detectable signal upon the occurrence of the desired binding event.

In addition, fluorescence activated cell sorting can be used to screen and isolate clones having an activity or sequence of interest. Previously, FACS machines have been employed in the studies focused on the analyses of eukaryotic and prokaryotic cell lines and cell culture processes. FACS has also been utilized to monitor production of foreign proteins in both eukaryotes and prokaryotes to study, for example, differential gene expression, and the like. The detection and counting capabilities of the FACS system have been applied in these examples. However, FACS has never previously been employed in a discovery process to screen for and recover bioactivities in prokaryotes. Furthermore, the present invention does not require cells to survive, as do previously described technologies, since the desired nucleic acid (recombinant clones) can be obtained from alive or dead cells. The cells only need to be viable long enough to produce the compound to be detected, and can thereafter be either viable or non-viable cells so long as the expressed biomolecule remains active. The present invention also solves problems that would have been associated with detection and sorting of E. coli expressing recombinant enzymes, and recovering encoding nucleic acids. Additionally, the present invention includes within its embodiments any apparatus capable of detecting fluorescent wavelengths associated with biological material, such apparatus are defined herein as fluorescent analyzers (one example of which is a FACS apparatus).

In some instances it is desirable to identify nucleic acid sequences from a mixed population of organisms, isolates, or enriched populations. In this embodiment, it is not necessary to express gene products. Nucleic acid sequences of interest can be identified or "biopanned" by contacting a clone, device (e.g. a gene chip), filter, or nucleic acid sample with a probe labeled with a detectable molecule. The probe will typically have a sequence that is substantially identical to the nucleic acid sequence of interest. Alternatively, the probe will be a fragment or full length nucleic acid sequence encoding a polypeptide of interest. The probe and nucleic acids are incubated under conditions and for such time as to allow the probe and a substantially complementary sequence to hybridize. Hybridization stringency will vary depending on, for example, the length and GC content of the probe. Such factors can be determined empirically (See, for example, Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement)). Once hybridized the complementary sequence can be PCR amplified, identified by hybridization techniques (e.g., exposing the probe and nucleic acid mixture to a film), or detecting the nucleic acid using a chip.

Prior to the present invention, the evaluation of complex gene libraries or environmental expression libraries was rate limiting. The present invention allows the rapid screening of complex environmental libraries, containing, for example, genomic sequences from thousands of different organisms or subsets and isolates thereof. The benefits of the present invention can be seen, for example, in screening a complex environmental sample. Screening of a complex sample previously required one to use labor-intensive methods to screen several million clones to cover the genomic biodiversity. The invention represents an extremely high-throughput screening method, which allows one to assess this enormous number of clones. The method disclosed allows the screening anywhere from about 30 million to about 200 million clones per hour for a desired nucleic acid sequence, biological activity, or biomolecule of interest. This allows the thorough screening of environmental libraries for clones expressing novel bioactivities or biomolecules.

Once a sequence or bioactivity of interest is identified (e.g., an enzyme of interest) the sequence or polynucleotide encoding the bioactivity of interest can be evolved, mutated or derived to modify the amino acid sequence to provide, for example, modified activities such as increased thermostability, specificity or activity.

The invention provides methods of identifying a nucleic acid sequence encoding a polypeptide having either known or unknown function. For example, much of the diversity in microbial genomes results from the rearrangement of gene clusters in the genome of microorganisms. These gene clusters can be present across species or phylogenetically related with other organisms.

For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function.

Some gene families consist of identical members. Clustering is a prerequisite for maintaining identity between genes, although clustered genes are not necessarily identical. Gene clusters range from extremes where a duplication is generated to adjacent related genes to cases where hundreds of identical genes lie in a tandem array. Sometimes no significance is discernable in a repetition of a particular gene. A principal example of this is the expressed duplicate insulin genes in some species, whereas a single insulin gene is adequate in other mammalian species.

Further, gene clusters undergo continual reorganization and, thus, the ability to create heterogeneous libraries of gene clusters from, for example, bacterial or other prokaryote sources is valuable in determining sources of novel proteins, particularly including enzymes such as, for example, the polyketide synthases that are responsible for the synthesis of polyketides having a vast array of useful activities. For example, polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of a huge variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins. Other types of proteins that are the product(s) of gene clusters are also contemplated, including, for example, antibiotics, antivirals, antitumor agents and regulatory proteins, such as insulin.

The ability to select and combine desired components from a library of polyketides and postpolyketide biosynthesis genes for generation of novel polyketides for study is appealing. The method(s) of the present invention make it possible to, and facilitate the cloning of, novel polyketide synthases and other gene clusters, since one can generate gene banks with clones containing large inserts (especially when using the f-factor based vectors), which facilitates cloning of gene clusters.

For example, a gene cluster can be ligated into a vector containing an expression of regulatory sequences, which can control and regulate the production of a detectable protein or protein-related array activity from the ligated gene clusters. Use of vectors which have an exceptionally large capacity for exogenous nucleic acid introduction are particularly appropriate for use with such gene clusters and are described by way of example herein to include the f-factor (or fertility factor) of E. coli. This f-factor of E. coli is a plasmid which affects high-frequency transfer of itself during conjugation and is ideal to achieve and stably propagate large nucleic acid fragments, such as gene clusters from mixed microbial samples.

The nucleic acid isolated or derived from these samples (e.g., a mixed population of microorganisms) or isolates thereof can be inserted into a vector or a plasmid prior to screening of the polynucleotides. Such vectors or plasmids are typically those containing expression regulatory sequences, including promoters, enhancers and the like.

Accordingly, the invention provides novel systems to clone and screen mixed populations of organisms, enriched samples, or isolates thereof for polynucleotides encoding molecules having an activity of interest, enzymatic activities and bioactivities of interest in vitro. The method(s) of the invention allow the cloning and discovery of novel bioactive molecules in vitro, and in particular novel bioactive molecules derived from uncultivated or cultivated samples. Large size gene clusters, genes and gene fragments can be cloned, sequenced and screened using the method(s) of the invention. Unlike previous strategies, the method(s) of the invention allow one to clone screen and identify polynucleotides and the polypeptides encoded by these polynucleotides in vitro from a wide range of environmental samples.

The invention allows one to screen for and identify polynucleotide sequences from complex environmental samples, enriched samples thereof, or isolates thereof. Gene libraries can be generated from cell free samples, so long as the sample contains nucleic acid sequences, or from samples containing cells, cellular material or viral particles. The organisms from which the libraries may be prepared include prokaryotic microorganisms, such as Eubacteria and Archaebacteria, lower eukaryotic microorganisms such as fungi, algae and protozoa, as well as mixed populations of plants, plant spores and pollen. The organisms may be cultured organisms or uncultured organisms, obtained from environmental samples and includes extremophiles, such as thermophiles, hyperthermophiles, psychrophiles and psychrotrophs.

Sources of nucleic acids used to generate a DNA library can be obtained from environmental samples, such as, but not limited to, microbial samples obtained from Arctic and Antarctic ice, water or permafrost sources, materials of volcanic origin, materials from soil or plant sources in tropical areas, droppings from various organisms including mammals and invertebrates, as well as dead and decaying matter and the like. The nucleic acids used to generate the gene libraries can be obtained, for example, from enriched subpopulations or isolates of the sample. In another embodiment, DNA of a plurality of isolates can be pooled to create a source of nucleic acids for generation of the library. Alternatively, the nucleic acids can be obtained from a plurality of isolates, a plurality of gene libraries generated from the plurality of isolates to obtain a plurality of gene libraries. Two or more of the gene libraries can be pooled or combined to obtain a pooled isolate library. Thus, for example, nucleic acids may be recovered from either a cultured or non-cultured organism and used to produce an appropriate gene library (e.g., a recombinant expression library) for subsequent determination of the identity of the particular biomolecule of interest (e.g., a polynucleotide sequence) or screened for a bioactivity of interest (e.g., an enzyme or biological activity).

The following outlines a general procedure for producing libraries from both culturable and non-culturable organisms, enriched populations, as well as mixed population of organisms and isolates thereof, which libraries can be probed, sequenced or screened to select therefrom nucleic acid sequences having an identified, desired or predicted biological activity (e.g., an enzymatic activity), which selected nucleic acid sequences can be further evolved, mutagenized or derived.

As used herein an environmental sample is any sample containing organisms or polynucleotides or a combination thereof. Thus, an environmental sample can be obtained from any number of sources (as described above), including, for example, insect feces, hot springs, soil and the like. Any source of nucleic acids in purified or non-purified form can be utilized as starting material. Thus, the nucleic acids may be obtained from any source, which is contaminated by an organism or from any sample containing cells. The environmental sample can be an extract from any bodily sample such as blood, urine, spinal fluid, tissue, vaginal swab, stool, amniotic fluid or buccal mouthwash from any mammalian organism. For non-mammalian (e.g., invertebrates) organisms the sample can be a tissue sample, salivary sample, fecal material or material in the digestive tract of the organism. An environmental sample also includes samples obtained from extreme environments including, for example, hot sulfur pools, volcanic vents, and frozen tundra. The sample can come from a variety of sources. For example, in horticulture and agricultural testing the sample can be a plant, fertilizer, soil, liquid or other horticultural or agricultural product; in food testing the sample can be fresh food or processed food (for example infant formula, seafood, fresh produce and packaged food); and in environmental testing the sample can be liquid, soil, sewage treatment, sludge and any other sample in the environment which is considered or suspected of containing an organism or polynucleotides.

When the sample is a mixture of material containing a mixed population of organisms, for example, blood, soil or sludge, it can be treated with an appropriate reagent which is effective to open the cells and expose or separate the strands of nucleic acids. Although not necessary, this lysing and nucleic acid denaturing step will allow cloning, amplification or sequencing to occur more readily. Further, if desired, the mixed population can be cultured prior to analysis in order to purify or enrich a particular population or a desired isolate (e.g., an isolate of a particular species, genus, or family of organisms) and thus obtaining a purer sample. This is not necessary, however. For example, culturing of organisms in the sample can include culturing the organisms in microdroplets and separating the cultured microdroplets with a cell sorter into individual wells of a multi-well tissue culture plate. Alternatively, the sample can be cultured on any number of selective media compositions designed to inhibit or promote growth of a particular sub-population of organisms.

Where isolates are derived from the sample containing mixed population of organisms, nucleic acids can be obtained from the isolates as described below. The nucleic acids obtained from the isolates can be used to generate a gene library or, alternatively, be pooled with other isolate fractions of the sample wherein the pooled nucleic acids are used to generate a gene library. The isolates can be cultured prior to extraction of nucleic acids or can be uncultured. Methods of isolating specific populations of organisms present in a mixed population.

Accordingly, the sample comprises nucleic acids from, for example, a diverse and mixed population of organisms (e.g., microorganisms present in the gut of an insect). Nucleic acids are isolated from the sample using any number of methods for DNA and RNA isolation. Such nucleic acid isolation methods are commonly performed in the art. Where the nucleic acid is RNA, the RNA can be reversed transcribed to DNA using primers known in the art. Where the DNA is genomic DNA, the DNA can be sheared using, for example, a 25-gauge needle.

The nucleic acids can be cloned into an appropriate vector. The vector used will depend upon whether the DNA is to be expressed, amplified, sequenced or manipulated in any number of ways known in the art (see, for example, U.S. Pat. No. 6,022,716 which discloses high throughput sequencing vectors). Cloning techniques are known in the art or can be developed by one skilled in the art, without undue experimentation. The choice of a vector will also depend on the size of the polynucleotide sequence and the host cell to be employed in the methods of the invention. Thus, the vector used in the invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are typically used where the specific nucleic acid sequence to be analyzed or modified is large because these vectors are able to stably propagate large polynucleotides.

The vector containing the cloned nucleic acid sequence can then be amplified by plating (i.e., clonal amplification) or transfecting a suitable host cell with the vector (e.g., a phage on an *E. coli* host). The cloned nucleic acid sequence is used to prepare a library for screening (e.g., expression screening, PCR screening, hybridization screening or the like) by transforming a suitable organism. Hosts, known in the art are transformed by artificial introduction of the vectors containing the nucleic acid sequence by inoculation under conditions conducive for such transformation. One could transform with double stranded circular or linear nucleic acid or there may also be instances where one would transform with single stranded circular or linear nucleic acid sequences. By transform or transformation is meant a permanent or transient genetic change induced in a cell following incorporation of new DNA (e.g., DNA exogenous to the cell). Where the cell is a mammalian cell, a permanent genetic change is generally achieved by introduction of the DNA into the genome of the cell. A transformed cell or host cell generally refers to a cell (e.g., prokaryotic or eukaryotic) into which (or into an ancestor of which) has been introduced, by means of recombinant DNA techniques, a DNA molecule not normally present in the host organism.

A particular type of vector for use in the invention contains an f-factor origin replication. The f-factor (or fertility factor) in *E. coli* is a plasmid which effects high-frequency transfer of itself during conjugation and less frequent transfer of the bacterial chromosome itself. In a particular embodiment cloning vectors referred to as "fosmids" or bacterial artificial chromosome (BAC) vectors are used. These are derived from *E. coli* f-factor which is able to stably integrate large segments of DNA. When integrated with DNA from a mixed uncultured environmental sample, this makes it possible to achieve large genomic fragments in the form of a stable environmental gene library.

The nucleic acids derived from a mixed population or sample may be inserted into the vector by a variety of procedures. In general, the nucleic acid sequence is inserted into an appropriate restriction endonuclease site(s) by procedures known in the art. Such procedures and others are deemed to be within the scope of those skilled in the art. A typical cloning scenario may have DNA "blunted" with an appropriate nuclease (e.g., Mung Bean Nuclease), methylated with, for example, EcoR I Methylase and ligated to EcoR I linkers GGAATTCC (SEQ ID NO:1). The linkers are then digested with an EcoR I Restriction Endonuclease and the DNA size fractionated (e.g., using a sucrose gradient). The resulting size fractionated DNA is then ligated into a suitable vector for sequencing, screening or expression (e.g., a lambda vector and packaged using an in vitro lambda packaging extract).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the CaCl2 method by procedures well known in the art. Alternatively, MgCl2 or RbCl can be used. Transformation can also be performed after forming a protoplast of the host cell or by electroporation.

When the host is a eukaryote, methods of transfection or transformation with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). The eukaryotic cell may be a yeast cell (e.g., *Saccharomyces cerevisiae*), an insect cell (e.g., *Drosophila* sp.) or may be a mammalian cell, including a human cell.

Eukaryotic systems, and mammalian expression systems, allow for post-translational modifications of expressed mammalian proteins to occur. Eukaryotic cells, which possess the cellular machinery for processing of the primary transcript, glycosylation, phosphorylation, or secretion of the gene product should be used. Such host cell lines may include, but are not limited to, CHO, VERO, BHK, HeLa, COS, MDCK, Jurkat, HEK-293, and W138.

In one aspect, once a library of clones is created using any number of methods, including those describe above, the clones are resuspended in a liquid media, for example, a nutrient rich broth or other growth media known in the art. Typically the media is a liquid media, which can be readily pipetted. One or more media types containing at least one clone of the library are then introduced either individually or together as a mixture, into capillaries (all or a portion thereof) in a capillary array.

In another aspect, the library is first biopanned prior to introduction or delivery into a capillary device or other screening technique. Such biopanning methods enrich the library for sequences or activities of interest. Examples of methods for biopanning or enrichment are described below.

In one aspect, the library can be screened or sorted to enrich for clones containing a sequence or activity of interested based on polynucleotide sequences present in the library or clone. Thus, the invention provides methods and compositions useful in screening organisms for a desired biological activity or biological sequence and to assist in obtaining sequences of interest that can further be used in directed evolution, molecular biology, biotechnological and industrial applications.

Accordingly, the invention provides methods to rapidly screen, enrich and/or identify sequences in a sample by screening and identifying the nucleic acid sequences present in the sample. Thus, the invention increases the repertoire of available sequences that can be used for the development of diagnostics, therapeutics or molecules for industrial applications. Accordingly, the methods of the invention can identify novel nucleic acid sequences encoding proteins or polypeptides having a desired biological activity.

After the gene libraries (e.g., an expression library) have been generated one can include the additional step of "biopanning" such libraries prior to expression screening. The "biopanning" procedure refers to a process for identifying clones having a specified biological activity by screening for sequence homology in a library of clones.

The probe sequence used for selectively interacting with the target sequence of interest in the library can be a full-length coding region sequence or a partial coding region sequence for a known bioactivity. The library can be probed using mixtures of probes comprising at least a portion of the sequence encoding a known bioactivity or having a desired bioactivity. These probes or probe libraries are preferably single-stranded. In one aspect, the library is preferably been converted into single-stranded form. The probes that are particularly suitable are those derived from DNA encoding bioactivities having an activity similar or identical to the specified bioactivity, which is to be screened. The probes can be used to PCR amplify and thus select target sequences. Alternatively, the probe sequences can be used as hybridization probes which can be used to identify sequences with substantial or a desired homology.

In another aspect, in vivo biopanning may be performed utilizing a FACS-based machine. Gene libraries or expression libraries are constructed with vectors, which contain elements, which stabilize transcribed RNA. For example, the inclusion of sequences which result in secondary structures such as hairpins, which are designed to flank the transcribed regions of the RNA would serve to enhance their stability, thus increasing their half life within the cell. The probe molecules used in the biopanning process consist of oligonucleotides labeled with detectable molecules that provide a detectable signal upon interaction with a target sequence (e.g., only fluoresce upon binding of the probe to a target molecule). Various dyes or stains well known in the art, for example those described in "Practical Flow Cytometry", 1995 Wiley-Liss, Inc., Howard M. Shapiro, M. D., can be used to intercalate or associate with nucleic acid in order to "label" the oligonucleotides. These probes are introduced into the recombinant cells of the library using one of several transformation methods. The probe molecules interact or hybridize to the transcribed target mRNA or DNA resulting in DNA/RNA heteroduplex molecules or DNA/DNA duplex molecules. Binding of the probe to a target will yield a detectable signal (e.g., a fluorescent signal), which is detected and sorted by a FACS machine, or the like, during the screening process.

The probe DNA should be at least about 10 bases and preferably at least 15 bases. In one aspect, an entire coding region of one part of a pathway may be employed as a probe. Where the probe is hybridized to the target DNA in an in vitro system, conditions for the hybridization in which target DNA is selectively isolated by the use of at least one DNA probe will be designed to provide a hybridization stringency of at least about 50% sequence identity, more particularly a stringency providing for a sequence identity of at least about 70%.

The resultant libraries of transformed clones can then be further screened for clones, which display an activity of interest. Clones can be shuttled in alternative hosts for expression of active compounds, or screened using methods described herein.

An alternative to the in vivo biopanning described above is an encapsulation technique such as, for example, gel microdroplets, which may be employed to localize multiple clones in one location to be screened on a FACS machine. Clones can then be broken out into individual clones to be screened again on a FACS machine to identify positive individual clones. Screening in this manner using a FACS machine is fully described in patent application Ser. No. 08/876,276 filed Jun. 16, 1997. Thus, for example, if a clone mixture has a desirable activity, then the individual clones may be recovered and rescreened utilizing a FACS machine to determine which of such clones has the specified desirable activity.

Different types of encapsulation strategies and compounds or polymers can be used with the present invention. For instance, high temperature agarose can be employed for making microdroplets stable at high temperatures, allowing stable encapsulation of cells subsequent to heat-kill steps utilized to remove all background activities when screening for thermostable bioactivities. Encapsulation can be in beads, high temperature agaroses, gel microdroplets, cells, such as ghost red blood cells or macrophages, liposomes, or any other means of encapsulating and localizing molecules.

For example, methods of preparing liposomes have been described (e.g., U.S. Pat. Nos. 5,653,996, 5,393,530 and 5,651,981), as well as the use of liposomes to encapsulate a variety of molecules (e.g., U.S. Pat. Nos. 5,595,756, 5,605, 703, 5,627,159, 5,652,225, 5,567,433, 4,235,871, 5,227, 170). Entrapment of proteins, viruses, bacteria and DNA in erythrocytes during endocytosis has been described, as well (see, for example, Journal of Applied Biochemistry U.S. Pat. No. 4,418,435 (1982)). Erythrocytes employed as carriers in vitro or in vivo for substances entrapped during hypoosmotic lysis or dielectric breakdown of the membrane have also been described (reviewed in Ihler, G. M. (1983) J. Pharm. Ther). These techniques are useful in the present invention to encapsulate samples in a microenvironment for screening.

"Microenvironment," as used herein, is any molecular structure, which provides an appropriate environment for facilitating the interactions necessary for the method of the invention. An environment suitable for facilitating molecular interactions includes, for example, liposomes. Liposomes can be prepared from a variety of lipids including phospholipids, glycolipids, steroids, long-chain alkyl esters;

e.g., alkyl phosphates, fatty acid esters; e.g., lecithin, fatty amines and the like. A mixture of fatty material may be employed such a combination of neutral steroid, a charge amphiphile and a phospholipid. Illustrative examples of phospholipids include lecithin, sphingomyelin and dipalmitoylphos-phatidylcholine. Representative steroids include cholesterol, cholestanol and lanosterol. Representative charged amphiphilic compounds generally contain from 12–30 carbon atoms. Exemplary compounds include mono- or dialkyl phosphate esters, or alkyl amines; e.g., diacetyl phosphate, stearyl amine, hexadecyl amine, dilauryl phosphate, and the like.

Further, it is possible to combine some or all of the above embodiments such that a normalization step is performed prior to generation of the expression library, the expression library is then generated, the expression library so generated is then biopanned, and the biopanned expression library is then screened using a high throughput cell sorting and screening instrument. Thus there are a variety of options, including: (i) generating the library and then screen it; (ii) normalize the target DNA, generate the library and screen it; (iii) normalize, generate the library, biopan and screen; or (iv) generate, biopan and screen the library. The nucleic acids used to generate a library can be obtained, for example, from environmental samples, mixed populations of organisms (e.g., cultured or uncultured), enriched populations thereof, and isolates thereof. In addition, the screening techniques include, for example, hybridization screening, PCR screening, expression screening, and the like.

The gel microdroplet technology has had significance in amplifying the signals available in flow cytometric analysis, and in permitting the screening of microbial strains in strain improvement programs for biotechnology. Wittrup et al., (Biotechnolo. Bioeng. (1993) 42:351–356) developed a microencapsulation selection method which allows the rapid and quantitative screening of >106 yeast cells for enhanced secretion of *Aspergillus awamori* glucoamylase. The method provides a 400-fold single-pass enrichment for high-secretion mutants.

Gel microdroplet or other related technologies can be used in the present invention to localize, sort as well as amplify signals in the high throughput screening of recombinant libraries. Cell viability during the screening is not an issue or concern since nucleic acid can be recovered from the microdroplet.

Following any number of biopanning techniques capable of enriching the library population for clones containing sequences of interest, the enriched clones are suspended in a liquid media such as a nutrient broth or other growth media. Accordingly, the enriched clones comprise a plurality of host cells transformed with constructs comprising vectors into which have been incorporated nucleic acid sequences derived from a sample (e.g., mixed populations of organisms, isolates thereof, and the like). Liquid media containing a subset of clones and one or more substrates having a detectable molecule (e.g., an enzyme substrate) is then introduced or contacted, either individually or together as a mixture, with the enriched clones (e.g., into capillaries in a capillary array). Interaction (including reaction) of the substrate and a clone expressing an enzyme having the desire enzyme activity produces a product or a detectable signal, which can be spatially detected to identify one or more clones or capillaries containing at least one signal-producing clone. The signal-producing clones or nucleic acids contained in the signal-producing clone can then be recovered using any number of techniques.

A "substrate" as used herein includes, for example, substrates for the detection of a bioactivity or biomolecule (e.g., an enzymes and their specific enzyme activities). Such substrates are well known in the art. For example, various enzymes and suitable substrates specific for such enzymes are provided in Molecular Probes, Handbook Of Fluorescent Probes and Research Chemical (Molecular Probes, Inc.; Eugene, Oreg.), the disclosure of which is incorporated herein by reference. The substrate can have a detectable molecule associated with it including, for example, chromagenic or fluorogenic molecules. A suitable substrate for use in the present invention is any substrate that produces an optically detectable signal upon interaction (e.g., reaction) with a given enzyme having a desired activity, or a given clone encoding such enzyme.

One skilled in the art can choose a suitable substrate based on a desired enzyme activity, for example. Examples of desired enzymes/enzymatic activities include those listed herein. A desired enzyme activity may also comprise a group of enzymes in an enzymatic pathway for which there exists an optical signal substrate. One example of this is the set of carotenoid synthesis enzymes.

Substrates are known and/or are commercially available for glycosidases, epoxide hydrolases, phosphatases, and monoxygenases, among others. Where the desired activity is in the same class as that of other biomolecules or enzymes having a number of known substrates, the activity can be examined using a cocktail of the known substrates. For example, substrates are known for approximately 20 commercially available esterases and the combination of these known substrates can provide detectable, if not optimal, signal production.

The optical signal substrate can be a chromogenic substrate, a fluorogenic substrate, a bio- or chemi-luminescent substrate, or a fluorescence resonance energy transfer (FRET) substrate. The detectable species can be one, which results from cleavage of the substrate or a secondary molecule which is so affected by the cleavage or other substrate/biomolecule interaction as to undergo a detectable change. Innumerable examples of detectable assay formats are known from the diagnostic arts which use immunoassay, chromogenic assay, and labeled probe methodologies.

In one aspect, the optical signal substrate can be a bio- or chemi-luminescent substrate. Chemiluminescent substrates for several enzymes are available from Tropix (Bedford, Mass.). Among the enzymes having known chemiluminescent substrates are alkaline phosphatase, beta-galactosidase, beta-glucouronidase, and beta-glucosidase.

In another embodiment, chromogenic substrates may be used, particularly for certain enzymes such as hydrolytic enzymes. For example, the optical signal substrate can be an indolyl derivative, which is enzymatically cleaved to yield a chromogenic product. Where chromogenic substrates are used, the optically detectable signal is optical absorbance (including changes in absorbance). In this aspect, signal detection can be provided by an absorbance measurement using a spectrophotometer or the like.

In another aspect, a fluorogenic substrate is used, such that the optically detectable signal is fluorescence. Fluorogenic substrates provide high sensitivity for improved detection, as well as alternate detection modes. Hydroxy- and amino-substituted coumarins are the most widely used fluorophores used for preparing fluorogenic substrates. A typical coumarin-based fluorogenic substrate is 7-hydroxycoumarin, commonly known as umbelliferone (Umb). Derivatives and analogs of umbelliferone are also used. Substrate based on derivative and analogs of fluorescein (such as FDG or C12-FDG) and rhodamine are also used. Substrates derived from resorufin (e.g., resorufin beta-D-galactopyranoside or resorufin beta-D-glucouronide) are particularly useful in the present invention. Resorufin-based substrates are useful, for example, in screening for glycosidases, hydrolases and dealkylases. Lipophilic derivatives of the foregoing substrates (e.g., alkylated derivatives) may be useful in certain embodiments, since they generally load more readily into cells and may tend to associate with lipid regions of the cell. Fluorescein and resorufin are available commercially as alkylated derivatives that form products that are relatively insoluble in water (i.e., lipophilic). For example, fluorescence imaging can be performed using C12-resorufin galactoside, produced by Molecular Probes (Eugene, Oreg.) as a substrate. The particular fluorogenic substrate used may be chosen based on the enzymatic activity being screened.

Typically, the substrates are able to enter the cell and maintain its presence within the cell for a period sufficient for analysis to occur (e.g., once the substrate is in the cell it does not "leak" back out before reacting with the enzyme being screened to an extend sufficient to produce a detectable response). Retention of the substrate in the cell can be enhanced by a variety of techniques. In one method, the substrate compound is structurally modified by addition of a hydrophobic (e.g., alkyl) tail. In another embodiment, a solvent, such as DMSO or glycerol, can be used to coat the exterior of the cell. Also the substrate can be administered to the cells at reduced temperature, which has been observed to retard leakage of substrates from cells. However, entry of the substrate into the cell is not necessary where, for example, the enzyme or polypeptide is secreted, present in a lysed cellular sample or the like, or where the substrate can act externally to the cell (e.g., an extracellular receptor-ligand complex).

The optical signal substrate can, in some embodiments, be a FRET substrate. FRET is a spectroscopic method that can monitor proximity and relative angular orientation of fluorophores. A fluorescent indicator system that uses FRET to measure the concentration of a substrate or products includes two fluorescent moieties having emission and excitation spectra that render one a "donor" fluorescent moiety and the other an "acceptor" fluorescent moiety. The two fluorescent moieties are chosen such that the excitation spectrum of the acceptor fluorescent moiety overlaps with the emission spectrum of the excited moiety (the donor fluorescence moiety). The donor moiety is excited by light of appropriate intensity within the excitation spectrum of the donor moiety and emits the absorbed energy as fluorescent light. When the acceptor fluorescent protein moiety is positioned to quench the donor moiety in the excited state, the fluorescence energy is transferred to the acceptor moiety, which can emit a second photon. The emission spectra of the donor and acceptor moieties have minimal overlap so that the two emissions can be distinguished. Thus, when acceptor emits fluorescence at longer wavelength that the donor, then the net steady state effect is that the donor's emission is quenched, and the acceptor now emits when excited at the donor's absorption maximum.

The detectable or optical signal can be measured using, for example, a fluorometer (or the like) to detect fluorescence, including fluorescence polarization, time-resolved fluorescence or FRET. In general, excitation radiation, from an excitation source having a first wavelength, causes the excitation radiation to excite the sample. In response, fluorescence compounds in the sample emit radiation having a wavelength that is different from the excitation wavelength. Methods of performing assays on fluorescent materials are well known in the art and are described, e.g., by Lakowicz (Principles of Fluorescence Spectroscopy, New York, Plenum Press, 1983) and Herman ("Resonance energy transfer microscopy," in: Fluorescence Microscopy of Living Cells in Culture, Part B, Methods in Cell Biology, vol. 30, ed. Taylor & Wang, San Diego, Academic Press, 1989, pp. 219–243). Examples of fluorescence detection techniques are described in further detail below.

In addition, several methods have been described in the literature for using reporter genes to measure gene expression. Nolan et al. describes a technique to analyze beta-galactosidase expression in mammalian cells. This technique employs fluorescein-di-beta-D-glactopyranoside (FDG) as a substrate for beta-galactosidase, which releases fluorescein, a product that can be detected by its fluorescence emission upon hydrolysis (Nolan et al., 1991). Other fluorogenic substrates have been developed, such as 5-dodecanoylamino fluorescein di-beta-D-galactopyranside (C12-FDG) (Molecular Probes), which differ from FDG in that they are lipophilic fluorescein derivatives that can easily cross most cell membranes under physiological culture conditions.

The above-mentioned beta-galactosidase assays may be employed to screen single *E. coli* cells, expressing recombinant beta-D-galactosidase isolated, for example, from a hyperthermophilic archaeon such as *Sulfolobus solfataricus*. Other reporter genes may be useful as substrates and are known for beta-glucouronidase, alkaline phosphatase, chloramphenical acetyltransferase (CAT) and luciferase.

The library may, for example, be screened for a specified enzyme activity. For example, the enzyme activity screened for may be as a catalyst for the modification of epoxides. The recombinant enzymes may then be rescreened for a more specific enzyme activity.

Alternatively, the library may be screened for a more specialized enzyme activity. For example, instead of generically screening for bioactivity, the library may be screened for a more specialized activity, i.e. the type of bond on which the epoxide hydrolase acts. Thus, for example, the library may be screened to ascertain those EHs, which act on one or more specified epoxide groups such as mono-substituted epoxides, 2,2-disubstituted epoxides, 2,3-disubstituted epoxides, trisubstituted epoxides and styrene oxides.

As described with respect to one of the above aspects, the invention provides a process for activity screening of clones containing selected DNA derived from a microorganism which method includes:

screening a library for a biomolecule of interest or bioactivity of interest, wherein the library includes a plurality of clones, the clones having been prepared by recovering nucleic acids (e.g., genomic DNA) from a mixed population of organisms, enriched populations thereof, or isolates thereof, and transforming a host with the nucleic acids to produce clones which are screened for the biomolecule or bioactivity of interest.

In another aspect, an enrichment step may be used before activity based screening. The enrichment step can be, for example, a biopanning method. This procedure of "biopanning" is described and exemplified in U.S. Pat. No. 6,054,002, issued Apr. 25, 2000, which is incorporated herein by reference.

In another aspect, polynucleotides are contained in clones, the clones having been prepared from nucleic acid sequences of a mixed population of organisms, wherein the nucleic acid sequences are used to prepare a gene library of the mixed population of organisms. The gene library is screened for a sequence of interest by transfecting a host cell containing the library with at least one nucleic acid sequence having a detectable molecule which is all or a portion of a DNA sequence encoding a bioactivity having a desirable activity and separating the library clones containing the desirable sequence by, for example, a fluorescent based analysis.

The biopanning approach described above can be used to create libraries enriched with clones carrying sequences homologous to a given probe sequence. Using this approach libraries containing clones with inserts of up to 40 kbp can be enriched approximately 1,000 fold after each round of panning. This enables one to reduce the number of clones to be screened after 1 round of biopanning enrichment. This approach can be applied to create libraries enriched for clones carrying sequence of interest related to a bioactivity of interest for example polyketide sequences.

Hybridization screening using high-density filters or biopanning has proven an efficient approach to detect homologues of pathways containing conserved genes. To discover novel bioactive molecules that may have no known counterparts, however, other approaches are necessary. Another approach of the present invention is to screen in $E.$ $coli$ for the expression of small molecule ring structures or "backbones". Because the genes encoding these polycyclic structures can often be expressed in $E.$ $coli$ the small molecule backbone can be manufactured albeit in an inactive form. Bioactivity is conferred upon transferring the molecule or pathway to an appropriate host that expresses the requisite glycosylation and methylation genes that can modify or "decorate" the structure to its active form. Thus, inactive ring compounds, recombinantly expressed in $E.$ $coli$ are detected to identify clones, which are then shuttled to a metabolically rich host, such as Streptomyces, for subsequent production of the bioactive molecule. The use of high throughput robotic systems allows the screening of hundreds of thousands of clones in multiplexed arrays in microtiter dishes.

One approach to detect and enrich for clones carrying these structures is to use the capillary screening methods or FACS screening, a procedure described and exemplified in U.S. Ser. No. 08/876,276, filed Jun. 16, 1997. Polycyclic ring compounds typically have characteristic fluorescent spectra when excited by ultraviolet light. Thus, clones expressing these structures can be distinguished from background using a sufficiently sensitive detection method. For example, high throughput FACS screening can be utilized to screen for small molecule backbones in $E.$ $coli$ libraries. Commercially available FACS machines are capable of screening up to 100,000 clones per second for UV active molecules. These clones can be sorted for further FACS screening or the resident plasmids can be extracted and shuttled to $Streptomyces$ for activity screening.

In an alternate screening approach, after shuttling to $Streptomyces$ hosts, organic extracts from candidate clones can be tested for bioactivity by susceptibility screening against test organisms such as $Staphylococcus$ $aureus,$ $E.$ $coli,$ or $Saccharomyces$ $cerevisiae.$ FACS screening can be used in this approach by co-encapsulating clones with the test organism.

An alternative to the above-mentioned screening methods provided by the present invention is an approach termed "mixed extract" screening. The "mixed extract" screening approach takes advantage of the fact that the accessory genes needed to confer activity upon the polycyclic backbones are expressed in metabolically rich hosts, such as $Streptomyces,$ and that the enzymes can be extracted and combined with the backbones extracted from $E.$ $coli$ clones to produce the bioactive compound in vitro. Enzyme extract preparations from metabolically rich hosts, such as $Streptomyces$ strains, at various growth stages are combined with pools of organic extracts from $E.$ $coli$ libraries and then evaluated for bioactivity.

Another approach to detect activity in the $E.$ $coli$ clones is to screen for genes that can convert bioactive compounds to different forms.

Capillary screening, for example, can also be used to detect expression of UV fluorescent molecules in metabolically rich hosts, such as $Streptomyces.$ Recombinant oxytetracylin retains its diagnostic red fluorescence when produced heterologously in $S.$ $lividans$ TK24. Pathway clones, which can be identified by the methods and systems of the invention, can thus be screened for polycyclic molecules in a high throughput fashion.

Recombinant bioactive compounds can also be screened in vivo using "two-hybrid" systems, which can detect enhancers and inhibitors of protein-protein or other interactions such as those between transcription factors and their activators, or receptors and their cognate targets. In this embodiment, both a small molecule pathway and a GFP reporter construct are co-expressed. Clones altered in GFP expression can then be identified and the clone isolated for characterization.

The present invention also allows for the transfer of cloned pathways derived from uncultivated samples into metabolically rich hosts for heterologous expression and downstream screening for bioactive compounds of interest using a variety of screening approaches briefly described above.

After viable or non-viable cells, each containing a different expression clone from the gene library, are screened, and positive clones are recovered, DNA can be isolated from positive clones utilizing techniques well known in the art. The DNA can then be amplified either in vivo or in vitro by utilizing any of the various amplification techniques known in the art. In vivo amplification would include transformation of the clone(s) or subclone(s) into a viable host, followed by growth of the host. In vitro amplification can be performed using techniques such as the polymerase chain reaction. Once amplified the identified sequences can be "evolved" or sequenced.

One advantage afforded by present invention is the ability to manipulate the identified biomolecules or bioactivities to generate and select for encoded variants with altered sequence, activity or specificity.

Clones found to have biomolecules or bioactivities for which the screen was performed can be subjected to directed mutagenesis to develop new biomolecules or bioactivities with desired properties or to develop modified biomolecules or bioactivities with particularly desired properties that are absent or less pronounced in nature (e.g., wild-type activity), such as stability to heat or organic solvents. Any of the known techniques for directed mutagenesis are applicable to the invention. For example, particularly preferred mutagenesis techniques for use in accordance with the invention include those described below.

Alternatively, it may be desirable to variegate a biomolecule (e.g., a peptide, protein, or polynucleotide sequence) or a bioactivity (e.g., an enzymatic activity) obtained, identified or cloned as described herein. Such variegation can modify the biomolecule or bioactivity in order to increase or decrease, for example, a polypeptide's activity, specificity, affinity, function, and the like. DNA shuffling can be used to increase variegation in a particular sample. DNA shuffling is meant to indicate recombination between substantially homologous but non-identical sequences, in some embodiments DNA shuffling may involve crossover via non-homologous recombination, such as via cer/lox and/or flp/frt systems and the like (see, for example, U.S. Pat. No. 5,939,250, issued to Dr. Jay Short on Aug. 17, 1999, and assigned to Diversa Corporation, the disclosure of which is incorporated herein by reference). Various methods for shuffling, mutating or variegating polynucleotide or polypeptide sequences are discussed below.

Nucleic acid shuffling is a method for in vitro or in vivo homologous recombination of pools of shorter or smaller polynucleotides to produce a polynucleotide or polynucleotides. Mixtures of related nucleic acid sequences or polynucleotides are subjected to sexual PCR to provide random polynucleotides, and reassembled to yield a library or mixed population of recombinant hybrid nucleic acid molecules or polynucleotides. In contrast to cassette mutagenesis, only shuffling and error-prone PCR allow one to mutate a pool of sequences blindly (without sequence information other than primers).

The advantage of the mutagenic shuffling of the invention over error-prone PCR alone for repeated selection can best be explained as follows. Consider DNA shuffling as compared with error-prone PCR (not sexual PCR). The initial library of selected or pooled sequences can consist of related sequences of diverse origin or can be derived by any type of mutagenesis (including shuffling) of a single gene. A collection of selected sequences is obtained after the first round of activity selection. Shuffling allows the free combinatorial association of all of the related sequences, for example.

This method differs from error-prone PCR, in that it is an inverse chain reaction. In error-prone PCR, the number of polymerase start sites and the number of molecules grows exponentially. However, the sequence of the polymerase start sites and the sequence of the molecules remains essentially the same. In contrast, in nucleic acid reassembly or shuffling of random polynucleotides the number of start sites and the number (but not size) of the random polynucleotides decreases over time. For polynucleotides derived from whole plasmids the theoretical endpoint is a single, large concatemeric molecule.

Since crossovers occur at regions of homology, recombination will primarily occur between members of the same sequence family. This discourages combinations of sequences that are grossly incompatible (e.g., having different activities or specificities). It is contemplated that multiple families of sequences can be shuffled in the same reaction. Further, shuffling generally conserves the relative order.

Rare shufflants will contain a large number of the best molecules (e.g., highest activity or specificity) and these rare shufflants may be selected based on their superior activity or specificity.

A pool of 100 different polypeptide sequences can be permutated in up to 103 different ways. This large number of permutations cannot be represented in a single library of DNA sequences. Accordingly, it is contemplated that multiple cycles of DNA shuffling and selection may be required depending on the length of the sequence and the sequence diversity desired. Error-prone PCR, in contrast, keeps all the selected sequences in the same relative orientation, generating a much smaller mutant cloud.

The template polynucleotide, which may be used in the methods of the invention may be DNA or RNA. It may be of various lengths depending on the size of the gene or shorter or smaller polynucleotide to be recombined or reassembled. Preferably, the template polynucleotide is from 50 bp to 50 kb. It is contemplated that entire vectors containing the nucleic acid encoding the protein of interest can be used in the methods of the invention, and in fact have been successfully used.

The template polynucleotide may be obtained by amplification using the PCR reaction (U.S. Pat. Nos. 4,683,202 and 4,683,195) or other amplification or cloning methods. However, the removal of free primers from the PCR products before subjecting them to pooling of the PCR products and sexual PCR may provide more efficient results. Failure to adequately remove the primers from the original pool before sexual PCR can lead to a low frequency of crossover clones.

The template polynucleotide often is double-stranded. A double-stranded nucleic acid molecule is recommended to ensure that regions of the resulting single-stranded polynucleotides are complementary to each other and thus can hybridize to form a double-stranded molecule.

It is contemplated that single-stranded or double-stranded nucleic acid polynucleotides having regions of identity to the template polynucleotide and regions of heterology to the template polynucleotide may be added to the template polynucleotide, at this step. It is also contemplated that two different but related polynucleotide templates can be mixed at this step.

The double-stranded polynucleotide template and any added double- or single-stranded polynucleotides are subjected to sexual PCR which includes slowing or halting to provide a mixture of from about 5 bp to 5 kb or more. Preferably the size of the random polynucleotides is from about 10 bp to 1000 bp, more preferably the size of the polynucleotides is from about 20 bp to 500 bp.

Alternatively, it is also contemplated that double-stranded nucleic acid having multiple nicks may be used in the methods of the invention. A nick is a break in one strand of the double-stranded nucleic acid. The distance between such nicks is preferably 5 bp to 5 kb, more preferably between 10 bp to 1000 bp. This can provide areas of self-priming to produce shorter or smaller polynucleotides to be included with the polynucleotides resulting from random primers, for example.

The concentration of any one specific polynucleotide will not be greater than 1% by weight of the total polynucleotides, more preferably the concentration of any one specific nucleic acid sequence will not be greater than 0.1% by weight of the total nucleic acid.

The number of different specific polynucleotides in the mixture will be at least about 100, preferably at least about 500, and more preferably at least about 1000.

At this step single-stranded or double-stranded polynucleotides, either synthetic or natural, may be added to the random double-stranded shorter or smaller polynucleotides in order to increase the heterogeneity of the mixture of polynucleotides.

It is also contemplated that populations of double-stranded randomly broken polynucleotides may be mixed or combined at this step with the polynucleotides from the sexual PCR process and optionally subjected to one or more additional sexual PCR cycles.

Where insertion of mutations into the template polynucleotide is desired, single-stranded or double-stranded polynucleotides having a region of identity to the template polynucleotide and a region of heterology to the template polynucleotide may be added in a 20 fold excess by weight as compared to the total nucleic acid, more preferably the single-stranded polynucleotides may be added in a 10 fold excess by weight as compared to the total nucleic acid.

Where a mixture of different but related template polynucleotides is desired, populations of polynucleotides from each of the templates may be combined at a ratio of less than about 1:100, more preferably the ratio is less than about 1:40. For example, a backcross of the wild-type polynucleotide with a population of mutated polynucleotide may be desired to eliminate neutral mutations (e.g., mutations yielding an insubstantial alteration in the phenotypic property being selected for). In such an example, the ratio of randomly provided wild-type polynucleotides which may be added to the randomly provided sexual PCR cycle hybrid polynucleotides is approximately 1:1 to about 100:1, and more preferably from 1:1 to 40:1.

The mixed population of random polynucleotides are denatured to form single-stranded polynucleotides and then re-annealed. Only those single-stranded polynucleotides having regions of homology with other single-stranded polynucleotides will re-anneal.

The random polynucleotides may be denatured by heating. One skilled in the art could determine the conditions necessary to completely denature the double-stranded nucleic acid. Preferably the temperature is from 80° C. to 100° C., more preferably the temperature is from 90° C. to 96° C. Other methods, which may be used to denature the polynucleotides include pressure and pH.

The polynucleotides may be re-annealed by cooling. Preferably the temperature is from 20° C. to 75° C., more preferably the temperature is from 40° C. to 65° C. If a high frequency of crossovers is needed based on an average of only 4 consecutive bases of homology, recombination can be forced by using a low annealing temperature, although the process becomes more difficult. The degree of renaturation, which occurs will depend on the degree of homology between the population of single-stranded polynucleotides.

Renaturation can be accelerated by the addition of polyethylene glycol ("PEG") or salt. The salt concentration is preferably from 0 mM to 200 mM, more preferably the salt concentration is from 10 mM to 100 mm. The salt may be KCl or NaCl. The concentration of PEG is preferably from 0% to 20%, more preferably from 5% to 10%.

The annealed polynucleotides are next incubated in the presence of a nucleic acid polymerase and dNTP's (i.e. dATP, dCTP, DGTP and dTTP). The nucleic acid polymerase may be the Klenow fragment, the Taq polymerase or any other DNA polymerase known in the art.

The approach to be used for the assembly depends on the minimum degree of homology that should still yield crossovers. If the areas of identity are large, Taq polymerase can be used with an annealing temperature of between 45□65 □C. If the areas of identity are small, Klenow polymerase can be used with an annealing temperature of between 20°–30° C. One skilled in the art could vary the temperature of annealing to increase the number of crossovers achieved.

The polymerase may be added to the random polynucleotides prior to annealing, simultaneously with annealing or after annealing.

The cycle of denaturation, renaturation and incubation in the presence of polymerase is referred to herein as shuffling or reassembly of the nucleic acid. This cycle is repeated for a desired number of times. Preferably the cycle is repeated from 2 to 50 times, more preferably the sequence is repeated from 10 to 40 times.

The resulting nucleic acid is a larger double-stranded polynucleotide of from about 50 bp to about 100 kb, preferably the larger polynucleotide is from 500 bp to 50 kb.

These larger polynucleotides may contain a number of copies of a polynucleotide having the same size as the template polynucleotide in tandem. This concatemeric polynucleotide is then denatured into single copies of the template polynucleotide. The result will be a population of polynucleotides of approximately the same size as the template polynucleotide. The population will be a mixed population where single or double-stranded polynucleotides having an area of identity and an area of heterology have been added to the template polynucleotide prior to shuffling. These polynucleotides are then cloned into the appropriate vector and the ligation mixture used to transform bacteria.

It is contemplated that the single polynucleotides may be obtained from the larger concatemeric polynucleotide by amplification of the single polynucleotide prior to cloning by a variety of methods including PCR (U.S. Pat. Nos. 4,683, 195 and 4,683,202), rather than by digestion of the concatemer.

The vector used for cloning is not critical provided that it will accept a polynucleotide of the desired size. If expression of the particular polynucleotide is desired, the cloning vehicle should further comprise transcription and translation signals next to the site of insertion of the polynucleotide to allow expression of the polynucleotide in the host cell.

The resulting bacterial population will include a number of recombinant polynucleotides having random mutations. This mixed population may be tested to identify the desired recombinant polynucleotides. The method of selection will depend on the polynucleotide desired.

For example, if a polynucleotide, identified by the methods of described herein, encodes a protein with a first binding affinity, subsequent mutated (e.g., shuffled) sequences having an increased binding efficiency to a ligand may be desired. In such a case the proteins expressed by each of the portions of the polynucleotides in the population or library may be tested for their ability to bind to the ligand by methods known in the art (i.e. panning, affinity chromatography). If a polynucleotide, which encodes for a protein with increased drug resistance is desired, the proteins expressed by each of the polynucleotides in the population or library may be tested for their ability to confer drug resistance to the host organism. One skilled in the art, given knowledge of the desired protein, could readily test the population to identify polynucleotides, which confer the desired properties onto the protein.

It is contemplated that one skilled in the art could use a phage display system in which fragments of the protein are expressed as fusion proteins on the phage surface (Pharmacia, Milwaukee Wis.). The recombinant DNA molecules are cloned into the phage DNA at a site, which results in the transcription of a fusion protein a portion of which is encoded by the recombinant DNA molecule. The phage containing the recombinant nucleic acid molecule undergoes replication and transcription in the cell. The leader sequence of the fusion protein directs the transport of the fusion protein to the tip of the phage particle. Thus, the fusion protein, which is partially encoded by the recombinant DNA molecule is displayed on the phage particle for detection and selection by the methods described above.

It is further contemplated that a number of cycles of nucleic acid shuffling may be conducted with polynucleotides from a sub-population of the first population, which sub-population contains DNA encoding the desired recombinant protein. In this manner, proteins with even higher binding affinities or enzymatic activity could be achieved.

It is also contemplated that a number of cycles of nucleic acid shuffling may be conducted with a mixture of wild type polynucleotides and a sub-population of nucleic acid from the first or subsequent rounds of nucleic acid shuffling in order to remove any silent mutations from the sub-population.

Any source of nucleic acid, in a purified form can be utilized as the starting nucleic acid. Thus the process may employ DNA or RNA including messenger RNA, which DNA or RNA may be single or double stranded. In addition, a DNA☐RNA hybrid, which contains one strand of each may be utilized. The nucleic acid sequence may be of various lengths depending on the size of the nucleic acid sequence to be mutated. Preferably the specific nucleic acid sequence is from 50 to 50,000 base pairs. It is contemplated that entire vectors containing the nucleic acid encoding the protein of interest may be used in the methods of the invention.

Any specific nucleic acid sequence can be used to produce the population of hybrids by the present process. It is only necessary that a small population of hybrid sequences of the specific nucleic acid sequence exist or be available for the present process.

A population of specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into *E. coli* and propagated as a pool or library of hybrid plasmids.

Alternatively, a small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once a mixed population of specific nucleic acid sequences is generated, the polynucleotides can be used directly or inserted into an appropriate cloning vector, using techniques well known in the art.

The choice of vector depends on the size of the polynucleotide sequence and the host cell to be employed in the methods of the invention. The templates of the invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are preferred where the specific nucleic acid sequence to be mutated is larger because these vectors are able to stably propagate large polynucleotides.

If a mixed population of the specific nucleic acid sequence is cloned into a vector it can be clonally amplified. Utility can be readily determined by screening expressed polypeptides.

The DNA shuffling method of the invention can be performed blindly on a pool of unknown sequences. By adding to the reassembly mixture oligonucleotides (with ends that are homologous to the sequences being reassembled) any sequence mixture can be incorporated at any specific position into another sequence mixture. Thus, it is contemplated that mixtures of synthetic oligonucleotides, PCR polynucleotides or even whole genes can be mixed into another sequence library at defined positions. The insertion of one sequence (mixture) is independent from the insertion of a sequence in another part of the template. Thus, the degree of recombination, the homology required, and the diversity of the library can be independently and simultaneously varied along the length of the reassembled DNA.

Shuffling requires the presence of homologous regions separating regions of diversity. Scaffold-like protein structures may be particularly suitable for shuffling. The conserved scaffold determines the overall folding by self-association, while displaying relatively unrestricted loops that mediate the specific binding. Examples of such scaffolds are the immunoglobulin beta-barrel, and the four helix bundle which are well-known in the art. This shuffling can be used to create scaffold like proteins with various combinations of mutated sequences for binding.

The equivalents of some standard genetic matings may also be performed by shuffling in vitro. For example, a "molecular backcross" can be performed by repeatedly mixing the hybrid's nucleic acid with the wild type nucleic acid while selecting for the mutations of interest. As in traditional breeding, this approach can be used to combine phenotypes from different sources into a background of choice. It is useful, for example, for the removal of neutral mutations that affect unselected characteristics (e.g., immunogenicity). Thus it can be useful to determine which mutations in a protein are involved in the enhanced biological activity and which are not, an advantage which cannot be achieved by error-prone mutagenesis or cassette mutagenesis methods.

Large, functional genes can be assembled correctly from a mixture of small random polynucleotides. This reaction may be of use for the reassembly of genes from the highly fragmented DNA of fossils. In addition random nucleic acid fragments from fossils may be combined with polynucleotides from similar genes from related species.

It is also contemplated that the method of the invention can be used for the in vitro amplification of a whole genome from a single cell as is needed for a variety of research and diagnostic applications. DNA amplification by PCR typically includes sequences of about 40 kb. Amplification of a whole genome such as that of *E. coli* (5,000 kb) by PCR would require about 250 primers yielding 125 forty kb polynucleotides. On the other hand, random production of polynucleotides of the genome with sexual PCR cycles, followed by gel purification of small polynucleotides will provide a multitude of possible primers. Use of this mix of random small polynucleotides as primers in a PCR reaction alone or with the whole genome as the template should result in an inverse chain reaction with the theoretical endpoint of a single concatamer containing many copies of the genome.

A 100 fold amplification in the copy number and an average polynucleotide size of greater than 50 kb may be obtained when only random polynucleotides are used. It is thought that the larger concatamer is generated by overlap of many smaller polynucleotides. The quality of specific PCR products obtained using synthetic primers will be indistinguishable from the product obtained from unamplified DNA. It is expected that this approach will be useful for the mapping of genomes.

The polynucleotide to be shuffled can be produced as random or non-random polynucleotides, at the discretion of the practitioner. Moreover, the invention provides a method of shuffling that is applicable to a wide range of polynucleotide sizes and types, including the step of generating polynucleotide monomers to be used as building blocks in the reassembly of a larger polynucleotide. For example, the building blocks can be fragments of genes or they can be comprised of entire genes or gene pathways, or any combination thereof.

In an aspect of in vivo shuffling, a mixed population of a specific nucleic acid sequence is introduced into bacterial or eukaryotic cells under conditions such that at least two different nucleic acid sequences are present in each host cell. The polynucleotides can be introduced into the host cells by a variety of different methods. The host cells can be transformed with the smaller polynucleotides using methods known in the art, for example treatment with calcium chloride. If the polynucleotides are inserted into a phage genome, the host cell can be transfected with the recombinant phage genome having the specific nucleic acid sequences. Alternatively, the nucleic acid sequences can be introduced into the host cell using electroporation, transfection, lipofection, biolistics, conjugation, and the like.

In general, in this aspect, specific nucleic acid sequences will be present in vectors, which are capable of stably replicating the sequence in the host cell. In addition, it is contemplated that the vectors will encode a marker gene such that host cells having the vector can be selected. This ensures that the mutated specific nucleic acid sequence can be recovered after introduction into the host cell. However, it is contemplated that the entire mixed population of the specific nucleic acid sequences need not be present on a vector sequence. Rather only a sufficient number of sequences need be cloned into vectors to ensure that after introduction of the polynucleotides into the host cells each host cell contains one vector having at least one specific nucleic acid sequence present therein. It is also contemplated that rather than having a subset of the population of the specific nucleic acids sequences cloned into vectors, this subset may be already stably integrated into the host cell.

It has been found that when two polynucleotides, which have regions of identity are inserted into the host cells homologous recombination occurs between the two polynucleotides. Such recombination between the two mutated specific nucleic acid sequences will result in the production of double or triple hybrids in some situations.

It has also been found that the frequency of recombination is increased if some of the mutated specific nucleic acid sequences are present on linear nucleic acid molecules. Therefore, in one aspect, some of the specific nucleic acid sequences are present on linear polynucleotides.

After transformation, the host cell transformants are placed under selection to identify those host cell transformants, which contain mutated specific nucleic acid sequences having the qualities desired. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the mutated population which shows enhanced binding to the ligand. Alternatively, the protein can be expressed in another system to ensure proper processing.

Once a subset of the first recombined specific nucleic acid sequences (daughter sequences) having the desired characteristics are identified, they are then subject to a second round of recombination. In the second cycle of recombination, the recombined specific nucleic acid sequences may be mixed with the original mutated specific nucleic acid sequences (parent sequences) and the cycle repeated as described above. In this way a set of second recombined specific nucleic acids sequences can be identified which have enhanced characteristics or encode for proteins having enhanced properties. This cycle can be repeated a number of times as desired.

It is also contemplated that in the second or subsequent recombination cycle, a backcross can be performed. A molecular backcross can be performed by mixing the desired specific nucleic acid sequences with a large number of the wild type sequences, such that at least one wild type nucleic acid sequence and a mutated nucleic acid sequence are present in the same host cell after transformation. Recombination with the wild type specific nucleic acid sequence will eliminate those neutral mutations that may affect unselected characteristics such as immunogenicity but not the selected characteristics.

In another aspect of the invention, it is contemplated that during the first round a subset of specific nucleic acid sequences can be generated as smaller polynucleotides by slowing or halting their PCR amplification prior to introduction into the host cell. The size of the polynucleotides must be large enough to contain some regions of identity with the other sequences so as to homologously recombine with the other sequences. The size of the polynucleotides will range from 0.03 kb to 100 kb more preferably from 0.2 kb to 10 kb. It is also contemplated that in subsequent rounds, all of the specific nucleic acid sequences other than the sequences selected from the previous round may be utilized to generate PCR polynucleotides prior to introduction into the host cells.

The shorter polynucleotide sequences can be single-stranded or double-stranded. The reaction conditions suitable for separating the strands of nucleic acid are well known in the art.

The steps of this process can be repeated indefinitely, being limited only by the number of possible hybrids, which can be achieved.

Therefore, the initial pool or population of mutated template nucleic acid is cloned into a vector capable of replicating in a bacteria such as *E. coli*. The particular vector is not essential, so long as it is capable of autonomous replication in *E. coli*. In a one embodiment, the vector is designed to allow the expression and production of any protein encoded by the mutated specific nucleic acid linked to the vector. It is also preferred that the vector contain a gene encoding for a selectable marker.

The population of vectors containing the pool of mutated nucleic acid sequences is introduced into the *E. coli* host cells. The vector nucleic acid sequences may be introduced by transformation, transfection or infection in the case of phage. The concentration of vectors used to transform the bacteria is such that a number of vectors is introduced into each cell. Once present in the cell, the efficiency of homologous recombination is such that homologous recombination occurs between the various vectors. This results in the generation of hybrids (daughters) having a combination of mutations, which differ from the original parent mutated sequences. The host cells are then clonally replicated and selected for the marker gene present on the vector. Only those cells having a plasmid will grow under the selection.

The host cells, which contain a vector are then tested for the presence of favorable mutations.

Once a particular daughter mutated nucleic acid sequence has been identified which confers the desired characteristics, the nucleic acid is isolated either already linked to the vector or separated from the vector. This nucleic acid is then mixed with the first or parent population of nucleic acids and the cycle is repeated.

The parent mutated specific nucleic acid population, either as polynucleotides or cloned into the same vector is introduced into the host cells already containing the daughter nucleic acids. Recombination is allowed to occur in the cells and the next generation of recombinants, or granddaughters are selected by the methods described above. This cycle can be repeated a number of times until the nucleic acid or peptide having the desired characteristics is obtained. It is contemplated that in subsequent cycles, the population of mutated sequences, which are added to the hybrids may come from the parental hybrids or any subsequent generation.

In an alternative embodiment, the invention provides a method of conducting a "molecular" backcross of the obtained recombinant specific nucleic acid in order to eliminate any neutral mutations. Neutral mutations are those mutations, which do not confer onto the nucleic acid or peptide the desired properties. Such mutations may however confer on the nucleic acid or peptide undesirable characteristics. Accordingly, it is desirable to eliminate such neutral mutations. The method of the invention provides a means of doing so.

In this aspect, after the hybrid nucleic acid, having the desired characteristics, is obtained by the methods of the embodiments, the nucleic acid, the vector having the nucleic acid or the host cell containing the vector and nucleic acid is isolated.

The nucleic acid or vector is then introduced into the host cell with a large excess of the wild type nucleic acid. The nucleic acid of the hybrid and the nucleic acid of the wild type sequence are allowed to recombine. The resulting recombinants are placed under the same selection as the hybrid nucleic acid. Only those recombinants, which retained the desired characteristics will be selected. Any silent mutations which do not provide the desired characteristics will be lost through recombination with the wild type DNA. This cycle can be repeated a number of times until all of the silent mutations are eliminated.

In another aspect, the invention provides for a method for shuffling, assembling, reassembling, recombining, and/or concatenating at least two polynucleotides to form a progeny polynucleotide (e.g., a chimeric progeny polynucleotide that can be expressed to produce a polypeptide or a gene pathway). In a particular embodiment, a double stranded polynucleotide (e.g., two single stranded sequences hybridized to each other as hybridization partners) is treated with an exonuclease to liberate nucleotides from one of the two strands, leaving the remaining strand free of its original partner so that, if desired, the remaining strand may be used to achieve hybridization to another partner.

In a particular aspect, a double stranded polynucleotide end (that may be part of—or connected to—a polynucleotide or a non-polynucleotide sequence) is subjected to a source of exonuclease activity. Enzyme with 3' exonuclease activity, an enzyme with 5' exonuclease activity, an enzyme with both 3' exonuclease activity and 5' exonuclease activity, and any combination thereof can be used in the invention. An exonuclease can be used to liberate nucleotides from one or both ends of a linear double stranded polynucleotide, and from one to all ends of a branched polynucleotide having more than two ends.

By contrast, a non-enzymatic step may be used to shuffle, assemble, reassemble, recombine, and/or concatenate polynucleotide building blocks that is comprised of subjecting a working sample to denaturing (or "melting") conditions (for example, by changing temperature, pH, and/or salinity conditions) so as to melt a working set of double stranded polynucleotides into single polynucleotide strands. For shuffling, it is desirable that the single polynucleotide strands participate to some extent in annealment with different hybridization partners (i.e. and not merely revert to exclusive re-annealment between what were former partners before the denaturation step). The presence of the former hybridization partners in the reaction vessel, however, does not preclude, and may sometimes even favor, re-annealment of a single stranded polynucleotide with its former partner, to recreate an original double stranded polynucleotide.

In contrast to this non-enzymatic shuffling step comprised of subjecting double stranded polynucleotide building blocks to denaturation, followed by annealment, the invention further provides an exonuclease-based approach requiring no denaturation—rather, the avoidance of denaturing conditions and the maintenance of double stranded polynucleotide substrates in annealed (i.e. non-denatured) state are necessary conditions for the action of exonucleases (e.g., exonuclease III and red alpha gene product). In further contrast, the generation of single stranded polynucleotide sequences capable of hybridizing to other single stranded polynucleotide sequences is the result of covalent cleavage—and hence sequence destruction—in one of the hybridization partners. For example, an exonuclease III enzyme may be used to enzymatically liberate 3' terminal nucleotides in one hybridization strand (to achieve covalent hydrolysis in that polynucleotide strand); and this favors hybridization of the remaining single strand to a new partner (since its former partner was subjected to covalent cleavage).

It is particularly appreciated that enzymes can be discovered, optimized (e.g., engineered by directed evolution), or both discovered and optimized specifically for the instantly disclosed approach that have more optimal rates and/or more highly specific activities &/or greater lack of unwanted activities. In fact it is expected that the invention may encourage the discovery and/or development of such designer enzymes.

Furthermore, it is appreciated that one can protect the end of a double stranded polynucleotide or render it susceptible to a desired enzymatic action of an exonuclease as necessary. For example, a double stranded polynucleotide end having a 3' overhang is not susceptible to the exonuclease action of exonuclease III. However, it may be rendered susceptible to the exonuclease action of exonuclease III by a variety of means; for example, it may be blunted by treatment with a polymerase, cleaved to provide a blunt end or a 5' overhang, joined (ligated or hybridized) to another double stranded polynucleotide to provide a blunt end or a 5' overhang, hybridized to a single stranded polynucleotide to provide a blunt end or a 5' overhang, or modified by any of a variety of means).

According to one aspect, an exonuclease may be allowed to act on one or on both ends of a linear double stranded polynucleotide and proceed to completion, to near completion, or to partial completion. When the exonuclease action is allowed to go to completion, the result will be that the length of each 5' overhang will be extend far towards the middle region of the polynucleotide in the direction of what might be considered a "rendezvous point" (which may be somewhere near the polynucleotide midpoint). Ultimately, this results in the production of single stranded polynucleotides (that can become dissociated) that are each about half the length of the original double stranded polynucleotide.

Thus, the exonuclease-mediated approach is useful for shuffling, assembling and/or reassembling, recombining, and concatenating polynucleotide building blocks. The polynucleotide building blocks can be up to ten bases long or tens of bases long or hundreds of bases long or thousands of bases long or tens of thousands of bases long or hundreds of thousands of bases long. or millions of bases long or even longer.

Substrates for an exonuclease may be generated by subjecting a double stranded polynucleotide to fragmentation. Fragmentation may be achieved by mechanical means (e.g., shearing, sonication, and the like), by enzymatic means (e.g., using restriction enzymes), and by any combination thereof. Fragments of a larger polynucleotide may also be generated by polymerase-mediated synthesis.

Additional examples of enzymes with exonuclease activity include red-alpha and venom phosphodiesterases. Red alpha (red alpha gene product (also referred to as lambda exonuclease) is of bacteriophage alpha origin. Red alpha gene product acts processively from 5'-phosphorylated termini to liberate mononucleotides from duplex DNA (Takahashi & Kobayashi, 1990). Venom phosphodiesterases (Laskowski, 1980) is capable of rapidly opening supercoiled DNA.

In one aspect, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. These exemplifications, while illustrating certain specific aspects of the invention, do not portray the limitations or circumscribe the scope of the disclosed invention.

Thus according to one aspect of the invention, the sequences of a plurality of progenitor nucleic acid templates identified using the methods of the invention are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, and preferably at almost all of the progenitor templates. Even more preferably still a demarcation point is an area of homology that is shared by all of the progenitor templates.

In another aspect, the ligation reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the invention, the possibility of unwanted side products is greatly reduced.

In yet another aspect, the invention provides that, the ligation reassembly process is performed systematically, for example in order to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. In a particularly embodiment, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one embodiment, this polynucleotide is a gene, which may be a man-made gene. According to another embodiment, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a demarcation point.

Thus, according to another aspect, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In a preferred instance, the recombination is facilitated by, or occurs at, areas of homology between the man-made intron-containing gene and a nucleic acid with serves as a recombination partner. In a particularly preferred instance, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic ligation reassembly method of the invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

An overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100, 000 bp (including every integer value in between).

Many methods exist by which a double-stranded nucleic acid building block can be generated that is serviceable for the invention; and these are known in the art and can be readily performed by the skilled artisan.

According to one aspect, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another aspect, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

The invention provides a method for selecting a subset of polynucleotides from a starting set of polynucleotides, which method is based on the ability to discriminate one or more selectable features (or selection markers) present anywhere in a working polynucleotide, so as to allow one to perform selection for (positive selection) and/or against (negative selection) each selectable polynucleotide. In a one aspect, a method is provided termed end-selection, which method is based on the use of a selection marker located in part or entirely in a terminal region of a selectable polynucleotide, and such a selection marker may be termed an "end-selection marker".

End-selection may be based on detection of naturally occurring sequences or on detection of sequences introduced experimentally (including by any mutagenesis procedure mentioned herein and not mentioned herein) or on both, even within the same polynucleotide. An end-selection marker can be a structural selection marker or a functional selection marker or both a structural and a functional selection marker. An end-selection marker may be comprised of a polynucleotide sequence or of a polypeptide sequence or of any chemical structure or of any biological or biochemical tag, including markers that can be selected using methods based on the detection of radioactivity, of enzymatic activity, of fluorescence, of any optical feature, of a magnetic property (e.g., using magnetic beads), of immunoreactivity, and of hybridization.

End-selection may be applied in combination with any method for performing mutagenesis. Such mutagenesis methods include, but are not limited to, methods described herein (supra and infra). Such methods include, by way of non-limiting exemplification, any method that may be referred herein or by others in the art by any of the following terms: "saturation mutagenesis", "shuffling", "recombination", "reassembly", "error-prone PCR", "assembly PCR", "sexual PCR", "crossover PCR", "oligonucleotide primer-directed mutagenesis", "recursive (and/or exponential) ensemble mutagenesis (see Arkin and Youvan, 1992)", "cassette mutagenesis", "in vivo mutagenesis", and "in vitro mutagenesis". Moreover, end-selection may be performed on molecules produced by any mutagenesis and/or amplification method (see, e.g., Arnold, 1993; Caldwell and Joyce, 1992; Stemmer, 1994) following which method it is desirable to select for (including to screen for the presence of) desirable progeny molecules.

In addition, end-selection may be applied to a polynucleotide apart from any mutagenesis method. In a one embodiment, end-selection, as provided herein, can be used in order to facilitate a cloning step, such as a step of ligation to another polynucleotide (including ligation to a vector). The invention thus provides for end-selection as a means to facilitate library construction, selection and/or enrichment for desirable polynucleotides, and cloning in general.

In another aspect, end-selection can be based on (positive) selection for a polynucleotide; alternatively end-selection can be based on (negative) selection against a polynucleotide; and alternatively still, end-selection can be based on both (positive) selection for, and on (negative) selection against, a polynucleotide. End-selection, along with other methods of selection and/or screening, can be performed in an iterative fashion, with any combination of like or unlike selection and/or screening methods and mutagenesis or directed evolution methods, all of which can be performed in an iterative fashion and in any order, combination, and permutation. It is also appreciated that end-selection may also be used to select a polynucleotide in a: circular (e.g., a plasmid or any other circular vector or any other polynucleotide that is partly circular), and/or branched, and/or modified or substituted with any chemical group or moiety.

In one non-limiting aspect, end-selection of a linear polynucleotide is performed using a general approach based on the presence of at least one end-selection marker located at or near a polynucleotide end or terminus (that can be either a 5' end or a 3' end). In one particular non-limiting exemplification, end-selection is based on selection for a specific sequence at or near a terminus such as, but not limited to, a sequence recognized by an enzyme that recognizes a polynucleotide sequence. An enzyme that recognizes and catalyzes a chemical modification of a polynucleotide is referred to herein as a polynucleotide-acting enzyme. In a preferred embodiment, polynucleotide-acting enzymes are exemplified non-exclusively by enzymes with polynucleotide-cleaving activity, enzymes with polynucleotide-methylating activity, enzymes with polynucleotide-ligating activity, and enzymes with a plurality of distinguishable enzymatic activities (including non-exclusively, e.g., both polynucleotide-cleaving activity and polynucleotide-ligating activity).

It is appreciated that relevant polynucleotide-acting enzymes include any enzymes identifiable by one skilled in the art (e.g., commercially available) or that may be developed in the future, though currently unavailable, that are useful for generating a ligation compatible end, preferably a sticky end, in a polynucleotide. It may be preferable to use restriction sites that are not contained, or alternatively that are not expected to be contained, or alternatively that are unlikely to be contained (e.g., when sequence information regarding a working polynucleotide is incomplete) internally in a polynucleotide to be subjected to end-selection. It is recognized that methods (e.g., mutagenesis methods) can be used to remove unwanted internal restriction sites. It is also appreciated that a partial digestion reaction (i.e. a digestion reaction that proceeds to partial completion) can be used to achieve digestion at a recognition site in a terminal region while sparing a susceptible restriction site that occurs internally in a polynucleotide and that is recognized by the same enzyme. In one aspect, partial digest are useful because it is appreciated that certain enzymes show preferential cleavage of the same recognition sequence depending on the location and environment in which the recognition sequence occurs.

It is also appreciated that protection methods can be used to selectively protect specified restriction sites (e.g., internal sites) against unwanted digestion by enzymes that would otherwise cut a working polypeptide in response to the presence of those sites; and that such protection methods include modifications such as methylations and base substitutions (e.g., U instead of T) that inhibit an unwanted enzyme activity.

In another aspect of the invention, a useful end-selection marker is a terminal sequence that is recognized by a polynucleotide-acting enzyme that recognizes a specific polynucleotide sequence. In one aspect of the invention, useful polynucleotide-acting enzymes also include other enzymes in addition to classic type II restriction enzymes. According to this aspect of the invention, useful polynucleotide-acting enzymes also include gyrases (e.g., topoisomerases), helicases, recombinases, relaxases, and any enzymes related thereto.

It is appreciated that, end-selection can be used to distinguish and separate parental template molecules (e.g., to be subjected to mutagenesis) from progeny molecules (e.g., generated by mutagenesis). For example, a first set of primers, lacking in a topoisomerase I recognition site, can be used to modify the terminal regions of the parental molecules (e.g., in polymerase-based amplification). A different second set of primers (e.g., having a topoisomerase I recognition site) can then be used to generate mutated progeny molecules (e.g., using any polynucleotide chimerization method, such as interrupted synthesis, template-switching polymerase-based amplification, or interrupted synthesis; or using saturation mutagenesis; or using any other method for introducing a topoisomerase I recognition site into a mutagenized progeny molecule) from the amplified template molecules. The use of topoisomerase I-based end-selection can then facilitate, not only discernment, but selective topoisomerase I-based ligation of the desired progeny molecules.

It is appreciated that an end-selection approach using topoisomerase-based nicking and ligation has several advantages over previously available selection methods. In sum, this approach allows one to achieve direction cloning (including expression cloning).

The present method can be used to shuffle, by in vitro and/or in vivo recombination by any of the disclosed methods, and in any combination, polynucleotide sequences selected by peptide display methods, wherein an associated polynucleotide encodes a displayed peptide which is screened for a phenotype (e.g., for affinity for a predetermined receptor (ligand).

An increasingly important aspect of bio-pharmaceutical drug development and molecular biology is the identification of peptide structures, including the primary amino acid sequences, of peptides or peptidomimetics that interact with biological macromolecules. One method of identifying peptides that possess a desired structure or functional property, such as binding to a predetermined biological macromolecule (e.g., a receptor), involves the screening of a large library or peptides for individual library members which possess the desired structure or functional property conferred by the amino acid sequence of the peptide.

In addition to direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members), which are bound to the immobilized macromolecule are then recovered and replicated to amplify the selected bacteriophage sub-population for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publications WO 91/17271, WO 91/18980, WO 91/19818 and WO 93/08278.

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of peptide library members that comprise displayed peptides or displayed single-chain antibodies attached to a polynucleotide template from which the displayed peptide was synthesized. The mode of attachment may vary according to the specific embodiment of the invention selected, and can include encapsulation in a phage particle or incorporation in a cell.

A significant advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

The invention also provides a method for shuffling a pool of polynucleotide sequences identified by the methods of the invention and selected by affinity screening a library of polysomes displaying nascent peptides (including single-chain antibodies) for library members which bind to a predetermined receptor (e.g., a mammalian proteinaceous receptor such as, for example, a peptidergic hormone receptor, a cell surface receptor, an intracellular protein which binds to other protein(s) to form intracellular protein complexes such as hetero-dimers and the like) or epitope (e.g., an immobilized protein, glycoprotein, oligosaccharide, and the like).

Polynucleotide sequences selected in a first selection round (typically by affinity selection for binding to a receptor (e.g., a ligand)) by any of these methods are pooled and the pool(s) is/are shuffled by in vitro and/or in vivo recombination to produce a shuffled pool comprising a population of recombined selected polynucleotide sequences. The recombined selected polynucleotide sequences are subjected to at least one subsequent selection round. The polynucleotide sequences selected in the subsequent selection round(s) can be used directly, sequenced, and/or subjected to one or more additional rounds of shuffling and subsequent selection. Selected sequences can also be back-crossed with polynucleotide sequences encoding neutral sequences (i.e., having insubstantial functional effect on binding), such as for example by back-crossing with a wild-type or naturally-occurring sequence substantially identical to a selected sequence to produce native-like functional peptides, which may be less immunogenic. Generally, during back-crossing subsequent selection is applied to retain the property of binding to the predetermined receptor (ligand).

Prior to or concomitant with the shuffling of selected sequences, the sequences can be mutagenized. In one embodiment, selected library members are cloned in a prokaryotic vector (e.g., plasmid, phagemid, or bacteriophage) wherein a collection of individual colonies (or plaques) representing discrete library members is produced. Individual selected library members can then be manipulated (e.g., by site-directed mutagenesis, cassette mutagenesis, chemical mutagenesis, PCR mutagenesis, and the like) to generate a collection of library members representing a kernal of sequence diversity based on the sequence of the selected library member. The sequence of an individual selected library member or pool can be manipulated to incorporate random mutation, pseudorandom mutation, defined kernal mutation (i.e., comprising variant and invariant residue positions and/or comprising variant residue positions which can comprise a residue selected from a defined subset of amino acid residues), codon-based mutation, and the like, either segmentally or over the entire length of the individual selected library member sequence. The mutagenized selected library members are then shuffled by in vitro and/or in vivo recombinatorial shuffling as disclosed herein.

The invention also provides peptide libraries comprising a plurality of individual library members of the invention, wherein (1) each individual library member of said plurality comprises a sequence produced by shuffling of a pool of selected sequences, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

The invention also provides a product-by-process, wherein selected polynucleotide sequences having (or encoding a peptide having) a predetermined binding specificity are formed by the process of: (1) screening a displayed peptide or displayed single-chain antibody library against a predetermined receptor (e.g., ligand) or epitope (e.g., antigen macromolecule) and identifying and/or enriching library members which bind to the predetermined receptor or epitope to produce a pool of selected library members, (2) shuffling by recombination the selected library members (or amplified or cloned copies thereof) which binds the predetermined epitope and has been thereby isolated and/or enriched from the library to generate a shuffled library, and (3) screening the shuffled library against the predetermined receptor (e.g., ligand) or epitope (e.g., antigen macromolecule) and identifying and/or enriching shuffled library members which bind to the predetermined receptor or epitope to produce a pool of selected shuffled library members.

The present method can be used to shuffle, by in vitro and/or in vivo recombination by any of the disclosed methods, and in any combination, polynucleotide sequences selected by antibody display methods, wherein an associated polynucleotide encodes a displayed antibody which is screened for a phenotype (e.g., for affinity for binding a predetermined antigen (ligand)).

Various molecular genetic approaches have been devised to capture the vast immunological repertoire represented by the extremely large number of distinct variable regions, which can be present in immunoglobulin chains. The naturally-occurring germ line immunoglobulin heavy chain locus is composed of separate tandem arrays of variable segment genes located upstream of a tandem array of diversity segment genes, which are themselves located upstream of a tandem array of joining (i) region genes, which are located upstream of the constant region genes. During B lymphocyte development, V-D-J rearrangement occurs wherein a heavy chain variable region gene (VH) is formed by rearrangement to form a fused D segment followed by rearrangement with a V segment to form a V-D-J joined product gene which, if productively rearranged, encodes a functional variable region (VH) of a heavy chain. Similarly, light chain loci rearrange one of several V segments with one of several J segments to form a gene encoding the variable region (VL) of a light chain.

The vast repertoire of variable regions possible in immunoglobulins derives in part from the numerous combinatorial possibilities of joining V and i segments (and, in the case of heavy chain loci, D segments) during rearrangement in B cell development. Additional sequence diversity in the heavy chain variable regions arises from non-uniform rearrangements of the D segments during V-D-J joining and from N region addition. Further, antigen-selection of specific B cell clones selects for higher affinity variants having non-germline mutations in one or both of the heavy and light chain variable regions; a phenomenon referred to as "affinity maturation" or "affinity sharpening". Typically, these "affinity sharpening" mutations cluster in specific areas of the variable region, most commonly in the complementarity-determining regions (CDRs).

In order to overcome many of the limitations in producing and identifying high-affinity immunoglobulins through antigen-stimulated 13 cell development (i.e., immunization), various prokaryotic expression systems have been developed that can be manipulated to produce combinatorial antibody libraries which may be screened for high-affinity antibodies to specific antigens. Recent advances in the expression of antibodies in *Escherichia coli* and bacteriophage systems (see "alternative peptide display methods", infra) have raised the possibility that virtually any specificity can be obtained by either cloning antibody genes from characterized hybridomas or by de novo selection using antibody gene libraries (e.g., from Ig cDNA).

Combinatorial libraries of antibodies have been generated in bacteriophage lambda expression systems which may be screened as bacteriophage plaques or as colonies of lysogens (Huse et al., 1989); Caton and Koprowski, 1990; Mullinax et al., 1990; Persson et al., 1991). Various embodiments of bacteriophage antibody display libraries and lambda phage expression libraries have been described (Kang et al., 1991; Clackson et al., 1991; McCafferty et al., 1990; Burton et al., 1991; Hoogenboom et al., 1991; Chang et al., 1991; Breitling et al., 1991; Marks et al., 1991, p. 581; Barbas et al, 1992; Hawkins and Winter, 1992; Marks et al., 1992, p. 779; Marks et al., 1992, p. 16007; and Lowman et al., 1991; Lerner et al., 1992; all incorporated herein by reference). Typically, a bacteriophage antibody display library is screened with a receptor (e.g., polypeptide, carbohydrate, glycoprotein, nucleic acid) that is immobilized (e.g., by covalent linkage to a chromatography resin to enrich for reactive phage by affinity chromatography) and/or labeled (e.g., to screen plaque or colony lifts).

One particularly advantageous approach has been the use of so-called single-chain fragment variable (scfv) libraries (Marks et al., 1992, p. 779; Winter and Milstein, 1991; Clackson et al., 1991; Marks et al., 1991, p. 581; Chaudhary et al., 1990; Chiswell et al., 1992; McCafferty et al., 1990; and Huston et al., 1988). Various embodiments of scfv libraries displayed on bacteriophage coat proteins have been described.

Beginning in 1988, single-chain analogues of Fv fragments and their fusion proteins have been reliably generated by antibody engineering methods. The first step generally involves obtaining the genes encoding VH and VL domains with desired binding properties; these V genes may be isolated from a specific hybridoma cell line, selected from a combinatorial V-gene library, or made by V gene synthesis. The single-chain Fv is formed by connecting the component V genes with an oligonucleotide that encodes an appropriately designed linker peptide, such as (Gly-Gly-Gly-Gly-Ser (SEQ ID NO:3)) or equivalent linker peptide(s). The linker bridges the C-terminus of the first V region and N-terminus of the second, ordered as either VH-linker-VL or VL-linker-VH' In principle, the scfv binding site can faithfully replicate both the affinity and specificity of its parent antibody combining site.

Thus, scfv fragments are comprised of VH and VL domains linked into a single polypeptide chain by a flexible linker peptide. After the scfv genes are assembled, they are cloned into a phagemid and expressed at the tip of the M13 phage (or similar filamentous bacteriophage) as fusion proteins with the bacteriophage PIII (gene 3) coat protein. Enriching for phage expressing an antibody of interest is accomplished by panning the recombinant phage displaying a population scfv for binding to a predetermined epitope (e.g., target antigen, receptor).

The linked polynucleotide of a library member provides the basis for replication of the library member after a screening or selection procedure, and also provides the basis for the determination, by nucleotide sequencing, of the identity of the displayed peptide sequence or VH and VL amino acid sequence. The displayed peptide (s) or single-chain antibody (e.g., scfv) and/or its VH and VL domains or their CDRs can be cloned and expressed in a suitable expression system. Often polynucleotides encoding the isolated VH and VL domains will be ligated to polynucleotides encoding constant regions (CH and CL) to form polynucleotides encoding complete antibodies (e.g., chimeric or fully-human), antibody fragments, and the like. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like.

Various methods have been reported for increasing the combinatorial diversity of a scfv library to broaden the repertoire of binding species (idiotype spectrum) The use of PCR has permitted the variable regions to be rapidly cloned either from a specific hybridoma source or as a gene library from non-immunized cells, affording combinatorial diversity in the assortment of VH and VL cassettes which can be combined. Furthermore, the VH and VL cassettes can themselves be diversified, such as by random, pseudorandom, or directed mutagenesis. Typically, VH and VL cassettes are diversified in or near the complementarity-determining regions (CDRS), often the third CDR, CDR3. Enzymatic inverse PCR mutagenesis has been shown to be a simple and reliable method for constructing relatively large libraries of scfv site-directed hybrids (Stemmer et al., 1993), as has error-prone PCR and chemical mutagenesis (Deng et al., 1994). Riechmann (Riechmann et al., 1993) showed semi-rational design of an antibody scfv fragment using site-directed randomization by degenerate oligonucleotide PCR and subsequent phage display of the resultant scfv hybrids. Barbas (Barbas et al., 1992) attempted to circumvent the problem of limited repertoire sizes resulting from using biased variable region sequences by randomizing the sequence in a synthetic CDR region of a human tetanus toxoid-binding Fab.

CDR randomization has the potential to create approximately $1 \times 10^{20}$ CDRs for the heavy chain CDR3 alone, and a roughly similar number of variants of the heavy chain CDR1 and CDR2, and light chain CDR1–3 variants. Taken individually or together, the combination possibilities of CDR randomization of heavy and/or light chains requires generating a prohibitive number of bacteriophage clones to produce a clone library representing all possible combinations, the vast majority of which will be non-binding. Generation of such large numbers of primary transformants is not feasible with current transformation technology and bacteriophage display systems. For example, Barbas (Barbas et al., 1992) only generated $5 \times 10^7$ transformants, which represents only a tiny fraction of the potential diversity of a library of thoroughly randomized CDRs.

Despite these substantial limitations, bacteriophage display of scfv have already yielded a variety of useful antibodies and antibody fusion proteins. A bispecific single chain antibody has been shown to mediate efficient tumor cell lysis (Gruber et al., 1994). Intracellular expression of an anti-Rev scfv has been shown to inhibit HIV-1 virus replication in vitro (Duan et al., 1994), and intracellular expression of an anti-p2lrar, scfv has been shown to inhibit meiotic maturation of *Xenopus* oocytes (Biocca et al., 1993). Recombinant scfv, which can be used to diagnose HIV infection have also been reported, demonstrating the diagnostic utility of scfv (Lilley et al., 1994). Fusion proteins wherein an scFv is linked to a second polypeptide, such as a toxin or fibrinolytic activator protein, have also been reported (Holvost et al., 1992; Nicholls et al., 1993).

If it were possible to generate scfv libraries having broader antibody diversity and overcoming many of the limitations of conventional CDR mutagenesis and randomization methods, which can cover only a very tiny fraction of the potential sequence combinations, the number and quality of scfv antibodies suitable for therapeutic and diagnostic use could be vastly improved. To address this, the in vitro and in vivo shuffling methods of the invention are used to recombine CDRs, which have been obtained (typically via PCR amplification or cloning) from nucleic acids obtained from selected displayed antibodies. Such displayed antibodies can be displayed on cells, on bacteriophage particles, on polysomes, or any suitable antibody display system wherein the antibody is associated with its encoding nucleic acid(s). In a variation, the CDRs are initially obtained from mRNA (or cDNA) from antibody-producing cells (e.g., plasma cells/splenocytes from an immunized wild-type mouse, a human, or a transgenic mouse capable of making a human antibody as in WO 92/03918, WO 93/12227, and WO 94/25585), including hybridomas derived therefrom.

Polynucleotide sequences selected in a first selection round (typically by affinity selection for displayed antibody binding to an antigen (e.g., a ligand) by any of these methods are pooled and the pool(s) is/are shuffled by in vitro and/or in vivo recombination, especially shuffling of CDRs (typically shuffling heavy chain CDRs with other heavy chain CDRs and light chain CDRs with other light chain CDRs) to produce a shuffled pool comprising a population of recombined selected polynucleotide sequences. The recombined selected polynucleotide sequences are expressed in a selection format as a displayed antibody and subjected to at least one subsequent selection round. The polynucleotide sequences selected in the subsequent selection round(s) can be used directly, sequenced, and/or subjected to one or more additional rounds of shuffling and subsequent selection until an antibody of the desired binding affinity is obtained. Selected sequences can also be back-crossed with polynucleotide sequences encoding neutral antibody framework sequences (i.e., having insubstantial functional effect on antigen binding), such as for example by back-crossing with a human variable region framework to produce human-like sequence antibodies. Generally, during back-crossing subsequent selection is applied to retain the property of binding to the predetermined antigen.

Alternatively, or in combination with the noted variations, the valency of the target epitope may be varied to control the average binding affinity of selected scfv library members. The target epitope can be bound to a surface or substrate at varying densities, such as by including a competitor epitope, by dilution, or by other method known to those in the art. A high density (valency) of predetermined epitope can be used to enrich for scfv library members, which have relatively low affinity, whereas a low density (valency) can preferentially enrich for higher affinity scfv library members.

For generating diverse variable segments, a collection of synthetic oligonucleotides encoding random, pseudorandom, or a defined sequence kemal set of peptide sequences can be inserted by ligation into a predetermined site (e.g., a CDR). Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification prior to shuffling, or can be used directly (i.e., may avoid loss of diversity which may occur upon propagation in a host cell) and the selected library members subsequently shuffled.

Displayed peptide/polynucleotide complexes (library members) which encode a variable segment peptide sequence of interest or a single-chain antibody of interest are selected from the library by an affinity enrichment technique. This is accomplished by means of a immobilized macromolecule or epitope specific for the peptide sequence of interest, such as a receptor, other macromolecule, or other epitope species. Repeating the affinity selection procedure provides an enrichment of library members encoding the desired sequences, which may then be isolated for pooling and shuffling, for sequencing, and/or for further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a scfv library can be simultaneously screened for a multiplicity of scfv which have different binding specificities. Given that the size of a scfv library often limits the diversity of potential scfv sequences, it is typically desirable to us scfv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scfv library under suitable binding conditions. The collection of beads, comprising multiple epitope species, can then be used to isolate, by affinity selection, scfv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

A variety of techniques can be used in the present invention to diversify a peptide library or single-chain antibody library, or to diversify, prior to or concomitant with shuffling, around variable segment peptides found in early rounds of panning to have sufficient binding activity to the predetermined macromolecule or epitope. In one approach, the positive selected peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences, which can then be shuffled. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive selected peptide/polynucleotide complexes (especially of the variable region sequences, the amplification products of which are shuffled in vitro and/or in vivo and one or more additional rounds of screening is done prior to sequencing. The same general approach can be employed with single-chain antibodies in order to expand the diversity and enhance the binding affinity/specificity, typically by diversifying CDRs or adjacent framework regions prior to or concomitant with shuffling. If desired, shuffling reactions can be spiked with mutagenic oligonucleotides capable of in vitro recombination with the selected library members can be included. Thus, mixtures of synthetic oligonucleotides and PCR produced polynucleotides (synthesized by error-prone or high-fidelity methods) can be added to the in vitro shuffling mix and be incorporated into resulting shuffled library members (shufflants).

The invention of shuffling enables the generation of a vast library of CDR-variant single-chain antibodies. One way to generate such antibodies is to insert synthetic CDRs into the single-chain antibody and/or CDR randomization prior to or concomitant with shuffling. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat (Kabat et al., 1991); the pool (s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human VH CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some embodiments, residues other than those which naturally-occur at a residue position in the collection of CDR sequences are incorporated: conservative amino acid substitutions are frequently incorporated and up to 5 residue positions may be varied to incorporate non-conservative amino acid substitutions as compared to known naturally-occurring CDR sequences. Such CDR sequences can be used in primary library members (prior to first round screening) and/or can be used to spike in vitro shuffling reactions of selected library member sequences. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about $1 \times 10^6$ unique CDR sequences are included in the collection, although occasionally $1 \times 10^7$ to $1 \times 10^8$ unique CDR sequences are present, especially if conservative amino acid substitutions are permitted at positions where the conservative amino acid substituent is not present or is rare (i.e., less than 0.1 percent) in that position in naturally-occurring human CDRS. In general, the number of unique CDR sequences included in a library should not exceed the expected number of primary transformants in the library by more than a factor of 10. Such single-chain antibodies generally bind of about at least $1 \times 10$ m-, preferably with an affinity of about at least $5 \times 10^7$ M-1, more preferably with an affinity of at least $1 \times 10^8$ M-1 to $1 \times 10^9$ M-1 or more, sometimes up to $1 \times 10^{10}$ M-1 or more. Frequently, the predetermined antigen is a human protein, such as for example a human cell surface antigen (e.g., CD4, CD8, IL-2 receptor, EGF receptor, PDGF receptor), other human biological macromolecule (e.g., thrombomodulin, protein C, carbohydrate antigen, sialyl Lewis antigen, L-selectin), or nonhuman disease associated macromolecule (e.g., bacterial LPS, virion capsid protein or envelope glycoprotein) and the like.

High affinity single-chain antibodies of the desired specificity can be engineered and expressed in a variety of systems. For example, scfv have been produced in plants (Firek et al., 1993) and can be readily made in prokaryotic systems (Owens and Young, 1994; Johnson and Bird, 1991). Furthermore, the single-chain antibodies can be used as a basis for constructing whole antibodies or various fragments thereof (Kettleborough et al., 1994). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, 1982). Once purified, partially or to homogeneity as desired, the polypeptides may then be used therapeutically or in developing and performing assay procedures, immunofluorescent stainings, and the like (see, generally, Lefkovits and Pernis, 1979 and 1981; Lefkovits, 1997).

The antibodies generated by the method of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens and binding members well known to those skilled in the art.

Shuffling can also be used to recombinatorially diversify a pool of selected library members obtained by screening a two-hybrid screening system to identify library members which bind a predetermined polypeptide sequence. The selected library members are pooled and shuffled by in vitro and/or in vivo recombination. The shuffled pool can then be screened in a yeast two hybrid system to select library members which bind said predetermined polypeptide sequence (e.g., and SH2 domain) or which bind an alternate predetermined polypeptide sequence (e.g., an SH2 domain from another protein species).

An approach to identifying polypeptide sequences which bind to a predetermined polypeptide sequence has been to use a so-called "two-hybrid" system wherein the predetermined polypeptide sequence is present in a fusion protein (Chien et al., 1991). This approach identifies protein-protein interactions in vivo through reconstitution of a transcriptional activator (Fields and Song, 1989), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacz, HIS3) which is operably linked to a Gal4 binding site. Typically, the two-hybrid method is used to identify novel polypeptide sequences which interact with a known protein (Silver and Hunt, 1993; Durfee et al., 1993; Yang et al., 1992; Luban et al., 1993; Hardy et al., 1992; Bartel et al., 1993; and Vojtek et al., 1993). However, variations of the two-hybrid method have been used to identify mutations of a known protein that affect its binding to a second known protein (Li and Fields, 1993; Lalo et al., 1993; Jackson et al., 1993; and Madura et al., 1993). Two-hybrid systems have also been used to identify interacting structural domains of two known proteins (Bardwell et al., 1993; Chakrabarty et al., 1992; Staudinger et al., 1993; and Milne and Weaver 1993) or domains responsible for oligomerization of a single protein (Iwabuchi et al., 1993; Bogerd et al., 1993). Variations of two-hybrid systems have been used to study the in vivo activity of a proteolytic enzyme (Dasmahapatra et al., 1992). Alternatively, an E. coli/BCCP interactive screening system (Germino et al., 1993; Guarente, 1993) can be used to identify interacting protein sequences (i.e., protein sequences which heterodimerize or form higher order heteromultimers). Sequences selected by a two-hybrid system can be pooled and shuffled and introduced into a two-hybrid system for one or more subsequent rounds of screening to identify polypeptide sequences which bind to the hybrid containing the predetermined binding sequence. The sequences thus identified can be compared to identify consensus sequence(s) and consensus sequence kernals.

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading polymerase (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

The invention is further directed to a method for generating a selected mutant polynucleotide sequence (or a population of selected polynucleotide sequences) typically in the form of amplified and/or cloned polynucleotides, whereby the selected polynucleotide sequences(s) possess at least one desired phenotypic characteristic (e.g., encodes a polypeptide, promotes transcription of linked polynucleotides, binds a protein, and the like) which can be selected for. One method for identifying hybrid polypeptides that possess a desired structure or functional property, such as binding to a predetermined biological macromolecule (e.g., a receptor), involves the screening of a large library of polypeptides for individual library members which possess the desired structure or functional property conferred by the amino acid sequence of the polypeptide.

In one aspect, the present invention provides a method for generating libraries of displayed polypeptides or displayed antibodies suitable for affinity interaction screening or phenotypic screening. The method comprises (1) obtaining a first plurality of selected library members comprising a displayed polypeptide or displayed antibody and an associated polynucleotide encoding said displayed polypeptide or displayed antibody, and obtaining said associated polynucleotides or copies thereof wherein said associated polynucleotides comprise a region of substantially identical sequences, optimally introducing mutations into said polynucleotides or copies, (2) pooling the polynucleotides or copies, (3) producing smaller or shorter polynucleotides by interrupting a random or particularized priming and synthesis process or an amplification process, and (4) performing amplification, preferably PCR amplification, and optionally mutagenesis to homologously recombine the newly synthesized polynucleotides.

It is an object of the invention to provide a process for producing hybrid polynucleotides which express a useful hybrid polypeptide by a series of steps comprising:

(a) producing polynucleotides by interrupting a polynucleotide amplification or synthesis process with a means for blocking or interrupting the amplification or synthesis process and thus providing a plurality of smaller or shorter polynucleotides due to the replication of the polynucleotide being in various stages of completion;

(b) adding to the resultant population of single- or double-stranded polynucleotides one or more single- or double-stranded oligonucleotides, wherein said added oligonucleotides comprise an area of identity in an area of heterology to one or more of the single- or double-stranded polynucleotides of the population;

(c) denaturing the resulting single- or double-stranded oligonucleotides to produce a mixture of single-stranded polynucleotides, optionally separating the shorter or smaller polynucleotides into pools of polynucleotides having various lengths and further optionally subjecting said polynucleotides to a PCR procedure to amplify one or more oligonucleotides comprised by at least one of said polynucleotide pools;

(d) incubating a plurality of said polynucleotides or at least one pool of said polynucleotides with a polymerase under conditions which result in annealing of said single-stranded polynucleotides at regions of identity between the single-stranded polynucleotides and thus forming of a mutagenized double-stranded polynucleotide chain;

(e) optionally repeating steps (c) and (d);

(f) expressing at least one hybrid polypeptide from said polynucleotide chain, or chains; and (g) screening said at least one hybrid polypeptide for a useful activity.

In one aspect of the invention, the means for blocking or interrupting the amplification or synthesis process is by utilization of UV light, DNA adducts, DNA binding proteins.

In one aspect of the invention, the DNA adducts, or polynucleotides comprising the DNA adducts, are removed from the polynucleotides or polynucleotide pool, such as by a process including heating the solution comprising the DNA fragments prior to further processing.

In another aspect, clones which are identified as having a biomolecule or bioactivity of interest may also be sequenced to identify the DNA sequence encoding a polypeptide (e.g., an enzyme) or the polypeptide sequence itself having the specified activity, for example. Thus, in accordance with the present invention it is possible to isolate and identify: (i) DNA encoding a bioactivity of interest (e.g., an enzyme having a specified enzyme activity), (ii) biomolecules (e.g., polynucleotides or enzymes having such activity (including the amino acid sequence thereof)) and (iii) produce recombinant biomolecules or bioactivities.

Suitable clones (e.g., 1–1000 or more clones) from the library are identified by the methods of the invention and sequenced using, for example, high through-put sequencing techniques. The exact method of sequencing is not a limiting factor of the invention. Any method useful in identifying the sequence of a particular cloned DNA sequence can be used. In general, sequencing is an adaptation of the natural process of DNA replication. Therefore, a template (e.g., the vector) and primer sequences are used. One general template preparation and sequencing protocol begins with automated picking of bacterial colonies, each of which contains a separate DNA clone which will function as a template for the sequencing reaction. The selected clones are placed into media, and grown overnight. The DNA templates are then purified from the cells and suspended in water. After DNA quantification, high-throughput sequencing is performed using a sequencers, such as Applied Biosystems, Inc., Prism 377 DNA Sequencers. The resulting sequence data can then be used in additional methods, including searching a database or databases.

A number of source databases are available that contain either a nucleic acid sequence and/or a deduced amino acid sequence for use with the invention in identifying or determining the activity encoded by a particular polynucleotide sequence. All or a representative portion of the sequences (e.g., about 100 individual clones) to be tested are used to search a sequence database (e.g., GenBank, PFAM or ProDom), either simultaneously or individually. A number of different methods of performing such sequence searches are known in the art. The databases can be specific for a particular organism or a collection of organisms. For example, there are databases for the *C. elegans, Arabadopsis*. sp., *M. genitalium, M. jannaschii, E. coli, H. influenzae, S. cerevisiae* and others. The sequence data of the clone is then aligned to the sequences in the database or databases using algorithms designed to measure homology between two or more sequences.

In some instances it may be desirable to express a particular cloned polynucleotide sequence once its identity or activity is determined or a suggested identity or activity is associated with the polynucleotide. In such instances the desired clone, if not already cloned into an expression vector, is ligated downstream of a regulatory control element (e.g., a promoter or enhancer) and cloned into a suitable host cell. Expression vectors are commercially available along with corresponding host cells for use in the invention.

As representative examples of expression vectors which may be used there may be mentioned viral particles, baculovirus, phage, plasmids, phagemids, cosmids, phosmids, bacterial artificial chromosomes, viral nucleic acid (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus*, yeast, and the like) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE70, pQE60, pQE-9 (Qiagen), psiX174, pBluescript SK, pBluescript KS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene), pSVK3, pBPV, pMSG, pSVL (Pharmacia). However, any other plasmid or vector may be used as long as they are replicable and viable in the host.

The nucleic acid sequence in the expression vector is operatively linked to an appropriate expression control sequence(s) (promoter) to direct mRNA synthesis. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors typically contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The nucleic acid sequence(s) selected, cloned and sequenced as hereinabove described can additionally be introduced into a suitable host to prepare a library, which is screened for the desired biomolecule or bioactivity. The selected nucleic acid is preferably already in a vector which includes appropriate control sequences whereby a selected nucleic acid encoding a biomolecule or bioactivity may be expressed, for detection of the desired activity. The host cell can be a higher eukaryotic cell, such as a mammalian cell, or a lower eukaryotic cell, such as a yeast cell, or the host cell can be a prokaryotic cell, such as a bacterial cell. The selection of an appropriate host is deemed to be within the scope of those skilled in the art from the teachings herein.

In some instances it may be desirable to perform an amplification of the nucleic acid sequence present in a sample or a particular clone that has been isolated. In this embodiment, the nucleic acid sequence is amplified by PCR reaction or similar reaction known to those of skill in the art. Commercially available amplification kits are available to carry out such amplification reactions.

In addition, it is important to recognize that the alignment algorithms and searchable database can be implemented in computer hardware, software or a combination thereof. Accordingly, the isolation, processing and identification of nucleic acid or polypeptide sequences can be implemented in an automated system.

In addition to the sequence-based techniques described above, a number of traditional assay system exist for measuring an enzymatic activity using multi-well plates. For example, existing screening technology usually relies on two-dimensional well (e.g., 96-, 384- and 1536-well) plates. The present invention also provides a capillary array-based approach of that has numerous advantages over well-based screening techniques, including the elimination of the need for fluid dispensers for dispensing fluids (e.g., reactants) into individual well reservoirs, and the reduced cost per array (e.g., glass capillaries are reusable) (see, for example, U.S. patent application Ser. No. 09/444,112, filed Nov. 22, 1999, which is incorporated herein by reference in its entirety).

Accordingly, the capillaries, capillary array and systems of the invention are particularly well suited for screening libraries for activity or biomolecules of interest including polynucleotides. The screening for activity may be effected on individual expression clones or may be initially effected on a mixture of expression clones to ascertain whether or not the mixture has one or more specified activities. If the mixture has a specified activity, then the individual clones may be rescreened for such activity or for a more specific activity after collection from the capillary array.

All headings and subheading used herein are provided for the convenience of the reader and should not be construed to limit the invention.

As used herein and in the appended claims, the singular forms "a," "and," and "the" include plural referents unless the context clearly dictates otherwise. Thus, for example, reference to "a clone" includes a plurality of clones and reference to "the nucleic acid sequence" generally includes reference to one or more nucleic acid sequences and equivalents thereof known to those skilled in the art, and so forth.

Unless defined otherwise, all technical and scientific terms used herein have the same meaning as commonly understood to one of ordinary skill in the art to which the invention belongs. Although any methods, devices and materials similar or equivalent to those described herein can be used in the practice or testing of the invention, the preferred methods, devices and materials described.

All publications mentioned herein are incorporated herein by reference in full for the purpose of describing and disclosing the databases, proteins, and methodologies, which are described in the publications, which might be used in connection with the described invention. The publications discussed above and throughout the text are provided solely for their disclosure prior to the filing date of the present application. Nothing herein is to be construed as an admission that the inventors are not entitled to antedate such disclosure by virtue of prior invention.

The invention will now be described in greater detail by reference to the following non-limiting examples.

EXAMPLES

Example 1

DNA Isolation

DNA is isolated using the IsoQuick Procedure as per manufacture's instructions (Orca Research Inc., Bothell, Wash.). The isolated DNA can optionally be normalized according to Example 2 (below). Upon isolation, the DNA is sheared by pushing and pulling the DNA through a 25-gauge double-hub needle and a 1-cc syringe about 500 times. A small amount is run on a 0.8% agarose gel to make sure the majority of the DNA is in the desired size range (about 3–6 kb).

Blunt-ending DNA. The DNA is blunt-ended by mixing 45 $\mu$l of 10× Mung Bean Buffer, 2.0 $\mu$l Mung Bean Nuclease (1050 u/$\mu$l) and water to a final volume of 405 $\mu$l. The mixture is incubated at 37° C. for 15 minutes. The mixture is phenol;chloroform extracted, followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol and repelleted in the microcentrifuge. Following centrifugation, the DNA is dried and gently resuspended in 26 $\mu$l of TE buffer.

Methylation of DNA. The DNA is methylated by mixing 4 $\mu$l of 10×EcoRI Methylase Buffer, 0.5 $\mu$l SAM (32 mM), 5.0 $\mu$l EcoRI Methylase (40 u/$\mu$l) and incubating at 37° C. for 1 hour. In order to insure blunt ends, the following can be added to the methylation reaction: 5.0 $\mu$l of 100 mM MgCl$_2$, 8.0 $\mu$l of dNTP mix (2.5 mM of each dGTP, dATP, dTTP, dCTP), 4.0 $\mu$l of Klenow (5 u/$\mu$l). The mixture is then incubated at 12° C. for 30 minutes.

After incubating for 30 minutes 450 $\mu$l 1×STE is added. The mixture is phenol/chloroform extracted once followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol, repelleted in the microcentrifuge and allowed to dry for 10 minutes.

Ligation. The DNA is ligated by gently resuspending the DNA in 8 $\mu$l EcoRI adapters (from Stratagene's cDNA Synthesis Kit), 1.0 $\mu$l of 10× ligation buffer, 1.0 $\mu$l of 10 mM rATP, 1.0 $\mu$l of T4 DNA Ligase (4 Wu/$\mu$l) and incubating at 4° C. for 2 days. The ligation reaction is terminated by heating for 30 minutes at 70° C.

Phosphorylation of adapters. The adapter ends are phosphorylated by mixing the ligation reaction with 1.0 $\mu$l of 10× Ligation Buffer, 2.0 $\mu$l of 10 mM rATP, 6.0 $\mu$l of H$_2$O, 1.0 $\mu$l of polynucleotide kinase (PNK), and incubating at 37° C. for 30 minutes. After incubating for 30 minutes, 31 $\mu$l of H$_2$O and 5 ml of 10×STE are added to the reaction and the sample is size fractionated on a Sephacryl S-500 spin column. The pooled fractions (1–3) are phenol/chloroform extracted once, followed by an additional chloroform extraction. The DNA is precipitated by the addition of ice cold ethanol on ice for 10 minutes. The precipitate is pelleted by centrifugation in a microcentrifuge at high speed for 30 minutes. The resulting pellet is washed with 1 ml 70% ethanol, repelleted by centrifugation and allowed to dry for 10 minutes. The sample is resuspended in 10.5 $\mu$l TE buffer. The sample is not plated, but is ligated directly to lambda arms as described above, except 2.5 $\mu$l of DNA and no water is used.

Sucrose Gradient (2.2 ml) Size Fractionation. Ligation is stopped by heating the sample to 65° C. for 10 minutes. The sample is gently loaded on a 2.2 ml sucrose gradient and centrifuged in a mini-ultracentrifuged 45 k rpm at 20° C. for 4 hours (no brake). Fractions are collected by puncturing the bottom of the gradient tube with a 20-gauge needle and allowing the sucrose to flow through the needle. The first 20 drops are collected in a Falcon 2059 tube, and then ten 1-drop fractions (labeled 1–10) are collected. Each drop is about 60 $\mu$l in volume. Five $\mu$l of each fraction are run on a 0.8% agarose gel to check the size. Fractions 1–4 (about 10–1.5 kb) are pooled and, in a separate tube, fractions 5–7 (about 5–0.5 kb) are pooled. One ml of ice cold ethanol is added to precipitate the DNA and then placed on ice for 10 minutes. The precipitate is pelleted by centrifugation in a microcentrifuge at high speed for 30 minutes. The pellets are washed by resuspending them in 1 ml of 70% ethanol and repelleting them by centrifugation in a microcentrifuge at high speed for 10 minutes, and then dried. Each pellet is then resuspended in 10 $\mu$l of TE buffer.

Test Ligation to Lambda Arms. The assay is plated by spotting 0.5 $\mu$l of the sample on agarose containing ethidium bromide along with standards (DNA sample of known concentration) to get an approximate concentration. The samples are then viewed using UV light and the estimated concentration is compared to the standards. The following ligation reaction (5 $\mu$l reactions) are prepared and incubated at 4° C. overnight, as shown in Table 1 below:

TABLE 1

| Sample | H$_2$O | 10× Ligase | 10 nM rATP | Lambda arms (ZAP) | Insert DNA | T4 DNA Ligase |
|---|---|---|---|---|---|---|
| Fraction 1–4 | 0.5 $\mu$l | 0.5 $\mu$l | 0.5 $\mu$l | 1.0 $\mu$l | 2.0 $\mu$l | 0.5 $\mu$l |
| Fraction 5–7 | 1.5 $\mu$l | 0.5 $\mu$l | 0.5 $\mu$l | 1.0 $\mu$l | 2.0 $\mu$l | 0.5 $\mu$l |

Test Package and Plate. The ligation reactions are packaged following manufacturer's protocol. Packaging reactions are stopped with 500 $\mu$l SM buffer and pooled with packaging that came from the same ligation. One $\mu$l of each pooled reaction is titered on an appropriate host (OD$_{600}$=1.0) (XL1-Blue MRF). 200 $\mu$l host (in MgSO$_4$) are added to Falcon 2059 tubes, inoculated with 1 $\mu$l packaged phage and incubated at 37° C. for 15 minutes. About 3 ml of 48° C. top agar (50 ml stock containing 150 $\mu$l IPTG (0.5 M) and 300 $\mu$l X-GAL (350 mg/ml)) are added and plated on 100 mm plates. The plates are incubated overnight at 37° C.

Amplification of Libraries (5.0×10$^5$ recombinants from each library). About 3.0 ml host cells (OD$_{600}$=1.0) are added to two 50 ml conical tubes, inoculated with 2.5×10$^5$ pfu of phage per conical tube, and then incubated at 37° C. for 20 minutes. Top agar is added to each tube to a final volume of 45 ml. Each tube is plated across five 150 mm plates. The plates are incubated at 37° C. for 6–8 hours or until plaques are about pin-head in size. The plates are overlaid with 8–10 ml SM Buffer and placed at 4° C. overnight (with gentle rocking if possible).

Harvest Phage. The phage suspension is recovered by pouring the SM buffer off each plate into a 50 ml conical tube. About 3 ml of chloroform are added, shaken vigorously and incubated at room temperature for 15 minutes. The tubes are centrifuged at 2K rpm for 10 minutes to remove cell debris. The supernatant is poured into a sterile flask, 500 µl chloroform are added and stored at 4° C.

Titer Amplified Library. Serial dilutions of the harvested phage are made (for example, $10^{-5}=1$ µl amplified phage in 1 ml SM Buffer; $10^{-6}=1$ µl of the $10^{-3}$ dilution in 1 ml SM Buffer and the like), and 200 µl host (in 10 mM $MgSO_4$) are added to two tubes. One tube is inoculated with 10 µl of $10^{-6}$ dilution ($10^{-5}$). The other tube is inoculated with 1 µl of $10^{-6}$ dilution ($10^{-6}$), and incubated at 37° C. for 15 minutes.

About 3 ml of 48° C. top agar (50 ml stock containing 150 µl IPTG (0.5 M) and 37 µl X-GAL (350 mg/ml)) are added to each tube and plated on 100 mm plates. The plates are incubated overnight at 37° C.

The ZAP II library is excised to create the pBLUESCRIPT library according to manufacturer's protocols (Stratagene).

The DNA library can be transformed into host cells (e.g., *E. coli*) to generate an expression library of clones.

Example 2

Normalization

Prior to library generation, purified DNA can be normalized. DNA is first fractionated according to the following protocol A sample composed of genomic DNA is purified on a cesium-chloride gradient. The cesium chloride (Rf= 1.3980) solution is filtered through a 0.2 µm filter and 15 ml is loaded into a 35 ml OptiSeal tube (Beckman) The DNA is added and thoroughly mixed. Ten micrograms of bisbenzimide (Sigma; Hoechst 33258) is added and mixed thoroughly. The tube is then filled with the filtered cesium chloride solution and spun in a Bti50 rotor in a Beckman L8-70 Ultracentrifuge at 33 k rpm for 72 hours. Following centrifugation, a syringe pump and fractionator (Brandel Model 186) are used to drive the gradient through an ISCO UA-5UV absorbance detector set to 280 nm. Peaks representing the DNA from the organisms present in an environmental sample are obtained. Eubacterial sequences can be detected by PCR amplification of DNA encoding rRNA from a 10 fold dilution of the *E. coli* peak using the following primers to amplify:

```
Forward primer:
5'-AGAGTTTGATCCTGGCTCAG-3'    (SEQ ID NO:93)

Reverse primer:
5'-GGTTACCTTGTTACGACTT-3'     (SEQ ID NO:94)
```

Recovered DNA is sheared or enzymatically digested to 3–6 kb fragments. Lone-linker primers are ligated and the DNA is size-selected. Size-selected DNA is amplified by PCR, if necessary.

Normalization is then accomplished by resuspending the double-stranded DNA sample in hybridization buffer (0.12 M $NaH_2PO_4$, pH 6.8/0.82 M NaCl/1 mM EDTA/0.1% SDS). The sample is overlaid with mineral oil and denatured by boiling for 10 minutes. The sample is incubated at 68° C. for 12–36 hours. Double-stranded DNA is separated from single-stranded DNA according to standard protocols (Sambrook, 1989) on hydroxyapatite at 60° C. The single-stranded DNA fraction is desalted and amplified by PCR. The process is repeated for several more rounds (up to 5 or more).

Example 3

Enzymatic Activity Assay

The following is a representative example of a procedure for screening an expression library, prepared in accordance with Example 1, for hydrolase activity.

Plates of the library prepared as described in Example 1 are used to multiply inoculate a single plate containing 200 µl of LB Amp/Meth, glycerol in each well. This step is performed using the High Density Replicating Tool (HDRT) of the Beckman BIOMEK™ with a 1% bleach, water, isopropanol, air-dry sterilization cycle between each inoculation. The single plate is grown for 2 h at 37° C. and is then used to inoculate two white 96-well Dynatech microtiter daughter plates containing 250 µl of LB Amp/Meth, glycerol in each well. The original single plate is incubated at 37° C. for 18 h, then stored at –80° C. The two condensed daughter plates are incubated at 37° C. also for 18 h. The condensed daughter plates are then heated at 70° C. for 45 mm. to kill the cells and inactivate the host *E. coli* enzymes. A stock solution of 5 mg/mL morphourea phenylalanyl-7-amino-4-trifluoromethyl coumarin (MuPheAFC, the "substrate") in DMSO is diluted to 600 µM with 50 mM pH 7.5 Hepes buffer containing 0.6 mg/mL of the detergent dodecyl maltoside. Fifty µl of the 600 µM MuPheAFC solution is added to each of the wells of the white condensed plates with one 100 µl mix cycle using the IBIOMEK to yield a final concentration of substrate of about 100 µM. The fluorescence values are recorded (excitation=400 nm, emission= 505 nm) on a plate reading fluorometer immediately after addition of the substrate (t=0). The plate is incubated at 70° C. for 100 min, then allowed to cool to ambient temperature for 15 additional minutes. The fluorescence values are recorded again (t=100). The values at t=0 are subtracted from the values at t=100 to determine if an active clone is present.

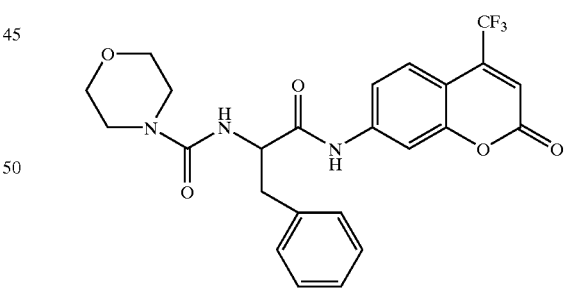

The data will indicate whether one of the clones in a particular well is hydrolyzing the substrate. In order to determine the individual clone which carries the activity, the source library plates are thawed and the individual clones are used to singly inoculate a new plate containing LB Amp/Meth, glycerol. As above, the plate is incubated at 37° C. to grow the cells, heated at 70° C. to inactivate the host enzymes, and 50 µl of 600 µM MuPheAFC is added using the Biomek.

After addition of the substrate the t=0 fluorescence values are recorded, the plate is incubated at 70° C., and the t=100 min. values are recorded as above. These data indicate which plate the active clone is in.

The enantioselectivity value, E, for the substrate is determined according to the equation below:

$$E = \frac{\ln[(1 - c(1 + ee_p)]}{\ln[(1 - c(1 + ee_p)]}$$

where $ee_p$=the enantiomeric excess (ee) of the hydrolyzed product and c=the percent conversion of the reaction. See Wong and Whitesides, Enzymes in Synthetic Organic Chemistry, 1994, Elsevier, Tarrytown, N.Y., pp. 9–12.

The enantiomeric excess is determined by either chiral high performance liquid chromatography (HPLC) or chiral capillary electrophoresis (CE). Assays are performed as follows: two hundred μl of the appropriate buffer is added to each well of a 96-well white microtiter plate, followed by 50 μl of partially or completely purified enzyme solution; 50 μl of substrate is added and the increase in fluorescence monitored versus time until 50% of the substrate is consumed or the reaction stops, whichever comes first.

Example 4

Directed Mutagenesis of Positive Enzyme Activity Clones

Directed mutagenesis was performed on two different enzymes (alkaline phosphatase and β-glycosidase) to generate new enzymes which exhibit a higher degree of activity than the wild-type enzymes.

Alkaline Phosphatase

The XL1-Red strain (Stratagene) was transformed with genomic clone 27a3a (in plasmid pBluescript) encoding the alkaline phosphatase gene from the organism OC9a, an organism isolated from the surface of a whale bone, according to the manufacturer's protocol. A 5 ml culture of LB+0.1 mg/ml ampicillin was inoculated with 200 μl of the transformation and the culture was allowed to grow at 37° C. for 30 hours. A miniprep was then performed on the culture, and the isolated DNA screened by transforming 2 μl of the resulting DNA into XL-1 Blue cells (Stratagene) according to the manufacturer's protocol and following the assay procedure outlined below. The mutated OC9a phosphatase took 10 minutes to develop color and the wild type enzyme took 30 minutes to develop color in the screening assay.

Standard Alkaline Phosphatase Screening Assay

Transformed XL1 Blue cells were plated on LB/amp plates. The resulting colonies were lifted with Duralon UV (Stratagene) or HATF (Millipore) membranes and lysed in chloroform vapors for 30 seconds. Cells were heat killed by incubating for 30 minutes at 85° C. The filters were developed at room temperature in BCIP buffer and the fastest developing colonies ("positives") were selected for restreaking the "positives" onto a BCIP plate (BCIP Buffer: 20 mm CAPS pH 9.0, 1 mm $MgCl_2$, 0.01 mm $ZnCl_2$, 0.1 mg/ml BCIP).

Beta-Glycosidase

This protocol was used to mutagenize Thermococcus 9N2 Beta-Glycosidase. PCR was carried out by incubating 2 microliters dNTP's (10 mM Stocks); 10 microliters 10×PCR Buffer; 0.5 microliters Vector DNA-31G1A-100 nanograms; 20 microliters 3' Primer (100 pmol); 20 microliters 5' Primer (100 pmol); 16 microliters $MnCl$ $4H_2O$ (1.25 mM Stock); 24.5 microliters $H_2O$; and 1 microliter Taq Polymerase (5.0 Units) in a total volume of 100 microliters. The PCR cycle was: 95° C. 15 seconds; 58° C. 30 seconds; 72° C. 90 seconds; 25 cycles (10 minute extension at 72° C.–4° C. incubation).

Five microliters of the PCR product was run on a 1% agarose gel to check the reaction. Purify on a QIAQUICK column (Qiagen). Resuspend in 50 microliters $H_2O$.

Twenty-five microliters of purified PCR product; 10 microliters NEB Buffer #2; 3 microliters Kpn I (1 OU/microliter); 3 microliters EcoRI (20 U/microliter); and 59 microliters $H_2O$. were incubated for 2 hours at 37° C. to digest the PCR products and purified on a QIAQUICK column (Qiagen). Elute with 35 microliters $H_2O$.

Ten microliters of digested PCR product, 5 microliters Vector (cut with EcoRI/KpnI and phosphatased with shrimp alkaline phosphatase, 4 microliters 5× Ligation Buffer, and 1 microliter T4 DNA Ligase (BRL) were incubated overnight to ligate the PCR products into the vector.

The resulting vector was transformed into M15pREP4 cells using electroporation. 100 or 200 microliters of the cells were plated onto LB amp meth kan plates, and grown overnight at 37° C.

Beta-galactosidase was assayed by (1) Perform colony lifts using Millipore HATF membrane filters; (2) lyse colonies with chloroform vapor in 150 mm glass petri dishes; (3) transfer filters to 100 mm glass petri dishes containing a piece of Whatman 3MM filter paper saturated with Z buffer containing 1 mg/ml XGLU (After transferring filter bearing lysed colonies to the glass petri dish, maintain dish at room temperature); and (4) "Positives" were observed as blue spots on the filter membranes ("positives" are spots which appear early). A Pasteur pipette (or glass capillary tube) was used to core blue spots on the filter membrane. Place the small filter disk in an Eppendorf tube containing 20 μl water. Incubate the Eppendorf tube at 75° C. for 5 minutes followed by vortexing to elute plasmid DNA off filter. Transform this DNA into electrocompetent E. coli cells and repeat filter-lift assay on transformation plates to identify "positives." Return transformation plates to 37° C. incubator after filter lift to regenerate colonies. Inoculate 3 ml LBamp liquid with repurified positives and incubate at 37° C. overnight. Isolate plasmid DNA from these cultures and sequence plasmid insert. The filter assay uses buffer Z (see recipe below) containing 1 mg/ml of the substrate 5-bromo-4-chloro-3-indolyl-.beta.-o-glucopyranoside (XGLU) (Diagnostic Chemicals Limited or Sigma). Z-Buffer: (referenced in Miller, J. H. (1992) A Short Course in Bacterial Genetics, p. 445.) per liter:

| | |
|---|---|
| $Na_2HPO_4$—$7H_2O$ | 16.1 g |
| $Na_2HPO_4$—$4H_2O$ | 5.5 g |
| KCl | 0.75 g |
| $Na_2HPO_4$—$7H_2O$ | 0.246 g |
| 6-mercaptoethanol | 2.7 ml |
| Adjust pH to 7.0 | |

Example 5

Construction of a Stable, Large Insert DNA Library of Picoplankton Genomic DNA

Cell collection and preparation of DNA. Agarose plugs containing concentrated picoplankton cells were prepared from samples collected on an oceanographic cruise from Newport, Oreg. to Honolulu, Hi. Seawater (30 liters) was collected in Niskin bottles, screened through 10 μm Nitex, and concentrated by hollow fiber filtration (Amicon DC 10) through 30,000 MW cutoff polyfulfone filters. The concentrated bacterioplankton cells were collected on a 0.22 μm, 47 mm Durapore filter, and resuspended in 1 ml of 2×STE buffer (1M NaCl, 0.1M EDTA, 10 mM Tris, pH 8.0) to a final density of approximately $1 \times 10^{10}$ cells per ml. The cell suspension was mixed with one volume of 1% molten Seaplaque LMP agarose (FMC) cooled to 40° C., and then immediately drawn into a 1 ml syringe. The syringe was sealed with parafilm and placed on ice for 10 min. The cell-containing agarose plug was extruded into 10 ml of Lysis Buffer (10 mM Tris pH 8.0, 50 mM NaCl, 0.1M EDTA, 1% Sarkosyl, 0.2% sodium deoxycholate, 1 mg/ml lysozyme) and incubated at 37° C. for one hour. The agarose plug was then transferred to 40 mls of ESP Buffer (1% Sarkosyl, 1 mg/ml proteinase K, in 0.5M EDTA), and incubated at 55° C. for 16 hours. The solution was decanted and replaced with fresh ESP Buffer, and incubated at 55° C. for an additional hour. The agarose plugs were then placed in 50 mM EDTA and stored at 4° C. shipboard for the duration of the oceanographic cruise.

One slice of an agarose plug (72 μl) prepared from a sample collected off the Oregon coast was dialyzed overnight at 4° C. against 1 mL of buffer A (100 mM NaCl, 10 mM Bis Tris Propane-HCl, 100 μg/ml acetylated BSA: pH 7.0 at 25° C.) in a 2 mL microcentrifuge tube. The solution was replaced with 250 μl of fresh buffer A containing 10 mM $MgCl_2$ and 1 mM DTT and incubated on a rocking platform for 1 hr at room temperature. The solution was then changed to 250 μl of the same buffer containing 4 U of Sau3A1 (NEB), equilibrated to 37° C. in a water bath, and then incubated on a rocking platform in a 37° C. incubator for 45 min. The plug was transferred to a 1.5 ml microcentrifuge tube and incubated at 68° C. for 30 min to inactivate the enzyme and to melt the agarose. The agarose was digested and the DNA dephosphorylated using Gelase and HK-phosphatase (Epicentre), respectively, according to the manufacturer's recommendations. Protein was removed by gentle phenol/chloroform extraction and the DNA was ethanol precipitated, pelleted, and then washed with 70% ethanol. This partially digested DNA was resuspended in sterile $H_2O$ to a concentration of 2.5 ng/l for ligation to the pFOS1 vector.

PCR amplification results from several of the agarose plugs indicated the presence of significant amounts of archaeal DNA. Quantitative hybridization experiments using rRNA extracted from one sample, collected at 200 m of depth off the Oregon Coast, indicated that planktonic archaea in (this assemblage comprised approximately 4.7% of the total picoplankton biomass (this sample corresponds to "PACI"-200 m in Table 1 of DeLong et al., Nature, 371:695–698, 1994). Results from archacal-biased rDNA PCR amplification performed on agarose plug lysates confirmed the presence of relatively large amounts of archaeal DNA in this sample. Agarose plugs prepared from this picoplankton sample were chosen for subsequent fosmid library preparation. Each 1 ml agarose plug from this site contained approximately $7.5 \times 10^5$ cells, therefore approximately $5.4 \times 10^5$ cells were present in the 72 μl slice used in the preparation of the partially digested DNA.

Vector arms were prepared from pFOS1 as described (Kim et al., Stable propagation of cosmid sized human DNA inserts in an F factor based vector, Nucl. Acids Res., 20:10832–10835, 1992). Briefly, the plasmid was completely digested with AstII, dephosphorylated with HK phosphatase, and then digested with BamHI to generate two arms, each of which contained a cos site in the proper orientation for cloning and packaging ligated DNA between 35–45 kbp. The partially digested picoplankton DNA was ligated overnight to the PFOS1 arms in a 15 μl ligation reaction containing 25 ng each of vector and insert and 1 U of T4 DNA ligase (Boehringer-Mannheim). The ligated DNA in four microliters of this reaction was in vitro packaged using the Gigapack XL packaging system (Stratagene), the fosmid particles transfected to E. coli strain DH10B (BRL), and the cells spread onto $LB_{cm15}$ plates. The resultant fosmid clones were picked into 96-well microliter dishes containing $LB_{cm15}$ supplemented with 7% glycerol. Recombinant fosmids, each containing ca. 40 kb of picoplankton DNA insert, yielded a library of 3.552 fosmid clones, containing approximately $1.4 \times 10^8$ base pairs of cloned DNA. All of the clones examined contained inserts ranging from 38 to 42 kbp. This library was stored frozen at −80° C. for later analysis.

Numerous modifications and variations of the present invention are possible in light of the above teachings; therefore, within the scope of the claims, the invention may be practiced other than as particularly described. While the invention has been described in detail with reference to certain preferred embodiments thereof, it will be understood that modifications and variations are within the spirit and scope of that which is described and claimed.

All publications, patents, patent applications, GenBank sequences and ATCC deposits, cited herein are hereby expressly incorporated by reference for all purposes.

A number of aspects of the invention have been described. Nevertheless, it will be understood that various modifications may be made without departing from the spirit and scope of the invention. Accordingly, other aspects are within the scope of the following claims.

What is claimed is:

1. An isolated or recombinant nucleic acid, wherein the nucleic acid comprises a sequence that hybridizes under stringent conditions to a nucleic acid comprising a sequence as set forth in SEQ ID NO:25 or a sequence encoding a polypeptide having an amino acid sequence as set forth in SEQ ID NO:26 or SEQ ID NO:85, wherein the nucleic acid encodes a polypeptide having an epoxide hydrolase activity.

2. The isolated or recombinant nucleic acid of claim 1, wherein the nucleic acid is at least about 100 residues in length.

3. The isolated or recombinant nucleic acid of claim 2, wherein the nucleic acid is at least about 200 residues in length.

4. The isolated or recombinant nucleic acid of claim 3, wherein the nucleic acid is about 300 residues in length.

5. The isolated or recombinant nucleic acid of claim 4, wherein the nucleic acid is at least about 400 residues in length.

6. The isolated or recombinant nucleic acid of claim 5, wherein the nucleic acid is at least about 500, 600, 700, 800, 900, or 1000 residues in a length or the full length of a gene or transcript.

7. The isolated or recombinant nucleic acid of claim 1, wherein the stringent conditions include a wash step comprising a wash in 0.2×SSC at a temperature of about 65° C. for about 15 minutes.

8. An isolated or recombinant nucleic acid having a sequence as set forth in SEQ ID NO:25.

9. An isolated or recombinant nucleic acid comprising a sequence encoding a polypeptide having a sequence as set forth in SEQ ID NO:26 or SEQ ID NO:85.

10. The isolated or recombinant nucleic acid of claim 1, wherein the nucleic acid sequence has at least 95% sequence identity to a sequence as set forth in SEQ ID NO:25, or to a sequence encoding polypeptide having an amino acid sequence as set forth in SEQ ID NO:26 or SEQ ID NO:85.

11. The isolated or recombinant nucleic acid of claim 10, wherein the nucleic acid sequence has at least 98% sequence identity to a sequence as set forth in SEQ ID NO.25, or to a sequence encoding polypeptide having an amino acid sequence as set forth in SEC ID NO:26 or SEQ ID NO:85.

12. The isolated or recombinant nucleic acid of claim 10, wherein the nucleic acid sequence has at least 99% sequence identity to a sequence as set forth in SEQ ID NO:25, or to a sequence encoding polypeptide having an amino acid sequence as set forth in SEQ ID NO:26 or SEQ ID NO:85.

13. The isolated or recombinant nucleic acid of claim 10, wherein the sequence comparison algorithm is a BLAST version 2.2.2 algorithm where a filtering setting is set to blastall -p blastp -d "nr pataa" -F F, and all other options are set to default.

14. The isolated or recombinant nucleic acid of claim 1, wherein the epoxide hydrolase activity comprises catalyzing the addition of water to an oxirane compound.

15. The isolated or recombinant nucleic acid of claim 1, wherein the epoxide hydrolase activity further comprises formation of a corresponding diol.

16. The isolated or recombinant nucleic acid of claim 1, wherein the epoxide hydrolase activity further comprises formation of an enantiomerically enriched epoxide.

17. The isolated or recombinant nucleic acid of claim 14, wherein the oxirane compound comprises an epoxide or arene oxide.

18. The isolated or recombinant nucleic acid of claim 14, wherein the oxirane compound or the corresponding diol is optically active.

19. The isolated or recombinant nucleic acid of claim 18, wherein the oxirane compound or the corresponding diol is enantiomerically pure.

20. The isolated or recombinant nucleic acid of claim 1, wherein the epoxide hydrolase activity is enantioselective.

21. The isolated or recombinant nucleic acid of claim 1, wherein the epoxide hydrolase activity is thermostable.

22. The isolated or recombinant nucleic acid of claim 21, wherein the polypeptide retains an epoxide hydrolase activity under conditions comprising a temperature range of between about 37° C. to about 70° C.

23. The isolated or recombinant nucleic acid of claim 1, wherein the epoxide hydrolase activity is thermotolerant.

24. The isolated or recombinant nucleic acid of claim 23, wherein the polypeptide retains an epoxide hydrolase activity after exposure to a temperature in the range from greater than 37° C. to about 90° C.

25. The isolated or recombinant nucleic acid of claim 24, wherein the polypeptide retains an epoxide hydrolase activity after exposure to a temperature in the range from greater than 37° C. to about 50° C.

26. An amplification primer sequence pair for amplifying a nucleic acid encoding a polypeptide having a epoxide hydrolase activity, wherein the primer pair is capable of amplifying a nucleic acid comprising a sequence as set forth in SEQ ID NO:25, or a sequence encoding a polypeptide having an amino acid sequence as set forth in SEQ ID NO:26 or SEQ ID NO:85.

27. The amplification primer pair of claim 26, wherein each member of the amplification primer sequence pair comprises an oligonucleotide comprising at least about 20 to 50 consecutive bases of the sequence.

28. A method of amplifying a nucleic acid encoding a polypeptide having an epoxide hydrolase activity comprising amplification of a template nucleic acid with an amplification primer sequence pair capable of amplifying a nucleic acid sequence as set forth in SEQ ID NO:25, or a sequence encoding a polypeptide having an amino acid sequence as set forth in SEQ ID NO:26 or SEQ ID NO:85.

29. An expression cassette comprising the nucleic acid of claim 1.

30. The expression cassette of claim 29, wherein the nucleic acid encodes a polypeptide having a sequence as set forth in SEQ ID NO:26 or SEQ ID NO:85.

31. A vector comprising a nucleic acid comprising:
the nucleic acid sequence of claim 1.

32. The vector of claim 31, wherein the nucleic acid encodes a polypeptide having a sequence as set forth in SEQ ID NO:26 or SEQ ID NO:85.

33. A cloning vehicle comprising the vector is set forth in claim 31 or the nucleic acid as set forth in claim 1, wherein the cloning vehicle comprises a viral vector, a plasmid, a phage, a phagemid, a cosmid, a fosmid, a bacteriophage or an artificial chromosome.

34. The cloning vehicle of claim 33, wherein the nucleic acid encodes a polypeptide having a sequence as set forth in SEQ ID NO:26 or SEQ ID NO:85.

35. The cloning vehicle claim 33, wherein the viral vector comprises an adenovirus vector, a retroviral vector or an adeno-associated viral vector.

36. The cloning vehicle of claim 33, comprising a bacterial artificial chromosome (BAC), a P1-derived vector (PAC), a yeast artificial chromosome (YAC), or a mammalian artificial chromosome (MAC).

37. A transformed cell comprising a vector, wherein the vector comprises the nucleic acid of claim 1.

38. A transformed cell comprising
the nucleic acid of claim 1.

39. The transformed cell of claim 37 or claim 38, wherein the cell is a bacterial cell, a mammalian cell, a fungal cell, a yeast cell, an insect cell or a plant cell.

40. The transformed cell of claim 37 or claim 38, wherein the nucleic acid encodes a polypeptide having a sequence as set forth in SEQ ID NO:26 or SEQ ID NO:85.

41. An antisense oligonucleotide comprising a nucleic acid sequence complementary to or capable of hybridizing under stringent conditions to
the nucleic acid of claim 1.

42. The antisense oligonucleotide of claim 41, wherein the antisense oligonucleotide is between about 20 to 50, about 20 to 60, about 30 to 70, about 40 to 80, or about 60 to 100 bases in length.

43. A method of inhibiting the translation of an epoxide hydrolase message in a cell comprising administering to the cell or expressing in the cell an antisense oligonucleotide comprising a nucleic acid sequence at least 20 residues in length that is complementary to or capable of hybridizing under stringent conditions to a nucleic acid comprising
the nucleic acid of claim 1.

44. The method of claim 43, wherein the nucleic acid encodes a polypeptide having a sequence as set forth in SEQ ID NO:26 or SEQ ID NO:85.

45. A method of determining whether a test compound specifically binds to a polypeptide comprising the following steps:
(a) expressing a nucleic acid or a vector comprising the nucleic acid under conditions permissive for translation of the nucleic acid to a polypeptide, wherein the nucleic acid has a sequence as set forth in claim 1;

(b) providing a test compound;

(c) contacting the polypeptide with the test compound; and (d) determining whether the test compound of step (b) specifically binds to the polypeptide.

46. The method of claim 45, wherein the nucleic acid encodes a polypeptide having a sequence as set forth in SEQ ID NO:26 or SEQ ID NO:85.

47. A method for identifying a modulator of an epoxide hydrolase activity comprising the following steps:

(a) providing a polypeptide encoded by the nucleic acid of claim 1;

(b) providing a test compound;

(c) contacting the polypeptide of step (a) with the test compound of step (b) and measuring an activity of the epoxide hydrolase, wherein a change in the epoxide hydrolase activity, which is measured in the presence of the test compound, is compared to the epoxide hydrolase activity in the absence of the test compound, thereby providing a determination whether the test compound modulates the epoxide hydrolase activity.

48. The method of claim 47, wherein the nucleic acid encodes a polypeptide having a sequence as set forth in SEQ ID NO:26 or SEQ ID NO:85.

49. The method of claim 47, wherein the epoxide hydrolase activity is measured by providing an epoxide hydrolase substrated and by detecting a decrease in the amount of the substrate or an increase in the amount of a reaction product, or, by detecting an increase in the amount of the substrate or a decrease in the amount of a reaction product.

50. The method of claim 49, wherein decrease in the amount of the substrate or an increase in the amount of the reaction product with the test compound as compared to the amount of substrate or reaction product without the test compound identifies the test compound as an activator of the epoxide hydrolase activity.

51. The method of claim 47, wherein an increase in the amount of the substrate or a decrease in the amount of the reaction product with the test compound as compared to the amount of substrate or reaction product without the test compound identifies the test compound as an inhibitor of the epoxide hydrolase activity.

52. A method for isolating or recovering a nucleic acid encoding a polypeptide with an epoxide hydrolase activity from an environmental sample comprising the steps of:

(a) providing an amplification primer sequence pair as set forth in claim 26;

(b) isolating a nucleic acid from the environmental sample or treating the environmental sample so that nucleic acid in the sample is accessible for hybridization to the amplification primer pair; and (c) combining the nucleic acid of step (b) with the amplification primer pair of step (a) and amplifying nucleic acid from the environmental sample, thereby isolating or recovering a nucleic acid encoding a polypeptide with an epoxide hydrolase activity from an environmental sample.

53. The method of claim 52, wherein each member of the amplification primer sequence pair comprises an oligonucleotide comprising at least about 20 to 50 consecutive bases of a sequence as set forth in SEQ ID NO:25, or a sequence encoding a polypeptide having an amino acid sequence as set forth in SEQ ID NO:26 or SEQ ID NO:85.

54. A method for isolating or recovering a nucleic acid encoding a polypeptide with an epoxide hydrolase activity from an environmental sample comprising the steps of:

(a) providing a polynucleotide probe comprising a sequence as set forth in claim 1;

(b) isolating a nucleic acid from the environmental sample or treating the environmental sample so that nucleic acid in the sample is accessible for hybridization to polynucleotide probe of step (a);

(c) combining the isolated nucleic acid or the treated environmental sample of step (b) with the polynucleotide probe of step (a); and (d) isolating a nucleic acid that specifically hybridizes with the polynucleotide probe of step (a), thereby isolating or recovering a nucleic acid encoding a polypeptide with an epoxide hydrolase activity from an environmental sample.

55. The method of claim 54, wherein the nucleic acid encodes a polypeptide having a sequence as set forth in SEQ ID NO:26 or SEQ ID NO:85.

56. The method of claim 52 or claim 54, wherein the environmental sample comprises a water sample, a liquid sample, a soil sample, an air sample or a biological sample.

57. The method of claim 56, wherein the biological sample is derived from a bacterial cell, a protozoan cell, an insect cell, a yeast cell, a plant cell, a fungal cell or a mammalian cell.

58. An isolated or recombinant nucleic acid comprising a nucleic acid that encodes a polypeptide comprising the amino acid sequence set forth in SEQ ID NO:85.

* * * * *